(12) United States Patent
De Lucca et al.

(10) Patent No.: US 8,586,751 B2
(45) Date of Patent: Nov. 19, 2013

(54) NICOTINAMIDE COMPOUNDS USEFUL AS KINASE MODULATORS

(75) Inventors: George V. De Lucca, Pennington, NJ (US); Qing Shi, Princeton, NJ (US); Chunjian Liu, Pennington, NJ (US); Jingwu Duan, Yardley, PA (US); Andrew J. Tebben, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/377,157

(22) PCT Filed: Jun. 10, 2010

(86) PCT No.: PCT/US2010/038079
§ 371 (c)(1),
(2), (4) Date: Dec. 9, 2011

(87) PCT Pub. No.: WO2010/144647
PCT Pub. Date: Dec. 16, 2010

(65) Prior Publication Data
US 2012/0082702 A1    Apr. 5, 2012

Related U.S. Application Data

(60) Provisional application No. 61/186,417, filed on Jun. 12, 2009.

(51) Int. Cl.
*A61K 31/4433* (2006.01)
*C07D 401/14* (2006.01)

(52) U.S. Cl.
USPC ........................... 546/268.4; 514/333

(58) Field of Classification Search
USPC ........................... 548/400; 546/268.4; 514/333
See application file for complete search history.

(56) References Cited

U.S. PATENT DOCUMENTS

| | | | |
|---|---|---|---|
| 3,375,257 | A | 3/1968 | Thiele |
| 5,104,877 | A | 4/1992 | Boger |
| 5,366,982 | A | 11/1994 | Dereu et al. |
| 5,691,364 | A | 11/1997 | Buckman et al. |
| 5,972,975 | A | 10/1999 | Esser et al. |
| 6,407,111 | B1 | 6/2002 | Bos et al. |
| 6,432,963 | B1 | 8/2002 | Hisamichi et al. |
| 6,797,706 | B1 | 9/2004 | Hisamichi et al. |
| 6,797,709 | B2 | 9/2004 | Yamada et al. |
| 7,273,868 | B2 | 9/2007 | Yamada et al. |
| 7,329,664 | B2 | 2/2008 | Bakthavatchalam et al. |
| 7,459,460 | B2 | 12/2008 | Yang et al. |
| 7,982,036 | B2 | 7/2011 | Singh et al. |
| 2002/0115674 | A1 | 8/2002 | Domagala et al. |
| 2002/0132836 | A1 | 9/2002 | Dairaghi et al. |
| 2004/0097563 | A1 | 5/2004 | Murata et al. |
| 2004/0116479 | A1 | 6/2004 | Haviv et al. |
| 2004/0132730 | A1 | 7/2004 | Axon et al. |
| 2004/0236084 | A1 | 11/2004 | Biwersi et al. |
| 2005/0090499 | A1 | 4/2005 | Currie et al. |
| 2005/0101604 | A1 | 5/2005 | Currie et al. |
| 2005/0182103 | A1 | 8/2005 | Finke et al. |
| 2005/0288502 | A1 | 12/2005 | Andersen et al. |
| 2006/0009453 | A1 | 1/2006 | Geuns-Meyer et al. |
| 2006/0069110 | A1 | 3/2006 | Andersen et al. |
| 2006/0084650 | A1 | 4/2006 | Dong et al. |
| 2006/0100246 | A1 | 5/2006 | Murata et al. |
| 2006/0217417 | A1 | 9/2006 | Brunette et al. |
| 2006/0229337 | A1 | 10/2006 | Brittelli et al. |
| 2006/0252819 | A1 | 11/2006 | Zolotoy et al. |
| 2006/0258672 | A1 | 11/2006 | Barbosa et al. |
| 2006/0258691 | A1 | 11/2006 | Barbosa et al. |
| 2006/0270686 | A1 | 11/2006 | Kelly et al. |
| 2007/0021611 | A1 | 1/2007 | McGuinness et al. |

(Continued)

FOREIGN PATENT DOCUMENTS

| JP | 2002/338466 | 11/2002 |
|---|---|---|
| JP | 4178816 B2 | 9/2008 |

(Continued)

OTHER PUBLICATIONS

Patani, et al., "Bioisosterism: A Rational Approach in Drug Design," Chemical Reviews, 96 (1996), pp. 3147-3176.
Nagashima, et al., "Synthesis and evaluation of 2-{[2-(4-hydroxyphenyl)-ethyl]amino}pyrimidine-5-carboxamide derivatives as novel STAT6 inhibitors," Bioorganic & Medicinal Chemistry, 15, 2 (2006), pp. 1044-1055.
Girgis, et al.. "Novel synthesis of nicotinamid derivatives of cytotoxic properties," Bioorganic & Medicinal Chemistry, 14(13), pp. 4466-4476 (2006).
Madkour, et al., "Reactions of 5-(*p*-Anisyl)-2-methyl-7-(*p*-tolyl)-4*H*-pyrido[2,3-*d*][1,3]oxazin-4-one," Heterocycles (1994), 38(1), pp. 57-69.

(Continued)

*Primary Examiner* — Yong Chu
*Assistant Examiner* — Sonya Wright
(74) *Attorney, Agent, or Firm* — Gary D. Greenblatt

(57) ABSTRACT

Disclosed are nicotinamide compounds of Formula (I): or stereoisomers or pharmaceutically acceptable salts thereof. Also disclosed are methods of using such compounds in the treatment of at least one Btk associated condition, such as, for example, inflammatory disease, and pharmaceutical compositions comprising such compounds.

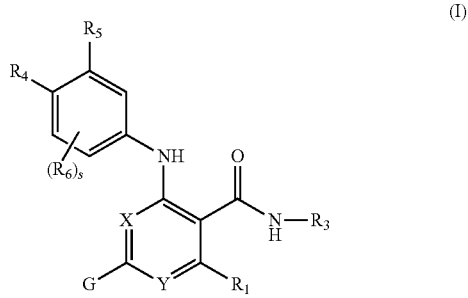

(I)

10 Claims, No Drawings

(56) References Cited

U.S. PATENT DOCUMENTS

| | | |
|---|---|---|
| 2007/0043063 A1 | 2/2007 | Salituro et al. |
| 2007/0066640 A1 | 3/2007 | Castiglioni et al. |
| 2007/0105861 A1 | 5/2007 | Lee et al. |
| 2007/0208164 A1 | 9/2007 | Olszewski et al. |
| 2008/0045536 A1 | 2/2008 | Vaccaro et al. |
| 2008/0076800 A1 | 3/2008 | Huang et al. |
| 2008/0132545 A1 | 6/2008 | Lu et al. |
| 2008/0200464 A1 | 8/2008 | Bellon et al. |
| 2009/0137588 A1 | 5/2009 | Singh et al. |
| 2009/0233900 A1 | 9/2009 | Kuramochi et al. |
| 2010/0029610 A1 | 2/2010 | Singh et al. |
| 2010/0222319 A1 | 9/2010 | Bernhart et al. |
| 2010/0249092 A1 | 9/2010 | Singh et al. |

FOREIGN PATENT DOCUMENTS

| | | |
|---|---|---|
| WO | WO 9809960 | 3/1998 |
| WO | WO 03/013523 | 2/2003 |
| WO | WO 2005/009443 | 2/2005 |
| WO | WO-2005/009443 * | 2/2005 |
| WO | WO-2005009443 * | 3/2005 |
| WO | WO 2005/040133 | 5/2005 |
| WO | WO 2006/075152 | 7/2006 |
| WO | WO 2007/029062 | 3/2007 |
| WO | WO 2007/038314 | 4/2007 |
| WO | WO 2007/042878 | 4/2007 |
| WO | WO 2007/087276 | 8/2007 |
| WO | WO 2007/124546 | 11/2007 |
| WO | WO 2008/005937 | 1/2008 |
| WO | WO 2008/009963 | 1/2008 |
| WO | WO 2008/016643 | 2/2008 |
| WO | WO 2008/019090 | 2/2008 |
| WO | WO 2008/024963 | 2/2008 |
| WO | WO 2008/044713 | 4/2008 |
| WO | WO 2008/053194 | 5/2008 |
| WO | WO 2008/079294 | 7/2008 |
| WO | WO 2009/158571 | 12/2009 |

OTHER PUBLICATIONS

Jure, Latvijas PSR Zinatnu Akademijas Vestis, Kimijas Seriga (1990), (4), pp. 439-444.
Ridi, Annali di Chimica (Rome, Italy) (1959), 49, pp. 944-957.
Robev, Doklady Bolgarskoi Akademii Nauk, Compte Rendus de l'Academie Bulgare des Sciences, (1978), 31(9), pp. 1131-1134.
1026181-11-2/RN Database: Chemscats, (2008).
1025928-91-9/RN Database: ChemsSpider, (2008).
1001050-64-1/RN Database: Chemcats, (2008).
International Search Report mailed Aug. 31, 2010.
IPRP issued Dec. 12, 2011.

* cited by examiner

NICOTINAMIDE COMPOUNDS USEFUL AS KINASE MODULATORS

This application is a 371 of International Application No. PCT/US2010/038079, filed on Jun. 10, 2010, which claims benefit of U.S. 61/186,417, filed on Jun. 12, 2009.

The present invention generally relates nicotinamide compounds useful as kinase modulators, including the modulation of Bruton's tyrosine kinase (Btk). Provided herein are certain nicotinamide compounds and related compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including Btk, in a mammal.

Protein kinases, the largest family of human enzymes, encompass well over 500 proteins. Bruton's Tyrosine Kinase (Btk) is a member of the Tec family of tyrosine kinases, and is a regulator of early B-cell development, as well as mature B-cell activation, signaling and survival.

B-cell signaling through the B-cell receptor (BCR) leads to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium sign upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice are also resistant to developing collagen-induced arthritis and are less susceptible to Staphylococcus-induced arthritis.

A large body of evidence supports the role of B-cells and the humoral immune system in the pathogenesis of autoimmune and/or inflammatory diseases. Protein-based therapeutics (such as Ritaxan) developed to deplete B-cells, represent an important approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases including, but not limited to: SLE, rheumatoid arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evan's syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

In addition, Btk has been reported to play a role in controlling B-cell survival in certain B-cell cancers. For example, Btk has been shown to be important for the survival of BCR-Abl-positive B-cell acute lymphoblastic leukemia cells. Thus inhibition of Btk activity can be useful for the treatment of B-cell lymphoma and leukemia.

In view of the numerous conditions that are contemplated to benefit by treatment involving modulation of protein kinases, it is immediately apparent that new compounds that modulate protein kinases such as Btk and methods of using these compounds should provide substantial therapeutic benefits to a wide variety of patients.

Inhibitors of protein kinases are widely sought and a number of publications report compounds effective in modulating protein kinases. For example, patent publications WO 2005/047290, WO 2005/14599, WO 2005/05429, WO 2006/99075, and WO 2006/53121 disclose certain imidazopyrazine compounds that are said to inhibit protein kinase activity, including Btk activity. Patent publication WO 2008/33858 discloses methods of inhibiting Btk activity with various Btk binding chemical compounds. U.S. Publication No. 2006/084650 discloses that fused heterocyclic compounds exemplified by imidazopyrimidines and pyrrolotriazines may be used as protein kinase inhibitors. In addition, certain imidazopyridazine and imidazotriazine compounds are disclosed in WO 2007/38314 (published Apr. 5, 2007) and WO 2008/045536 (published Feb. 21, 2008), both of which are assigned to the present assignee.

The present invention relates to a class of nicotinamide compounds found to be effective inhibitors of protein kinases, particularly Btk. These compounds are provided to be useful as pharmaceuticals with desirable stability, bioavailability, therapeutic index, and toxicity values that are important to their drugability.

SUMMARY OF THE INVENTION

The first aspect of the invention provides nicotinamide compounds of Formula (I):

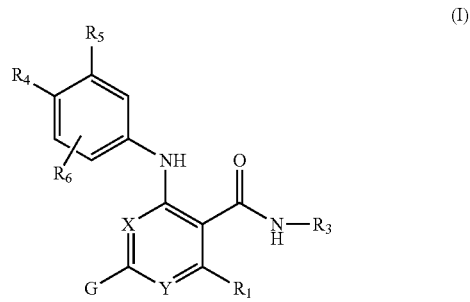

or stereoisomers or pharmaceutically acceptable salts thereof, wherein:
one of X and Y is N, and the other of X and Y is $CR_2$;
G is:
  i) —$NR_b(CR_bR_b)_q$(phenyl); or
  ii) a cyclic group selected from 1- to 2-ring carbocyclyl, 1- to 2-ring aryl, 1- to 2-ring heterocyclyl, and 1- to 2-ring heteroaryl, each substituted with zero to 3 $R_f$;

$R_1$ is H or —$OR_a$;
$R_2$ is H, —$OCH_3$, halo, —$CH_3$, —$CF_3$, —$OCF_3$, or —CN;
$R_3$ is H or —$CH_3$;
$R_6$ is H, alkoxy, halo, —$CH_3$, —$CF_3$, —$OCF_3$, or —CN;
one of $R_4$ and $R_5$ is H, halo, —$CH_3$, —$CF_3$, —CN, —$NH_2$, —OH, alkoxy, —$OCF_3$, —$NR_dR_d$, —$NR_bS(O)_2$(alkyl), —$NR_bS(O)_2$(aryl), —$NR_bC(O)$(phenyl), —$NR_bC(O)NR_b$(phenyl), —$S(O)_2(C_{1-4}$alkyl), —$NR_bS(O)_2$(heterocyclyl), —$NR_b(S(O)_2(C_{1-4}$haloalkyl), —$NR_bS(O)_2$(fluorophenyl), —$NR_bS(O)_2$(biphenyl), —$NR_bS(O)_2$(heteroaryl), —$NR_bS(O)_2$(benzyl), —$N(S(O)_2(C_{1-4}$haloalkyl))$_2$, pyrrolidine-2,5-dione, —$NR_bC(O)O$(alkyl) or -L-C(O)-A;
and the other of $R_4$ and $R_5$ is:
a) H, halo, —CN, or alkoxy;
b) -L-A; or
c) -L-C(O)-A;
wherein L is a bond or —$(CR_cR_c)_t$—; and A is selected from $A_1$, $A_2$, and $A_3$, wherein:
$A_1$ is alkyl or cycloalkyl, each independently substituted with 0 to 5 substituents independently selected from —OH, =O, alkyl, —OH, alkoxy, —C(O)(alkyl), —C(O)$OR_d$, —$NR_dR_d$, —C(O)$NR_dR_d$, —C(O)$NR_b$(hydroxyalkyl), —C(O)$NR_b$(heterocyclyl), —C(O)$NR_b(CR_bR_b)_qNR_dR_d$, and/or —$NR_bC(O)$(alkyl);
$A_2$ is heterocyclyl or heteroaryl having 1- to 3-heteroatoms independently selected from N, O, and/or S, and substituted with zero to 5 substituents independently selected from —OH, =O, alkyl, hydroxyalkyl, cycloalkyl, —C(O)(alkyl), —$NR_dR_d$, —C(O)$NR_dR_d$, —C(O)$NR_b$(hydroxyalkyl), —C(O)$NR_b$(cycloalkyl), C(O)$NR_b(CR_bR_b)_qNR_dR_d$, —C(O)$NR_b$(phenyl), —$NR_bC(O)$(alkyl), —C(O)O(alkyl), and/or —C(O)O(benzyl);
$A_3$ is —OH, alkoxy, —$NR_dR_d$, di-$(C_{1-2}$alkyl) N-oxide, —$NR_b$(hydroxyalkyl), —$NR_b$(cycloalkyl), —$NR_b(CR_bR_b)_qNR_dR_d$, —$NR_b$(phenyl), —$NR_bC(O)$(alkyl), —S(alkyl), —S(O)(alkyl), —S(O)(fluoroalkyl), —$S(O)_2NR_dR_d$, —$S(O)_2(CR_bR_b)_qNR_dR_d$, —$O(CR_bR_b)_qCR_b$(alkoxy)$_2$, —$O(CR_bR_b)_qNR_b$(cycloalkyl), —$O(CR_bR_b)_qNR_dR_d$, —$NR_bS(O)_2$(alkyl), —$NR_bS(O)_2$(aryl), —$NR_bS(O)_2$(heteroaryl), —$NR_bC(O)NR_bA_2$, —$NR_bC(O)A_2$, —$NR_bA_2$, —$NR_bC(O)(CR_bR_b)_qA_2$, or —$O(CR_cR_c)_qA_2$;
$R_a$ is H, alkyl, hydroxyalkyl, or —$(CH_2)_{17}$-phenyl, wherein said phenyl in turn is substituted with zero to 4 $R_h$;
each $R_b$ is independently H and/or —$CH_3$;
each $R_c$ is independently H, —OH, —$CH_3$, F, and/or —$CH_2OH$;
each $R_d$ is independently H and/or alkyl;
each $R_f$ is independently H, $Q_1$, $R_g$, —C(O)$Q_2$, —C(O)$(CR_bR_b)_tQ_2$, —C(O)$NR_bQ_2$, —C(O)$N(Q_2)_2$, —$NR_bQ_2$, —$NR_bCR_bR_bQ_2$, —$N(Q_2)_2$, —$(CR_bR_b)_tQ_2$, —$(CR_bR_b)_tNR_bC(O)Q_2$, —C(O)$NR_b(CR_bR_b)_tQ_2$, —$NR_bS(O)_2Q_2$, —$NR_bS(O)_2Q_2$, —$(CR_bR_b)_tNR_bQ_2$, and/or 5- to 6-membered heterocyclyl substituted with 0-3 $R_g$;
each $R_g$ is independently $Q_2$, =O, =$CR_bR_b$, —OH, halo, —CN, alkyl, hydroxyalkyl, haloalkyl, aminoalkyl, phenyl, phenoxy, alkoxy, aryl, heteroaryl, heterocyclyl, —$NR_dR_d$, —C(O)(alkyl), —C(O)$CR_bR_b$(phenyl), —$CR_bR_bC(O)$(phenyl), and/or —C(O)$NR_dR_d$; and/or two $R_g$ together with the carbon atom to which they are attached form a 5- to 7-membered cycloalkyl or heterocyclyl ring substituted with zero to 2 substituents independently selected from —OH, alkyl, cycloalkyl, halo, fluoroalkyl, =O, 1- to 2-ring aryl, and/or 1- to 2-ring heteroaryl;
each $Q_1$ is independently:
a) H, —OH, —C(O)$OR_d$, —C(O)$NR_b$(phenyl), —C(O)$NR_b$(alkyl phenyl), —OC(O)(phenyl), —O(phenyl), phenyl, —$NR_dR_d$, —$NR_b$(pyrimidinyl), —N(pyrimidinyl)$_2$, hydroxyalkyl, aminoalkyl, —$(CR_bR_b)_qC(O)O$(alkyl), —$(CR_bR_b)_qNR_bC(O)$(alkyl), indolyl, imidazolidinonyl, and/or pyrrolidinonyl;
b) —$NR_dC(O)$-$Q_2$;
c) —$NR_bC(O)(CR_bR_b)_t$-$Q_2$;
d)

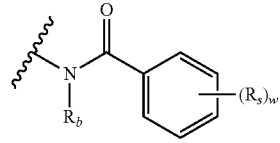

wherein each $R_s$ is independently selected from alkyl, fluoroalkyl, halo, —OH, —C(O)(alkyl), —$NR_bC(O)$(alkyl), —C(O)$OR_d$, alkoxy, fluoroalkoxy, —$NR_dR_d$, —$S(O)_2$(alkyl), —$NR_bC(O)O$(alkyl), phenoxy, —$CR_bR_bNR_bC(O)$(alkyl), and/or a cyclic group independently selected from aryl, heteroaryl, and/or heterocyclyl, wherein said cyclic group is substituted with zero or more substituents independently selected from alkyl, —OH, halo, haloalkyl, —$NR_dR_d$, alkoxy, =O, and/or —CN;
e) —$NR_bS(O)_2$-$Q_2$;
f) —$(CR_bR_b)_tC(O)$-$Q_2$;
g) $NR_bC(O)NR_b$-$Q_2$; and/or
h) $(CR_bR_b)_tC(O)NR_b$-$Q_2$;
each $Q_2$ is independently:
a) H, —OH, alkyl, haloalkyl, —$NR_dR_d$, alkoxy, phenoxy, and/or benzophenonyl;
b) cycloalkyl, aryl, heterocyclyl, and/or heteroaryl, each of which is substituted with zero or more substituents independently selected from alkyl, fluoroalkyl, cycloalkyl, halo, —CN, —OH, =O, —$NR_dR_d$, alkoxy, fluoroalkoxy, —C(O)(alkyl), —C(O)O(alkyl), phenoxy, —O(cycloalkyl), —$NR_bC(O)$(alkyl), —S(alkyl), —$S(O)_2$(alkyl), —$NR_bC(O)O$(alkyl), —$CR_bR_bNR_bC(O)$(alkyl), and/or a cyclic group independently selected from aryl, heteroaryl, and/or heterocyclyl, wherein said cyclic group is substituted with zero or more substituents independently selected from alkyl, —OH, halo, —$NR_dR_d$, alkoxy, =O, —CN, and/or haloalkyl; and/or
c) —$(CR_bR_b)_qN$(alkyl)$_2$, —$(CR_bR_b)_q$(aryl), and/or —$(CR_bR_b)_q$(heteroaryl);
each $R_h$ is independently —OH, —$NH_2$, alkyl, halo, haloalkyl, alkoxy, and/or haloalkoxy;
n is zero, 1, 2, 3, 4, 5, or 6;
each q is independently 1, 2, and/or 3;
each t is independently 1, 2, 3, and/or 4; and
w is zero, 1, 2, or 3.

The present invention also provides pharmaceutical compositions comprising at least one nicotinamide compound of Formula (I), or stereoisomers or pharmaceutically acceptable salts thereof; and a pharmaceutically acceptable carrier or diluent.

The present invention also provides a method of inhibiting of Btk activity comprising administering to a mammal in need thereof at least one compound of Formula (I), or a stereoisomer or a pharmaceutically acceptable salt thereof.

The present invention also provides a method for treating allergic disorders and/or autoimmune and/or inflammatory diseases, comprising administering to a mammal in need thereof at least one compound of Formula (I), or a stereoisomer or a pharmaceutically acceptable salt thereof.

The present invention also provides a method for treating cancer comprising administering to a mammal in need thereof at least one compound of Formula (I), or a stereoisomer or a pharmaceutically acceptable salt thereof.

The present invention also provides the compounds of Formula (I), or stereoisomers or pharmaceutically acceptable salts thereof, for use in therapy.

The present invention also provides the use of the compounds of Formula (I), stereoisomers or pharmaceutically acceptable salts thereof, for the manufacture of a medicament for the treatment or prophylaxis of an allergic disorder and/or autoimmune and/or inflammatory disease.

The present invention also provides the use of the compounds of Formula (I) or pharmaceutically acceptable salts thereof, for the manufacture of a medicament for treatment of cancer.

These and other features of the invention will be set forth in expanded form as the disclosure continues.

DETAILED DESCRIPTION

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The term "halo" or "halogen" refers to fluoro, chloro, bromo, and iodo.

The term "hydroxy" refers to the group —OH.

The term "amino" refers to the group —NH$_2$.

In the chemical structures shown herein, a dashed line represents either a single or double bond. For example,

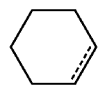

represents either

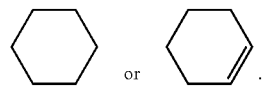

As used herein, the term "alkyl" or "alkylene" is intended to include both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "C$_{1-6}$alkyl" denotes straight and branched chain alkyl groups with one to six carbon atoms. The alkyl group can be unsubstituted or substituted with at least one hydrogen being replaced by another chemical group.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and C$_{1-4}$hydroxyalkyl. "C$_{1-4}$hydroxyalkyl" is intended to include C$_1$, C$_2$, C$_3$, and C$_4$ alkyl groups substituted with one or more hydroxyl groups.

The subscript "0" refers to a bond. Thus, the term "C$_{0-2}$hydroxyalkyl" includes hydroxy, hydroxymethyl and hydroxyethyl.

The term "haloalkyl" includes both branched and straight-chain saturated aliphatic hydrocarbon groups substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. For example, "C$_{1-4}$haloalkyl" is intended to include C$_1$, C$_2$, C$_3$, and C$_4$ alkyl groups substituted with one or more halogens.

The term "fluoroalkyl" as used herein is intended to include both branched and straight-chain saturated aliphatic hydrocarbon groups substituted with one or more fluorine atoms. For example, "C$_{1-4}$fluoroalkyl" is intended to include C$_1$, C$_2$, C$_3$, and C$_4$ alkyl groups substituted with one or more fluorine atoms.

The term "alkoxy" and "—O(alkyl)" represent an alkyl group bonded through an oxygen linkage. For example, "C$_{1-6}$alkoxy" or "—O(C$_{1-6}$alkyl)" are intended to include C$_1$, C$_2$, C$_3$, C$_4$, C$_5$, and C$_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group bonded through a sulfur linkage; for example —S—CH$_3$, and —S—CH$_2$CH$_3$.

The term "haloalkoxy" refers to a haloalkyl group bonded through an oxygen linkage (—O—), wherein the haloalkyl group has one or more halo substituents. For example, "C$_1$-

6haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluoroethoxy.

"Fluoroalkoxy" and "—O(fluoroalkyl)" represent a fluoroalkyl group as defined above attached through an oxygen linkage (—O—). For example, "$C_{1-4}$fluoroalkoxy" is intended to include $C_1$, $C_2$, $C_3$, and $C_4$ fluoroalkoxy groups.

The terms "hydroxyalkoxy" and "—O(hydroxyalkyl)" refers to an alkoxy group substituted with a single or more hydroxyl groups. For example, "hydroxyalkoxy" includes —OCH$_2$OH, —OCH$_2$CH$_2$OH, and $C_{1-4}$hydroxyalkoxy.

The term "alkylthio" refers to an alkyl bonded through a sulfur linkage (—S—). For example, the term "thioalkyl" includes the group —S($C_{1-6}$alkyl).

The term "cycloalkyl" refers to a fully saturated hydrocarbon group containing from 1 to 2 rings and 3 to 8 carbons per ring. The term "$C_{3-7}$cycloalkyl" is intended to include $C_3$, $C_4$, $C_5$, $C_6$, and $C_7$ cycloalkyl groups. Exemplary cycloalkyl groups include, but are not limited to, cyclopropyl, cyclobutyl, cyclopentyl, cyclohexyl, and cycloheptyl. Branched cycloalkyl groups such as 1-methylcyclopropyl and 2-methylcyclopropyl are included in the definition of "cycloalkyl".

The term "cycloalkenyl" refers to a nonaromatic, partially unsaturated hydrocarbon group containing from 1 to 2 rings and 3 to 8 carbons per ring, which have one or more double carbon-carbon bonds that may occur in any stable point along the ring. The term "$C_{3-7}$cycloalkenyl" is intended to include $C_3$, $C_4$, $C_5$, $C_6$, and $C_7$ cycloalkenyl groups. Exemplary cycloalkenyl groups include, but are not limited to, cyclopropenyl, cyclobutenyl, cyclopentenyl, cyclohexenyl, and cycloheptenyl. Branched cycloalkenyl groups such as 1-methylcyclopropenyl and 2-methylcyclopropenyl are included in the definition of "cycloalkenyl".

The term "aminoalkyl" refers to an alkyl group substituted with one or more amine groups. Exemplary aminoalkyl groups include aminomethyl, aminoethyl, and $C_{1-6}$-aminoalkyl.

The term "alkylamino" refers to an amino group substituted with an alkyl group as defined above. For example, the term "alkylamino" includes the group —NH($C_{1-6}$alkyl).

The term "dialkylamino" refers to an amino group substituted with two alkyl groups as defined above. For example, the term "dialkylamino" includes the group —N(CH$_3$)($C_{1-12}$alkyl).

The term "carbonyl" refers to a bivalent carbonyl group —C(O)—.

The term "CO$_2$" is used herein, this is refers to the group

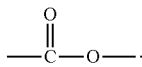

The term "cyano" refers to the group —CN.

The term "nitro" refers to the group —NO$_2$.

The term "carbamoyl" refers to the group —C(O)NH— which is bonded on one end to the remainder of the molecule and on the other to hydrogen or an organic moiety, such as, for example, alkyl, haloalkyl, hydroxyalkyl, aryl, alkylaryl, heterocycle, heteroaryl, alkylcarbonyl, and hydroxyl.

The term "aryl" refers to cyclic aromatic hydrocarbon groups having from 1 to 3 aromatic rings, especially monocyclic or bicyclic groups, such as, for example, phenyl, biphenyl, fluorenyl, 1-naphthyl and 2-naphthyl. When the aryl group contains two or more aromatic rings (e.g., bicyclic, etc.), the aromatic rings may be joined at a single point (e.g., biphenyl) or fused (e.g., naphthyl and phenanthrenyl). The aryl can be optionally substituted with at least one substituent, preferably 1 to 5 substituents, at any available and substitutable ring position, or where valence allows on any rings fused or attached thereto. Exemplary substituents include, but are not limited to, for example, hydroxy, alkyl, halo, haloalkyl, amine, cyano, and alkoxy.

The term "alkylaryl" refers to an aryl group substituted with an alkyl group. The term "alkylphenyl" refers to a phenyl group substituted with an alkyl group. For example, the term "alkylphenyl" includes methylphenyl, ethylphenyl, and $C_{1-4}$alkylphenyl.

The term "hydroxyphenyl" refers to an aryl group substituted with a hydroxy group.

The term "halophenyl" refers to an aryl group substituted with one or more halo groups. Exemplary halophenyl groups include fluorophenyl, difluorophenyl, and chlorophenyl. The halo group(s) may be attached at any available position on the phenyl.

The term "fluoroalkylphenyl" refers to an aryl group substituted with a fluoroalkyl group, wherein the fluoroalkyl group contains one or more fluoro atoms. For example, the term "fluoroalkylphenyl" includes monofluoromethylphenyl, trifluoromethylphenyl, and ($C_{1-2}$fluoroalkyl)phenyl.

The term "aryloxy" refers to an aryl group bonded through an oxygen linkage (—O—). For example, the term "aryloxy" includes phenoxy (—O-phenyl).

The term "benzyl" refers to phenyl group bonded through a methylene group and is also represented by —CH$_2$(phenyl).

The term "heteroatom" refers to oxygen (O), sulfur (S), and nitrogen (N).

The term "heterocyclo" or "heterocyclyl" may be used interchangeably and refer to non-aromatic 3- to 7-membered monocyclic groups, 6- to 11-membered bicyclic groups, and 10- to 15-membered tricyclic groups, in which at least one of the rings has at least one heteroatom (O, S or N), said heteroatom containing ring preferably having 1 to 3 heteroatoms independently selected from O, S, and/or N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The heterocyclo ring may contain zero, one, two or three substituents, for example, substituents selected from halogen, trifluoromethyl, trifluoromethoxy, alkyl, haloalkyl, hydroxyalkyl, aminoalkyl, alkenyl, nitro, cyano, oxo (=O), alkoxy, haloalkoxy, alkylthio, —NH(alkyl), —N(alkyl)$_2$, —C(=O)(alkyl), —CO$_2$(alkyl), —C(=O)NH(alkyl), —C(=O)N(alkyl)$_2$, aryl, and/or cycloalkyl, heterocyclo. As valence allows, if said further ring is cycloalkyl or heterocyclo it is additionally optionally substituted with =O (oxo).

Exemplary monocyclic heterocyclyl groups include oxetanyl, azetidinyl, pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl. Exemplary bicyclic heterocyclo groups include quinuclidinyl.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the substituents defined above for heterocyclyl rings.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and tetrahydroquinolinyl.

Exemplary tricyclic heteroaryl groups include carbazolyl, benzidolyl, phenanthrollinyl, acridinyl, phenanthridinyl, and xanthenyl.

The term "carbocyclyl" means a saturated or partially unsaturated ring(s) in which all atoms of all rings are carbon. Thus, the term includes nonaromatic rings such as, for example, cycloalkyl and cycloalkenyl rings.

When the term "optionally substituted" is used herein to refer to a ring or group, the ring or group may be substituted or unsubstituted.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

It should be understood that the selections for all groups will be made by one skilled in the field to provide stable compounds.

Compounds of this invention may have one or more asymmetric centers. Compounds of the present invention containing an asymmetrically substituted atom may be isolated in optically active or racemic forms. It is well known in the art how to prepare optically active forms, such as by resolution of racemic forms or by synthesis using optically active starting materials or optically active catalysts. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, (enantiomeric and diastereomeric) racemic forms and all geometric isomeric forms of a structure are intended, unless the specific stereochemistry or isomeric form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The molecular weight of compounds of the present invention is preferably less than about 800 grams per mole.

The compounds of the present invention are intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The compounds of Formula (I) can form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Prodrugs and solvates of the inventive compounds are also contemplated. The term "prodrug" denotes a compound which, upon administration to a subject, undergoes chemical conversion by metabolic or chemical processes to yield a compound of the Formula (I), and/or a salt and/or solvate thereof. Any compound that will be converted in vivo to provide the bioactive agent (i.e., the compound for Formula (I)) is a prodrug within the scope and spirit of the invention. For example, compounds containing a carboxy group can form physiologically hydrolyzable esters which serve as prodrugs by being hydrolyzed in the body to yield Formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
  a) *Design of Prodrugs*, H. Bundgaard, ed., Elsevier (1985), and *Methods in Enzymology*, 112:309-396, K. Widder et al., eds., Academic Press (1985);
  b) Bundgaard, H., Chapter 5, "Design and Application of Prodrugs," *A Textbook of Drug Design and Development*, pp. 113-191, P. Krosgaard-Larsen et al., eds., Harwood Academic Publishers (1991); and
  c) Bundgaard, H., *Adv. Drug Deliv. Rev.*, 8:1-38 (1992), each of which is incorporated herein by reference.

Compounds of the Formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization. The inventive compounds may be in the free or hydrate form.

It should further be understood that solvates (e.g., hydrates) of the compounds of Formula (I) are also with the scope of the present invention. Methods of solvation are generally known in the art.

In one embodiment, the compounds of Formula (I) are provided wherein X is N and Y is $CR_2$. The compounds of this embodiment have structures represented by Formula (Ia):

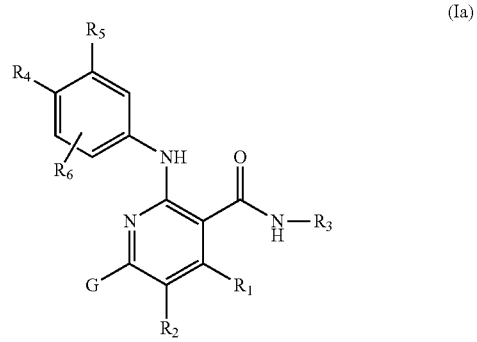

(Ia)

or stereoisomers or pharmaceutically acceptable salts thereof, wherein G, $R_1$, $R_2$, $R_3$, $R_4$, $R_5$, and $R_6$ are defined in the first aspect hereinabove. Preferably, $R_3$ is H.

In one embodiment, the compounds of Formula (I) are provided wherein X is $CR_2$ and Y is N. The compounds of this embodiment have structures represented by Formula (Ib):

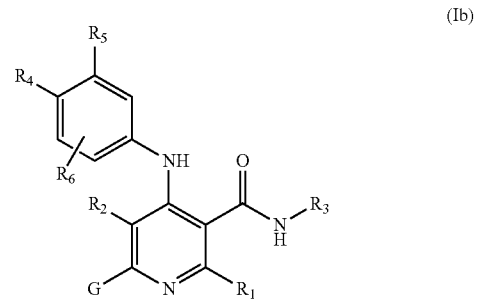

(Ib)

or stereoisomers or pharmaceutically acceptable salts thereof, wherein G, $R_1$, $R_2$, $R_3$, $R_4$, $R_5$, and $R_6$ are defined in the first aspect hereinabove. Preferably, $R_3$ is H.

In one embodiment, the compounds of Formula (I) are provided wherein G is —$NR_b(CR_bR_b)_q$(phenyl). The compounds of this embodiment have structures represented by Formula (Ic):

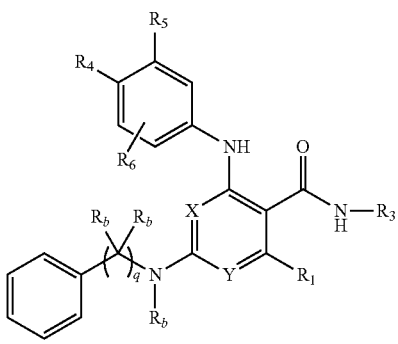

(Ic)

or stereoisomers or pharmaceutically acceptable salts thereof, wherein: X, Y, $R_1$, $R_3$, $R_4$, $R_5$, $R_6$, $R_b$, and q are defined in the first aspect hereinabove. Preferably, $R_3$ is H.

In one embodiment, the compounds of Formula (I) are provided wherein G is a cyclic group. The compounds of this embodiment have structures represented by Formula (Id):

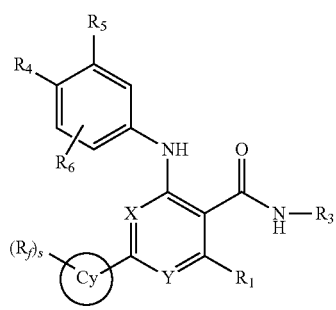

(Id)

or stereoisomers or pharmaceutically acceptable salts thereof, wherein: Cy is a cyclic group selected from 1- to 2-ring carbocyclyl, 1- to 2-ring aryl, 1- to 2-ring heterocyclyl, and 1- to 2-ring heteroaryl, and s is zero, 1, 2, or 3. Preferably, $R_3$ is H.

In one example of this embodiment, X is N and Y is $CR_2$. In another example of this embodiment, X is $CR_2$ and Y is N. X, Y, $R_1$, $R_2$, $R_3$, $R_4$, $R_5$, $R_6$, and $R_f$ are defined in the first aspect hereinabove.

In one embodiment, the compounds of Formula (I) are provided wherein G is a mono- or bi-cyclic carbocyclyl group, each substituted with zero to 3 $R_f$. The compounds of this embodiment have structures represented by Formula (Ie):

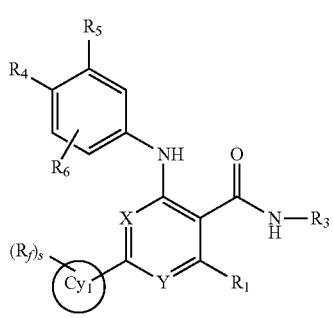

(Ie)

or stereoisomers or pharmaceutically acceptable salts thereof, wherein: $Cy_1$ is a cyclic group selected from 1- to 2-ring carbocyclyl; and s is zero, 1, 2, or 3. X, Y, $R_1$, $R_3$, $R_4$, $R_5$, $R_6$, and $R_f$ are defined in the first aspect hereinabove. Examples of suitable 1-ring carbocyclyl groups include, cyclopentyl, cyclohexyl, cyclopentenyl, and cyclohexenyl groups. Examples of bicyclic carbocyclyl groups include bicyclo[2.1.1]hexyl, bicyclo[2.2.1]heptanyl, bicyclo[2.2.2.]octanyl, bicyclo[2.1.1]hexenyl, bicyclo[2.2.1]heptenyl, and bicyclo[2.2.2]octenyl groups. Preferably, $R_3$ is H. In one example of this embodiment, X is N and Y is $CR_2$. In another example of this embodiment, X is $CR_2$ and Y is N. $R_2$ is defined in the first aspect hereinabove.

In one embodiment, the compounds of Formula (I) are provided wherein G is a 1- to 2-ring aryl group, each substituted with zero to 3 $R_f$. The compounds of this embodiment have structures represented by Formula (If):

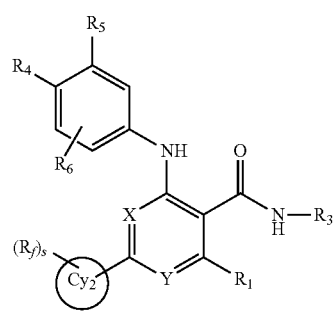

(If)

or stereoisomers or pharmaceutically acceptable salts thereof, wherein: $Cy_2$ is a cyclic group selected from 1- to 2-ring aryl groups; s is zero, 1, 2, or 3; and X, Y, $R_1$, $R_3$, $R_4$, $R_5$, $R_6$, and $R_f$ are defined in the first aspect hereinabove. Examples of suitable monocyclic aryl groups include phenyl. Examples of suitable bicyclic aryl groups include naphthalenyl, 1,2,3,4-tetrahydronaphthalenyl, 1,2-dihydronaphthalenyl, 2,3-dihydro-1H-indenyl, and 1H-indenyl. Preferably, $R_3$ is H. In one example of this embodiment, X is N and Y is $CR_2$. In another example of this embodiment, X is $CR_2$ and Y is N. $R_2$ is defined in the first aspect hereinabove.

In one embodiment, the compounds of Formula (I) are provided wherein G is a mono- or bi-cyclic heterocyclyl group. The compounds of this embodiment have structures represented by Formula (Ig):

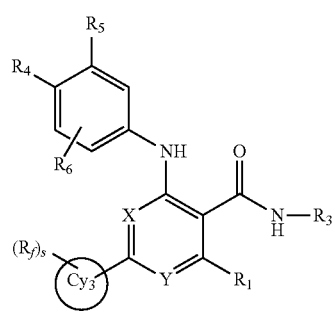

(Ig)

or stereoisomers or pharmaceutically acceptable salts thereof, wherein: $Cy_3$ is a cyclic group selected from 1- to 2-ring heterocyclyl, each substituted with zero to 3 $R_f$; s is zero, 1, 2, or 3; and X, Y, $R_1$, $R_3$, $R_4$, $R_5$, $R_6$, and $R_f$ are defined in the first aspect hereinabove. Examples of 5- to 6-membered monocyclic heterocyclyl groups include, but are not limited to, pyrrolidinyl, piperidinyl, piperazinyl, and morpholinyl. Examples of suitable 6- to 10-membered bicyclic heterocyclyl groups include 1,2,3,4-tetrahydroquinolinyl, 1,2,3,4-tetrahydroisoquinolinyl, indolinyl, isoindolinyl, and 2,5-diazabicyclo[2.2.1]heptane. Preferably, $R_3$ is H. In one example of this embodiment, X is N and Y is $CR_2$. In another example of this embodiment, X is $CR_2$ and Y is N. $R_2$ is defined in the first aspect hereinabove.

In one embodiment, the compounds of Formula (I) are provided wherein G is a 1- to 2-ring heteroaryl group, each substituted with zero to 3 $R_f$. The compounds of this embodiment have structures represented by Formula (Ih):

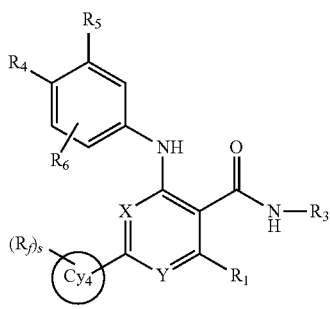

(Ih)

or stereoisomers or pharmaceutically acceptable salts thereof, wherein: $Cy_4$ is a cyclic group selected from 1-ring heteroaryl and 2-ring heteroaryl groups; s is zero, 1, 2, or 3; and X, Y, $R_1$, $R_3$, $R_4$, $R_5$, $R_6$, and $R_f$ are defined in the first aspect hereinabove. Examples of suitable 1-ring heteroaryl groups include thiophenyl, pyrazolyl, thiazolyl, and pyridinyl. Examples of suitable 2-ring heteroaryl groups include indolyl and benzofuranyl. Preferably, $R_3$ is H. In one example of this embodiment, X is N and Y is $CR_2$. In another example of this embodiment, X is $CR_2$ and Y is N. $R_2$ is defined in the first aspect hereinabove.

Another embodiment provides a compound having Formula (I) or stereoisomers or pharmaceutically acceptable salts thereof, wherein:

G is:
i) —$NR_b(CR_bR_b)_q$(phenyl);
ii) 1- to 2-ring heteroaryl or 1- to 2-ring heterocyclyl substituted with zero to 3 substituents independently selected from alkyl, phenyl, —$NR_dR_d$, —$NR_dC(O)O$(alkyl), —C(O)(alkyl), —C(O)(phenyl), and/or —C(O)(benzyl);
iii)

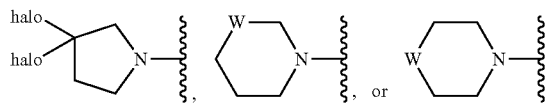

wherein W is $CR_b(OR_b)$, C=$CR_bR_b$, $NR_d$, or NC(O)$CR_bR_b$(phenyl); or W is $CR_gR_g$ and
a) each $R_g$ is halo; or
b) $R_g$ and $R_g$ together with the carbon atom to which they are attached, form a 5- to 7-membered cycloalkyl or heterocyclyl ring substituted with zero to 2 substituents independently selected from —OH, alkyl, cycloalkyl, halo, —$CF_3$, =O, —C(O)OH, —C(O)($C_{1-6}$alkyl), 1- to 2-ring aryl, and/or 1- to 2-ring heteroaryl;

iv) naphthalenyl; or phenyl substituted with zero to 3 substituents independently selected from —OH, alkyl, fluoroalkyl, halo, —CN, —$NR_bR_b$, —C(O)OH, alkoxy, —$CR_bR_bO$(alkyl), —$CH_2NR_bC(O)$(alkyl), —$CH_2NR_bC(O)$(phenyl), —C(O)(alkyl), —C(O)(heterocyclyl), phenoxy, —C(O)O(alkyl), —C(O)$NR_b$(alkyl), —C(O)N(alkyl)$_2$, —C(O)$NR_bCR_bR_b$(heteroaryl), —$NR_bS(O)_2$(alkyl), —$NR_bS(O)_2$(phenyl), —$NR_bC(O)$(phenyl), —$NR_bC(O)$(alkyl phenyl), and/or —$NR_bC(O)NR_b$(phenyl); or v)

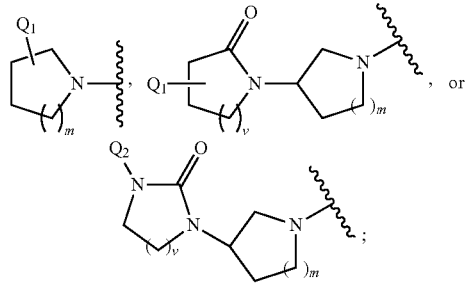

vi) cycloalkyl or cycloalkenyl substituted with zero to 2 substituents independently selected from —OH, halo, —$CF_3$, =O, —OC(O)(phenyl), —$NR_bC(O)$(phenyl), —$NR_bCR_bR_b$(methoxyphenyl), —$NR_bC(O)NR_b$(thiazolyl),

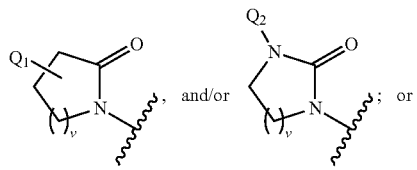

vii)

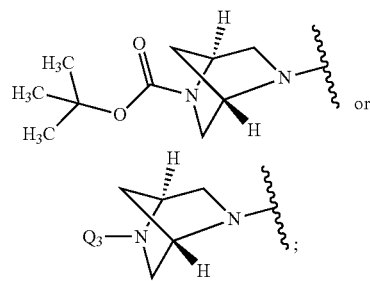

$Q_3$ is H, —C(O)O($C_{1-4}$alkyl), —C(O)$NR_b$($C_{1-4}$alkyl), or —C(O)$NR_b$(1-ring heteroaryl);
each $R_d$ is independently H and/or $C_{1-6}$alkyl; m is 1 or 2; v is 1 or 2; and X, Y, $R_1$, $R_3$, $R_4$, $R_5$, $R_6$, $R_b$, $R_f$, $R_g$, $Q_1$, $Q_2$, and q are defined in the first aspect hereinabove. Preferably, $R_3$ is H. In one example of this embodiment, X is N and Y is $CR_2$. In another example of this embodiment, X is $CR_2$ and Y is N.

Another embodiment provides a compound having Formula (I) or stereoisomers or pharmaceutically acceptable salts thereof, wherein:

G is:
i) 1- to 2-ring heteroaryl or 1- to 2-ring heterocyclyl substituted with zero to 3 substituents independently selected from alkyl, phenyl, —NR$_d$R$_d$, —NR$_d$C(O)O(alkyl), —C(O)(alkyl), —C(O)(phenyl), and/or —C(O)(benzyl);

ii)

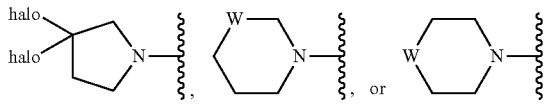

wherein W is CR$_b$(OR$_b$), C=CR$_b$R$_b$, NR$_d$, or NC(O)CR$_b$R$_b$(phenyl); or W is CR$_g$R$_g$ and
a) each R$_g$ is halo; or
b) R$_g$ and R$_g$ together with the carbon atom to which they are attached, form a 5- to 7-membered cycloalkyl or heterocyclyl ring substituted with zero to 2 substituents independently selected from —OH, alkyl, cycloalkyl, halo, —CF$_3$, =O, 1- to 2-ring aryl, and/or 1- to 2-ring heteroaryl;

iii) naphthalenyl; or phenyl substituted with zero to 3 substituents independently selected from —OH, alkyl, fluoroalkyl, halo, —CN, —NR$_b$R$_b$, alkoxy, —CR$_b$R$_b$O(alkyl), —CH$_2$NR$_b$C(O)(alkyl), —CH$_2$NR$_b$C(O)(phenyl), —C(O)(alkyl), —C(O)(heterocyclyl), phenoxy, —C(O)O(alkyl), —C(O)NR$_b$(alkyl), —C(O)N(alkyl)$_2$, —C(O)NR$_b$CR$_b$R$_b$(heterocyclyl), —NR$_b$S(O)$_2$(alkyl), —NR$_b$S(O)$_2$(phenyl), —NR$_b$C(O)(phenyl), —NR$_b$C(O)(alkyl phenyl), and/or —NR$_b$C(O)NR$_b$(phenyl);

iv)

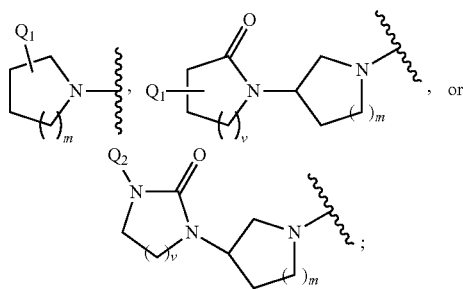

v) cycloalkyl or cycloalkenyl substituted with zero to 2 substituents independently selected from —OH, halo, —CF$_3$, =O, —OC(O)(phenyl), —NR$_b$C(O)(phenyl), —NR$_b$CR$_b$R$_b$(methoxyphenyl), —NR$_b$C(O)NR$_b$(thiazolyl),

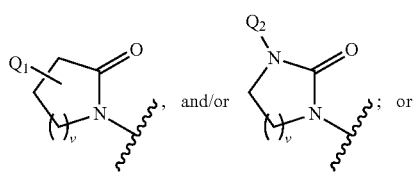

vi)

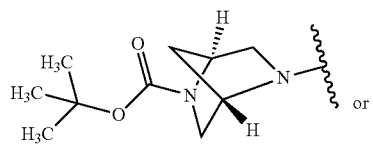

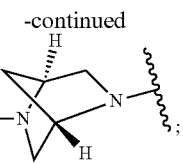

Q$_3$ is H, —C(O)O(C$_{1-4}$alkyl), —C(O)NR$_b$(C$_{1-4}$alkyl), or —C(O)NR$_b$(1-ring heteroaryl);
each R$_d$ is independently H and/or C$_{1-6}$alkyl; m is 1 or 2; v is 1 or 2; and X, Y, R$_1$, R$_3$, R$_4$, R$_5$, R$_6$, R$_b$, R$_f$, R$_g$, Q$_1$, Q$_2$, and q are defined in the first aspect hereinabove. Preferably, R$_3$ is H. In one example of this embodiment, X is N and Y is CR$_2$. In another example of this embodiment, X is CR$_2$ and Y is N.

One embodiment provides a compound having Formula (I) or stereoisomers or pharmaceutically acceptable salts thereof, wherein:
R$_a$ is H, C$_{1-6}$alkyl, C$_{1-6}$hydroxyalkyl, or —(CH$_2$)$_n$phenyl, wherein said phenyl in turn is substituted with zero to 4 R$_h$;
one of R$_4$ and R$_5$ is H, halo, —CH$_3$, —CF$_3$, —CN, —NH$_2$, —OH, C$_{1-3}$alkoxy, —OCF$_3$, —C(O)NR$_b$(C$_{1-2}$alkyl), —NR$_b$(C$_{1-2}$alkyl), —NR$_b$S(O)$_2$(C$_{1-2}$alkyl), —NR$_b$S(O)$_2$(phenyl), —NR$_b$C(O)(phenyl), pyrrolidine-2,5-dione, —NR$_b$C(O)NR$_b$(phenyl), —NR$_b$S(O)$_2$(pyrrolidinyl), —S(O)$_2$(C$_{1-4}$alkyl), —NR$_b$S(O)$_2$(C$_{1-4}$ alkyl), —NR$_b$S(O)$_2$(fluorophenyl), —NR$_b$S(O)$_2$(biphenyl), —NR$_b$S(O)$_2$(naphthalenyl), —NR$_b$S(O)$_2$(imidazolyl), —NR$_b$S(O)$_2$(chlorothiophenyl), —NR$_b$S(O)$_2$(benzyl), —NR$_b$S(O)$_2$(pyridinyl), —NR$_b$(S(O)$_2$(C$_{1-4}$haloalkyl), —N(S(O)$_2$(C$_{1-4}$haloalkyl))$_2$, or —NR$_b$C(O)O(C$_{1-4}$alkyl);
and the other of R$_4$ and R$_5$ is:
a) H, halo, —CN, or C$_{1-6}$alkoxy;
b) -L-A; or
c) -L-C(O)-A;
wherein L is a bond or —(CR$_c$R$_c$)$_t$—; and A is selected from A$_1$, A$_2$, and A$_3$, wherein:
A$_1$ is C$_{1-6}$alkyl or C$_{5-7}$cycloalkyl, each independently substituted with 0 to 3 substituents independently selected from —OH, —NH$_2$, C$_{1-3}$alkoxy, —C(O)NH$_2$, —C(O)(C$_{1-6}$alkyl), —C(O)OR$_b$, —NH(C$_{1-6}$alkyl), —N(C$_{1-6}$alkyl)$_2$, —C(O)NR$_b$(C$_{1-6}$alkyl), —C(O)NR$_b$(C$_{1-6}$hydroxyalkyl), —C(O)NR$_b$(heterocyclyl), —NR$_b$C(O)(C$_{1-6}$alkyl), —C(O)NR$_b$(CR$_b$R$_b$)$_q$NH(C$_{1-6}$alkyl), and/or —C(O)NR$_b$(CR$_b$R$_b$)$_q$N(C$_{1-6}$alkyl)$_2$;
A$_2$ is 4- to 6-membered heterocyclyl or 5- to 6-membered heteroaryl having 1- to 3-heteroatoms independently selected from N, O, and/or S, and substituted with zero to 4 substituents independently selected from —OH, =O, C$_{1-6}$alkyl, C$_{1-4}$hydroxyalkyl, C$_{3-6}$cycloalkyl, —C(O)(C$_{1-6}$alkyl), —NH(C$_{1-6}$alkyl), —N(C$_{1-6}$alkyl)$_2$, —C(O)NR$_b$(C$_{1-6}$alkyl), —C(O)NR$_b$(C$_{1-6}$hydroxyalkyl), —C(O)NR$_b$(C$_{3-6}$cycloalkyl), —C(O)NR$_b$(CR$_b$R$_b$)$_q$NH(C$_{1-6}$alkyl), —C(O)NR$_b$(phenyl), —C(O)NR$_b$(CR$_b$R$_b$)$_q$N(C$_{1-6}$alkyl)$_2$, —C(O)NR$_b$R$_b$, —NR$_b$C(O)(C$_{1-6}$alkyl), —C(O)O(C$_{1-4}$alkyl), and/or —C(O)O(benzyl);
A$_3$ is —OH, —NH$_2$, C$_{1-6}$alkoxy, —NH(C$_{1-6}$alkyl), —N(C$_{1-6}$alkyl)$_2$, di-(C$_{1-2}$alkyl) N-oxide, —NR$_b$(C$_{1-6}$hydroxyalkyl), —NR$_b$(C$_{3-7}$cycloalkyl), —NR$_b$(CR$_b$R$_b$)$_q$NH(C$_{1-6}$alkyl), —NR$_b$(CR$_b$R$_b$)$_q$N(C$_{1-6}$alkyl)$_2$, —NR$_b$(phenyl), —NR$_b$C(O)(C$_{1-6}$alkyl), —S(C$_{1-6}$alkyl), —S(O)$_2$(C$_{1-6}$alkyl), —S(O)$_2$(C$_{1-4}$fluoroalkyl), —S(O)$_2$NR$_d$R$_d$, —S(O)$_2$(CR$_b$R$_b$)$_q$N(C$_{1-2}$alkyl)$_2$, —O(CR$_b$R$_b$)$_q$CR$_b$(C$_{1-2}$alkoxy)$_2$, —O(CR$_b$R$_b$)$_q$NR$_b$(C$_{3-6}$cycloalkyl), —O(CR$_b$R$_b$)$_q$N $(C_{1-2}alkyl)_2$, —$NR_bC(O)NR_bA_2$, —$NR_bC(O)A_2$, —$NR_bA_2$, —$NR_bC(O)(CR_bR_b)_qA_2$, or —$O(CR_cR_c)_qA_2$;

G is:

i) —$NR_b(CR_bR_b)_q$(phenyl);

ii) 1- to 2-ring heteroaryl or 1- to 2-ring heterocyclyl substituted with zero to 3 substituents independently selected from —OH, =O, $C_{1-6}$alkyl, —$CR_bR_bC(O)OH$, —$CR_bR_bC(O)O(C_{1-4}alkyl)$, —$CR_bR_bC(O)NH(phenyl)$, —$CR_bR_bS(O)_2(phenyl)$, phenyl, —$NR_b(C_{1-6}alkyl)$, —$N(C_{1-6}alkyl)C(O)O(C_{1-6}alkyl)$, —$C(O)(C_{1-4}alkyl)$, —C(O)(phenyl), and/or —C(O)(benzyl);

iii)

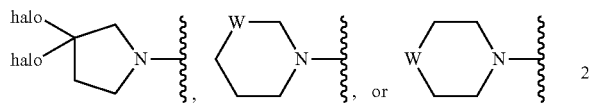

wherein W is $CR_b(OR_b)$, $C=CR_bR_b$, NH, $N(C_{1-6}alkyl)$, or $NC(O)CR_bR_b$(phenyl); or W is $CR_gR_g$ and a) each $R_g$ is halo; or b) $R_g$ and $R_g$ together with the carbon atom to which they are attached, form a 5- to 7-membered cycloalkyl or heterocyclyl ring substituted with zero to 2 substituents independently selected from —OH, —C(O)OH, —$C(O)(C_{1-4}alkyl)$, $C_{1-6}$alkyl, $C_{3-6}$cycloalkyl, halo, —$CF_3$, =O, 1- to 2-ring aryl, and/or 1- to 2-ring heteroaryl;

iv) naphthalenyl; or phenyl substituted with zero to 3 substituents independently selected from —OH, $C_{1-6}$alkyl, $C_{1-4}$fluoroalkyl, halo, —CN, —$NR_bR_b$, $C_{1-4}$alkoxy, —C(O)OH, —$CR_bR_bO(C_{1-6}alkyl)$, —$CH_2NR_bC(O)(C_{1-6}alkyl)$, —$CH_2NR_bC(O)(phenyl)$, —$C(O)(C_{1-6}alkyl)$, —C(O)(heterocyclyl), phenoxy, —$C(O)O(C_{1-6}alkyl)$, —$C(O)NR_b(C_{1-6}alkyl)$, —$C(O)N(C_{1-6}alkyl)_2$, —$C(O)NR_bCR_bR_b$(heterocyclyl), —$NR_bS(O)_2(C_{1-6}alkyl)$, —$NR_bS(O)_2(phenyl)$, —$NR_bC(O)(phenyl)$, —$NR_bC(O)(C_{1-6}alkyl phenyl)$, and/or —$NR_bC(O)NR_b(phenyl)$; or v)

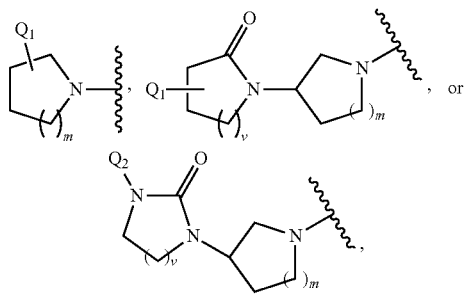

vi) $C_{3-6}$cycloalkyl or $C_{4-6}$cycloalkenyl substituted with zero to 2 substituents independently selected from —OH, halo, —$CF_3$, =O, —OC(O)(phenyl), —$NR_bC(O)(phenyl)$, —$NR_bCR_bR_b$(methoxyphenyl), —$NR_bC(O)NR_b$(thiazolyl),

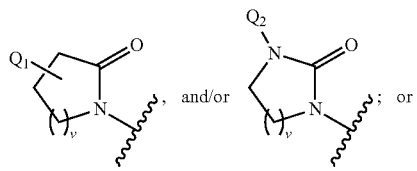

vii)

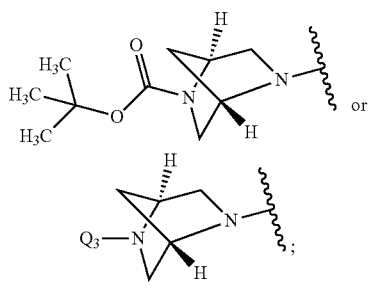

$Q_1$ is:

a) H, —OH, —$C(O)OR_b$, —$C(O)NR_b$(phenyl), —$C(O)NR_b(C_{1-6}alkyl\ phenyl)$, —OC(O)(phenyl), —O(phenyl), phenyl, —$NR_bR_b$, —$NR_b$(pyrimidinyl), —N(pyrimidinyl)$_2$, $C_{1-4}$hydroalkyl, $C_{1-4}$-aminoalkyl, —$(CR_bR_b)_qC(O)O(C_{1-4}alkyl)$, —$(CR_bR_b)_qNR_bC(O)O(C_{1-4}alkyl)$, indolyl, imidazolidinonyl, or pyrrolidinonyl;

b) —$NR_bC(O)$-$Q_2$;

c) —$NR_bC(O)CR_bR_b$-$Q_2$;

d)

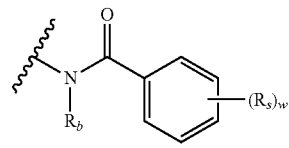

wherein each $R_s$ is independently selected from $C_{1-6}$alkyl, $C_{1-6}$fluoroalkyl, halo, —OH, —$C(O)(C_{1-6}alkyl)$, —$NR_bC(O)(C_{1-6}alkyl)$, —$C(O)O(C_{1-6}alkyl)$, $C_{1-6}$alkoxy, $C_{1-6}$fluoroalkoxy, —$NR_bR_b$, —$N(C_{1-6}alkyl)_2$, —$S(O)_2(C_{1-6}alkyl)$, —$NR_bC(O)O(C_{1-6}alkyl)$, phenoxy, —$CR_bR_bNR_bC(O)(C_{1-6}alkyl)$, and/or a cyclic group independently selected from aryl, heteroaryl, and/or heterocyclyl, wherein said cyclic group is substituted with zero or more substituents independently selected from $C_{1-6}$alkyl, —OH, halo, $C_{1-2}$haloalkyl, —$NR_bR_b$, $C_{1-4}$alkoxy, =O, and/or —CN;

e) —$NR_bS(O)_2$-$Q_2$; or f) —$NR_bC(O)NR_b$-$Q_2$;

$Q_2$ is:

a) H, $C_{1-6}$alkyl, $C_{1-6}$haloalkyl, —$N(C_{1-6}alkyl)_2$, $C_{1-6}$alkoxy, phenoxy, or benzophenonyl;

b) $C_{3-7}$cycloalkyl, aryl, heterocyclyl, or heteroaryl, each of which is substituted with zero or more substituents independently selected from $C_{1-6}$alkyl, $C_{3-7}$cycloalkyl, halo, —CN, —OH, =O, —$NR_bR_b$, $C_{1-6}$fluoroalkyl, $C_{1-6}$alkoxy, —$S(C_{1-6}alkyl)$, —$C(O)(C_{1-6}alkyl)$, —$C(O)O(C_{1-6}alkyl)$, —$C_{3-7}$cycloalkyl, $C_{1-6}$alkylphenyl, hydroxyphenyl, halophenyl, $(C_{1-6}fluoroalkyl)phenyl$, and/or pyridinyl; or c) —(CR$_b$R$_b$)$_q$N(C$_{1-6}$alkyl)$_2$, —(CR$_b$R$_b$)$_q$(phenyl), or —(CR$_b$R$_b$)$_q$(furanyl); and each R$_h$ is independently —OH, —NH$_2$, C$_{1-6}$alkyl, halo, C$_{1-6}$haloalkyl, C$_{1-6}$alkoxy, and/or C$_{1-6}$haloalkoxy;

m is 1 or 2; v is 1 or 2; and R$_b$, R$_c$, n, q, t, v, and w are defined in the first aspect hereinabove. Preferably, R$_3$ is H. In one example of this embodiment, X is N and Y is CR$_2$. In another example of this embodiment, X is CR$_2$ and Y is N.

One embodiment provides a compound having Formula (I) or stereoisomers or pharmaceutically acceptable salts thereof, wherein:

R$_6$ is H or C$_{1-2}$alkoxy;

one of R$_4$ and R$_5$ is H, halo, C$_{1-2}$alkoxy, —C(O)NR$_b$(C$_{1-2}$alkyl), —NR$_b$(C$_{1-2}$alkyl), —NR$_b$S(O)$_2$(C$_{1-2}$alkyl), —NR$_b$S(O)$_2$(phenyl), —C(O)NH(C$_{1-2}$alkyl), —N(CH$_3$)C(O)(phenyl), pyrrolidine-2,5-dione, —NR$_b$C(O)NR$_b$(phenyl), —CH$_2$S(O)$_2$(pyrrolidinyl), —S(O)$_2$(C$_{1-2}$alkyl), —NR$_b$S(O)$_2$(C$_{1-2}$alkyl), —NR$_b$S(O)$_2$(fluorophenyl), —NR$_b$S(O)$_2$(biphenyl), —NR$_b$S(O)$_2$(naphthalenyl), —NR$_b$S(O)$_2$(imidazolyl), —NR$_b$S(O)$_2$(chlorothiophenyl), —NR$_b$S(O)$_2$(benzyl), —NR$_b$S(O)$_2$(pyridinyl), —NR$_b$(S(O)$_2$(C$_{1-4}$-chloroalkyl), —N(S(O)$_2$(C$_{1-4}$-chloroalkyl))$_2$, or —NR$_b$C(O)O(C$_{1-4}$alkyl);

and the other of R$_4$ and R$_5$ is:

a) H, halo, —CN, or C$_{1-2}$alkoxy;
b) -L-A; or
c) -L-C(O)-A;

wherein L is a bond or —(CR$_c$R$_c$)$_t$—; and A is selected from A$_1$, A$_2$, and A$_3$, wherein:

A$_1$ is C$_{1-4}$alkyl or C$_{5-7}$cycloalkyl, each independently substituted with 0 to 2 substituents independently selected from —OH, —NH$_2$, C$_{1-2}$alkoxy, —C(O)(C$_{1-6}$alkyl), —C(O)OR$_b$, —NH(C$_{1-4}$alkyl), —N(C$_{1-6}$alkyl)$_2$, —C(O)NR$_b$(C$_{1-6}$alkyl), —C(O)NR$_b$(C$_{1-6}$hydroxyalkyl), —C(O)NR$_b$(heterocyclyl), —C(O)NR$_b$(CR$_b$R$_b$)$_q$NH(C$_{1-6}$alkyl), —C(O)NR$_b$(CR$_b$R$_b$)$_q$N(C$_{1-6}$alkyl)$_2$, and/or —NR$_b$C(O)(C$_{1-6}$alkyl);

A$_2$ is 4- to 6-membered heterocyclyl or 5- to 6-membered heteroaryl having 1- to 3-heteroatoms independently selected from N, O, and/or S, and substituted with zero to 4 substituents independently selected from —OH, =O, C$_{1-4}$alkyl, C$_{1-4}$hydroxyalkyl, C$_{3-5}$cycloalkyl, —C(O)(C$_{1-4}$alkyl), —NH(C$_{1-4}$alkyl), —N(C$_{1-4}$alkyl)$_2$, —C(O)NR$_b$(C$_{1-4}$alkyl), —C(O)NR$_b$(C$_{1-4}$hydroxyalkyl), —C(O)NR$_b$(C$_{3-4}$cycloalkyl), —C(O)NR$_b$(CR$_b$R$_b$)$_q$NH(C$_{1-4}$alkyl), —C(O)NR$_b$(phenyl), —C(O)NR$_b$(CR$_b$R$_b$)$_q$N(C$_{1-4}$alkyl)$_2$, —C(O)NR$_b$R$_b$, —NR$_b$C(O)(C$_{1-4}$alkyl), —C(O)O(C$_{1-4}$alkyl), and/or —C(O)O(benzyl);

A$_3$ is —OH, —NH$_2$, C$_{1-4}$alkoxy, —NH(C$_{1-6}$alkyl), —N(C$_{1-6}$alkyl)$_2$, di-(C$_{1-2}$alkyl) N-oxide, —NR$_b$(C$_{1-4}$hydroxyalkyl), —NR$_b$(C$_{3-6}$cycloalkyl), —NR$_b$(CR$_b$R$_b$)$_q$NH(C$_{1-4}$alkyl), —NR$_b$(CR$_b$R$_b$)$_q$N(C$_{1-4}$alkyl)$_2$, —NR$_b$(phenyl), —NR$_b$C(O)(C$_{1-4}$alkyl), —NR$_b$C(O)(C$_{1-4}$alkyl), —S(C$_{1-4}$alkyl), —S(O)$_2$(C$_{1-4}$alkyl), —S(O)$_2$(C$_{1-3}$fluoroalkyl), —S(O)$_2$NR$_d$R$_d$, —S(O)$_2$(CR$_b$)$_q$N(C$_{1-2}$alkyl)$_2$, —O(CR$_b$R$_b$)$_q$CR$_b$(C$_{1-2}$alkoxy)$_2$, —O(CR$_b$R$_b$)$_q$NR$_b$(C$_{3-6}$cycloalkyl), —O(CR$_b$R$_b$)$_q$N(C$_{1-2}$alkyl)$_2$, —NR$_b$C(O)NR$_b$A$_2$, —NR$_b$C(O)A$_2$, —NR$_b$A$_2$, —NR$_b$C(O)(CR$_b$R$_b$)$_q$A$_2$, or —O(CR$_c$R$_c$)$_q$A$_2$;

G is:

i) —NR$_b$(CR$_b$R$_b$)$_q$(phenyl);

ii) 1- to 2-ring heteroaryl or heterocyclyl substituted with zero to 3 substituents independently selected from —OH, =O, C$_{1-6}$alkyl, —CR$_b$R$_b$C(O)OH, —CR$_b$R$_b$C(O)O(C$_{1-4}$alkyl), —CR$_b$R$_b$C(O)NH(phenyl), —CR$_b$R$_b$S(O)$_2$(phenyl), phenyl, —NR$_b$(C$_{1-6}$alkyl), —N(C$_{1-6}$alkyl)C(O)O(C$_{1-6}$alkyl), —C(O)(C$_{1-4}$alkyl), —C(O)(phenyl), and/or —C(O)(benzyl);

iii)

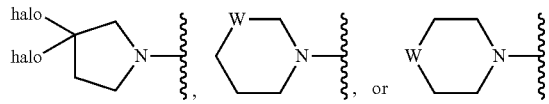

wherein W is CR$_b$(OR$_b$), C=CR$_b$R$_b$, NH, N(C$_{1-6}$alkyl), or NC(O)CR$_b$R$_b$(phenyl); or W is CR$_g$R$_g$ and a) each R$_g$ is halo; or
b) R$_g$ and R$_g$ together with the carbon atom to which they are attached, form a 5- to 7-membered cycloalkyl or heterocyclyl ring substituted with zero to two substituents independently selected from C$_{1-4}$alkyl, —C(O)OH, —C(O)O(C$_{1-4}$alkyl), =O, 1- to 2-ring aryl, and/or 1- to 2-ring heteroaryl;

iv) naphthalenyl; or phenyl substituted with zero to 3 substituents independently selected from —OH, C$_{1-6}$alkyl, C$_{1-2}$fluoroalkyl, halo, —CN, —NR$_b$R$_b$, C$_{1-4}$alkoxy, —C(O)OH, —CR$_b$R$_b$O(C$_{1-4}$alkyl), —CH$_2$NR$_b$C(O)(C$_{1-4}$alkyl), —CH$_2$NR$_b$C(O)(phenyl), —C(O)(C$_{1-4}$alkyl), —C(O)-(heterocyclyl), phenoxy, —C(O)O(C$_{1-6}$alkyl), —C(O)NR$_b$(C$_{1-4}$alkyl), —C(O)N(C$_{1-4}$alkyl)$_2$, —C(O)NR$_b$CR$_b$R$_b$ (heteroaryl), —NR$_b$S(O)$_2$(C$_{1-4}$alkyl), —NR$_b$S(O)$_2$(phenyl), —NR$_b$C(O)(phenyl), —NR$_b$C(O)(C$_{1-6}$alkyl phenyl), and/or —NR$_b$C(O)NR$_b$(phenyl); or v)

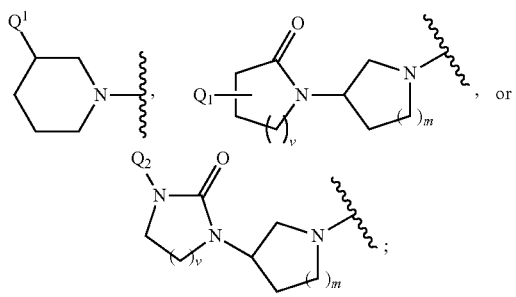

vi)

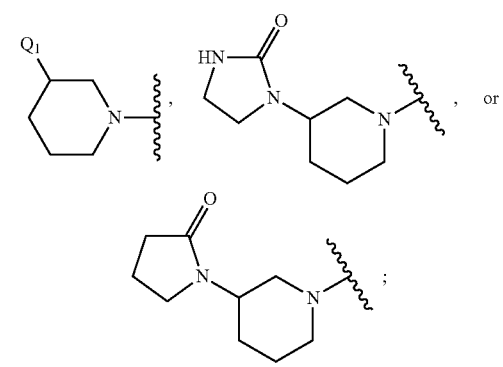

vii) cyclohexyl or cyclohexenyl substituted with zero to 2 substituents independently selected from —OH, =O, —OC(O)(phenyl), —NR$_b$C(O)(phenyl),

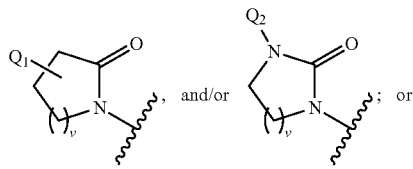

—NR$_b$CR$_b$R$_b$(methoxyphenyl), —NR$_b$C(O)NR$_b$(thiazolyl), viii)

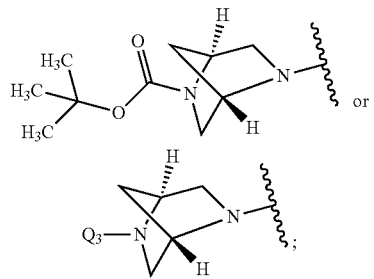

wherein Q$_1$ is:
a) H, —OH, —C(O)OR$_b$, —C(O)NR$_b$(phenyl), —C(O)NR$_b$(C$_{1-6}$alkyl phenyl), —OC(O)(phenyl), —O(phenyl), phenyl, —NR$_b$R$_b$, —NR$_b$(pyrimidinyl), —N(pyrimidinyl)$_2$, C$_{1-4}$hydroalkyl, C$_{1-4}$-aminoalkyl, —(CR$_b$R$_b$)$_q$C(O)O(C$_{1-4}$ alkyl), —(CR$_b$R$_b$)$_q$NR$_b$C(O)O(C$_{1-4}$ alkyl), indolyl, imidazolidinonyl, or pyrrolidinonyl;
b) —NR$_b$C(O)—B$_1$, wherein B$_1$ is C$_{1-4}$alkyl; C$_{1-4}$alkoxy; C$_{3-6}$cycloalkyl optionally substituted with C$_{1-4}$alkyl or C$_{1-4}$alkoxy; phenoxy; benzophenonyl; or 1- to 3-ring aryl optionally substituted with C$_{1-4}$alkyl, C$_{1-2}$fluoroalkyl, or C$_{1-4}$alkoxy;
c) —NR$_b$C(O)—B$_2$, wherein B$_2$ is 1- to 2-ring heterocyclyl or heteroaryl substituted with zero or more substituents independently selected from C$_{1-4}$alkyl, —NR$_b$R$_b$, halo, C$_{1-2}$fluoroalkyl, —CN, =O, C$_{1-4}$alkoxy, —C(O)(C$_{1-4}$alkyl), and/or pyridinyl;
d) —NR$_b$C(O)CR$_b$R$_b$—B$_3$, wherein B$_3$ is —N(C$_{1-6}$alkyl)$_2$, phenyl, or 1- to 2-ring heteroaryl substituted with zero or more substituents independently selected from C$_{1-4}$alkyl, —OH, —CN, halo, and/or C$_{1-4}$alkoxy;
e)

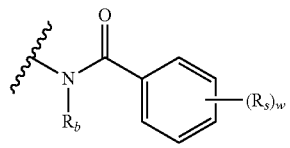

wherein each R$_s$ is independently selected from C$_{1-6}$alkyl, C$_{1-2}$fluoroalkyl, halo, —OH, —C(O)(C$_{1-4}$alkyl), —NR$_b$C(O)(C$_{1-4}$alkyl), —C(O)O(C$_{1-4}$alkyl), C$_{1-4}$alkoxy, C$_{1-4}$fluoroalkoxy, —NR$_b$R$_b$, —N(C$_{1-4}$alkyl)$_2$, —S(O)$_2$(C$_{1-4}$alkyl), —NR$_b$C(O)O (C$_{1-6}$alkyl), —CR$_b$R$_b$NR$_b$C(O)(C$_{1-6}$alkyl), phenoxy, and/or a cyclic group independently selected from aryl, heteroaryl, and/or heterocyclyl, wherein said cyclic group is substituted with zero or more substituents independently selected from C$_{1-6}$alkyl, —OH, halo, C$_{1-2}$haloalkyl, —NR$_b$R$_b$, C$_{1-4}$alkoxy, =O, and/or —CN;
f) —NHS(O)$_2$—B$_4$ wherein B$_4$ is phenyl or 1-ring heteroaryl substituted with zero to 3 substituents independently selected from C$_{1-4}$alkyl, halo, —NR$_b$R$_b$, C$_{1-4}$alkoxy, and/or C$_{1-2}$fluoroalkyl;
g) —NR$_b$C(O)NR$_b$—B$_5$ wherein B$_5$ is phenyl substituted with zero to 2 substituents independently selected from halo, C$_{1-6}$alkyl, —CN, —NR$_b$R$_b$, C$_{1-2}$fluoroalkyl, C$_{1-4}$alkoxy, —C(O)O(C$_{1-6}$alkyl), —S(C$_{1-2}$alkyl), —C(O)(C$_{1-4}$alkyl), and/or —O(C$_{3-6}$cycloalkyl);
h) —NR$_b$C(O)NR$_b$—B$_6$ wherein B$_6$ is a 1-ring heteroaryl substituted with zero to 2 substituents independently selected from C$_{1-4}$alkyl, halo, C$_{1-4}$fluoroalkyl, C$_{3-6}$cycloalkyl, —S(C$_{1-3}$alkyl), and/or —C(O)O(C$_{1-4}$alkyl); or
i) —NR$_b$C(O)NR$_b$—B$_7$ wherein B$_7$ is C$_{1-6}$alkyl, C$_{1-4}$haloalkyl, C$_{3-6}$cycloalkyl, —(CR$_b$R$_b$)$_q$(phenyl), or —(CR$_b$R$_b$)$_q$(furanyl); and
each R$_h$ is independently —OH, —NH$_2$, C$_{1-6}$alkyl, halo, C$_{1-4}$haloalkyl, C$_{1-4}$alkoxy, and/or C$_{1-4}$haloalkoxy;
m is 1 or 2;
v is 1 or 2; and R$_b$, R$_c$, q, t, v, and w are defined in the first aspect hereinabove.

Preferably, R$_3$ is H. In one example of this embodiment, X is N and Y is CR$_2$.

In another example of this embodiment, X is CR$_2$ and Y is N.

One embodiment provides a compound having Formula (I) or stereoisomers or pharmaceutically acceptable salts thereof, wherein:
R$_1$ is H;
R$_2$ is H, F, or Br;
R$_6$ is C$_{1-2}$alkoxy, R$_5$ is H, and R$_4$ is H; or
R$_6$ is H, R$_5$ is halo, and R$_4$ is 5- to 6-membered heterocyclyl having 1- to 3-heteratoms independently selected from N, O, and/or S, and substituted with zero to 2 substituents independently selected from C$_{1-4}$alkyl, C$_{1-4}$hydroxyalkyl, and/or —C(O)(C$_{1-4}$alkyl); or
R$_6$ is H, R$_5$ is H, —OCH$_3$, —NH(CH$_3$), —C(O)NHCH$_3$, —N(CH$_3$)C(O)(phenyl), pyrrolidine-2,5-dione, —N(CH$_3$)C(O)NH(phenyl), —CH$_2$S(O)$_2$(pyrrolidinyl), —S(O)$_2$CH$_3$, —NR$_b$S(O)$_2$CH$_3$, —NR$_b$S(O)$_2$CH$_2$CH$_3$, —NR$_b$S(O)$_2$(phenyl), —NR$_b$S(O)$_2$(fluorophenyl), —NR$_b$S(O)$_2$(biphenyl), —NR$_b$S(O)$_2$(naphthalenyl), —NR$_b$S(O)$_2$(chlorothiophenyl), —NR$_b$S(O)$_2$(imidazolyl), —NR$_b$S(O)$_2$(benzyl), —NR$_b$S(O)$_2$(pyridinyl), —NR$_b$(S(O)$_2$CH$_2$CH$_2$CH$_2$Cl), —N(S(O)$_2$CH$_2$CH$_2$CH$_2$Cl)$_2$, or —NR$_b$C(O)O(butyl), and R$_4$ is:
a) H, halo, or —CN;
b) -L-A; or
c) -L-C(O)-A;
wherein L is a bond or —(CR$_c$R$_c$)$_t$—; and A is selected from A$_1$, A$_2$, and A$_3$; wherein:
A$_1$ is C$_{1-4}$alkyl substituted with 0 to 2 substituents independently selected from —OH, —NH$_2$, —OCH$_3$, —C(O)OH, —NH(C$_{1-2}$alkyl), and/or —N(C$_{1-2}$alkyl)$_2$;
A$_2$ is 4- to 6-membered heterocyclyl or 5- to 6-membered heteroaryl having 1- to 3-heteroatoms independently selected from N, O, and/or S, and substituted with zero to 4 substituents independently selected from —OH, =O, C$_{1-3}$alkyl, C$_{1-2}$hydroxyalkyl, C$_{3-4}$cycloalkyl, —C(O)(C$_{1-2}$alkyl), —C(O)O(C$_{1-4}$alkyl), and/or —C(O)O(benzyl);

A₃ is —OH, —NH₂, C₁₋₄alkoxy, —OCH₂CH(OCH₂CH₃)₂, —OCH₂CH₂NH(cyclopropyl), —OCH₂CH₂(pyrrolidinyl)), —OCH₂CH₂N(CH₃)₂, N,N-dimethylethamine oxide, —NH(C₁₋₄alkyl), —N(C₁₋₂alkyl)₂, —NH(C₁₋₂hydroxyalkyl), —NH(C₃₋₆cycloalkyl), —NH(CH₂)qNH(C₁₋₄alkyl), —NH(CH₂)qN(C₁₋₂alkyl)₂, —NH(phenyl), —NHC(O)(C₁₋₂alkyl), —S(C₁₋₄alkyl), —S(O)₂(C₁₋₄alkyl), —S(O)₂(C₁₋₂fluoroalkyl), —S(O)₂NRdRd, —S(O)₂(C₁₋₂)qN(C₁₋₂alkyl)₂, —NHC(O)A₂, —NHA₂, —NHC(O)(CH₂)qA₂, or —O(CH₂)qA₂;

G is:
i) —NRb(CRbRb)q(phenyl);
ii) 1- to 2-ring heteroaryl or heterocyclyl substituted with zero to 3 substituents independently selected from —OH, =O, C₁₋₄alkyl, —CH₂C(O)OH, —CH₂C(O)NH(phenyl), —CH₂C(O)O(C₁₋₂alkyl), —CH₂S(O)₂(phenyl), phenyl, —NRb(C₁₋₄alkyl), —N(C₁₋₄alkyl)C(O)O(C₁₋₄alkyl), —C(O)(C₁₋₄alkyl), —C(O)(phenyl), and/or —C(O)(benzyl);
iii)

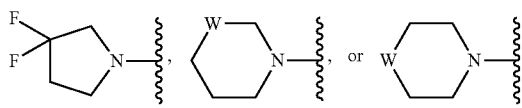

wherein W is CH(OH), C=CH₂, NH, N(C₁₋₄alkyl), or NC(O)CRbRb(phenyl); or W is CRgRg and
a) each Rg is halo; or
b) Rg and Rg together with the carbon atom to which they are attached, form a 5- to 6-membered cycloalkyl or heterocyclyl ring substituted with zero to two substituents independently selected from —C(O)OH, —CH(CH₃)₂, —C(O)OCH₂CH₃, =O, phenyl, pyridinyl, and/or naphthalenyl;
iv) naphthalenyl; or phenyl substituted with zero to 3 substituents independently selected from —OH, C₁₋₄alkyl, C₁₋₂fluoroalkyl, halo, —CN, —NRbRb, C₁₋₄alkoxy, —CH₂O(C₁₋₄alkyl), —CH₂NHC(O)(C₁₋₄alkyl), —CH₂NRbC(O)(phenyl), —C(O)(C₁₋₄alkyl), —C(O)(heterocyclyl), phenoxy, —C(O)OH, —C(O)O(C₁₋₄alkyl), —C(O)NRb(C₁₋₂alkyl), —C(O)N(C₁₋₄alkyl)₂, —C(O)NRbCRbRb(furanyl), —NRbS(O)₂(C₁₋₄alkyl), —NRbS(O)₂(phenyl), —NRbC(O)(phenyl), —NRbC(O)(C₁₋₄alkyl phenyl), and/or —NRbC(O)NRb(phenyl);
v)

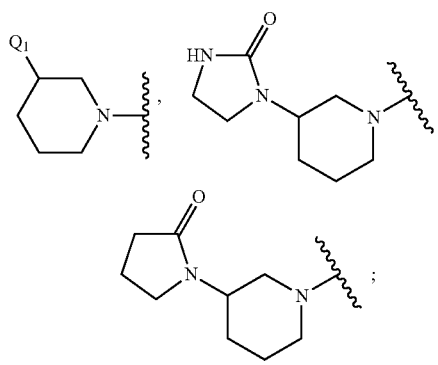

vi)

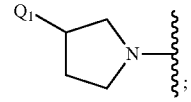

vii) cyclohexyl or cyclohexenyl substituted with zero to 1 substituent selected from —OH, =O, —OC(O)(phenyl), —NHC(O)(phenyl), —NHCH(CH₃)(methoxyphenyl), or —NHC(O)NH(thiazolyl); or
viii)

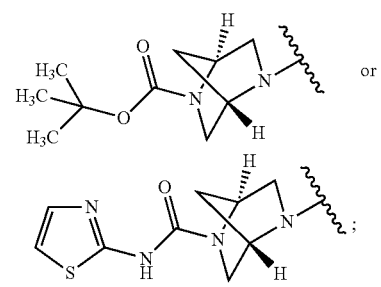

wherein Q₁ is:
a) H, —OH, —C(O)OH, —C(O)NRb(phenyl), —C(O)NRb(C₁₋₄alkyl phenyl), —OC(O)(phenyl), —O(phenyl), —NRbRb, —NRb(pyrimidinyl), —N(pyrimidinyl)₂, —CH₂OH, —CH₂NH₂, —CH₂C(O)OCH₂CH₃, —CH₂NHC(O)O(butyl), —CH₂CH₂NHC(O)O(butyl), phenyl, indolyl, imidazolidinonyl, or pyrrolidinonyl;
b) —NHC(O)—B₁, wherein B₁ is C₁₋₄alkyl; C₁₋₄alkoxy; C₃₋₆cycloalkyl optionally substituted with C₁₋₄alkyl or C₁₋₄alkoxy; phenoxy; benzophenonyl; or 2- or 3-ring aryl optionally substituted with C₁₋₄alkyl or C₁₋₄alkoxy;
c) —NHC(O)—B₂, wherein B₂ is 1- to 2-ring heterocyclyl or heteroaryl substituted with zero or more substituents independently selected from C₁₋₄alkyl, —NRbRb, halo, C₁₋₂fluoroalkyl, —CN, =O, C₁₋₄alkoxy, —C(O)O(C₁₋₄alkyl), and/or pyridinyl;
d) —NHC(O)CH₂—B₃, wherein B₃ is a —N(C₁₋₄alkyl)₂, phenyl, 1- to 2-ring heteroaryl substituted with zero or more substituents independently selected from C₁₋₄alkyl, —OH, —CN, halo, and/or C₁₋₃alkoxy;
e)

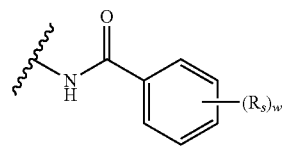

wherein each Rs is independently C₁₋₄alkyl, C₁₋₂fluoroalkyl, halo, —OH, —C(O)(C₁₋₄alkyl), —NRbC(O)(C₁₋₄alkyl), —C(O)O(C₁₋₄alkyl), C₁₋₄alkoxy, —O(C₁₋₄fluoroalkyl), —NH₂, —N(C₁₋₄alkyl)₂, —S(O)₂(C₁₋₂alkyl), —NRbC(O)O(C₁₋₄alkyl), —CRbRbNRbC(O)(C₁₋₄alkyl), phenoxy, phenyl, 1- to 3-ring heterocyclyl, or 1- to 3-ring heteroaryl, wherein said phenyl, said heterocyclyl, and said heteroaryl are substituted with zero or more substituents independently selected from C₁₋₄alkyl, —OH, halo, C₁₋₂haloalkyl, —NRbRb, C₁₋₄alkoxy, =O, and/or —CN;

f) —NHS(O)₂—B₄ wherein B₄ is phenyl or 1-ring heteroaryl substituted with zero to 3 substituents independently selected from C₁₋₄alkyl, halo, —NR_bR_b, C₁₋₄alkoxy, and/or C₁₋₂fluoroalkyl;

g) —NHC(O)NH—B₅ wherein B₅ is phenyl substituted with zero to two substituents independently selected from halo, C₁₋₄alkyl, —CN, —NR_bR_b, C₁₋₂fluoroalkyl, C₁₋₄alkoxy, —C(O)O(C₁₋₄alkyl), —S(C₁₋₂alkyl), —C(O)(C₁₋₄alkyl), and/or —O(C₃₋₆cycloalkyl);

h) —NHC(O)NH—B₆ wherein B₆ is 1-ring heteroaryl substituted with zero to two substituents independently selected from C₁₋₄alkyl, halo, C₁₋₄fluoroalkyl, C₃₋₆cycloalkyl, —S(C₁₋₂alkyl), and/or —C(O)O(C₁₋₄alkyl);

i) —NHC(O)NH—B₇ wherein B₇ is C₁₋₄alkyl, C₁₋₄haloalkyl, C₃₋₆cycloalkyl, benzyl, —CR_bR_bCR_bR_b-(phenyl), or —CR_bR_b-(furanyl);

each R_c is independently H, —CH₃, and/or —CH₂OH;
each q is independently 1 or 2; and
t is 1 or 2; and R_b and w are defined in the first aspect hereinabove. Preferably, R₃ is H. In one example of this embodiment, X is N and Y is CR₂. In another example of this embodiment, X is CR₂ and Y is N.

One embodiment provides a compound having Formula (I) or stereoisomers or pharmaceutically acceptable salts thereof, wherein:

R₆ is —OCH₃, R₅ is H, and R₄ is H; or

R₆ is H, R₅ is F, and R₄ is morpholinyl or N-methyl piperazinyl; or

R₆ is H, R₅ is —OCH₃, and R₄ is H, —OCH₂CH(OCH₂CH₃)₂, —OCH₂CH₂N(CH₃)₂, —OCH₂CH₂NH(cyclopropyl), or —OCH₂CH₂(pyrrolidinyl); or R₆ is H, R₅ is —NH(CH₃), —C(O)NHCH₃, —N(CH₃)C(O)(phenyl), pyrrolidine-2,5-dione, —N(CH₃)C(O)NH(phenyl), —CH₂S(O)₂(pyrrolidinyl), —S(O)₂CH₃, —NR_bS(O)₂CH₃, —NR_bS(O)₂CH₂CH₃, —NR_bS(O)₂(phenyl), —N(CH₃)S(O)₂(fluorophenyl), —N(CH₃)S(O)₂(biphenyl), —N(CH₃)S(O)₂(naphthalenyl), —N(CH₃)S(O)₂(imidazolyl), —N(CH₃)S(O)₂(chlorothiophenyl), —N(CH₃)S(O)₂(benzyl), —N(CH₃)S(O)₂(pyridinyl), —NH(S(O)₂CH₂CH₂CH₂Cl), —N(S(O)₂CH₂CH₂CH₂Cl)₂, or —N(CH₃)C(O)O(butyl), and R₄ is H or —C(O)(morpholinyl); or R₆ is H, R₅ is H, and R₄ is H, F, —CN, ethyl, butyl, hydroxyethyl, dimethylaminoethyl, N,N-dimethylethamine oxide, —OCH₃, —NHC(O)CH₃, —NH₂, —N(ethyl)₂, —C(O)CH₃, —C(O)OH, —C(O)O(butyl), —C(O)NH(cyclopropyl), —C(O)NH(butyl), —C(O)NH(phenyl), —C(O)N(CH₃)₂, —C(O)N(ethyl)₂, —C(O)NHCH₂CH₂N(CH₃)₂, —C(O)NH(hydroxyethyl), —C(CH₃)₂CH₂OH, —C(CH₃)₂C(O)OCH₂CH₃, —CH₂CH₂NH(butyl), —CH₂CH₂(azetidinyl), —CH₂CH₂(imidazolyl), —CH₂CH₂(pyrrolidinyl), —C(CH₃)₂C(O)NH(oxetanyl), —CH₂CH(CH₂OH)NHC(O)(pyrrolidinyl), —CH₂CH(CH₂OH)NHC(O)(piperidinyl), —C(CH₃)₂C(O)NHCH₂CH₂N(CH₃)₂, —NHC(O)CH₂(pyrrolidinyl), —C(CH₃)₂C(O)NH(cyclopropyl), —C(CH₃)₂C(O)NHCH₂CH₂OH, —S(O)₂N(CH₃)₂, —C(CH₃)₂C(O)OH, —S(O)₂CH₃, —S(O)₂CF₃, —S(O)₂CH₂CH₂N(CH₂CH₃)₂, pyrrolidinyl, oxazolyl, tetrahydropyranyl, morpholinyl, 4-hydroxymorpholinyl, morpholinonyl, piperidinyl, N-methyl piperidinyl, N-(butyl-OC(O))piperidinyl, 1-(ethyl-OC(O))-4-methylpiperidinyl, 1,4-dimethyl piperidinyl, N-acetyl piperazinyl, piperazinyl, N-methyl piperazinyl, N-ethyl piperazinyl, N-propyl piperazinyl, N-cyclopropyl-piperazinyl, N-cyclobutyl piperazinyl, N-(benzyl-OC(O))piperazinyl, —C(O)(azetidinyl), —C(O)(pyrrolidinyl), —C(O)(morpholinyl), —C(O)(piperidinyl), —C(O)(N-methyl piperazinyl), —C(O)(N-hydroxyethyl piperazinyl), —CH₂(morpholinyl), —CH₂(oxazolidinonyl),

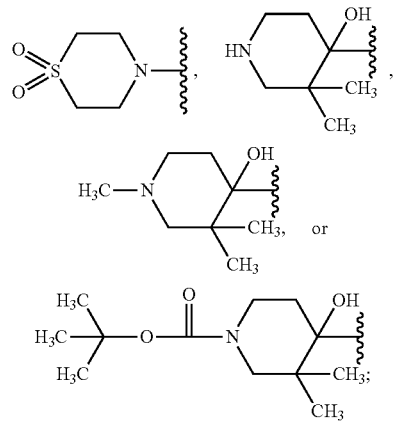

G is:

i) —NR_bCH₂—(phenyl) or —NR_bCH₂CH₂—(phenyl);

ii) thiophenyl; methylpyrrolidinyl, hydroxypyrrolidinyl, pyridinyl; indolyl; isoindolinyl; benzofuranyl; N-methylpyrazolyl; dimethyl morpholinyl; morpholinyl optionally substituted with phenyl, —CH₂C(O)OH, —CH₂C(O)NH(phenyl), or —CH₂S(O)₂(phenyl); piperizinyl optionally substituted with =O, —CH₂C(O)OCH₃, or —C(O)(benzyl); N-methyl piperazinyl substituted with —CH₂C(O)OCH₃; thiazolyl substituted with —NH(propyl) or —N(propyl)(C(O)(O-butyl); or 1,2,3,4-tetrahydroisoquinolinyl substituted with zero or one substituents selected from —C(O)(phenyl), —C(O)CH₃, or —C(O)butyl;

iii)

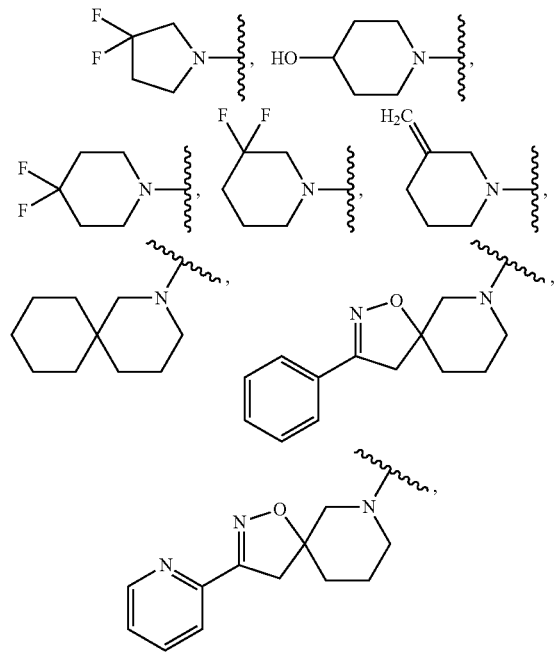

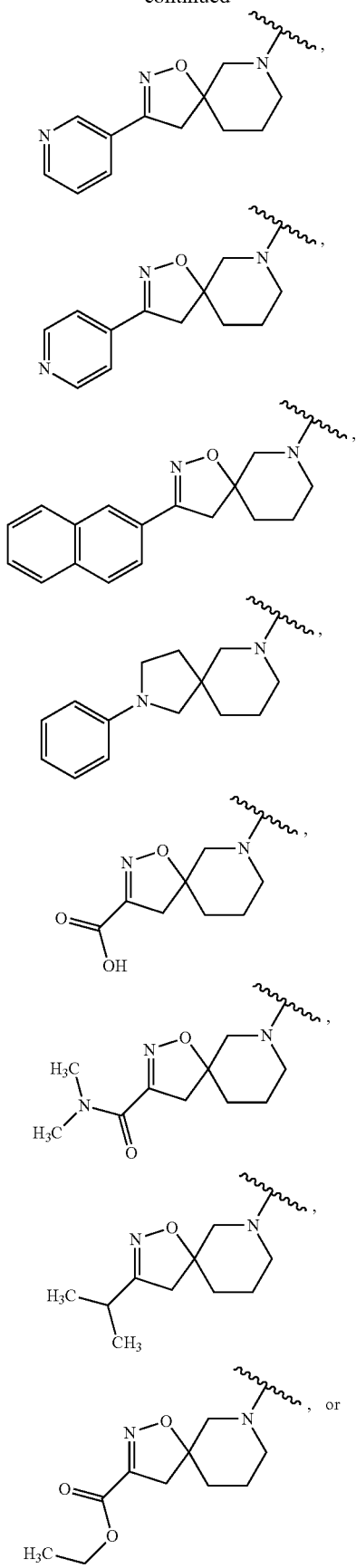

vi) naphthalenyl; or phenyl substituted with zero to 3 substituents independently selected from —OH, —CH₃, propyl, F, Cl, —CF₃, —CN, —NH₂, C$_{1-3}$alkoxy, —CH₂OCH₃, —CH₂NHC(O)CH₃, —CH₂NHC(O)(phenyl), —C(O)CH₃, —C(O)-(pyrrolidinyl), phenoxy, —C(O)OH, —C(O)O-(t-butyl), —C(O)NHCH₃, —C(O)N(CH₃)₂, —C(O)NHCH₂(furanyl), —NHS(O)₂(CH₃), —NHS(O)₂(phenyl), —NHC(O)(phenyl), —NHC(O)(t-butyl phenyl), and/or —NHC(O)NH(phenyl);

v)

wherein

Q₁ is:

a) H, —C(O)OH, —C(O)NH(t-butyl phenyl), —O(phenyl), —NH₂, —NH(pyrimidinyl), —N(pyrimidinyl)₂, —N(CH₃)C(O)(phenyl), —CH₂OH, —CH₂NH₂, —CH₂C(O)OCH₂CH₃, —CH₂NHC(O)O(butyl), —CH₂CH₂NHC(O)O(butyl), or indolyl;

b) —NHC(O)—B₁, wherein B₁ is —CH₃, propyl, cyclopropyl, cyclohexyl, butyl cyclohexyl, t-butoxy, phenoxy, benzophenonyl, naphthalenyl, methoxynaphthalenyl, or anthracenyl;

c) —NHC(O)—B₂, wherein B₂ is piperidinyl, furanyl, morpholinyl, pyrazinyl, indolyl, benzothiazolyl, benzotriazolyl, benzimidazolyl, quinolinyl, quinolinonyl, quinoxalinyl, 2,3-dihydrobenzodioxinyl, fluorenonyl, thiophenyl, pyrazolyl, imidazolyl, isoxazolyl, oxazolyl, thiazolyl, pyridinyl, pyridazinyl, or pyrimidinyl, each of which is substituted with zero or more substituents independently selected from —CH₃, propyl, butyl, —NH₂, Cl, —CF₃, —C(O)O(butyl), and/or pyridinyl;

d) —NHC(O)CH₂—B₃, wherein B₃ is a —N(CH₃)₂, phenyl, pyridinyl, or methyl indolyl;

e)

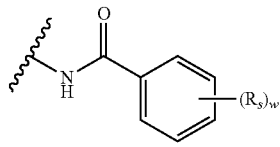

wherein each $R_s$ is independently —$CH_3$; butyl; —$CF_3$; halo; —OH; —C(O)$CH_3$; —NHC(O)$CH_3$; —C(O)O$CH_3$; —C(O)O$CH_2CH_3$; —O$CH_3$; propoxy; —O$CF_2CHF_2$; —N($CH_3$)$_2$; —S(O)$_2CH_3$; —NHC(O)O(butyl); —$CH_2$NHC(O)(t-butyl); phenoxy; pyrrolyl; thiophenyl; pyrazolyl; imidazolyl; methyl oxadiazolyl; triazolyl; tetrazolyl; methyl tetrazolyl; pyridinyl; pyrimidinyl; pyridinonyl; N-methyl piperizinyl, indolyl, benzimidazolyl, chromenonyl, or phenyl substituted with zero or more substituents independently selected from —$CH_3$, —OH, F, and/or Cl;

f) —NHS(O)$_2$—$B_4$ wherein $B_4$ is phenyl, trifluoromethyl phenyl, thiophenyl, dimethyl isoxazolyl, or methyl imidazolyl;

g) —NHC(O)NH—$B_5$ wherein $B_5$ is phenyl substituted with zero to two substituents independently selected from halo, —$CH_3$, ethyl, butyl, —CN, —$CF_3$, —O$CH_3$, —C(O)O(ethyl), —C(O)O(t-butyl), —S$CH_3$, —C(O)$CH_3$, and/or —O(cyclopentyl);

h) —NHC(O)NH—$B_6$ wherein $B_6$ is pyrazolyl, isoxazolyl, thiazolyl, thiadiazolyl, tetrazolyl, or pyridinyl, each of which is substituted with zero to two substituents independently selected from —$CH_3$, butyl, Br, —$CF_3$, cyclopropyl, —S(ethyl), and/or —C(O)O(ethyl); or i) —NHC(O)NH—$B_7$ wherein $B_7$ is propyl, chloroethyl, $C_{5-6}$cycloalkyl, benzyl, —$CH_2CH_2$— (phenyl), or —$CH_2$— (furanyl);

vi)

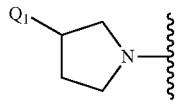

wherein $Q_1$ is H, —$NH_2$, phenyl, —C(O)OH, —NHC(O)(t-butyl), —NHC(O)(phenyl), —NHC(O)(trifluoromethyl phenyl), —NHC(O)O(t-butyl), —C(O)NH(phenyl), —C(O)NH(t-butyl phenyl), or —NHC(O)NH(methyl thiazolyl);

vii)

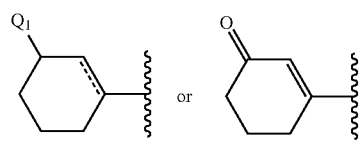

wherein $Q_1$ is H, —OH, —OC(O)(phenyl), —NHC(O)(phenyl), —NHCH($CH_3$)(methoxyphenyl), or —NHC(O)NH(thiazolyl); or viii)

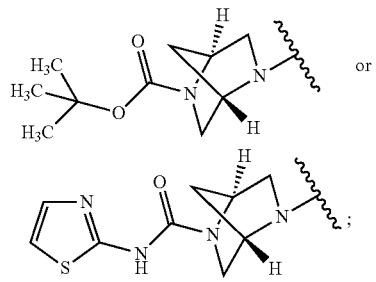

wherein $R_b$ is H or $CH_3$. Preferably, $R_3$ is H. In one example of this embodiment, X is N and Y is $CR_2$. In another example of this embodiment, X is $CR_2$ and Y is N.

Another embodiment provides a compound having Formula (I) or stereoisomers or pharmaceutically acceptable salts thereof, wherein G is: phenyl substituted with zero to 3 substituents. The compounds of this embodiment have structures represented by Formula (Ij):

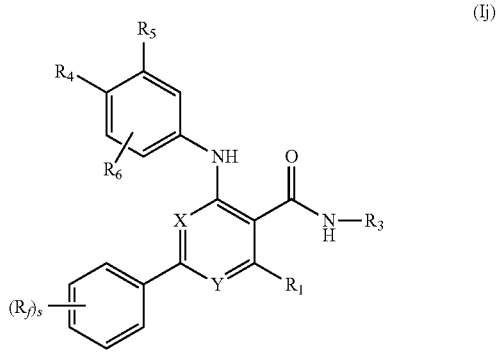

(Ij)

or stereoisomers or pharmaceutically acceptable salts thereof, wherein each $R_f$ is independently selected from —OH, alkyl, fluoroalkyl, halo, —CN, —$NR_bR_b$, —C(O)OH, alkoxy, —$CR_bR_b$O(alkyl), —$CH_2NR_b$C(O)(alkyl), —$CH_2NR_b$C(O)(phenyl), —C(O)(alkyl), —C(O)(heterocyclyl), phenoxy, —C(O)O(alkyl), —C(O)$NR_b$(alkyl), —C(O)N(alkyl)$_2$, —C(O)$NR_bCR_bR_b$(heteroaryl), —$NR_b$S(O)$_2$(alkyl), —$NR_b$S(O)$_2$(phenyl), —$NR_b$C(O)(phenyl), —$NR_b$C(O)(alkyl phenyl), and/or —$NR_b$C(O)$NR_b$(phenyl); each $R_b$ is independently H and/C—$CH_3$; s is zero, 1, 2, or 3; and X, Y, $R_1$, $R_3$, $R_4$, $R_5$, $R_6$, and $R_b$, are defined in the first aspect hereinabove. Preferably, each $R_f$ is independently selected from —OH, $C_{1-6}$alkyl, $C_{1-4}$fluoroalkyl, halo, —CN, —$NR_bR_b$, $C_{1-4}$alkoxy, —C(O)OH, —$CR_bR_b$O($C_{1-6}$alkyl), —$CH_2NR_b$C(O)($C_{1-6}$alkyl), —$CH_2NR_b$C(O)(phenyl), —C(O)($C_{1-6}$alkyl), —C(O)(heterocyclyl), phenoxy, —C(O)O($C_{1-6}$alkyl), —C(O)$NR_b$($C_{1-6}$alkyl), —C(O)N($C_{1-6}$alkyl)$_2$, —C(O)$NR_bCR_bR_b$ (heteroaryl), —$NR_b$S(O)$_2$($C_{1-6}$alkyl), —$NR_b$S(O)$_2$(phenyl), —$NR_b$C(O)(phenyl), —$NR_b$C(O)($C_{1-6}$alkyl phenyl), and/or —$NR_b$C(O)$NR_b$(phenyl). Preferably, $R_3$ is H. In one example of this embodiment, X is N and Y is $CR_2$. In another example of this embodiment, X is $CR_2$ and Y is N.

Another embodiment provides a compound having Formula (I) or stereoisomers or pharmaceutically acceptable salts thereof, wherein G is a 5- to 6-membered monocyclic heterocyclyl substituted with zero to 3 $R_f$. Examples of suitable 5- to 6-membered monocyclic heterocyclyl groups include:

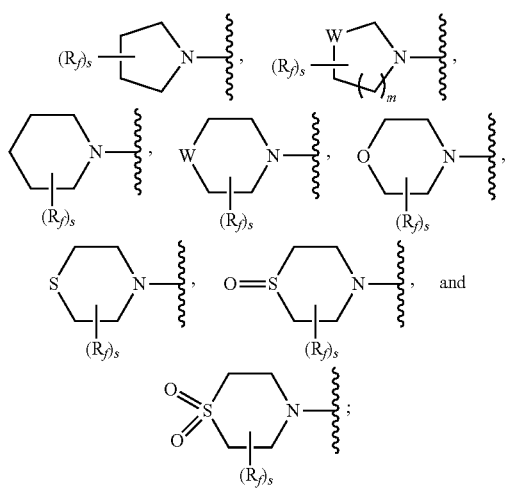

wherein W is CH(OH), C=$CR_bR_b$, NH, N(alkyl), NC(O)(phenyl), NC(O)$CR_bR_b$(phenyl), or W is $CR_gR_g$; each $R_g$ is halo; or $R_g$ and $R_g$ together with the carbon atom to which they are attached, form a 5- to 7-membered cycloalkyl or heterocyclyl ring substituted with zero to 2 substituents independently selected from —OH, alkyl, cycloalkyl, halo, —$CF_3$, =O, 1- to 2-ring aryl, and/or 1- to 2-ring heteroaryl; m is 1 or 2; and s is zero, 1, 2, or 3, provided that the total number of substituents to the 5- to 6-membered monocyclic heterocyclyl is 3 or less; and X, Y, $R_1$, $R_3$, $R_4$, $R_5$, $R_6$, $R_b$, and $R_f$ are defined in the first aspect hereinabove. Preferably, $R_3$ is H. In one example of this embodiment, X is N and Y is $CR_2$. In another example of this embodiment, X is $CR_2$ and Y is N. Examples of suitable $R_f$ groups include $Q_1$, $C_{1-6}$alkyl, phenyl, —$NR_b$($C_{1-6}$alkyl), —N($C_{1-6}$alkyl)C(O)O($C_{1-6}$alkyl), —C(O)($C_{1-4}$alkyl), —C(O)(phenyl), and/or —C(O)(benzyl),

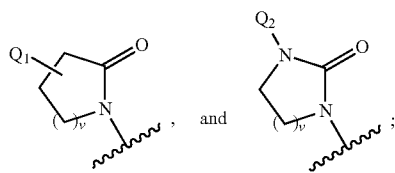

wherein:
$Q_1$ is:
a) H, —OH, —C(O)$OR_b$, —C(O)$NR_b$(phenyl), —C(O)$NR_b$($C_{1-6}$alkyl phenyl), —OC(O)(phenyl), —O(phenyl), phenyl, —$NR_bR_b$, —$NR_b$(pyrimidinyl), —N(pyrimidinyl)$_2$, $C_{1-4}$hydroalkyl, $C_{1-4}$-aminoalkyl, —($CR_bR_b$)$_q$C(O)O($C_{1-4}$alkyl), —($CR_bR_b$)$_q$$NR_b$C(O)O($C_{1-4}$alkyl), indolyl, imidazolidinonyl, or pyrrolidinonyl;
b) —$NR_b$C(O)-$Q_2$;
c) —$NR_b$C(O)$CR_bR_b$-$Q_2$;
d)

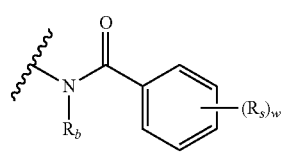

wherein each $R_s$ is independently selected from $C_{1-6}$alkyl, $C_{1-6}$fluoroalkyl, halo, —OH, —C(O)($C_{1-6}$alkyl), —$NR_b$C(O)($C_{1-6}$alkyl), —C(O)O($C_{1-6}$alkyl), $C_{1-6}$alkoxy, $C_{1-6}$fluoroalkoxy, —$NR_bR_b$, —N($C_{1-6}$alkyl)$_2$, —S(O)$_2$($C_{1-6}$alkyl), —$NR_b$C(O)O ($C_{1-6}$alkyl), phenoxy, —$CR_bR_bNR_b$C(O)($C_{1-6}$alkyl), and/or a cyclic group independently selected from aryl, heteroaryl, and/or heterocyclyl, wherein said cyclic group is substituted with zero or more substituents independently selected from $C_{1-6}$alkyl, —OH, halo, $C_{1-2}$haloalkyl, —$NR_bR_b$, $C_{1-4}$alkoxy, =O, and/or —CN;
e) —$NR_b$S(O)$_2$-$Q_2$; or
f) —$NR_b$C(O)$NR_b$-$Q_2$;
$Q_2$ is:
a) H, $C_{1-6}$alkyl, $C_{1-6}$haloalkyl, —N($C_{1-6}$alkyl)$_2$, $C_{1-6}$alkoxy, phenoxy, or benzophenonyl;
b) $C_{3-7}$cycloalkyl, aryl, heterocyclyl, or heteroaryl, each of which is substituted with zero or more substituents independently selected from $C_{1-6}$alkyl, $C_{3-7}$cycloalkyl, halo, —CN, —OH, =O, —$NR_bR_b$, $C_{1-6}$fluoroalkyl, $C_{1-6}$alkoxy, —S($C_{1-6}$alkyl), —C(O)($C_{1-6}$alkyl), —C(O)O($C_{1-6}$alkyl), —O($C_{3-7}$cycloalkyl), $C_{1-6}$alkylphenyl, hydroxyphenyl, halophenyl, ($C_{1-6}$fluoroalkyl)phenyl, and/or pyridinyl; or
c) —($CR_bR_b$)$_q$N($C_{1-6}$alkyl)$_2$, —($CR_bR_b$)$_q$(phenyl), or —($CR_bR_b$)$_q$(furanyl); and
each q is independently 1, 2, and/or 3; and
v is 1 or 2. Included in this embodiment are compounds in which G is:

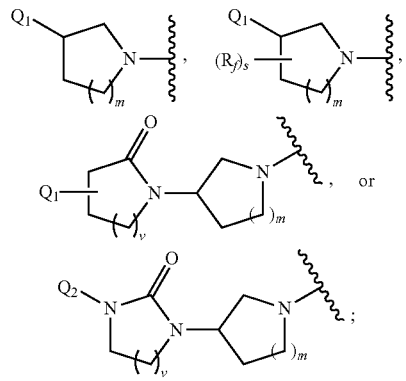

wherein s is zero, 1, 2, or 3, provided that the total number of substituents to the 5- to 6-membered monocyclic heterocyclyl is 3 or less.

Another embodiment provides a compound having Formula (I) or stereoisomers or pharmaceutically acceptable salts thereof, wherein:
G is:

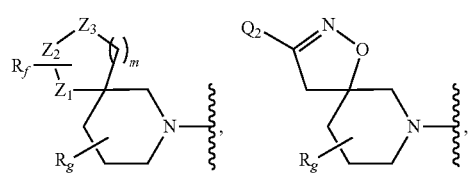

-continued

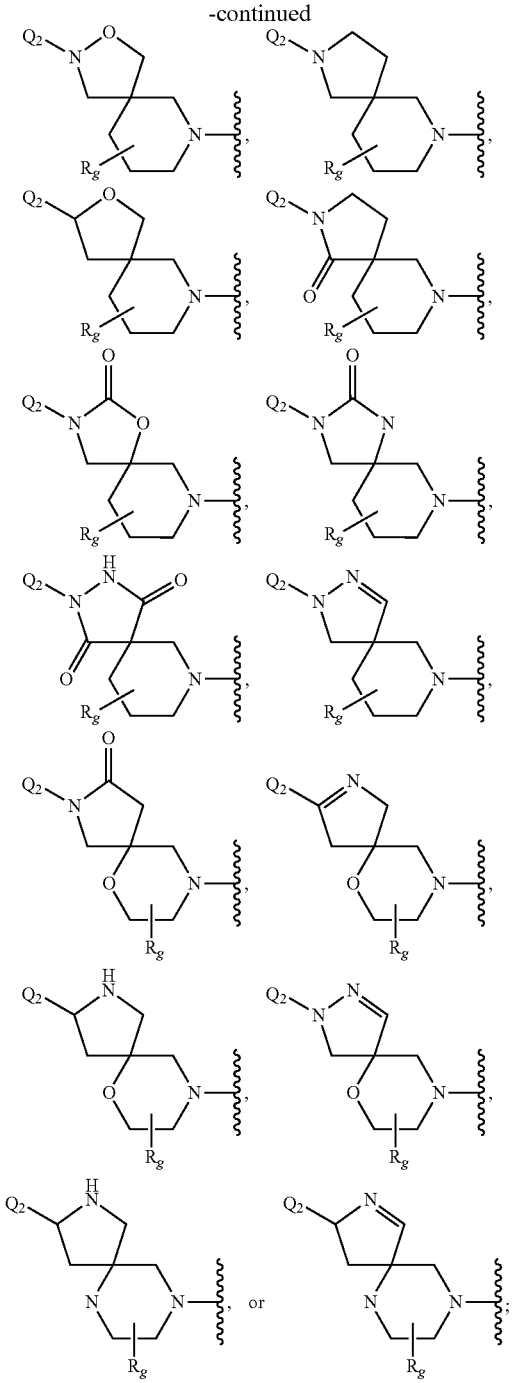

wherein m is 1 or 2; $Z_1$, $Z_2$, and $Z_3$ are independently $CH_2$, $CHR_f$, NH, $NR_f$, O, and/or S, and are chosen to provide a stable heterocyclyl ring; $Q_2$ is: a) H, $C_{1-6}$alkyl, $C_{1-6}$haloalkyl, —N($C_{1-6}$alkyl)$_2$, $C_{1-6}$alkoxy, phenoxy, or benzophenonyl; b) $C_{3-7}$cycloalkyl, aryl, heterocyclyl, or heteroaryl, each of which is substituted with zero or more substituents independently selected from $C_{1-6}$alkyl, $C_{3-7}$cycloalkyl, halo, —CN, —OH, =O, —$NR_bR_b$, $C_{1-6}$-fluoroalkyl, $C_{1-6}$alkoxy, —S($C_{1-6}$alkyl), —C(O)($C_{1-6}$alkyl), —C(O)O($C_{1-6}$alkyl), —O($C_{3-7}$cycloalkyl), $C_{1-6}$alkylphenyl, hydroxyphenyl, halophenyl, ($C_{1-6}$fluoroalkyl)phenyl, and/or pyridinyl; or c) —(CR$_b$R$_b$)$_q$N(C$_{1-6}$alkyl)$_2$, —(CR$_b$R$_b$)$_q$(phenyl), or —(CR$_b$R$_b$)$_q$(furanyl); and R$_b$, R$_f$, R$_g$, and q are defined in the first aspect hereinabove. Preferably, R$_3$ is H. In one example of this embodiment, X is N and Y is CR$_2$. In another example of this embodiment, X is CR$_2$ and Y is N.

Another embodiment provides a compound having Formula (I) or stereoisomers or pharmaceutically acceptable salts thereof, wherein G is cyclohexyl or cyclohexenyl substituted with zero to 3 R$_f$. The compounds of this embodiment include compounds having structures represented by Formula (Ik):

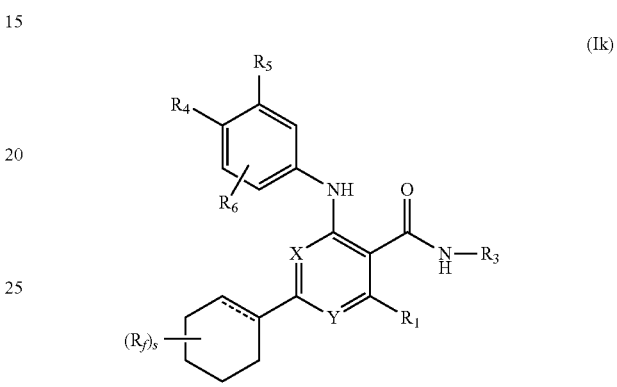

or stereoisomers or pharmaceutically acceptable salts thereof, wherein s is zero, 1, 2, or 3; and X, Y, R$_1$, R$_3$, R$_4$, R$_5$, R$_6$, and R$_f$ are defined in the first aspect hereinabove. Preferably, R$_3$ is H. In one example of this embodiment, X is N and Y is CR$_2$. In another example of this embodiment, X is CR$_2$ and Y is N. Suitable R$_f$ groups include Q$_1$, —OH, halo, —CF$_3$, =O, —OC(O)(phenyl), —NR$_b$C(O)(phenyl), —NR$_b$CR$_b$R$_b$(methoxyphenyl), —NR$_b$C(O)NR$_b$(thiazolyl),

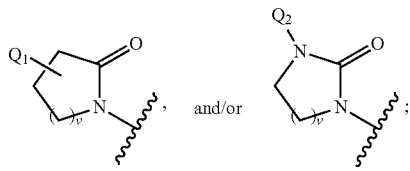

wherein v is 1 or 2, and Q$_1$ and Q$_2$ are defined in the first aspect hereinabove. For example, the present embodiment includes compounds in which G is:

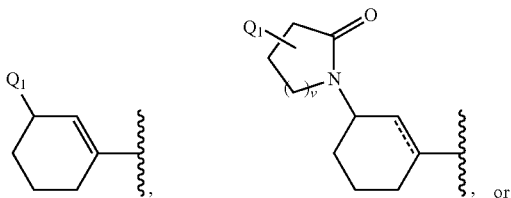

-continued

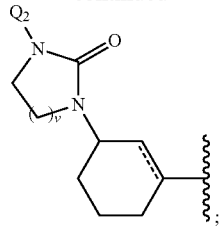

wherein v is 1 or 2; and $Q_1$ and $Q_2$ are defined in the first aspect hereinabove.

One embodiment provides a compound having Formula (I) or stereoisomers or pharmaceutically acceptable salts thereof, wherein:
X is N and Y is $CR_2$;
$R_3$ is H;
$R_6$ is H;
one of $R_4$ and $R_5$ is H, halo, $C_{1-2}$alkoxy, —C(O)$NR_b$($C_{1-2}$alkyl), —$NR_b$($C_{1-2}$alkyl), —$NR_b$S(O)$_2$($C_{1-2}$alkyl), —$NR_b$S(O)$_2$(phenyl), —C(O)NH($C_{1-2}$alkyl), —N(CH$_3$)C(O)(phenyl), pyrrolidine-2,5-dione, —$NR_b$C(O)$NR_b$(phenyl), —CH$_2$S(O)$_2$(pyrrolidinyl), —S(O)$_2$($C_{1-2}$alkyl), —$NR_b$S(O)$_2$($C_{1-2}$alkyl), —$NR_b$S(O)$_2$(fluorophenyl), —$NR_b$S(O)$_2$(biphenyl), —$NR_b$S(O)$_2$(naphthalenyl), —$NR_b$S(O)$_2$(imidazolyl), —$NR_b$S(O)$_2$(chlorothiophenyl), —$NR_b$S(O)$_2$(benzyl), —$NR_b$S(O)$_2$(pyridinyl), —$NR_b$(S(O)$_2$($C_{1-4}$-chloroalkyl), —N(S(O)$_2$($C_{1-4}$-chloroalkyl))$_2$, or —$NR_b$C(O)O($C_{1-4}$alkyl);
and the other of $R_4$ and $R_5$ is:
a) H, halo, —CN, or $C_{1-2}$alkoxy;
b) -L-A; or
c) -L-C(O)-A;
wherein L is a bond or —($CR_cR_c$)$_t$—; and
A is selected from $A_1$, $A_2$, and $A_3$, wherein:
$A_1$ is $C_{1-4}$alkyl or $C_{5-7}$cycloalkyl, each independently substituted with 0 to 2 substituents independently selected from —OH, —NH$_2$, —OCH$_3$, —C(O)NH$_2$, —C(O)($C_{1-6}$alkyl), —C(O)$OR_b$, —NH($C_{1-4}$alkyl), —N($C_{1-6}$alkyl)$_2$, —C(O)$NR_b$($C_{1-6}$alkyl), —C(O)$NR_b$($C_{1-6}$hydroxyalkyl), —C(O)$NR_b$(heterocyclyl), —C(O)$NR_bR_b$, —C(O)$NR_b$($CR_bR_b$)$_q$NH($C_{1-6}$alkyl), —C(O)$NR_b$($CR_bR_b$)$_q$N($C_{1-6}$alkyl)$_2$, and/or —$NR_b$C(O)($C_{1-6}$alkyl);
$A_2$ is 4- to 6-membered heterocyclyl or 5- to 6-membered heteroaryl having 1- to 3-heteroatoms independently selected from N, O, and/or S, and substituted with zero to 2 substituents independently selected from =O, $C_{1-4}$alkyl, $C_{1-3}$hydroxyalkyl, $C_{3-5}$cycloalkyl, —C(O)($C_{1-4}$alkyl), —NH($C_{1-4}$alkyl), —N($C_{1-4}$alkyl)$_2$, —C(O)$NR_b$($C_{1-4}$alkyl), —C(O)$NR_b$($C_{1-4}$hydroxyalkyl), —C(O)$NR_b$($C_{3-4}$cycloalkyl), —C(O)$NR_b$($CR_bR_b$)$_q$NH($C_{1-4}$alkyl), —C(O)$NR_b$(phenyl), —C(O)$NR_b$($CR_bR_b$)$_q$N($C_{1-4}$alkyl)$_2$, —C(O)$NR_bR_b$, —$NR_b$C(O)($C_{1-4}$alkyl), and/or —C(O)O(benzyl);
$A_3$ is —OH, —NH$_2$, $C_{1-4}$alkoxy, —NH($C_{1-6}$alkyl), —N($C_{1-6}$alkyl)$_2$, —$NR_b$($C_{1-4}$hydroxyalkyl), —$NR_b$($C_{3-6}$cycloalkyl), —$NR_b$($CR_bR_b$)$_q$NH($C_{1-4}$alkyl), —$NR_b$($CR_bR_b$)$_q$N($C_{1-4}$alkyl)$_2$, —$NR_b$(phenyl), —$NR_b$C(O)($C_{1-4}$alkyl), —S($C_{1-4}$alkyl), —S(O)$_2$($C_{1-4}$alkyl), —S(O)$_2$($C_{1-3}$fluoroalkyl), —S(O)$_2$N($C_{1-6}$alkyl)$_2$, —S(O)$_2$NH($C_{1-6}$alkyl), —$NR_b$S(O)$_2$(alkyl), —$NR_b$S(O)$_2$(aryl), —$NR_b$S(O)$_2$(heteroaryl), —$NR_b$C(O)$NR_bA_2$, —$NR_b$C(O)$A_2$, —$NR_bA_2$, —$NR_b$C(O)($CR_bR_b$)$_qA_2$, or —O($CR_cR_c$)$_qA_2$;

G is:
i) 1- to 2-ring heteroaryl or 1- to 2-ring heterocyclyl substituted with zero to 3 substituents independently selected from $C_{1-6}$alkyl, phenyl, —$NR_b$($C_{1-6}$alkyl), —N($C_{1-6}$alkyl)C(O)O($C_{1-6}$alkyl), —C(O)($C_{1-4}$alkyl), —C(O)(phenyl), and/or —C(O)(benzyl); or
ii) naphthalenyl; or phenyl substituted with zero to 3 substituents independently selected from —OH, $C_{1-6}$alkyl, $C_{1-6}$fluoroalkyl, halo, —CN, —$NR_bR_b$, $C_{1-4}$alkoxy, —$CR_bR_b$($C_{1-6}$alkoxy), —CH$_2NR_b$C(O)($C_{1-6}$alkyl), —CH$_2NR_b$C(O)(phenyl), —C(O)($C_{1-6}$alkyl), —C(O)(heterocyclyl), phenoxy, —C(O)O($C_{1-6}$alkyl), —C(O)$NR_b$($C_{1-6}$alkyl), —C(O)N($C_{1-4}$alkyl)$_2$, —C(O)$NR_b$$CR_bR_b$(heterocyclyl), —$NR_b$S(O)$_2$($C_{1-6}$alkyl), —$NR_b$S(O)$_2$(phenyl), —$NR_b$C(O)(phenyl), —$NR_b$C(O)($C_{1-6}$alkyl phenyl), and/or —$NR_b$C(O)$NR_b$(phenyl);
wherein $R_1$, $R_b$, $R_c$, m, q, s, t, v, and w are defined in the first aspect hereinabove.

One embodiment provides a compound having Formula (I) or stereoisomers or pharmaceutically acceptable salts thereof, wherein:
$R_1$ is H;
$R_6$ is H;
$R_2$ is H, F, Br, —CH$_3$, or —CN;
$R_5$ is halo and $R_4$ is 5- to 6-membered heterocyclyl having 1- to 3-heteroatoms independently selected from N, O, and/or S, and substituted with zero to 2 substituents independently selected from $C_{1-4}$alkyl, $C_{1-4}$hydroxyalkyl, and/or —C(O)($C_{1-4}$alkyl); or
$R_5$ is H, —NH(CH$_3$), —C(O)NHCH$_3$, —N(CH$_3$)C(O)(phenyl), pyrrolidine-2,5-dione, —N(CH$_3$)C(O)NH(phenyl), —CH$_2$S(O)$_2$(pyrrolidinyl), —S(O)$_2$CH$_3$, —$NR_b$S(O)$_2$CH$_3$, —$NR_b$S(O)$_2$CH$_2$CH$_3$, —$NR_b$S(O)$_2$(phenyl), —$NR_b$S(O)$_2$(fluorophenyl), —$NR_b$S(O)$_2$(biphenyl), —$NR_b$S(O)$_2$(naphthalenyl), —$NR_b$S(O)$_2$(chlorothiophenyl), —$NR_b$S(O)$_2$(imidazolyl), —$NR_b$S(O)$_2$(benzyl), —$NR_b$S(O)$_2$(pyridinyl), —$NR_b$(S(O)$_2$CH$_2$CH$_2$CH$_2$Cl), —N(S(O)$_2$CH$_2$CH$_2$CH$_2$Cl)$_2$, or —$NR_b$C(O)O(butyl); and
$R_4$ is H; or
$R_5$ is H or —OCH$_3$, and $R_4$ is:
a) H, halo, or —CN;
b) -L-A; or
c) -L-C(O)-A;
wherein L is a bond or —($CR_cR_c$)$_t$—; and A is selected from $A_1$, $A_2$, and $A_3$; wherein:
$A_1$ is $C_{1-4}$alkyl substituted with 0 to 2 substituents independently selected from —OH, —NH$_2$, —OCH$_3$, —C(O)OH, —NH($C_{1-2}$alkyl), and/or —N($C_{1-2}$alkyl)$_2$;
$A_2$ is 4- to 6-membered heterocyclyl or 5- to 6-membered heteroaryl having 1- to 3-heteroatoms independently selected from N, O, and/or S, and substituted with zero to 4 substituents independently selected from OH, =O, $C_{1-3}$alkyl, $C_{1-2}$hydroxyalkyl, $C_{3-4}$cycloalkyl, —C(O)($C_{1-2}$alkyl), —C(O)O($C_{1-4}$alkyl), and/or —C(O)O(benzyl);
$A_3$ is —OH, —NH$_2$, $C_{1-4}$alkoxy, —OCH$_2$CH(OCH$_2$CH$_3$)$_2$, —OCH$_2$CH$_2$NH(cyclopropyl), —OCH$_2$CH$_2$(pyrrolidinyl), —OCH$_2$CH$_2$N(CH$_3$)$_2$, N,N-dimethylethamine oxide, —NH($C_{1-4}$alkyl), —N($C_{1-2}$alkyl)$_2$, —NH($C_{1-2}$hydroxyalkyl), —NH($C_{3-6}$cycloalkyl), —NH(CH$_2$)$_q$NH($C_{1-4}$alkyl), —NH(CH$_2$)$_q$N($C_{1-2}$alkyl)$_2$, —NH(phenyl), —NHC(O)($C_{1-2}$alkyl), —S($C_{1-4}$alkyl), —S(O)$_2$($C_{1-4}$alkyl), —S(O)$_2$($C_{1-2}$fluoroalkyl), —S(O)$_2NR_dR_d$, —S(O)$_2$(CH$_2$)$_q$N($C_{1-2}$alkyl)$_2$, —NHC(O)$A_2$, —NH$A_2$, —NHC(O)(CH$_2$)$_qA_2$, or —O(CH$_2$)$_qA_2$;

G is:

i)

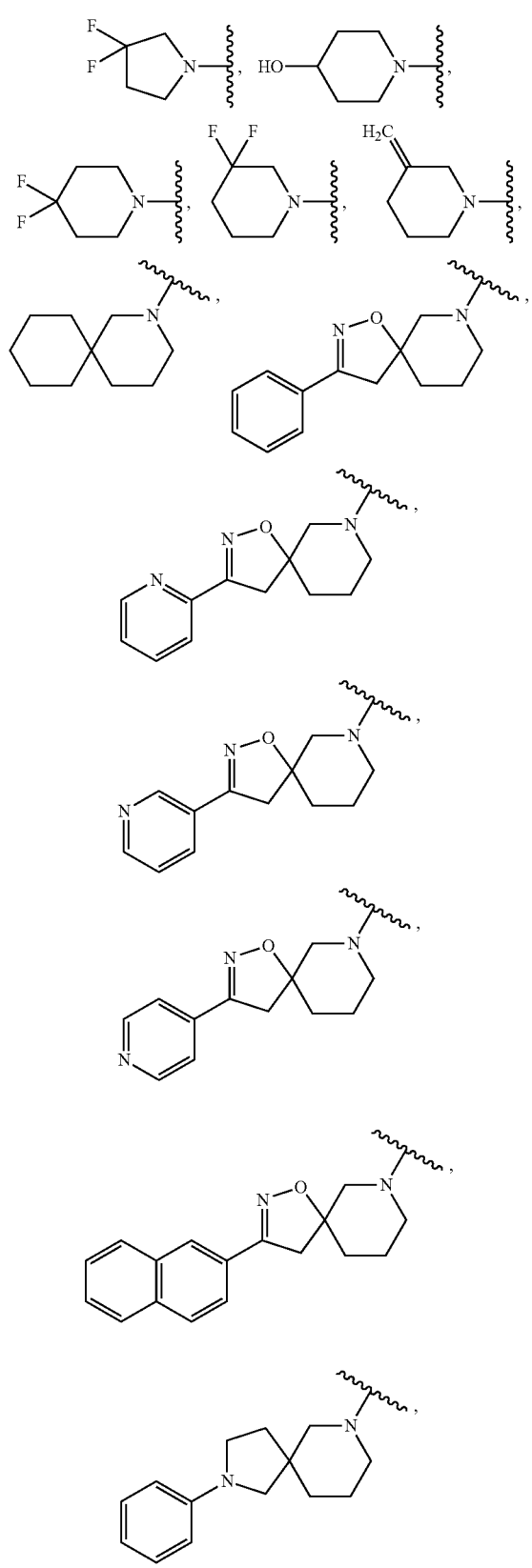

ii)

(cyclohexenyl group)

iii)

(pyrrolidine with Q₁ substituent)

wherein Q₁ is H, —NH₂, phenyl, —C(O)OH, —NHC(O)(C₁₋₄alkoxy), —NHC(O)(phenyl), —NHC(O)(trifluoromethyl phenyl), —C(O)NH(phenyl), —C(O)NH(C₁₋₄alkyl phenyl), or —NHC(O)NH(methyl thiazolyl);
each $R_c$ is independently H, —CH₃, and/or —CH₂OH;
each q is independently 1 or 2;
t is 1 or 2; and $R_e$, s, and w are defined in the first aspect hereinabove. Preferably, $R_3$ is H. In one example of this embodiment, X is N and Y is $CR_2$.

One embodiment provides a compound having Formula (I) or stereoisomers or pharmaceutically acceptable salts thereof, wherein:

X is N and Y is CR$_2$:

R$_1$ is H;

R$_3$ is H;

R$_6$ is H;

R$_2$ is H, F, Br, —CH$_3$, or CN;

R$_5$ is F, and R$_4$ is morpholinyl or N-methyl piperazinyl; or

R$_5$ is —OCH$_3$, and R$_4$ is H or —OCH$_2$CH$_2$(pyrrolidinyl); or

R$_5$ is H, and R$_4$ is H, F, —CN, ethyl, hydroxyethyl, dimethylaminoethyl, —OCH$_3$, —NHC(O)CH$_3$, —NH$_2$, —N(ethyl)$_2$, —C(O)CH$_3$, —C(O)OH, —C(O)O(butyl), —C(O)NH(cyclopropyl), —C(O)NH(butyl), —C(O)NH(phenyl), —C(O)N(CH$_3$)$_2$, —C(O)N(ethyl)$_2$, —C(O)NHCH$_2$CH$_2$N(CH$_3$)$_2$, —C(O)NH(hydroxyethyl), —CH$_2$CH(CH$_2$OH)NHC(O)(pyrrolidinyl), —CH$_2$CH(CH$_2$OH)NHC(O)(piperidinyl), —C(CH$_3$)$_2$C(O)NHCH$_2$CH$_2$N(CH$_3$)$_2$, —C(CH$_3$)$_2$C(O)NH(oxetanyl), —C(CH$_3$)$_2$C(O)NH(pyrrolidinyl), —C(CH$_3$)$_2$C(O)NH(cyclopropyl), —C(CH$_3$)$_2$C(O)NHCH$_2$CH$_2$OH, —CH$_2$C(CH$_3$)$_2$C(O)OH, —S(O)$_2$CH$_3$, —S(O)$_2$N(CH$_3$)$_2$, —S(O)$_2$CF$_3$, —S(O)$_2$CH$_2$CH$_2$N(CH$_2$CH$_3$)$_2$, —NHS(O)$_2$CH$_3$, —NCH$_3$S(O)$_2$CH$_3$ —NCH$_3$S(O)$_2$-phenyl, pyrrolidinyl, oxazolyl, morpholinyl, morpholinonyl, piperidinyl, N-methyl piperidinyl, N-acetyl piperazinyl, piperazinyl, N-methyl piperazinyl, N-ethyl piperazinyl, N-propyl piperazinyl, N-cyclopropyl-piperazinyl, N-cyclobutyl piperazinyl, N-(benzyl-OC(O))piperazinyl, —C(O)(azetidinyl), —C(O)(pyrrolidinyl), —C(O)(morpholinyl), —C(O)(piperidinyl), —C(O)(N-methyl piperazinyl), —C(O)(N-hydroxyethyl piperazinyl), —CH$_2$(morpholinyl), or

G is:

i) thiophenyl; pyridinyl; indolyl; isoindolinyl; benzofuranyl; N-methyl pyrazolyl; morpholinyl; dimethyl morpholinyl; phenyl morpholinyl; piperizinyl optionally substituted with —C(O)(benzyl); thiazolyl substituted with —NH(propyl) or —N(propyl)(C(O)O(butyl); NR$_b$(benzyl); or 1,2,3,4-tetrahydroisoquinolinyl substituted with zero or one substituent selected from —C(O)(phenyl), —C(O)CH$_3$, or —C(O)butyl;

ii)

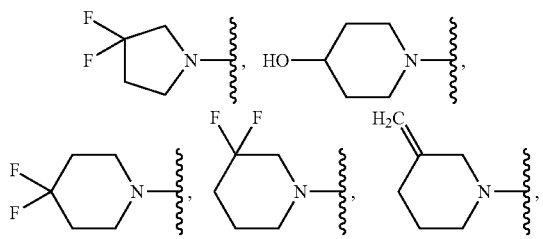

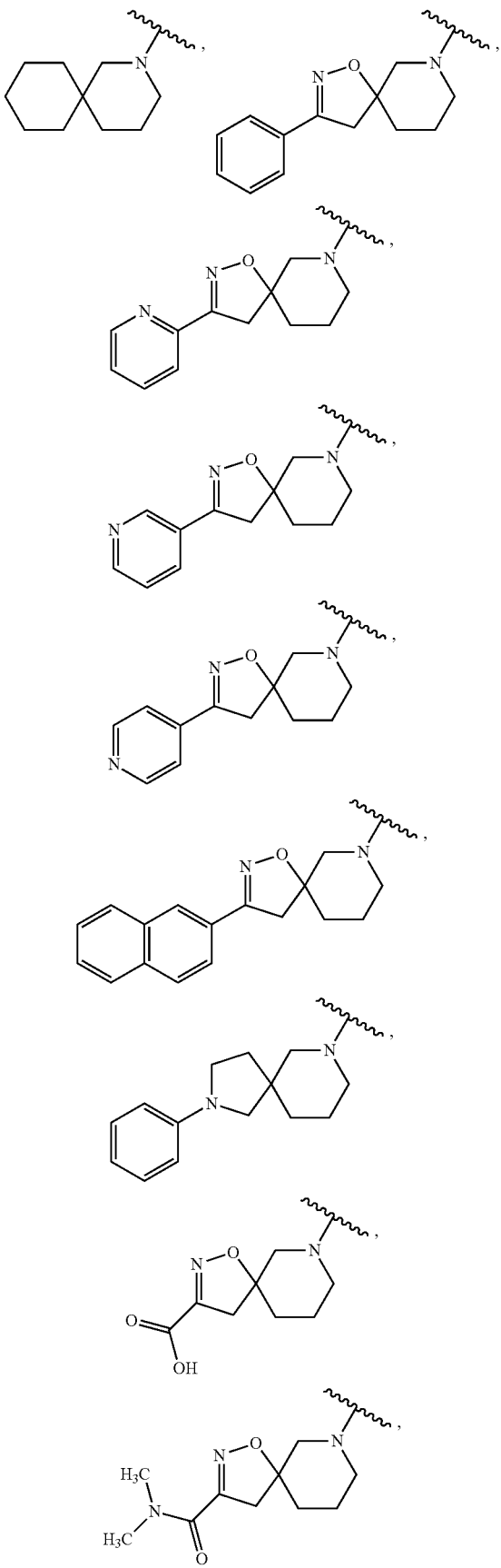

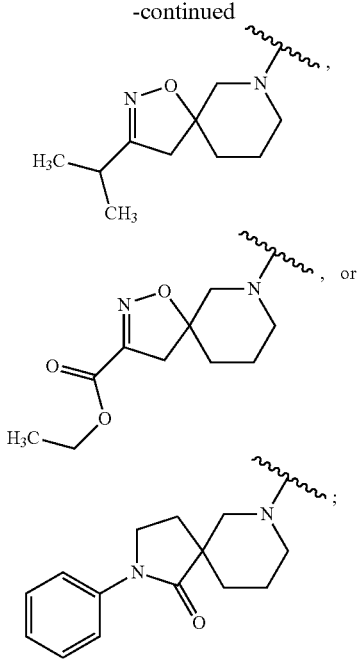

iii)

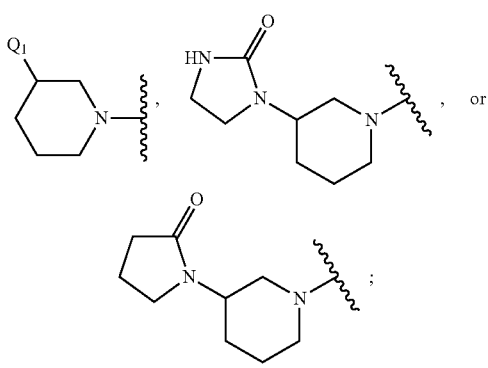

iv)

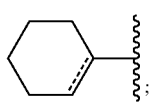

wherein Q₁ is
a) H, —C(O)OH, —C(O)NH(t-butyl phenyl), —O(phenyl), —NH₂, —NH(pyrimidinyl), —N(pyrimidinyl)₂, —N(CH₃)C(O)(phenyl), —CH₂OH, —CH₂NH₂, —CH₂C(O)OCH₂CH₃, —CH₂NHC(O)O(butyl), —CH₂CH₂NHC(O)O(butyl), or indolyl;
b) —NHC(O)—B₁, wherein B₁ is —CH₃, propyl, cyclopropyl, cyclohexyl, butyl cyclohexyl, t-butoxy, phenoxy, benzophenonyl, naphthalenyl, methoxynaphthalenyl, anthracenyl, or piperidinyl optionally substituted with —C(O)O(t-butyl);
c) —NHC(O)—B₂, wherein B₂ is piperidinyl, furanyl, morpholinyl, pyrazinyl, indolyl, benzothiazolyl, benzotriazolyl, benzimidazolyl, quinolinyl, quinolinonyl, quinoxalinyl, 2,3-dihydrobenzodioxinyl, fluorenonyl, thiophenyl, pyrazolyl, imidazolyl, isoxazolyl, oxazolyl, thiazolyl, pyridinyl, pyridazinyl, or pyrimidinyl, each of which is substituted with zero or more substituents independently selected from —CH₃, propyl, butyl, —NH₂, Cl, —CF₃, —C(O)O(butyl), and/or pyridinyl;
d) —NHC(O)CH₂—B₃, wherein B₃ is a —N(CH₃)₂, phenyl, pyridinyl, or methyl indolyl;
e) —NHS(O)₂—B₄ wherein B₄ is phenyl, trifluoromethyl phenyl, thiophenyl, dimethyl isoxazolyl, or methyl imidazolyl;
f) —NHC(O)NH—B₅ wherein B₅ is phenyl substituted with zero to two substituents independently selected from halo, —CH₃, ethyl, butyl, —CN, —CF₃, —OCH₃, —C(O)O(ethyl), —C(O)O(t-butyl), —SCH₃, —C(O)CH₃, and/or —O(cyclopentyl);
g) —NHC(O)NH—B₆ wherein B₆ is pyrazolyl, isoxazolyl, thiazolyl, thiadiazolyl, tetrazolyl, or pyridinyl, each of which is substituted with zero to two substituents independently selected from —CH₃, butyl, Br, —CF₃, cyclopropyl, —S(ethyl), and/or —C(O)O(ethyl);
h) —NHC(O)NH—B₇ wherein B₇ is propyl, chloroethyl, C₅₋₆cycloalkyl, benzyl, —CH₂CH₂-(phenyl), or —CH₂-(furanyl); or v)

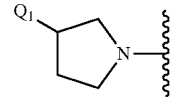

wherein Q₁ is H, —NH₂, phenyl, —C(O)OH, —NHC(O)(t-butyl), —NHC(O)(phenyl), —NHC(O)(trifluoromethyl phenyl), —C(O)NH(phenyl), —C(O)NH(t-butyl phenyl), or —NHC(O)NH(methyl thiazolyl). Preferably, R₃ is H.

In one embodiment, the compounds of Formula (I) or stereoisomers or pharmaceutically acceptable salts thereof are provided, wherein:
G is:

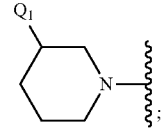

and
Q₁ is:
a)

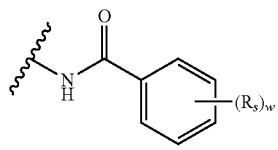

wherein each R$_s$ is independently —CH₃; butyl; —CF₃; halo; —OH; —C(O)CH₃; —NHC(O)CH₃; —C(O)OCH₃; —C(O)OCH₂CH₃; —OCH₃; propoxy; —OCF₂CHF₂; —N(CH₃)₂; —S(O)₂CH₃; —NHC(O)O(butyl); —CH₂NHC(O)(t-butyl); phenoxy; pyrrolyl; thiophenyl; pyrazolyl; imidazolyl; methyl oxadiazolyl;

triazolyl; tetrazolyl; methyl tetrazolyl; pyridinyl; pyrimidinyl; pyridinonyl; N-methyl piperizinyl, indolyl, benzimidazolyl, chromenonyl, or phenyl substituted with zero or more substituents independently selected from —CH₃, —OH, F, and/or Cl; and w is zero, 1, 2, or 3;

b) —NHC(O)NH—B₅ wherein B₅ is phenyl substituted with zero to two substituents independently selected from halo, —CH₃, ethyl, butyl, —CN, —CF₃, —OCH₃, —C(O)O(ethyl), —C(O)O(t-butyl), —SCH₃, —C(O)CH₃, and/or —O(cyclopentyl); or c) —NHC(O)NH—B₆ wherein B₆ is pyrazolyl, isoxazolyl, thiazolyl, thiadiazolyl, tetrazolyl, or pyridinyl, each of which is substituted with zero to two substituents independently selected from —CH₃, butyl, Br, —CF₃, cyclopropyl, —S(ethyl), and/or —C(O)O(ethyl). Preferably, R₂ is H, F, Cl, —CH₃, or —CN. Preferably, R₃ is H. Preferably, R₅ is H. Preferably, R₆ is H. In one example of this embodiment, X is N and Y is CR₂. In another example of this embodiment, X is CR₂ and Y is N.

In one embodiment, the compounds of Formula (I) or stereoisomers or pharmaceutically acceptable salts thereof are provided, wherein:

G is:

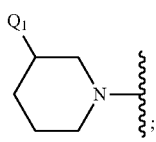

and

Q₁ is:

a) —NHC(O)NH—B₅ wherein B₅ is phenyl substituted with zero to two substituents independently selected from halo, —CH₃, ethyl, butyl, —CN, —CF₃, —OCH₃, —C(O)O(ethyl), —C(O)O(t-butyl), —SCH₃, —C(O)CH₃, and/or —O(cyclopentyl); or b) —NHC(O)NH—B₆ wherein B₆ is pyrazolyl, isoxazolyl, thiazolyl, thiadiazolyl, tetrazolyl, or pyridinyl, each of which is substituted with zero to two substituents independently selected from —CH₃, butyl, Br, —CF₃, cyclopropyl, —S(ethyl), and/or —C(O)O(ethyl). Preferably, R₂ is H, F, Cl, —CH₃, or —CN. Preferably, R₃ is H. Preferably, R₅ is H. Preferably, R₆ is H. In one example of this embodiment, X is N and Y is CR₂. In another example of this embodiment, X is CR₂ and Y is N.

In one embodiment, the compounds of Formula (I) or stereoisomers or pharmaceutically acceptable salts thereof are provided, wherein:

G is

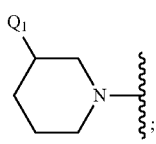

and

Q₁ is —NHC(O)NH—B₆ wherein B₆ is pyrazolyl, isoxazolyl, thiazolyl, thiadiazolyl, tetrazolyl, or pyridinyl, each of which is substituted with zero to two substituents independently selected from —CH₃, butyl, Br, —CF₃, cyclopropyl, —S(ethyl), and/or —C(O)O(ethyl). Preferably, R₂ is H, F, Cl, —CH₃, or —CN. Preferably, R₃ is H. Preferably, R₅ is H. Preferably, R₆ is H. In one example of this embodiment, X is N and Y is CR₂. In another example of this embodiment, X is CR₂ and Y is N.

One embodiment provides a compound having Formula (II):

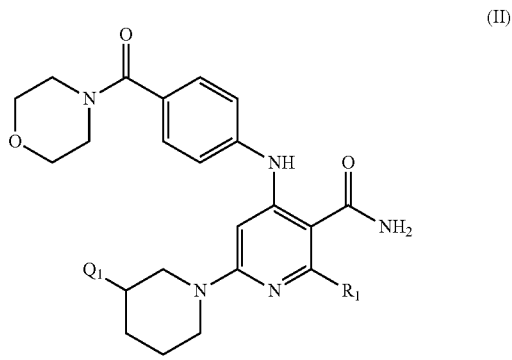

or stereoisomers or pharmaceutically acceptable salts thereof, wherein:

R₁ is H or C₃alkoxy;

Q₁ is: H, —NH₂, —NHC(O)O-(t-butyl), —NHC(O)NH—B₈; and

B₈ is phenyl or thiazolyl, each of which is optionally substituted with one or two methyl groups.

Another embodiment provides a compound having Formula (I) or stereoisomers or pharmaceutically acceptable salts thereof, wherein R₁ is H.

Another embodiment provides a compound having Formula (I) or stereoisomers or pharmaceutically acceptable salts thereof, wherein R₁ is —OR_a and R_a is H, alkyl, hydroxyalkyl, or —(CH₂)ₙ-phenyl, wherein said phenyl in turn is substituted with zero to 4 R_h. Preferably, R_a is C₁₋₆alkyl or C₁₋₆hydroxyalkyl. Suitable alkyl groups include C₁₋₄alkyl groups such as methyl, ethyl, propyl, and butyl.

Another embodiment provides a compound having Formula (I) or stereoisomers or pharmaceutically acceptable salts thereof, wherein R₂ is H, F, Cl, Br, —CH₃, or —CN. Preferably, R₂ is H, F, Cl, or Br. More preferably, R₂ is H or F.

Another embodiment provides a compound having Formula (I) or stereoisomers or pharmaceutically acceptable salts thereof, wherein R₃ is H.

Another embodiment provides a compound having Formula (I) or stereoisomers or pharmaceutically acceptable salts thereof, wherein R₅ is H, halo, or —OCH₃. Preferably, R₅ is H, F, or —OCH₃.

Another embodiment provides a compound having Formula (I) or stereoisomers or pharmaceutically acceptable salts thereof, wherein R₅ is H.

Another embodiment provides a compound having Formula (I) or stereoisomers or pharmaceutically acceptable salts thereof, wherein R₆ is H.

One embodiment provides a compound having Formula (I) or stereoisomers or pharmaceutically acceptable salts thereof, wherein one of X and Y is N, the other of X and Y is CR₂, and R₂ is halo. Preferably, R₃ is H. In one example of this embodiment, R₂ is F or Br. In another example of this embodiment, X is N and Y is CF or CBr. In a further example of this embodiment, Y is N, and X is CF or CBr. Preferably, R₃ is H.

One embodiment provides a compound having Formula (I) or stereoisomers or pharmaceutically acceptable salts thereof, wherein R₃ is H; and X, Y, G, R₁, R₃, R₄, R₅, R₆, and s are defined in the first aspect hereinabove.

One embodiment provides a compound having Formula (I) or stereoisomers or pharmaceutically acceptable salts thereof, wherein $R_1$ is H or —$OR_a$; $R_a$ is H, $C_{1-6}$alkyl, $C_{1-6}$hydroalkyl, or —$(CH_2)_n$phenyl, wherein said phenyl is substituted with zero to 4 $R_h$; and each $R_h$ is independently —OH, —$NH_2$, $C_{1-6}$alkyl, halo, $C_{1-6}$haloalkyl, $C_{1-6}$alkoxy, and/or $C_{1-6}$haloalkoxy. In one example of this embodiment, $R_1$ is H, —OH, or $C_{1-4}$alkoxy. In another example of this embodiment, $R_1$ is H. Preferably, $R_3$ is H.

Methods of Preparation

In general, the compounds of Formula (I) can be prepared in accordance with the following Schemes and the general knowledge of one skilled in the art and/or using methods set forth in the Examples that follow. Solvents, temperatures, pressures, and other reaction conditions can readily be selected by one of ordinary skill in the art. Starting materials are commercially available or readily prepared by one skilled in the art. Combinatorial techniques can be employed in the preparation of compounds, for example, where intermediates possess groups suitable for these techniques.

The synthesis of the compounds of this invention can be made using the methods summarized in Schemes 1 to 3.

SCHEME 1

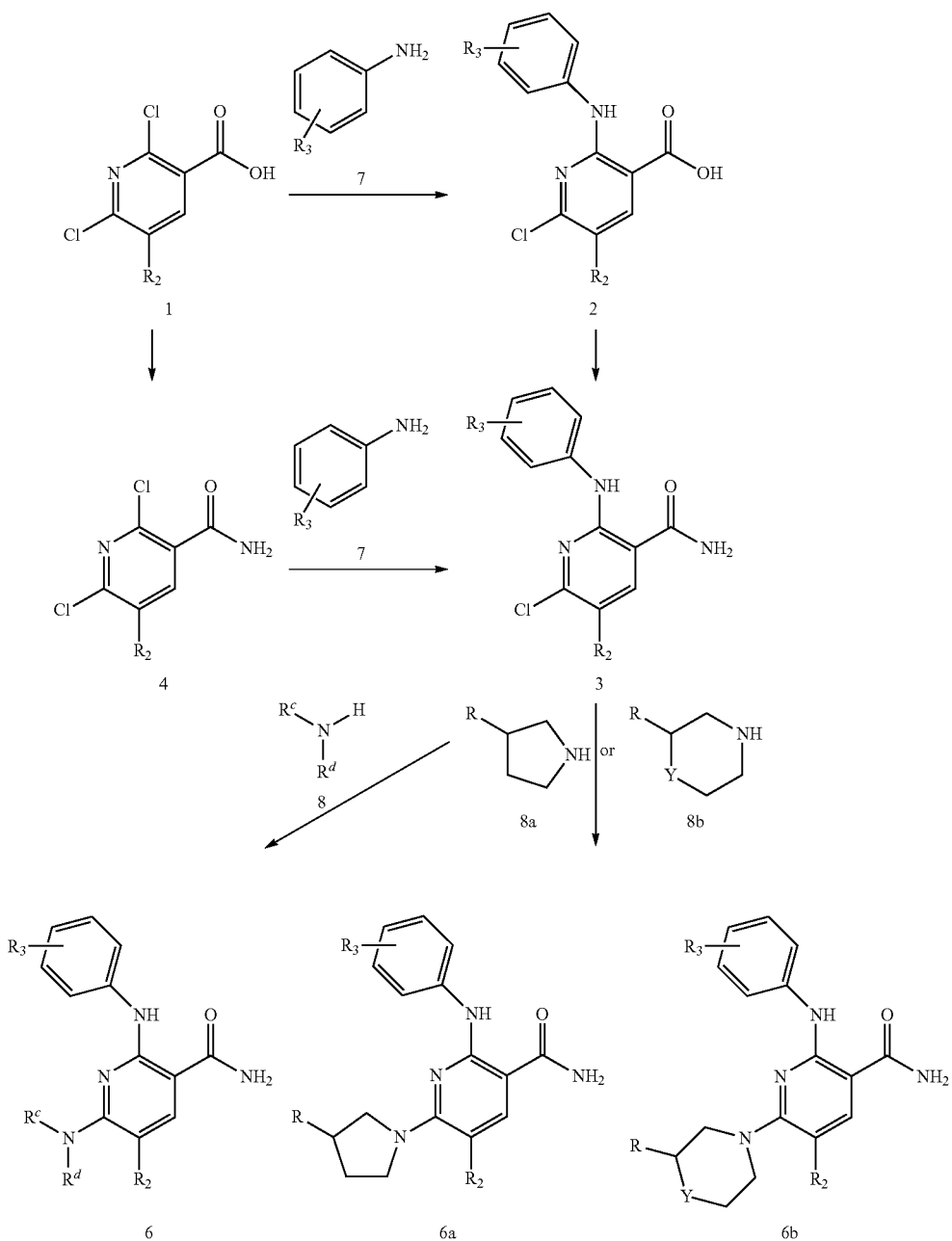

As shown in Scheme 1, the starting commercially available substituted 2,6-dichloronicotinic acids 1, are treated with the appropriate substituted aniline 7 in the presence of a base to give nicotinic acid 2. The acid is then converted to the 6-chloro-nicotinamide 3 using ammonia and either one of the various coupling reagents available commercially or through the synthesis of the corresponding acid chloride (using oxalyl chloride).

Alternatively, the reaction order could be reversed and the acid 1, can be first be converted to the amide 4 and then reacted with aniline 7 in the presence of a base to give to give the 6-chloro-nicotinamide 3. The 6-chloro-nicotinamide 3 can be reacted with an appropriate amine 8 to give the desired 6-amino substituted nicotinamide 6. The amine used can vary widely from acyclic amines to a substituted cyclic amine heterocycle such as a pyrrolidine 6a, piperidine (6b, where Y is C), morpholine (6b, where Y is O), or piperazine (6b, where Y is N), as in the examples shown in Scheme 1.

SCHEME 2

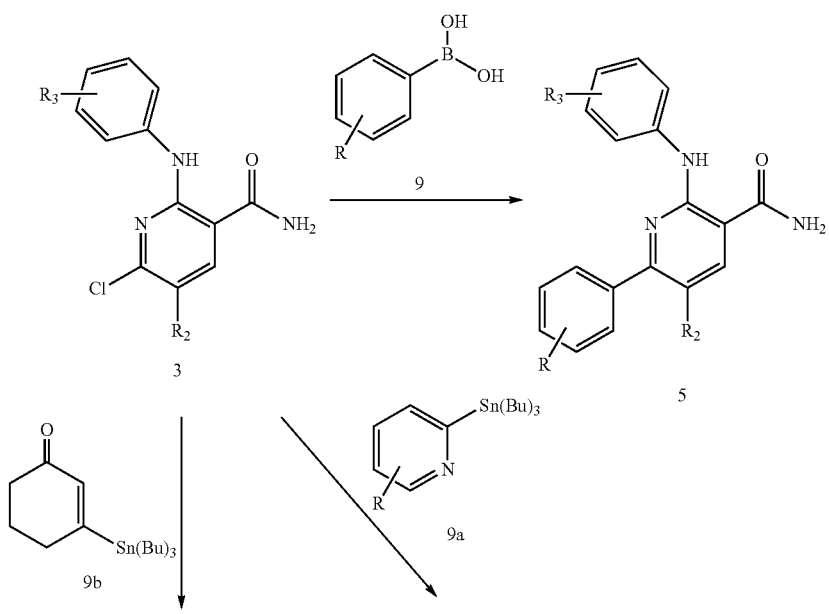

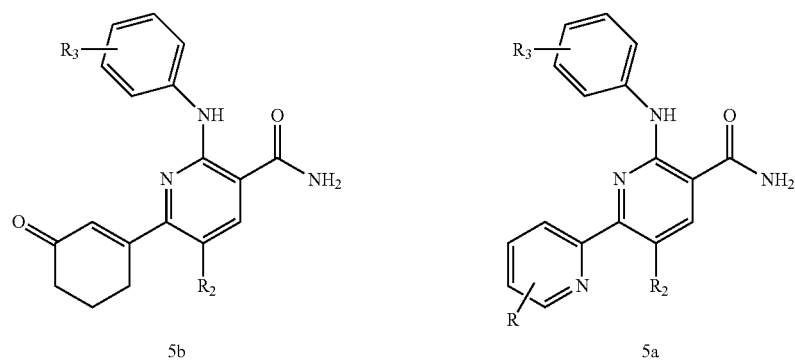

As shown in Scheme 2, the 6-chloro-nicotinamide 3 can also be substituted under Pd catalyzed Suzuki coupling reaction conditions such as with a variety of aryl boronic acids 9 (or heteroaryl boric acids) to give the corresponding 6-substituted nicotinamide 5. Alternatively, Stille cross-coupling with heteroaryl stannanes such as 9a can be used. Coupling using the known stannanes 9b (*Tet. Lett.*, 31:1837-1840 (1990)) gives the 6-substituted cyclohexene compound 5b, that can then be further elaborated.

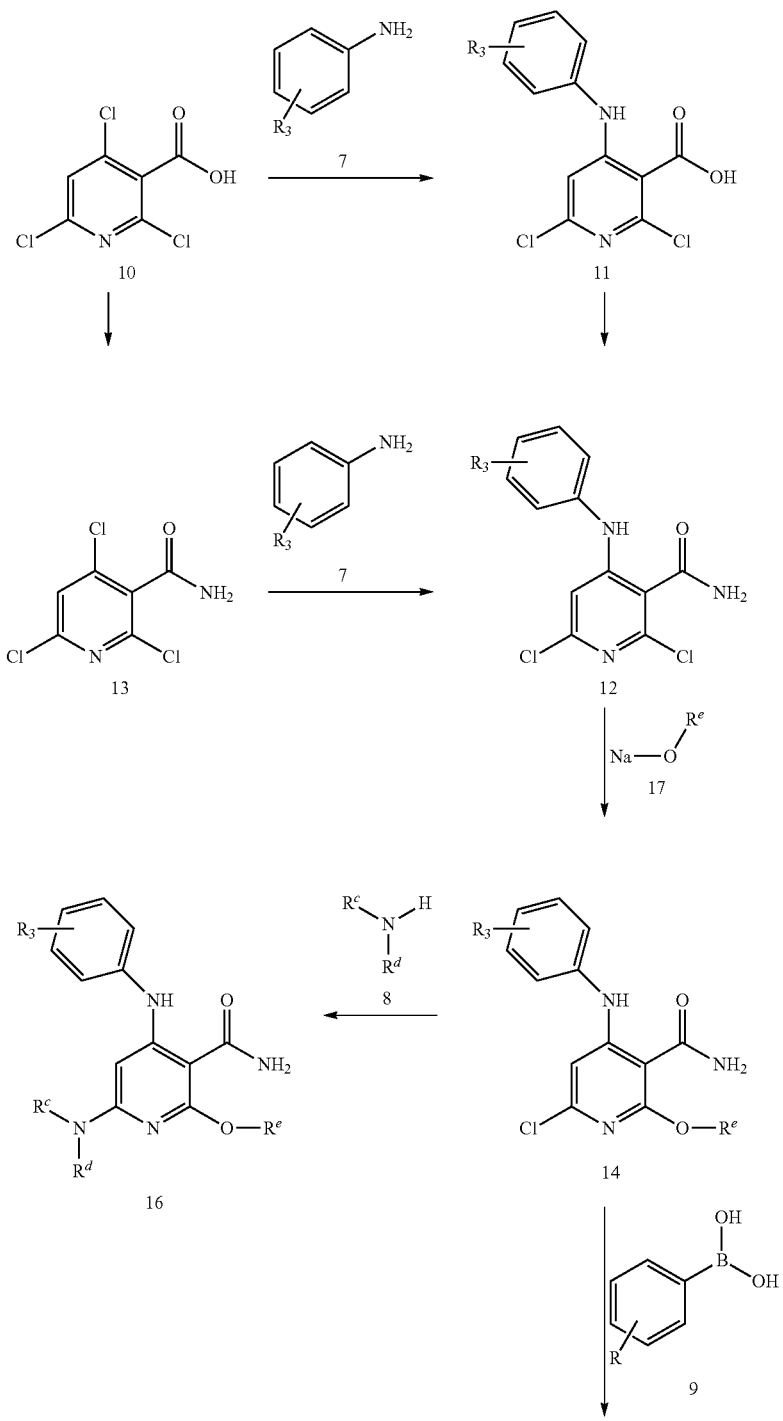

-continued

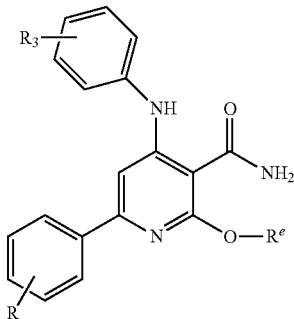

15

Isomeric nicotinamides are synthesized in an analogous fashion as summarized in Scheme 3. Thus, starting with the nicotinic acid 10, synthesized according to the literature procedure (J. Med. Chem., 47:2097-2109 (2004)), treatment with the appropriate aniline 7 in the presence of a base gives the substituted nicotinic acid 11. The acid is converted to the amide 12. The sequence can be reversed and the amide 13 synthesized first and then reacted with the aniline 7 to give the same intermediate 12. The 2-chloro substituent of amide 12 can be substituted with the sodium salt of an appropriate alcohol 17 to give the corresponding ether 14. Finally, the 6-chloro-nicotinamide 14 can be reacted with an appropriate amine 8 to give the desired 6-amino substituted nicotinamide 16. The 6-chloro-nicotinamide 14 can be also be treated with cyclic amine heterocycles (such as 8a, and 8b) to give the corresponding 6-substituted heterocyclic compounds similar to that discussed for Scheme 1. The 6-chloro-nicotinamide 14 can also be substituted under Pd catalyzed coupling conditions such as with a boronic acid 9 (or stannanes 9a/9b) to give the corresponding 6-substituted nicotinamide 15.

Utility

The compounds of the invention modulate kinase activity, including the modulation of Btk. Other types of kinase activity that may be modulated by the compounds of the instant invention include, but are not limited to, the Tec family of compounds, such as BMX, Btk, ITK, TXK and Tec, and mutants thereof.

Accordingly, compounds of Formula (I) have utility in treating conditions associated with the modulation of kinase activity, and particularly the selective inhibition of Btk activity. Such conditions include B-cell mediated diseases in which cytokine levels are modulated as a consequence of intracellular signaling.

As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

In view of their activity as selective inhibitors of Btk, compounds of Formula (I) are useful in treating cytokine-associated conditions including, but not limited to, inflammatory diseases such as Crohn's and ulcerative colitis, asthma, graft versus host disease, chronic obstructive pulmonary disease; autoimmune diseases such as Graves' disease, rheumatoid arthritis, systemic lupus erythematosis, psoriasis; destructive bone disorders such as bone resorption disease, osteoporosis, osteoarthritis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's and ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In addition, the Btk inhibitors of the present invention inhibit the expression of inducible pro-inflammatory proteins such as prostaglandin endoperoxide synthase-2 (PGHS-2), also referred to as cyclooxygenase-2 (COX-2). Accordingly, additional Btk-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "Btk-associated condition" or "Btk-associated disease or disorder" are used herein, each is intended to encompass all of the conditions identified above as if repeated at length, as well as any other condition that is affected by Btk kinase activity.

Therapeutically effective amount" is intended to include an amount of a compound of the present invention that is effective when administered alone or in combination to inhibit Btk.

One embodiment provides methods for treating such Btk kinase-associated conditions, comprising administering to a subject in need thereof at least one compound of Formula (I) or a pharmaceutically acceptable salt thereof. A therapeutically-effective amount for treating such conditions may be administered. The methods of the present embodiment may be employed to treat Btk kinase-associated conditions such as treatment of allergic disorders and/or autoimmune and/or inflammatory diseases including, but not limited to, SLE, rheumatoid arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evan's syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

The methods of treating Btk kinase-associated conditions may comprise administering at least one compound of Formula (I) alone or in combination with each other and/or other suitable therapeutic agents useful in treating such conditions. Therapeutically-effective amounts of at least one compound of Formula (I) and other suitable therapeutic agents for treating such conditions may be administered. Accordingly, "therapeutically effective amount" is also intended to include an amount of the combination of compounds claimed that is effective to inhibit Btk. The combination of compounds is preferably a synergistic combination. Synergy, as described, for example, by Chou et al., *Adv. Enzyme Regul.*, 22:27-55 (1984), occurs when the effect (in this case, inhibition of Btk) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-Btk effect, or some other beneficial effect of the combination compared with the individual components.

Exemplary of such other therapeutic agents include corticosteroids, rolipram, calphostin, cytokine-suppressive anti-inflammatory drugs (CSAIDs), 4-substituted imidazo[1,2-A] quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating Btk kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Another embodiment provides the compounds of Formula (I), or stereoisomers or pharmaceutically acceptable salts thereof, for use in therapy. In the present embodiment, the use in therapy may include the administration of a therapeutically-effective amount of a compound of Formula (I), or stereoisomers or pharmaceutically acceptable salts thereof.

The present invention also provides the use of the compounds of Formula (I), stereoisomers or pharmaceutically acceptable salts thereof, for the manufacture of a medicament for the treatment or prophylaxis of an allergic disorder and/or autoimmune and/or inflammatory disease. In the present embodiment, the use for the manufacture of a medicament may include the administration of a therapeutically-effective amount of a compound of Formula (I), or stereoisomers or pharmaceutically acceptable salts thereof for the treatment of prophylaxis of an allergic disorder and/or autoimmune and/or inflammatory disease.

The present invention also provides the use of the compounds of Formula (I) or pharmaceutically acceptable salts thereof, for the manufacture of a medicament for treatment of cancer. The present embodiment may include the use for the manufacture of a medicament includes the administration of a therapeutically-effective amount of a compound of Formula (I), or stereoisomers or pharmaceutically acceptable salts thereof for the treatment of prophylaxis of an allergic disorder and/or autoimmune and/or inflammatory disease.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed. (1985), which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., Gantrez); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of Btk enzyme levels.

Examples of compounds of Formula (I) as specified in the "Examples" section below, have been tested in one or more of the assays described below.

Preferred compounds of Formula (I) inhibit BTK enzymes with $IC_{50}$ values, below 10 µM, for example, from 0.001 to 10 µM, as measured by the Human Recombinant BTK enzyme assay. More preferably, the compounds of Formula (I) inhibit BTK enzymes with $IC_{50}$ values of less than 2 µM, for example, from 0.001 to 2 µM.

Biological Assays

Human Recombinant Btk Enzyme Assay

To V-bottom 384-well plates were added test compounds, human recombinant Btk (1 nM, Invitrogen Corporation), fluoresceinated peptide (1.5 µM), ATP (20 µM), and assay buffer (20 mM HEPES pH 7.4, 10 mM $MgCl_2$, 0.015% Brij35 and 4 mM DTT in 1.6% DMSO), with a final volume of 30

µL. After incubating at room temperature for 60 min, the reaction was terminated by adding 45 µl of 35 mM EDTA to each sample. The reaction mixture was analyzed on the Caliper LABCHIP® 3000 (Caliper, Hopkinton, Mass.) by electrophoretic separation of the fluorescent substrate and phosphorylated product. Inhibition data were calculated by comparison to no enzyme control reactions for 100% inhibition and no inhibitor controls for 0% inhibition. Dose response curves were generated to determine the concentration required inhibiting 50% of kinase activity ($IC_{50}$). Compounds were dissolved at 10 mM in dimethylsulfoxide (DMSO) and evaluated at eleven concentrations.

Using this assay, the following $IC_{50}$ values derived by non-linear regression analysis were determined and compared to those values of certain compounds in U.S. Publication No. 2007/078136 and U.S. Publication No. 2008/045536.

Mouse Splenic B Cell Proliferation Assay

Spleens from Balb/c mice (<12 weeks old) were mashed through screens and red blood cells were removed from splenocytes with RBC lysing buffer (Sigma-Aldrich Chemical Co, St. Louis, Mo.). T cells were depleted by incubation on nylon wool columns (Wako, Richmond, Va.). Resulting splenic B cells prepared this way were routinely>90% $CD19^+$ as measured by FACS analysis. B cells ($1\times10^5$ cells per well) were added to serial dilutions of compounds in triplicate in 96-well flat-bottom plates in RPMI 1640 (Invitrogen, Grand Island, N.Y.), supplemented with 10% heat-inactivated fetal calf serum (FCS, Summit Biotechnology, Fort Collins, Colo.), containing 1% L-glutamine (Invitrogen), 50 µg/ml gentamicin (Invitrogen) and $5\times10^{-5}$M β-mercaptoethanol (Sigma-Aldrich). Cells were stimulated with 10 µg/ml of AffiniPure $F(ab')_2$ fragment goat anti-mouse IgG IgM (Jackson Immunoresearch, West Grove, Pa.). Cultures were incubated for 72 hours, and pulsed for the last 6 hours with one µCi/well of $^3$-[H]-thymidine (PerkinElmer, Boston, Mass.) prior to harvest on a Packard cell harvester (PerkinElmer), and counted by liquid scintillation on a Packard TOPCOUNT® NXT (PerkinElmer).

Human Tonsillar B Cell Proliferation Assay

Tonsils were excised from patients undergoing routine tonsillectomy. Tonsil tissue was minced, mashed through screens and mononuclear cells were isolated on ficoll density gradients (Lymphocyte Separation Media; Mediatech Inc., Herndon, Va.). T cells were depleted from mononuclear cells by rosetting with sheep red blood cells (SRBC, Colorado Serum Company; Denver, Colo.). Tonsillar B cells prepared by this method were routinely>95% $CD19^+$ as measured by FACS analysis. B cells ($1\times10^5$ cells per well) were added to serial dilutions of compounds in triplicate in 96-well flat-bottom plates in RPMI 1640, (Invitrogen, Grand Island, N.Y.), supplemented with 10% heat-inactivated fetal calf serum (FCS, Summit Biotechnology, Fort Collins, Colo.), and containing antibiotic/antimycotic (Invitrogen, 1:100 dilution) and gentamicin (Invitrogen, 5 µg/ml). Cells were stimulated with 40 µg/ml AffiniPure F(ab')2 Fragment Goat anti Human IgG+IgM (Jackson Immunoresearch, West Grove, Pa.) in a total volume of 0.2 ml. Cultures were incubated for 72 hours, and pulsed for the last 6 hours with one µCi/well of $^3$[H]-thymidine (PerkinElmer, Boston, Mass.) prior to harvest on a Packard cell harvester (PerkinElmer), and counted by liquid scintillation on a Packard TOPCOUNT® NXT (PerkinElmer). $IC_{50}$ values of representative compounds are shown in Table 3.

Btk Phosphorylation Assay

Ramos cells (~$6\times10^6$ cells/ml) were incubated in the presence of Btk inhibitors for 1 hr at 37° C. before being stimulated with anti-human IgM+IgG (F(ab')2 fragment, Jackson ImmunoResearch, catalog #109-006-127) at 50 µg/mL for exactly 2 min at 37° C. Cells were immediately fixed by adding an equal volume of pre-warmed BD Phosflow Fix buffer I (BD Biosciences, catalog number 557870) to the cell suspension. After incubating at 37° C. for 10 minutes, the cells were washed once with 3 mL FACS washing buffer (1% FBS/PBS) and permeabilized by adding 0.5 mL of cold BD Phosflow Perm Buffer III (BD Biosciences, catalog number 558050) and incubating for 30 minutes on ice. The cells were washed an additional two times with 3 mL BD FACS washing buffer, re-suspended in 100 µL FACS washing buffer, stained with 20 µL Alexa 647 anti-Btk (pY551) (BD Biosciences, catalog number 558134), incubated at room temperature for 30 minutes in the dark, and washed once with 3 ml of FACS washing buffer. The cells were re-suspended in 100 µL FACS wash buffer and analyzed using FACSCalibur (BD Biosciences). Median fluorescent intensity (MFI) on Alexa 647 (FL-4) data were collected and used for calculations of inhibition.

Ramos FLIPR® Assay

Ramos RA1 B cells (ATCC® CRL-1596) at a density of $2\times10^6$ cells/ml in RPMI minus phenol red (Invitrogen 11835-030) and 50 mM HEPES (Invitrogen 15630-130) containing 0.1% BSA (Sigma A8577) were added to one half volume of calcium loading buffer (BD bulk kit for probenecid sensitive assays, #640177) and incubated at room temperature in the dark for 1 hour. Dye-loaded cells were pelleted (Beckmann GS-CKR, 1200 rpm, RT, 5 minutes) and resuspended in RT RPMI minus phenol red with 50 mM HEPES and 10% FBS to a density of $1\times10^6$ cells/ml. 150 µl aliquots (150,000/well) were plated into 96 well poly-D-lysine coated assay plates (BD 35 4640) and briefly centrifuged (Beckmann GS-CKR 800 rpm, 5 minutes, without brake). 50 µl compound dilutions in 0.4% DMSO/RPMI minus phenol red+50 mM HEPES+ 10% FBS were added to the wells and the plate was incubated at RT in the dark for 1 hour. Assay plate was briefly centrifuged as above prior to measuring calcium levels.

Using the FLIPR® 1 (Molecular devices), cells were stimulated by adding 50 µl 200 µg/ml F(ab')2 anti-IgM/IgG (Jackson ImmunoResearch 109-006-127) diluted in 1×HBSS (Invitrogen 14025-076), 50 mM HEPES, 0.1% BSA. Changes in intracellular calcium concentrations were measured for 180 seconds and percent inhibition was determined relative to peak calcium levels seen in the presence of F(ab')2 anti-IgM/IgG only.

NFAT-bla RA1 Reporter Assay

Ramos B cells containing a stable integration of a beta-lactamase reporter gene under the control of an NFAT response element (NFAT-bla RA1, Invitrogen, K1434) at a density of $100\times10^3$ cells/well were incubated with test compounds at 37° C. for 30 min prior to stimulation with $F(ab')_2$ anti-human IgM (Jackson ImmunoResearch, 109-006-129) at 2.5 µg/ml for 4.5 hrs at 37° C. After stimulation, Live-BLAzer-FRET B/G substrate (CCF2/AM, or CCF4/AM, Invitrogen) was added to each well and incubated for 90 min at room temperature in the dark. Assay plates were read on an LJL Analyst, with raw emission values subtracted from a media-only blank containing substrate in assay media (no cells). The ratios of 460 nm/530 nm emission (405 nm excitation) were used to calculate the amount of stimulation.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather defined by the claims appended hereto.

ABBREVIATIONS

CH₂Cl₂ dichloromethane
DIEA diisopropylethylamine
DMF dimethylformamide
EDC 1-[3-(dimethylamino)propyl]-3-ethyl-carbodiimide hydrochloride
EtOH ethanol
h. hour(s)
HATU O-(7-azabenzotriazol-1-yl)-1,1,3,3-tetramethyluronium hexafluorophosphate
HCl hydrochloric acid
HOBT 1-hydroxybenzotriazole
MeOH methanol
min. minute(s)
NaH sodium hydride
NaOH sodium hydroxide
NBS N-bromosuccinimide
Pd(Ph₃)₄ palladium tetrakis triphenylphosphine
rt. room temperature
t-butyl tertiary butyl
TFA trifluoroacetic acid
THF tetrahydrofuran Example 1

(R)-tert-Butyl 1-(5-carbamoyl-6-(4-(morpholine-4-carbonyl)phenylamino)pyridin-2-yl)piperidin-3-yl-carbamate

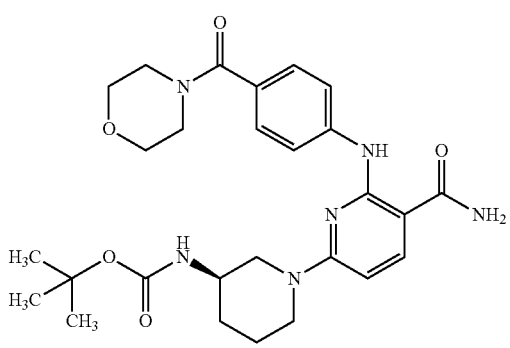 [SMILES: CC(C)(C)OC(=O)N[C@@H]1CCCN(c2ccc(C(N)=O)c(Nc3ccc(C(=O)N4CCOCC4)cc3)n2)C1]

A. 6-Chloro-2-(4-(morpholine-4-carbonyl)phenylamino)nicotinic acid

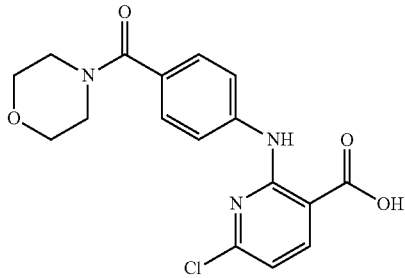 [SMILES: O=C(O)c1ccc(Cl)nc1Nc1ccc(C(=O)N2CCOCC2)cc1]

To a suspension of (4-aminophenyl)(morpholino)methanone (9.02 g, 43.8 mmol) in THF (20 mL) was added lithium bis(trimethylsilyl)amide (66.7 mL, 66.7 mmol, 1M solution in THF) dropwise over 15 min. at −78° C. under nitrogen. The reaction mixture was stirred for one hour at −78° C. To the resulting brown solution was added a solution of 2,6-dichloronicotinic acid (4 g, 20.83 mmol) in THF (12 ml) dropwise at −78° C. The reaction mixture was removed from the dry ice bath and stirred overnight at rt. The resulting dark solids were washed with a small amount of THF to remove (4-aminophenyl)(morpholino)methanone on the surface, followed by the addition of water and 18 ml of 6N HCl (pH of 2). The solids were filtered and the resulting pink filter cake was washed with water (~1 i) until the filter cake was white powder and the filtrate was colorless. The filter cake was transferred to a flask with MeOH and CH₂Cl₂, and dried on a rotary evaporator with MeOH to give 6.60 g of 6-chloro-2-(4-(morpholine-4-carbonyl)phenylamino)nicotinic acid as a white solid.
LCMS: (M+H)⁺=362.02, 364.03 (Cl pattern).

B. 6-Chloro-2-(4-(morpholine-4-carbonyl)phenylamino)nicotinamide

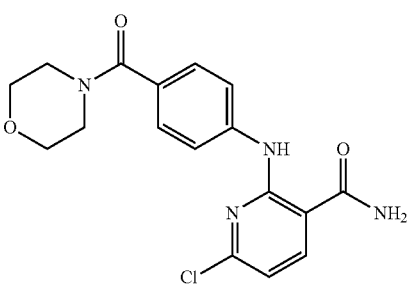 [SMILES: NC(=O)c1ccc(Cl)nc1Nc1ccc(C(=O)N2CCOCC2)cc1]

To a solution of 6-chloro-2-(4-(morpholine-4-carbonyl)phenylamino)nicotinic acid (6.60 g, 18.24 mmol), NH₄OH (40.1 mL, 20.07 mmol), and N-ethyl-N-isopropylpropan-2-amine (3.54 g, 27.4 mmol) in DMF (40 mL) was added HATU (13.87 g, 36.5 mmol) at rt. The solution became cloudy but eventually cleared up as the HATU was added. The reaction was completed after 1 h. The reaction mixture was diluted with 10% LiCl and extracted with ethyl acetate three times. The organic extracts was washed with 10% LiCl, water twice, and then concentrated. The light yellow solid was triturated with CH₂Cl₂ to give 3.8 g. A second trituration gave 1.95 g, and a third trituration gave 462 mg. A total of 6.2 g of 6-chloro-2-(4-(morpholine-4-carbonyl)phenylamino)nicotinamide was obtained.
LCMS: (M+H)⁺=361.03, 362.95 (Cl pattern).

C. (R)-tert-Butyl-1-(5-carbamoyl-6-(4-(morpholine-4-carbonyl)phenylamino) pyridin-2-yl)piperidin-3-ylcarbamate

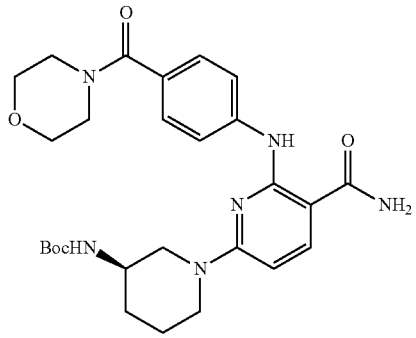 [SMILES: CC(C)(C)OC(=O)N[C@@H]1CCCN(c2ccc(C(N)=O)c(Nc3ccc(C(=O)N4CCOCC4)cc3)n2)C1]

A solution of (R)-tert-butyl piperidin-3-ylcarbamate (416 mg, 2.079 mmol), 6-chloro-2-(4-(morpholine-4-carbonyl)phenylamino)nicotinamide (500 mg, 1.386 mmol), and N,N-diisopropylethylamine (0.484 mL, 2.77 mmol) in N-methyl-2-pyrrolidinone (3 mL) was heated to 120° C. overnight. The reaction mixture was diluted with water. The grey precipitate was filtered and the solid was purified by chromatography (ISCO, 5% NH$_4$OH/MeOH/CH$_2$Cl$_2$, 40 g+12 g stack silica gel columns) to give 485 mg of (R)-tert-butyl-1-(5-carbamoyl-6-(4-(morpholine-4-carbonyl)phenylamino)pyridin-2-yl)piperidin-3-ylcarbamate as a yellow solid.

LCMS: (M+H)$^+$=525.20. $^1$H NMR (400 MHz, CDCl$_3$) δ ppm 11.19 (1H, s), 7.70 (2H, d, J=8.81 Hz), 7.51 (1H, d, J=8.81 Hz), 7.39 (2H, d, J=8.56 Hz), 6.14 (1H, d, J=9.06 Hz), 5.50 (2H, s), 4.59-4.67 (1H, m), 3.93-4.02 (1H, m), 3.83-3.92 (1H, m), 3.70 (8H, br s), 3.39-3.51 (1H, m), 3.25-3.37 (1H, m), 1.92-2.04 (1H, m), 1.72-1.84 (1H, m), 1.45 (9H, s).

Example 2

(R)-6-(3-Aminopiperidin-1-yl)-2-(4-(morpholine-4-carbonyl)phenylamino)nicotinamide

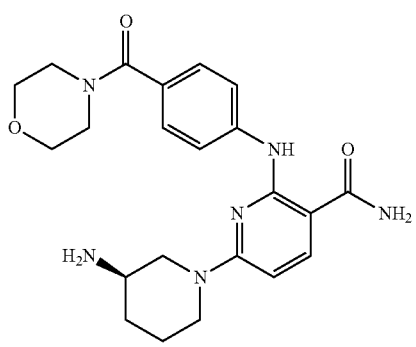 [SMILES: NC(=O)c1ccc(N2CCC[C@@H](N)C2)nc1Nc1ccc(C(=O)N2CCOCC2)cc1]

A solution of (R)-tert-butyl 1-(5-carbamoyl-6-(4-(morpholine-4-carbonyl)phenylamino)pyridin-2-yl)piperidin-3-ylcarbamate (1.7 g) in CH$_2$Cl$_2$ (3 ml) was treated with 3 ml of TFA and stirred at rt for 2 h. The reaction mixture was concentrated, basified with 1N NaOH, and extracted three times with CH$_2$Cl$_2$. The resulting organic layer was concentrated to obtained 1.367 g of (R)-6-(3-aminopiperidin-1-yl)-2-(4-(morpholine-4-carbonyl)phenylamino)nicotinamide as a pale yellow solid. LCMS: (M+H)+=425.08. $^1$H NMR (400 MHz, CDCl$_3$) δ ppm 11.21 (1H, s), 7.71 (2H, d, J=8.56 Hz), 7.52 (1H, d, J=8.81 Hz), 7.38 (2H, d, J=8.56 Hz), 6.06 (1H, d, J=8.80 Hz), 5.62 (2H, s), 4.19 (1H, d, J=9.57 Hz), 4.06-4.14 (1H, m, J=13.35 Hz), 3.59-3.79 (8H, m), 3.03-3.13 (1H, m), 2.78-2.92 (2H, m), 1.95-2.06 (1H, m), 1.73-1.86 (1H, m), 1.51-1.64 (1H, m), 1.30-1.46 (1H, m).

Example 3

(R)-6-(3-Benzamidopiperidin-1-yl)-2-(4-(morpholine-4-carbonyl)phenylamino)nicotinamide

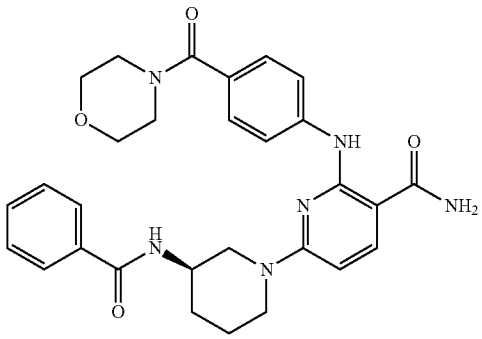 [SMILES: NC(=O)c1ccc(N2CCC[C@@H](NC(=O)c3ccccc3)C2)nc1Nc1ccc(C(=O)N2CCOCC2)cc1]

To a solution of (R)-6-(3-aminopiperidin-1-yl)-2-(4-(morpholine-4-carbonyl)phenylamino)nicotinamide (27.5 mg, 0.065 mmol) and Et$_3$N (0.014 mL, 0.097 mmol) in THF (2 mL) was added benzoyl chloride (10.93 mg, 0.078 mmol). The reaction mixture was stirred at rt for 10 min, quenched with satd. NaHCO$_3$, extracted twice with CH$_2$Cl$_2$, separated, and concentrated. The residue was purified by ISCO (100% ethyl acetate, 12 g column) to obtain 24 mg of (R)-6-(3-benzamidopiperidin-1-yl)-2-(4-(morpholine-4-carbonyl)phenylamino)nicotinamide as a white solid. LCMS: (M+H)$^+$=529.38. $^1$H NMR (400 MHz, CDCl$_3$) δ ppm 11.22 (1H, s), 7.66 (2H, d, J=8.56 Hz), 7.59-7.64 (2H, m), 7.53 (1H, d, J=9.06 Hz), 7.42-7.49 (1H, m), 7.37 (1H, d, J=7.81 Hz), 7.31 (1H, d, J=8.56 Hz), 6.55 (1H, d, J=6.80 Hz), 6.11-6.18 (1H, m), 5.60 (2H, s), 4.17-4.28 (1H, m), 3.86-3.94 (1H, m), 3.53-3.83 (11H, m), 1.96-2.06 (1H, m), 1.88-1.95 (1H, m), 1.74-1.85 (1H, m), 1.67-1.73 (1H, m).

Example 4

(R)-6-(3-(3-Isopropylureido)piperidin-1-yl)-2-(4-(morpholine-4-carbonyl)phenylamino)nicotinamide

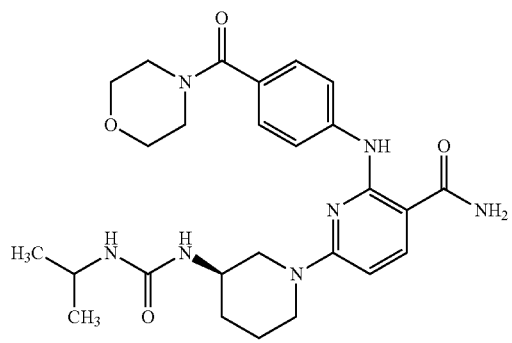 [SMILES: CC(C)NC(=O)N[C@@H]1CCCN(c2ccc(C(N)=O)c(Nc3ccc(C(=O)N4CCOCC4)cc3)n2)C1]

To a solution of (R)-6-(3-aminopiperidin-1-yl)-2-(4-(morpholine-4-carbonyl)phenylamino)nicotinamide (35 mg, 0.082 mmol) in THF (2 mL) was added 2-isocyanatopropane (14.03 mg, 0.165 mmol) and stirred at rt for 10 min. The reaction mixture was diluted with CH$_2$Cl$_2$, washed with satd NaHCO$_3$, separated, and concentrated. The residue was purified (ISCO, 5% NH$_4$OH/MeOH/CH$_2$Cl$_2$, 40 g silica gel column) to obtained 30.2 mg of (R)-6-(3-(3-isopropylureido) piperidin-1-yl)-2-(4-(morpholine-4-carbonyl)phenylamino) nicotinamide as a light yellow solid.

LCMS: (M+H)$^+$=510.34. $^1$H NMR (400 MHz, CDCl$_3$) δ ppm 11.20 (1H, s), 7.68 (2H, d, J=8.56 Hz), 7.48 (1H, d, J=8.81 Hz), 7.37 (2H, d, J=8.56 Hz), 6.08 (1H, d, J=8.81 Hz), 5.61 (2H, s), 4.58 (1H, d, J=7.05 Hz), 4.37 (1H, d, J=7.81 Hz), 3.58-3.93 (12H, m), 3.31-3.43 (1H, m), 3.20 (1H, dd, J=12.97, 7.68 Hz), 1.85-1.98 (1H, m), 1.66-1.76 (1H, m), 1.46-1.60 (2H, m), 1.11 (6H, d, J=6.55 Hz).

Example 5

(R)-6-(3-(3-(5-Cyclopropyl-1,3,4-thiadiazol-2-yl) ureido)piperidin-1-yl)-2-(4-(morpholine-4-carbonyl) phenylamino)nicotinamide

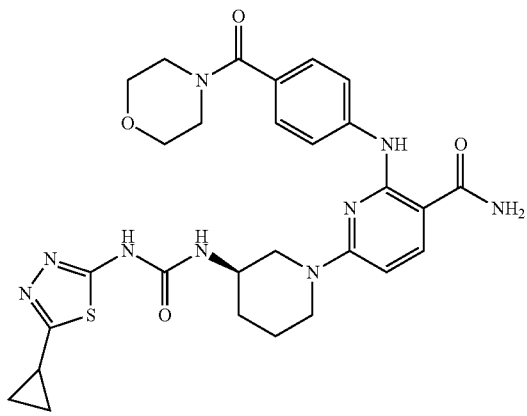 [SMILES: NC(=O)c1ccc(N2CCC[C@@H](NC(=O)Nc3nnc(C4CC4)s3)C2)nc1Nc1ccc(C(=O)N2CCOCC2)cc1]

A suspension of (R)-6-(3-aminopiperidin-1-yl)-2-(4-(morpholine-4-carbonyl)phenylamino)nicotinamide (40 mg, 0.094 mmol), phenyl 5-cyclopropyl-1,3,4-thiadiazol-2-ylcarbamate (29.5 mg, 0.113 mmol), and Et$_3$N (0.016 mL, 0.113 mmol) in CH$_2$Cl$_2$ (2 mL) was stirred at rt overnight. The reaction mixture was diluted with CH$_2$Cl$_2$, washed with water, and concentrated. The residue was purified by prep-HPLC. The product containing fractions were collected, neutralized with saturated NaHCO$_3$, extracted with CH$_2$Cl$_2$, separated, and concentrated to give 28 mg of (R)-6-(3-(3-(5-cyclopropyl-1,3,4-thiadiazol-2-yl)ureido)piperidin-1-yl)-2-(4-(morpholine-4-carbonyl)phenylamino)nicotinamide as a light pink solid. LCMS: (M+H)+=592.18. $^1$H NMR (400 MHz, CDCl$_{3-MIX}$) δ ppm 11.09 (1H, s), 7.59 (2H, d, J=8.79 Hz), 7.55 (1H, d, J=9.23 Hz), 7.24-7.28 (2H, m), 6.04 (1H, d, J=8.79 Hz), 3.93 (1H, dd, J=13.18, 3.08 Hz), 3.73-3.86 (2H, m), 3.53 (7H, d, J=6.15 Hz), 3.31-3.41 (1H, m), 3.22-3.31 (2H, m), 2.11-2.21 (1H, m), 1.90-2.00 (1H, m), 1.67-1.79 (1H, m), 1.51-1.65 (2H, m), 1.03-1.12 (2H, m), 0.89-0.96 (2H, m).

Example 6

(R)-6-(3-(2-(Dimethylamino)acetamido)piperidin-1-yl)-2-(4-(morpholine-4-carbonyl)phenylamino)nicotinamide

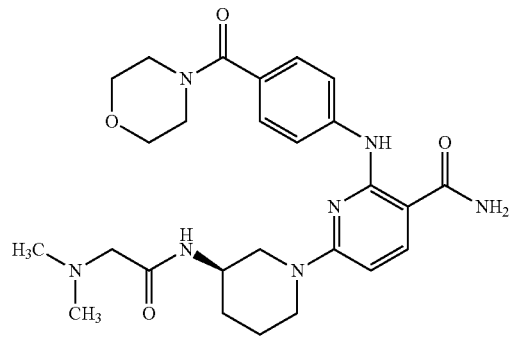 [SMILES: CN(C)CC(=O)N[C@@H]1CCCN(c2ccc(C(N)=O)c(Nc3ccc(C(=O)N4CCOCC4)cc3)n2)C1]

A solution of (R)-6-(3-aminopiperidin-1-yl)-2-(4-(morpholine-4-carbonyl)phenylamino)nicotinamide (40 mg, 0.094 mmol), 2-(dimethylamino)acetic acid (19.43 mg, 0.188 mmol), N,N-diisopropylethylamine (0.033 mL, 0.188 mmol), and HATU (71.7 mg, 0.188 mmol) in DMF was stirred at rt for 1 h. The reaction mixture was diluted with CH$_2$Cl$_2$, washed with satd NaHCO$_3$, separated, and concentrated. The residue was purified (ISCO, 5% NH$_4$OH/MeOH/CH$_2$Cl$_2$, 40 g silica gel column) to obtain 20 mg of (R)-6-(3-(2-(dimethylamino) acetamido)piperidin-1-yl)-2-(4-(morpholine-4-carbonyl)phenylamino)nicotinamide as a light yellow solid. LCMS: (M+H)$^+$=510.40. $^1$H NMR (400 MHz, CDCl$_3$) δ ppm 11.21 (1H, s), 7.69 (2H, d, J=8.56 Hz), 7.53 (1H, d, J=9.06 Hz), 7.37 (2H, d, J=8.56 Hz), 7.30 (1H, d, J=7.81 Hz), 6.12 (1H, d, J=8.81 Hz), 5.60 (1H, s), 3.96 (1H, dd, J=13.22, 3.15 Hz), 3.78-3.88 (1H, m), 3.60-3.78 (8H, m), 3.41-3.56 (2H, m), 2.92 (2H, s), 2.22 (6H, s), 1.65-2.03 (4H, m).

Example 7

(R)-Phenyl 1-(5-carbamoyl-6-(4-(morpholine-4-carbonyl)phenylamino)pyridin-2-yl)piperidin-3-ylcarbamate

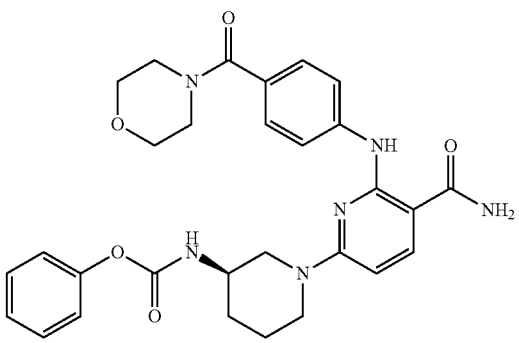 [SMILES: NC(=O)c1ccc(N2CCC[C@@H](NC(=O)Oc3ccccc3)C2)nc1Nc1ccc(C(=O)N2CCOCC2)cc1]

To a suspension of (R)-6-(3-aminopiperidin-1-yl)-2-(4-(morpholine-4-carbonyl)phenylamino)nicotinamide (140 mg, 0.330 mmol) and Et₃N (0.069 mL, 0.495 mmol) in CH₂Cl₂ (3 mL) was added phenyl carbonochloridate (51.6 mg, 0.330 mmol) at 0° C. and stirred for 10 min. The reaction mixture was quenched with satd. NaHCO₃, extracted with CH₂Cl₂, separated, and concentrated. The residue was purified (ISCO, 100% ethyl acetate, 12 g silica gel column) to obtained 93 mg of (R)-phenyl 1-(5-carbamoyl-6-(4-(morpholine-4-carbonyl)phenylamino)pyridin-2-yl)piperidin-3-yl-carbamate as a white solid. LCMS: (M+H)⁺=545.31. ¹H NMR (400 MHz, CDCl₃) δ ppm 11.20 (1H, s), 7.69 (2H, d, J=8.79 Hz), 7.50 (1H, d, J=8.79 Hz), 7.31-7.39 (4H, m, J=7.91, 7.91 Hz), 7.19 (1H, t, J=7.47 Hz), 7.08 (2H, d, J=7.47 Hz), 6.10 (1H, d, J=8.79 Hz), 5.64 (1H, s), 5.35 (1H, d, J=7.47 Hz), 5.30 (1H, s), 4.03 (1H, dd, J=12.96, 2.86 Hz), 3.78-3.91 (1H, m), 3.64 (7H, s), 3.38-3.53 (2H, m), 1.98-2.12 (1H, m), 1.76-1.87 (1H, m), 1.63-1.76 (1H, m), 1.19-1.34 (1H, m).

Example 8

(R)—N-(1-(5-Carbamoyl-6-(4-(morpholine-4-carbonyl)phenylamino)pyridin-2-yl)piperidin-3-yl)morpholine-4-carboxamide

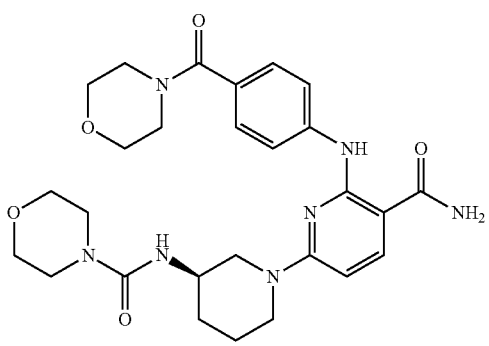 [SMILES: NC(=O)c1ccc(N2CCC[C@@H](NC(=O)N3CCOCC3)C2)nc1Nc1ccc(C(=O)N2CCOCC2)cc1]

A solution of (R)-phenyl 1-(5-carbamoyl-6-(4-(morpholine-4-carbonyl)phenylamino)pyridin-2-yl)piperidin-3-yl-carbamate (30 mg, 0.055 mmol), morpholine (7.20 mg, 0.083 mmol), and Et₃N (0.012 mL, 0.083 mmol) in CH₂Cl₂ (2 mL) was heated at 50° C. overnight. The reaction mixture was diluted with CH₂Cl₂, washed with satd. NaHCO₃ and water, and concentrated. The residue was purified by prep-HPLC and the product containing fractions were collected, neutralized with saturated NaHCO₃, extracted with CH₂Cl₂, separated, and concentrated to obtain 13.5 mg of (R)—N-(1-(5-carbamoyl-6-(4-(morpholine-4-carbonyl)phenylamino)pyridin-2-yl)piperidin-3-yl)morpholine-4-carboxamide as a light yellow solid as free base.

LCMS: (M+H)⁺=538.26. ¹H NMR (400 MHz, CDCl₃) δ ppm 11.25 (1H, s), 7.69 (2 H, d, J=8.35 Hz), 7.53 (1H, d, J=8.79 Hz), 7.38 (2H, d, J=8.35 Hz), 6.15 (1H, d, J=9.23 Hz), 5.58 (1H, s), 4.76 (1H, d, J=6.15 Hz), 3.88-3.97 (1H, m), 3.79-3.85 (1 H, m), 3.50-3.78 (15H, m), 3.14-3.29 (4H, m), 1.88-1.97 (1H, m), 1.70-1.81 (2H, m), 1.61-1.69 (1H, m).

Example 9

(R)-2-(4-(Morpholine-4-carbonyl)phenylamino)-6-(3-(phenylsulfonamido)piperidin-1-yl)nicotinamide

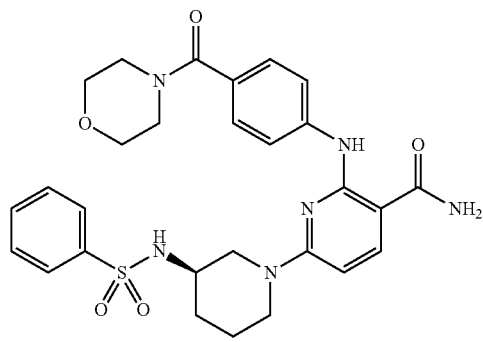 [SMILES: NC(=O)c1ccc(N2CCC[C@@H](NS(=O)(=O)c3ccccc3)C2)nc1Nc1ccc(C(=O)N2CCOCC2)cc1]

To a solution of (R)-6-(3-aminopiperidin-1-yl)-2-(4-(morpholine-4-carbonyl)phenylamino)nicotinamide (30 mg, 0.071 mmol) and Et₃N (0.049 mL, 0.353 mmol) in THF (2 mL) was added benzenesulfonyl chloride (18.72 mg, 0.106 mmol). The solution was stirred at rt for 10 min. The reaction mixture was diluted with CH₂Cl₂, washed with satd NaHCO₃, separated, and concentrated. The residue was purified (ISCO, 5% NH₄OH/MeOH/CH₂Cl₂, 40 g silica gel column) to obtain 30 mg of (R)-2-(4-(morpholine-4-carbonyl)phenylamino)-6-(3-(phenylsulfonamido)piperidin-1-yl)nicotinamide as a light yellow solid. LCMS: (M+H)+=465.40. ¹H NMR (400 MHz, CDCl₃) δ ppm 11.13 (1H, s), 7.84-7.90 (2 H, m), 7.58-7.63 (2H, m), 7.54-7.57 (1H, m), 7.44-7.52 (3H, m), 7.33 (2H, d, J=8.56 Hz), 5.99 (1H, d, J=8.81 Hz), 5.71-5.87 (2H, m), 3.85 (1H, d, J=10.83 Hz), 3.38-3.79 (12H, m), 1.67-1.79 (2H, m), 1.44-1.57 (2H, m).

Example 10

2-(4-(Morpholine-4-carbonyl)phenylamino)-6-(piperazin-1-yl)nicotinamide

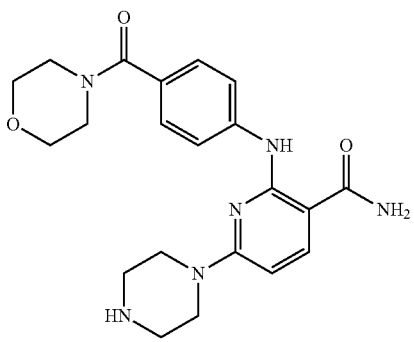 [SMILES: NC(=O)c1ccc(N2CCNCC2)nc1Nc1ccc(C(=O)N2CCOCC2)cc1]

A solution of 6-chloro-2-(4-(morpholine-4-carbonyl)phenylamino)nicotinamide (100 mg, 0.277 mmol) and piperazine (477 mg, 5.54 mmol) in NMP (2 mL) was heated to 120° C. overnight. The reaction mixture was diluted with CH₂Cl₂, washed with satd NaHCO₃, separated, and concentrated. The residue was purified by MPLC chromatography (ISCO, 8%

NH₄OH/MeOH/CH₂Cl₂, 40 g silica gel column) to give 72 mg of 2-(4-(morpholine-4-carbonyl)phenylamino)-6-(piperazin-1-yl)nicotinamide as a white solid. LCMS: (M+H)⁺=411.35. ¹H NMR (400 MHz, CDCl₃) δ ppm 11.20 (1H, s), 7.70 (2H, d, J=8.56 Hz), 7.54 (1H, d, J=9.06 Hz), 7.38 (2H, d, J=8.56 Hz), 6.04 (1H, d, J=8.81 Hz), 5.58 (2H, s), 3.58-3.78 (12H, m), 2.92-3.01 (4H, m).

Example 11

2-(4-(Morpholine-4-carbonyl)phenylamino)-6-(4-(2-phenylacetyl)piperazin-1-yl)nicotinamide

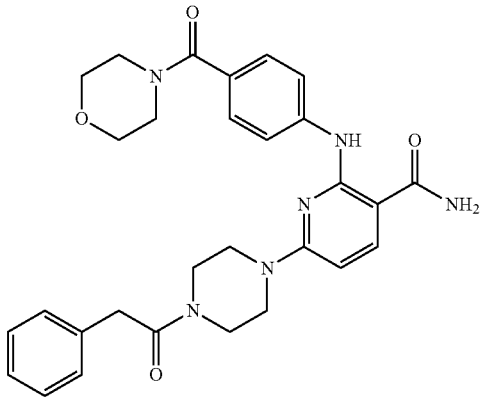 [SMILES: NC(=O)c1ccc(N2CCN(C(=O)Cc3ccccc3)CC2)nc1Nc1ccc(C(=O)N2CCOCC2)cc1]

To a suspension of 2-(4-(morpholine-4-carbonyl)phenylamino)-6-(piperazin-1-yl)nicotinamide (28 mg, 0.068 mmol) and Et₃N (0.019 mL, 0.136 mmol) in THF (2 mL) and CH₂Cl₂ (2.000 mL) was added 2-phenylacetyl chloride (10.55 mg, 0.068 mmol). The reaction mixture was stirred at rt for 10 min, diluted with CH₂Cl₂, washed with satd NaHCO₃, separated, and concentrated. The residue was purified by prep-HPLC. The product containing fractions were collected, basified with 1N NaOH, extracted with CH₂Cl₂, separated, and concentrated to give 14 mg of 2-(4-(morpholine-4-carbonyl)phenylamino)-6-(4-(2-phenylacetyl)piperazin-1-yl)nicotinamide as a white solid. LCMS: (M+H)⁺=529.40. ¹H NMR (400 MHz, CDCl₃) δ ppm 11.17 (1H, s), 7.63 (2H, d, J=8.56 Hz), 7.55 (1H, d, J=8.81 Hz), 7.35-7.40 (2H, m), 7.31-7.35 (2H, m), 7.23-7.31 (3H, m), 5.99 (1H, d, J=8.81 Hz), 5.59 (2H, s), 3.50-3.81 (18H, m).

Example 12

(R)-2-(4-(4-Methylpiperazin-1-yl)phenylamino)-6-(3-(3-(4-methylthiazol-2-yl)ureido)piperidin-1-yl)nicotinamide

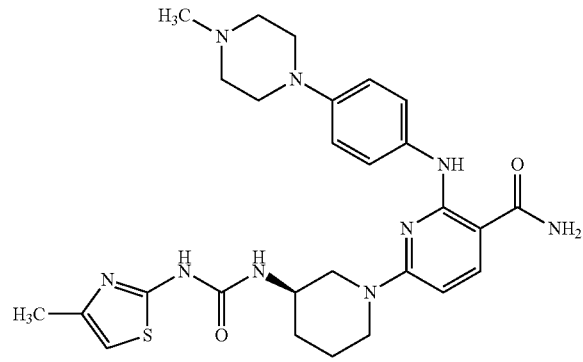 [SMILES: Cc1csc(NC(=O)N[C@@H]2CCCN(c3ccc(C(N)=O)c(Nc4ccc(N5CCN(C)CC5)cc4)n3)C2)n1]

A. 2,6-Dichloronicotinamide

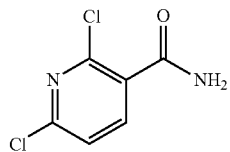 [SMILES: NC(=O)c1ccc(Cl)nc1Cl]

A suspension of 2,6-dichloronicotinic acid (5 g, 26.0 mmol) in CH₂Cl₂ (20 mL) was treated with oxalyl dichloride (3.97 g, 31.3 mmol) and few drops of DMF, and stirred at rt. The generation of bubbles was observed and the reaction mixture gradually became clear. The resulting clear solution was concentrated on a rotary evaporator to remove traces of oxalyl chloride, dissolved in CH₂Cl₂ (20 mL), treated with aqueous NH₄OH (3.47 mL, 52.1 mmol) added drop-wise, and stirred at rt for 1 h. The resulting mixture was diluted with CH₂Cl₂ (white precipitate doesn't all dissolve), washed with satd. NaHCO₃, and concentrated to obtain 2.97 g of 2,6-dichloronicotinamide as a white solid. LCMS: (M+H)⁺=190.96 (100%) 192.93 (70%) 194.93 (20%).

B. 6-Chloro-2-(4-(4-methylpiperazin-1-yl)phenylamino)nicotinamide

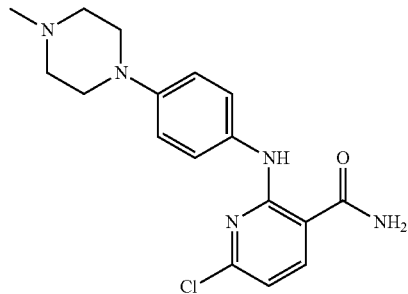 [SMILES: CN1CCN(c2ccc(Nc3nc(Cl)ccc3C(N)=O)cc2)CC1]

A solution of 2,6-dichloronicotinamide (100 mg, 0.524 mmol) and 4-(4-methylpiperazin-1-yl)aniline (300 mg, 1.571 mmol) in THF (5 mL) was cooled to −78° C. and treated with 1 M solution of lithium bis(trimethylsilyl)amide (3.14 mL, 3.14 mmol) in THF. The reaction mixture was stirred at −78° C. for 1 h and then at rt for 1 h. The reaction mixture was diluted with ethyl acetate, washed with water, and concentrated. The residue was purified by MPLC chromatography (ISCO, 5% NH₄OH/MeOH/CH₂Cl₂, 40 g silica gel column) to give 131 mg of 6-chloro-2-(4-(4-methylpiperazin-1-yl)phenylamino)nicotinamide as a yellow solid. LCMS: (M+H)⁺=346.09, 348.05 (Cl pattern). ¹H NMR (400 MHz, CDCl₃₋ₘᵢₓ) δ ppm 10.56 (1H, s), 7.59 (1H, d, J=7.91 Hz), 7.56 (2H, d, J=8.79 Hz), 6.93 (2H, d, J=9.23 Hz), 6.61 (1H, d, J=7.91 Hz), 5.76 (2H, br. s.), 3.16-3.21 (4H, m), 2.57-2.62 (4H, m), 2.36 (3 H, s).

C. (R)-2-(4-(4-Methylpiperazin-1-yl)phenylamino)-6-(3-(3-(4-methylthiazol-2-yl)ureido)piperidin-1-yl)nicotinamide A mixture of 6-chloro-2-(4-(4-methylpiperazin-1-yl)phenylamino)nicotinamide (60 mg, 0.173 mmol), (R)-1-(4-methylthiazol-2-yl)-3-(piperidin-3-yl)urea hydrochloride (96 mg, 0.347 mmol), and DIEA (0.182 mL, 1.041 mmol) in N-methyl-2-pyrrolidinone (2 mL) was heated at 120° C. overnight. The reaction mixture was quenched with water, resulting in the formation of light brown precipitate. The solid was filtered, washed with water, and dried under vacuum. The residue was purified by MPLC chromatography (ISCO, 7% NH$_4$OH/MeOH/CH$_2$Cl$_2$, 40 g silica gel column) to give 22 mg of (R)-2-(4-(4-methylpiperazin-1-yl)phenylamino)-6-(3-(3-(4-methylthiazol-2-yl)ureido)piperidin-1-yl)nicotinamide as a yellow solid. LCMS: (M+H)$^+$=550.08; $^1$H NMR (400 MHz, CDCl$_3$) δ ppm 10.62 (1H, s), 7.47 (2H, d, J=9.23 Hz), 7.33 (1H, d, J=8.79 Hz), 6.85 (2H, d, J=9.23 Hz), 6.28 (1H, s), 5.91 (1H, d, J=8.79 Hz), 5.69 (2H, br. s.), 4.00 (1H, d, J=7.47 Hz), 3.65-3.79 (2H, m), 3.55-3.64 (1H, m), 3.40-3.50 (1H, m), 3.07-3.14 (4H, m), 2.52-2.58 (4H, m), 2.33 (3H, s), 2.19 (3H, s), 1.87-1.98 (1H, m), 1.55-1.82 (3H, m).

Example 13

(R)-6-(3-(3-tert-Butyl-1H-pyrazole-5-carboxamido) piperidin-1-yl)-2-(4-(diethylamino)phenylamino) nicotinamide

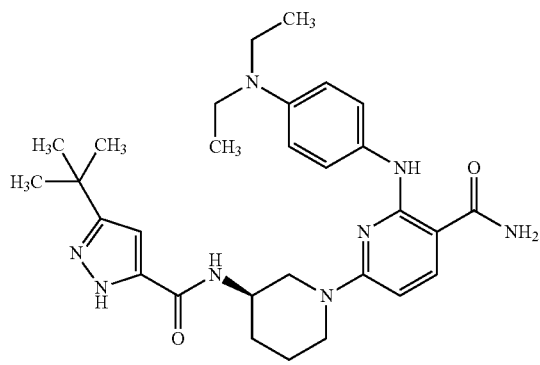 [SMILES: CCN(CC)c1ccc(Nc2nc(N3CCC[C@@H](NC(=O)c4cc(C(C)(C)C)n[nH]4)C3)ccc2C(N)=O)cc1]

A. 6-Chloro-2-(4-(diethylamino)phenylamino)nicotinamide

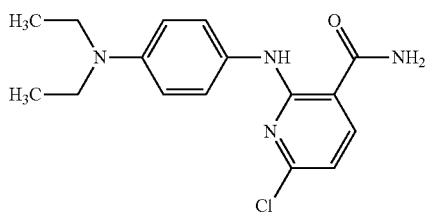 [SMILES: CCN(CC)c1ccc(Nc2nc(Cl)ccc2C(N)=O)cc1]

To a mixture of 2,6-dichloronicotinamide (1 g, 5.24 mmol) and N1,N1-diethylbenzene-1,4-diamine (2.150 g, 13.09 mmol) in THF (50 mL) was added lithium bis(trimethylsilyl) amide (26.2 mL, 26.2 mmol) drop-wise at first then portion-wise at −78° C. The reaction mixture was stirred at rt for 30 min. The ice bath was removed and the reaction mixture was stirred at rt overnight. The reaction mixture was diluted with water, extracted twice with ethyl acetate, and the combined organic layers were washed with water and concentrated. The residue was purified by MPLC (ISCO, hexane/ethyl acetate, 120 g silica gel column) to give 6-chloro-2-(4-(diethylamino) phenylamino)nicotinamide. LCMS: (M+H)$^+$=319.10. $^1$H NMR (400 MHz, CDCl$_3$) δ ppm 10.44 (1H, s), 7.56 (1H, d, J=7.91 Hz), 7.47 (2H, d, J=9.23 Hz), 6.69 (2H, d, J=9.23 Hz), 6.55 (1H, d, J=7.91 Hz), 5.73 (2H, br. s.), 3.33 (4H, q, J=7.03 Hz), 1.15 (6H, t, J=7.03 Hz).

The product, which was contaminated with N1,N1-diethylbenzene-1,4-diamine, was used without further purification in the next step.

B. (R)-tert-Butyl 1-(5-carbamoyl-6-(4-(diethylamino)phenylamino)pyridin-2-yl)piperidin-3-ylcarbamate

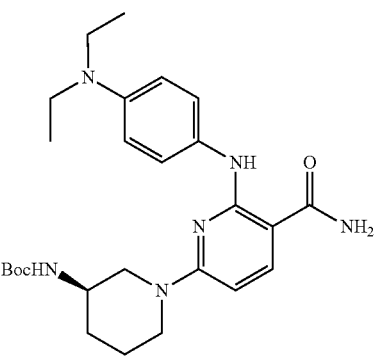 [SMILES: CCN(CC)c1ccc(Nc2nc(N3CCC[C@@H](NC(=O)OC(C)(C)C)C3)ccc2C(N)=O)cc1]

A mixture of 6-chloro-2-(4-(diethylamino)phenylamino) nicotinamide (1.669 g, 5.24 mmol), (R)-tert-butyl piperidin-3-ylcarbamate (1.573 g, 7.85 mmol), and DIEA (1.829 mL, 10.47 mmol) in N-methyl-2-pyrrolidinone (10 mL) was heated at 100° C. overnight. The reaction mixture was diluted with ethyl acetate, washed with satd. NaHCO$_3$, water, and concentrated. The resulting residue was purified by MPLC (ISCO, hexane/ethyl acetate, 80 g silica gel column) to give 1.41 g (R)-tert-butyl 1-(5-carbamoyl-6-(4-(diethylamino) phenylamino)pyridin-2-yl)piperidin-3-ylcarbamate as a yellow solid. LCMS: (M+H)+=483.3.

C. (R)-6-(3-Aminopiperidin-1-yl)-2-(4-(diethylamino)phenylamino)nicotinamide

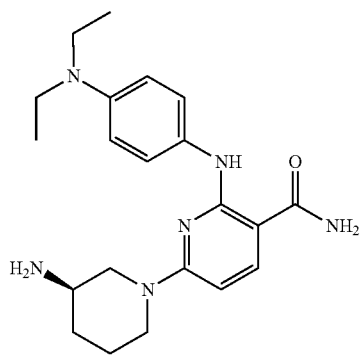 [SMILES: CCN(CC)c1ccc(Nc2nc(N3CCC[C@@H](N)C3)ccc2C(N)=O)cc1]

A solution of (R)-tert-butyl 1-(5-carbamoyl-6-(4-(diethylamino)phenylamino) pyridin-2-yl)piperidin-3-ylcarbamate (1.41 g, 2.92 mmol) in CH$_2$Cl$_2$ (2 mL) was treated with TFA (4 ml) and stirred at rt for 4 h. The reaction mixture was concentrated and the residue dissolved in CH$_2$Cl$_2$ and washed with 1N NaOH and concentrated to give 1.07 g of (R)-6-(3- aminopiperidin-1-yl)-2-(4-(diethylamino)phenylamino) nicotinamide as a yellow solid. LCMS: (M+H)+=383.25.

D. (R)-6-(3-(3-tert-Butyl-1H-pyrazole-5-carboxamido) piperidin-1-yl)-2-(4-(diethylamino)phenylamino)nicotinamide A solution of (R)-6-(3-aminopiperidin-1-yl)-2-(4-(diethylamino)phenylamino)nicotinamide (40 mg, 0.105 mmol), 3-tert-butyl-1H-pyrazole-5-carboxylic acid (21.11 mg, 0.125 mmol), EDC (30.1 mg, 0.157 mmol), HOBT (24.02 mg, 0.157 mmol), and Et$_3$N (0.022 mL, 0.157 mmol) in THF (1 mL) was stirred at rt for 4 h. The reaction mixture was diluted with CH$_2$Cl$_2$, washed with satd. NaHCO$_3$, and concentrated. The residue was purified by prep-HPLC. The product containing fractions were collected, basified with satd. Na$_2$CO$_3$, separated, and concentrated to give 33 mg of (R)-6-(3-(3-tert-butyl-1H-pyrazole-5-carboxamido) piperidin-1-yl)-2-(4-(diethylamino)phenylamino) nicotinamide as a yellow solid. LCMS: (M+H)+=533.30. $^1$H NMR (400 MHz, CDCl$_3$) δ ppm 10.96 (1H, br. s.), 10.52 (1H, s), 7.44 (1H, d, J=8.79 Hz), 7.36 (2H, d, J=8.79 Hz), 7.06 (1 H, br. s.), 6.59 (2H, d, J=9.23 Hz), 6.00 (1H, d, J=8.79 Hz), 5.75 (1H, br. s.), 4.16-4.27 (1H, m), 3.82 (1H, br. s.), 3.58-3.72 (3H, m), 3.27 (4H, q, J=7.18 Hz), 1.86-1.96 (2H, m), 1.78 (1H, d, J=5.71 Hz), 1.62-1.70 (1H, m), 1.60 (2H, s), 1.33 (9H, s), 1.10 (6H, t, J=7.03 Hz).

Example 14

6-(2,4-Difluorophenyl)-2-(4-(4-methylpiperazine-1-carbonyl)phenylamino)nicotinamide

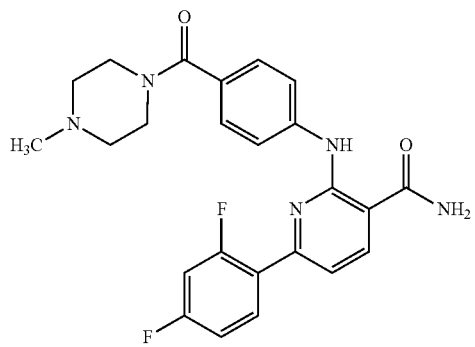 [SMILES: CN1CCN(C(=O)c2ccc(Nc3nc(-c4ccc(F)cc4F)ccc3C(N)=O)cc2)CC1]

A. 2,6-Dichloronicotinamide

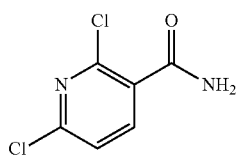 [SMILES: NC(=O)c1ccc(Cl)nc1Cl]

To a suspension of 2,6-dichloronicotinic acid (10 g, 52.1 mmol) in CH$_2$Cl$_2$ (100 mL) was added oxalyl chloride (5.02 mL, 57.3 mmol) and 3 drops of DMF and stirred at rt for 2 h. The suspension gradually became clear. The resulting clear solution was concentrated to give the acid chloride as a yellow solid. The acid chloride was dissolved in CH$_2$Cl$_2$ and treated with aqueous NH$_4$OH (5.64 mL, 260 mmol) and stirred at rt for 0.5 h. The reaction mixture was washed with water twice and concentrated to give 6.5 g of 2,6-dichloronicotinamide as a light yellow solid.

LCMS: (M+H)+=191.06, 193.03 (Cl pattern).

B. Methyl 4-(3-carbamoyl-6-chloropyridin-2-ylamino)benzoate

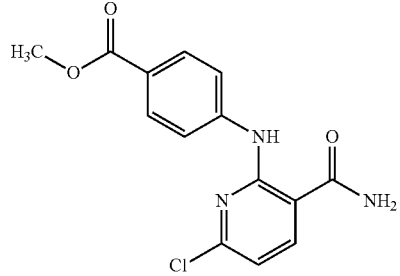 [SMILES: COC(=O)c1ccc(Nc2nc(Cl)ccc2C(N)=O)cc1]

To a solution of 2,6-dichloronicotinamide (1 g, 5.24 mmol) and methyl 4-aminobenzoate (0.950 g, 6.28 mmol) in THF (30 mL) was added lithium bis(trimethylsilyl)amide (18.32 mL, 18.32 mmol) at −78° C. The reaction mixture was stirred for 10 min. The dry ice bath was removed and the reaction mixture was stirred at rt for 3.5 h. The reaction mixture was diluted with water and the resulting yellow precipitate was filtered to give 1.7 g of methyl 4-(3-carbamoyl-6-chloropyridin-2-ylamino)benzoate as a yellow solid.

C. 4-(3-Carbamoyl-6-chloropyridin-2-ylamino)benzoic acid

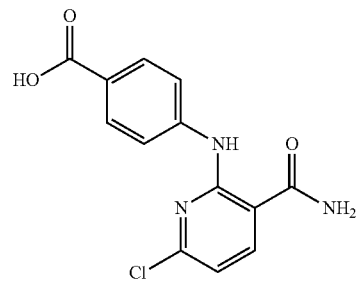 [SMILES: NC(=O)c1ccc(Cl)nc1Nc1ccc(C(=O)O)cc1]

Methyl 4-(3-carbamoyl-6-chloropyridin-2-ylamino)benzoate was dissolved in 20 mL of MeOH, treated with 10 mL of 30% NaOH, and stirred at rt for 3 h. The reaction mixture was acidified with 1N HCl and the resulting solid was filtered and air dried to give 1.43 g of 4-(3-carbamoyl-6-chloropyridin-2-ylamino)benzoic acid as a yellow solid. LCMS: (M+H)+=292.06, 294.00 (Cl pattern).

D. 6-Chloro-2-(4-(4-methylpiperazine-1-carbonyl) phenylamino)nicotinamide

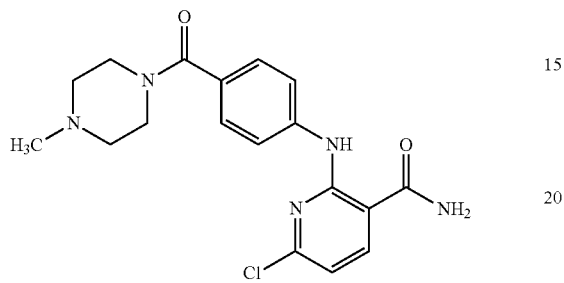

A suspension of 4-(3-carbamoyl-6-chloropyridin-2-ylamino)benzoic acid (700 mg, 2.400 mmol), 1-methylpiperazine (288 mg, 2.88 mmol), HOBT (441 mg, 2.88 mmol), and EDC (552 mg, 2.88 mmol) in DMF (4 mL) was stirred at rt for 2 h. The reaction mixture was diluted with water and the resulting precipitate filtered and purified by MPLC chromatography (ISCO, solid loaded on CELITE®, 10% NH$_4$OH/MeOH/CH$_2$Cl$_2$, 40 g silica gel column) to give 175 mg of 6-chloro-2-(4-(4-methylpiperazine-1-carbonyl)phenylamino)nicotinamide. LCMS: (M+H)$^+$=374.05, 376.07 (Cl pattern); $^1$H NMR (400 MHz, CDCl$_3$) δ ppm 10.74 (1H, s), 7.64 (3H, dd, J=8.13, 5.49 Hz), 7.21 (2H, d, J=8.79 Hz), 6.67 (1H, d, J=7.91 Hz), 3.38-3.97 (4 H, m), 2.34-2.59 (4H, m), 2.33 (3H, s), 1.70 (2H, s).

E. 6-(2,4-difluorophenyl)-2-(4-(4-methylpiperazine-1-carbonyl)phenylamino)nicotinamide A mixture of 6-chloro-2-(4-(4-methylpiperazine-1-carbonyl)phenylamino)nicotinamide (40 mg, 0.107 mmol), 2,4-difluorophenylboronic acid (16.90 mg, 0.107 mmol), K$_2$CO$_3$ (29.6 mg, 0.214 mmol), and Pd(Ph$_3$P)$_4$ (12.36 mg, 10.70 µmol) in THF (2 mL) in a microwave vial was degassed by passing nitrogen through briefly. The vial was sealed and heated to 90° C. overnight. The reaction mixture was diluted with CH$_2$Cl$_2$, washed with satd. NaHCO$_3$, water, and concentrated. The residue was purified by prep-HPLC. The product containing fractions were collected, basified by 1N NaOH, extracted with CH$_2$Cl$_2$, washed with water, concentrated to give 17 mg of 6-(2,4-difluorophenyl)-2-(4-(4-methylpiperazine-1-carbonyl)phenylamino)nicotinamide as a yellow solid. LCMS: (M+H)$^+$=452.08 $^1$H NMR (400 MHz, CDCl$_3$) δ ppm 10.80 (1H, s), 8.08 (1H, td, J=8.79, 6.59 Hz), 7.79-7.83 (1H, m), 7.77 (2H, d, J=8.35 Hz), 7.35 (2H, d, J=8.79 Hz), 7.23-7.27 (1H, m), 6.98-7.06 (1H, m), 6.93 (1H, ddd, J=11.42, 8.79, 2.64 Hz), 3.67 (4H, br. s.), 2.36-2.61 (4H, m), 2.33 (3H, s).

Example 15

5-Fluoro-2-(4-fluorophenylamino)-6-(piperidin-1-yl) nicotinamide

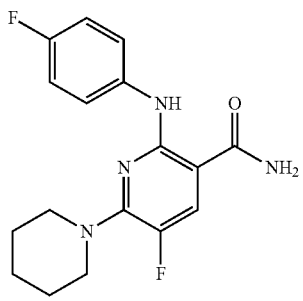 [SMILES: NC(=O)c1cc(F)c(N2CCCCC2)nc1Nc1ccc(F)cc1]

A. 6-Chloro-5-fluoro-2-(4-fluorophenylamino)nicotinic acid

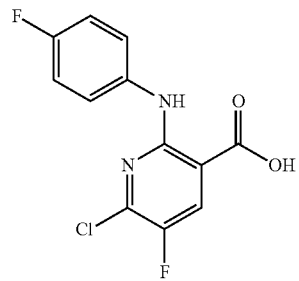 [SMILES: O=C(O)c1cc(F)c(Cl)nc1Nc1ccc(F)cc1]

A solution of 2,6-dichloro-5-fluoronicotinic acid (500 mg, 2.381 mmol) and 4-fluoroaniline (265 mg, 2.381 mmol) in THF (30 mL) was treated with 1 M lithium bis(trimethylsilyl) amide in THF (7.14 mL, 7.14 mmol) slowly and stirred at rt. Solvent was removed on rotary evaporator. The residue acidified with 1 N HCl, extracted into ethyl acetate, and concentrated to give a dark solid. LCMS: (M+H)$^+$=285.12.

B. 6-Chloro-5-fluoro-2-(4-fluorophenylamino)nicotinamide

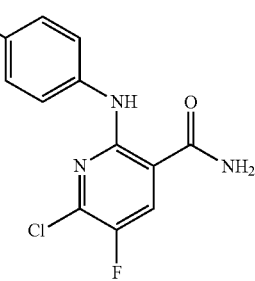

A suspension of crude 6-chloro-5-fluoro-2-(4-fluorophenylamino)nicotinic acid (687 mg, 2.414 mmol) in $CH_2Cl_2$ (20 mL) was treated with excess oxalyl chloride (0.423 mL, 4.83 mmol) and stirred at rt. Next, three drops of DMF was added, and the reaction mixture began to bubble. The reaction mixture was stirred at rt. The reaction mixture gradually becomes a clear solution. After 1 hr, solvent was removed on a rotary evaporator to give the acid chloride as a dark yellow solid. The acid chloride was dissolved in $CH_2Cl_2$ (20 mL) and treated with aqueous ammonium hydroxide (1 mL, 14.80 mmol) and stirred at rt for several minutes. The mixture was concentrated on a rotary evaporator and the resulting solid was dissolved in mixture of $CH_2Cl_2$ and MeOH, washed with water, and concentrated to give 630 mg of a brown solid. LCMS: $(M+H)^+$=284.11, 286.12 (Cl pattern). $^1$H NMR (400 MHz, $CDCl_3$) δ ppm 10.46 (1H, br. s.), 7.51-7.66 (3H, m), 7.03 (2H, t, J=8.79 Hz), 5.84 (2H, br. s).

C. 5-Fluoro-2-(4-fluorophenylamino)-6-(piperidin-1-yl)nicotinamide

A solution of 6-chloro-5-fluoro-2-(4-fluorophenylamino)nicotinamide (50 mg, 0.176 mmol) and piperidine (1 mL, 10.12 mmol) was sealed in a small microwave vial and heated in a heating block at 100° C. for 2 hrs. The reaction mixture was diluted with $CH_2Cl_2$ and washed with bicarbonate and water. The reaction mixture was concentrated and the dark crude material was chromatographed (ISCO Companion 40 g silica gel column and eluted with (90:9:1 $CH_2Cl_2$:MeOH:$NH_4OH)_x/CH_2Cl_2$ gradient (20-100%)) to give 50 mg of 5-fluoro-2-(4-fluorophenylamino)-6-(piperidin-1-yl)nicotinamide as a brown solid. LCMS: $(M+H)^+$=333.21. $^1$H NMR (400 MHz, $CDCl_3$) δ ppm 10.68 (1H, s), 7.52-7.57 (2 H, m), 7.22 (1H, d, J=14.06 Hz), 6.94-7.00 (2H, m), 5.47 (2H, br. s.), 3.64 (4H, d, J=6.15 Hz), 1.62-1.72 (6H, m).

Example 16

5-Bromo-2-(4-(morpholine-4-carbonyl)phenylamino)-6-(piperidin-1-yl)nicotinamide

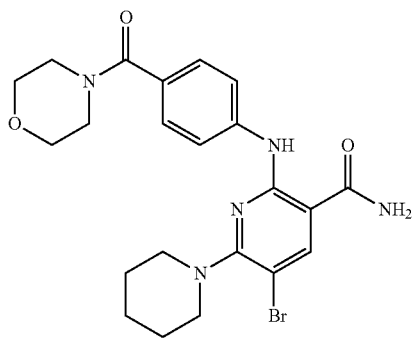 [SMILES: NC(=O)c1cc(Br)c(N2CCCCC2)nc1Nc1ccc(C(=O)N2CCOCC2)cc1]

A. 5-Bromo-6-chloro-2-(4-(morpholine-4-carbonyl)phenylamino)nicotinamide

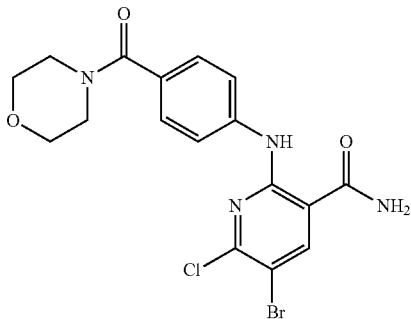 [SMILES: NC(=O)c1cc(Br)c(Cl)nc1Nc1ccc(C(=O)N2CCOCC2)cc1]

A suspension of 6-chloro-2-(4-(morpholine-4-carbonyl)phenylamino)nicotinamide (500 mg, 1.385 mmol) and NBS (250 mg, 1.4 mmol) in acetonitrile (10 mL) was stirred at overnight. The reaction mixture was treated with 1M $NaHSO_3$ and stirred at rt for 2 h. Next, the reaction mixture was diluted with ethyl acetate and the precipitate filtered to give a solid. The organic layer of the filtrate was separated and concentrated to an additional amount of solid. The above solids were combined and triturated with 250 mL of MeOH/$CH_2Cl_2$ (~1:1 ratio) to give 235 mg of 5-bromo-6-chloro-2-(4-(morpholine-4-carbonyl)phenylamino)nicotinamide as a grey solid. LCMS: $(M+H)^+$=338.80, 440.83, 442.87 (Br, Cl pattern). $^1$H NMR (400 MHz, methanol-$d_{3-MIX}$) δ ppm 8.38 (1H, s), 7.77 (2H, d, J=8.35 Hz), 7.42 (2H, d, J=8.79 Hz), 3.69 (8H, br. s.).

B. 5-Bromo-2-(4-(morpholine-4-carbonyl)phenylamino)-6-(piperidin-1-yl)nicotinamide A solution of 5-bromo-6-chloro-2-(4-(morpholine-4-carbonyl)phenylamino)nicotinamide (200 mg, 0.454 mmol) in piperidine (1 ml) was stirred at rt for 2 h and heated to 70° C. for 1 h. The mixture was diluted with $CH_2Cl_2$, washed with water three times, and concentrated. The residue was purified by chromatography (ISCO, hexane/ethyl acetate gradient, 40 g silica gel column) to give 210 mg of 5-bromo-2-(4-(morpholine-4-carbonyl)phenylamino)-6-(piperidin-1-yl)nicotinamide as a white solid. LCMS: $(M+H)^+$=488.02, 489.96 (Br pattern). $^1$H NMR (400 MHz, $CDCl_{3-MIX}$) δ ppm 11.11 (1H, s), 7.89 (1H, s), 7.76 (2H, d, J=8.79 Hz), 7.38 (2H, d, J=8.79 Hz), 3.72 (8H, br. s.), 3.46-3.52 (4H, m), 1.73 (6 H, m).

Example 17

(R)-2-(4-(Morpholine-4-carbonyl)phenylamino)-6-(3-(2-oxopyrrolidin-1-yl)piperidin-1-yl)nicotinamide (17)

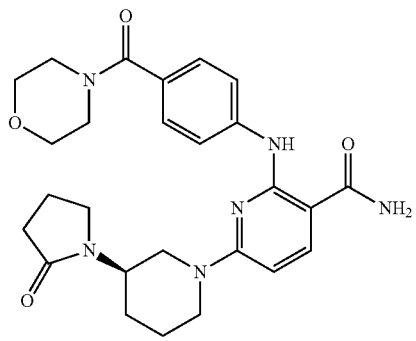

A solution of (R)-6-(3-aminopiperidin-1-yl)-2-(4-(morpholine-4-carbonyl)phenylamino)nicotinamide (80 mg) and ethyl 4-bromobutanoate (37 mg, 1 eq.) in DMF (1 mL) was treated with Cs$_2$CO$_3$ (184 mg, 3 eq) and heated at 100° C. for 2 days. The reaction mixture was diluted with ethyl acetate, washed with water, 10% LiCl, and concentrated. The residue was purified by MPLC chromatography (ISCO, 7% NH$_4$OH/MeOH/CH$_2$Cl$_2$, 40 g silica gel column) to give 26 mg of (R)-2-(4-(morpholine-4-carbonyl)phenylamino)-6-(3-(2-oxopyrrolidin-1-yl)piperidin-1-yl)nicotinamide as a light yellow solid. LCMS: (M+H)$^+$=493.27. $^1$H NMR (500 MHz, CDCl$_3$) δ ppm 11.18 (1H, s), 7.67 (2H, d, J=8.80 Hz), 7.53 (1H, d, J=8.80 Hz), 7.36 (2H, d, J=8.80 Hz), 6.06 (1H, d, J=8.80 Hz), 5.68 (2H, br. s.), 4.20-4.45 (2H, m), 3.98-4.19 (1H, m), 3.71 (8H, br. s.), 3.42-3.49 (1H, m), 3.33-3.41 (1H, m), 2.92-3.00 (1H, m), 2.83-2.91 (1H, m), 2.44 (2H, t, J=8.25 Hz), 2.05 (2H, qd, J=7.61, 7.42 Hz), 1.94 (1H, dd, J=11.82, 3.57 Hz), 1.81-1.89 (1H, m), 1.59-1.80 (2H, m).

Example 18

(R)-6-(3-(3-(2-Chloroethyl)ureido)piperidin-1-yl)-2-(4-(morpholine-4-carbonyl)phenylamino)nicotinamide

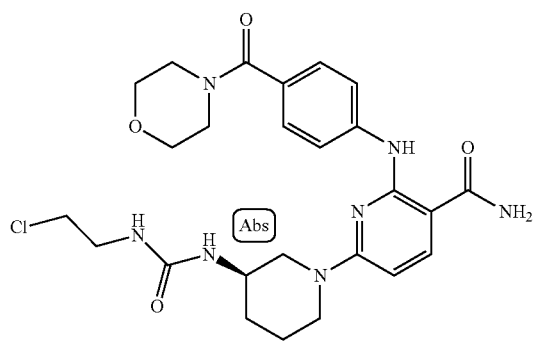 [SMILES: NC(=O)c1ccc(N2CCC[C@@H](NC(=O)NCCCl)C2)nc1Nc1ccc(C(=O)N2CCOCC2)cc1]

To a solution of (R)-6-(3-aminopiperidin-1-yl)-2-(4-(morpholine-4-carbonyl)phenylamino)nicotinamide (80 mg, 0.188 mmol) and 1-chloro-2-isocyanatoethane (24 mg, 0.226 mmol) in THF (1 mL) was added DIEA (36 mg, 0.282 mmol) and stirred at rt for 1 h. The reaction mixture was quenched with water, extracted twice into CH$_2$Cl$_2$, and the combined organic extracts were washed with water and concentrated to give 92 mg white solid as crude product. This was purified by MPLC chromatography (ISCO, 7% NH$_4$OH/MeOH/CH$_2$Cl$_2$, 40 g silica gel column) to give 82 mg of (R)-6-(3-(3-(2-chloroethyl)ureido)piperidin-1-yl)-2-(4-(morpholine-4-carbonyl)phenylamino)nicotinamide as a white solid. LCMS: (M+H)$^+$=530.22, 532.20 (Cl pattern). $^1$H NMR (500 MHz, CDCl$_3$) δ ppm 11.17 (1H, s), 7.65 (2H, d, J=8.80 Hz), 7.42 (1H, d, J=9.35 Hz), 7.33 (2H, d, J=8.80 Hz), 5.94 (1 H, d, J=8.80 Hz), 5.42 (1H, t, J=5.77 Hz), 5.15 (1H, d, J=7.15 Hz), 3.79-3.85 (1H, m), 3.62-3.78 (10H, m), 3.56-3.60 (2H, m), 3.47-3.51 (2H, m), 3.18 (1H, s), 2.88-2.96 (1H, m), 1.81-1.90 (1H, m), 1.47-1.57 (1H, m), 1.32-1.42 (1H, m), 1.21-1.30 (1H, m).

Example 19

(R)-2-(4-(Morpholine-4-carbonyl)phenylamino)-6-(3-(2-oxoimidazolidin-1-yl)piperidin-1-yl)nicotinamide

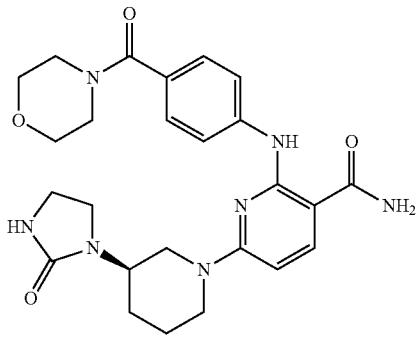 [SMILES: NC(=O)c1ccc(N2CCC[C@@H](N3CCNC3=O)C2)nc1Nc1ccc(C(=O)N2CCOCC2)cc1]

To a solution of (R)-6-(3-(3-(2-chloroethyl)ureido)piperidin-1-yl)-2-(4-(morpholine-4-carbonyl)phenylamino)nicotinamide (86 mg, 0.162 mmol) in DMF (1 mL) was added NaH (32.4 mg, 0.811 mmol) and stirred at rt for 1 h. The reaction mixture was quenched with water, extracted twice into CH$_2$Cl$_2$ twice. The combined organic extracts were washed with 10% LiCl and concentrated. The residue was purified by MPLC chromatography (ISCO, 6% NH$_4$OH/MeOH/CH$_2$Cl$_2$, 40 g silica gel column) and further purified by HPLC. The product containing fractions were collected, basified with 1N NaOH, and extracted with CH$_2$Cl$_2$ twice. The combined organic layers were concentrated to give 13 mg of (R)-2-(4-(morpholine-4-carbonyl)phenylamino)-6-(3-(2-oxoimidazolidin-1-yl)piperidin-1-yl)nicotinamide as a light yellow solid. LCMS: (M+H)+=494.23. $^1$H NMR (400 MHz, CDCl$_3$) δ ppm 11.17 (1H, s), 7.66-7.71 (2H, m), 7.52 (1H, d, J=8.79 Hz), 7.34-7.39 (2H, m), 6.07 (1H, d, J=8.79 Hz), 5.62-5.84 (2H, m), 4.54 (1H, s), 4.26-4.38 (2H, m), 3.76-3.88 (2H, m), 3.57-3.75 (8H, m), 3.43 (4H, d, J=4.39 Hz), 2.94-3.03 (1H, m), 1.92-2.02 (1H, m), 1.80-1.89 (1H, m), 1.68 (2H, m).

Example 20

(R)-2-(4-(Morpholine-4-carbonyl)phenylamino)-6-(3-(pyrimidin-2-ylamino)piperidin-1-yl)nicotinamide

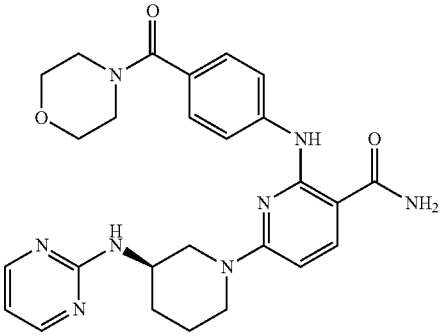 [SMILES: NC(=O)c1ccc(N2CCC[C@@H](Nc3ncccn3)C2)nc1Nc1ccc(C(=O)N2CCOCC2)cc1]

A mixture of (R)-6-(3-aminopiperidin-1-yl)-2-(4-(morpholine-4-carbonyl)phenylamino)nicotinamide (50 mg, 0.118 mmol), 2-bromopyrimidine (22.47 mg, 0.141 mmol), and DIEA (0.041 mL, 0.236 mmol) in THF (1 mL) was stirred at 100° C. overnight. The reaction mixture was diluted with ethyl acetate, washed with water, 10% LiCl, and concentrated. The residue was purified by prep-HPLC and the product containing fractions were collected, basified with 1N NaOH, extracted with $CH_2Cl_2$, washed with water, and concentrated to give 18 mg of (R)-2-(4-(morpholine-4-carbonyl)phenylamino)-6-(3-(pyrimidin-2-ylamino)piperidin-1-yl)nicotinamide as a light yellow solid. LCMS: (M+H)+=503.23. $^1$H NMR (500 MHz, $CDCl_3$) δ ppm 11.19 (1H, s), 8.27 (2H, d, J=4.58 Hz), 7.68 (2H, d, J=8.71 Hz), 7.51 (1H, d, J=8.71 Hz), 7.27 (2H, d, J=8.71 Hz), 6.56 (1H, t, J=4.81 Hz), 6.12 (1H, d, J=9.16 Hz), 5.57 (2H, br. s.), 5.26 (1H, d, J=7.79 Hz), 4.20 (1H, dd, J=12.83, 3.21 Hz), 4.09 (1H, dt, J=7.79, 3.89 Hz), 3.89-3.98 (1H, m), 3.49-3.83 (8H, m), 3.42-3.48 (1H, m), 3.39 (1H, dd, J=12.83, 7.79 Hz), 2.04-2.13 (2H, m), 1.69-1.92 (2H, m).

Example 21

(R)-Benzyl 4-(4-(6-(3-benzamidopiperidin-1-yl)-3-carbamoylpyridin-2-ylamino)phenyl)piperazine-1-carboxylate

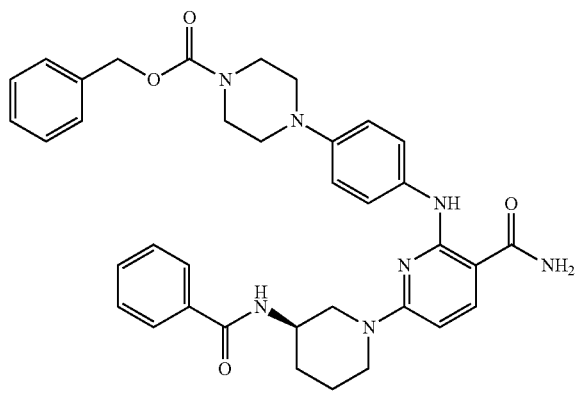 [SMILES: NC(=O)c1ccc(N2CCC[C@@H](NC(=O)c3ccccc3)C2)nc1Nc1ccc(N2CCN(C(=O)OCc3ccccc3)CC2)cc1]

A. Benzyl 4-(4-nitrophenyl)piperazine-1-carboxylate

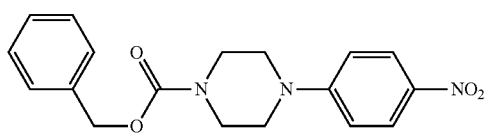

To a mixture of 1-(4-nitrophenyl)piperazine (5 g, 24.13 mmol) and $Et_3N$ (5.04 mL, 36.2 mmol) in THF (20 mL) was added benzyl chloroformate (3.79 mL, 26.5 mmol) portionwise at 0° C. The reaction mixture was stirred at 0° C. for 1 h and then at rt for 2 h. The reaction mixture was diluted with $CH_2Cl_2$, washed with satd $NaHCO_3$ and water, and concentrated to give 8.06 g of benzyl 4-(4-nitrophenyl)piperazine-1-carboxylate as yellow solid. LCMS: (M+H)+=342.15.

B. Benzyl 4-(4-aminophenyl)piperazine-1-carboxylate

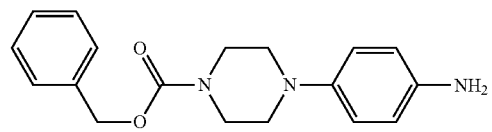 [SMILES: O=C(OCc1ccccc1)N1CCN(c2ccc([N+](=O)[O-])cc2)CC1]

To a mixture of 8.0 g benzyl 4-(4-nitrophenyl)piperazine-1-carboxylate (23.5 mmol) and 11 g $CoCl_2$ (47 mmol) in 100 mL MeOH was added 8.6 g (225 mmol) of $NaBH_4$ portionwise and then stirred at rt for 1 hr. To the reaction mixture was added 3N HCl until the black precipitate dissolved. The resulting mixture was concentrated to remove MeOH and the residue was extracted twice with ether. The aqueous layer was basified with 1N NaOH and then extracted twice with ethyl acetate. The combined extracts were concentrated to give an oil that was purified by MPLC chromatography (ISCO, 50% hexane/ethyl acetate, 40 g+12 g stacked column) to give 5.8 g of benzyl 4-(4-aminophenyl)piperazine-1-carboxylate. LCMS: (M+H)+=312.25.

C. Benzyl 4-(4-(3-carbamoyl-6-chloropyridin-2-ylamino)phenyl)piperazine-1-carboxylate

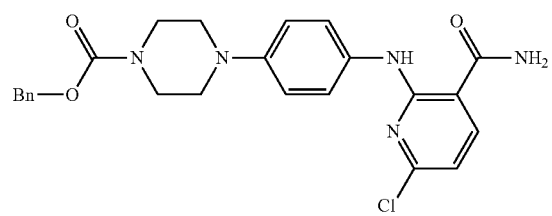 [SMILES: NC(=O)c1ccc(Cl)nc1Nc1ccc(N2CCN(C(=O)OCc3ccccc3)CC2)cc1]

To a mixture of 2,6-dichloronicotinamide (3 g, 15.71 mmol) and benzyl 4-(4-aminophenyl)piperazine-1-carboxylate (5.38 g, 17.28 mmol) in THF (100 mL) was added lithium bis(trimethylsilyl)amide (55.0 mL, 55.0 mmol) at −78° C. The reaction mixture was stirred at −78° C. for 20 min. and at rt for 2 h. The reaction was quenched with water and extracted three times with ethyl acetate. The combined organic layers were washed with water and concentrated. The residue was purified by MPLC chromatography (ISCO, 6% $NH_4OH/MeOH/CH_2Cl_2$, 40 g+12 g stacked column) to give 6.8 g of benzyl 4-(4-(3-carbamoyl-6-chloropyridin-2-ylamino)phenyl)piperazine-1-carboxylate as a brown solid. LCMS: (M+H)+=466.2, 468.2 (Cl pattern).

D. ((R)-Benzyl 4-(4-(6-(3-(tert-butoxycarbonylamino)piperidin-1-yl)-3-carbamoylpyridin-2-ylamino)phenyl)piperazine-1-carboxylate)

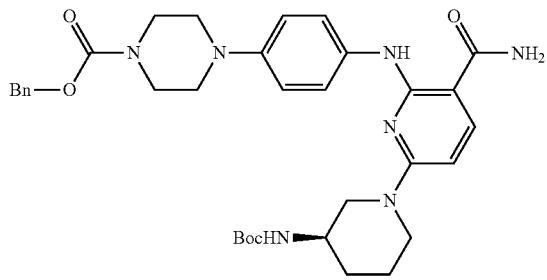 [SMILES: CC(C)(C)OC(=O)N[C@@H]1CCCN(c2ccc(C(N)=O)c(Nc3ccc(N4CCN(C(=O)OCc5ccccc5)CC4)cc3)n2)C1]

A mixture of benzyl 4-(4-(3-carbamoyl-6-chloropyridin-2-ylamino)phenyl)piperazine-1-carboxylate (4 g, 8.58 mmol), (R)-tert-butyl piperidin-3-ylcarbamate (2.58 g, 12.88 mmol), and DIEA (3.00 mL, 17.17 mmol) in N-methyl-2-pyrrolidinone (6 mL) was placed in two capped scintillation vials and heated at 100° C. overnight. The reaction mixtures were quenched with water and filtered. The solid was purified by MPLC chromatography (ISCO, 6% NH₄OH/MeOH/CH₂Cl₂, two 40 g stacked silica gel columns) to give 4.71 g of ((R)-benzyl 4-(4-(6-(3-(tert-butoxycarbonylamino)piperidin-1-yl)-3-carbamoylpyridin-2-ylamino)phenyl)piperazine-1-carboxylate).

E. (R)-Benzyl 4-(4-(6-(3-aminopiperidin-1-yl)-3-carbamoylpyridin-2-ylamino) phenyl)piperazine-1-carboxylate

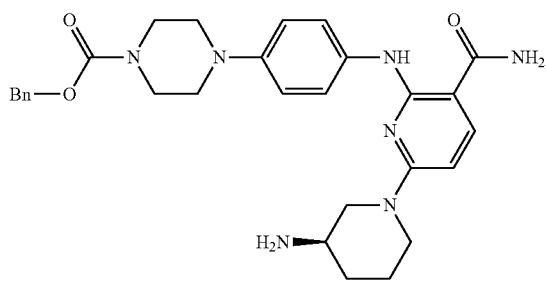 [SMILES: NC(=O)c1ccc(N2CCC[C@@H](N)C2)nc1Nc1ccc(N2CCN(C(=O)OCc3ccccc3)CC2)cc1]

A solution of ((R)-benzyl 4-(4-(6-(3-(tert-butoxycarbonylamino)piperidin-1-yl)-3-carbamoylpyridin-2-ylamino)phenyl)piperazine-1-carboxylate) (4.71 g, 7.5 mmol) in CH₂Cl₂ (5 ml) was treated with 5 mL of TFA and stirred at rt for 5 h. The reaction mixture was concentrated and the residue was partitioned between 1N NaOH and CH₂Cl₂. The aqueous phase was extracted with CH₂Cl₂ and the combined organic layers were concentrated. The brown residue was purified by MPLC (ISCO, 8% NH₄OH/MeOH/CH₂Cl₂, 120 g silica gel column) and the fractions containing product were combined and concentrated. The resulting solid was triturated with CH₂Cl₂ to obtain 1.9 g of (R)-benzyl 4-(4-(6-(3-aminopiperidin-1-yl)-3-carbamoylpyridin-2-ylamino) phenyl)piperazine-1-carboxylate as a white solid. A second trituration gave an additional 320 mg of product as a light yellow solid.
LCMS: (M+H)⁺=530.3.

F. (R)-Benzyl 4-(4-(6-(3-benzamidopiperidin-1-yl)-3-carbamoylpyridin-2-ylamino)phenyl)piperazine-1-carboxylate To a mixture of (R)-benzyl 4-(4-(6-(3-aminopiperidin-1-yl)-3-carbamoylpyridin-2-ylamino)phenyl)piperazine-1-carboxylate (1.1 g, 2.077 mmol) and Et₃N (0.579 mL, 4.15 mmol) in THF (10 mL) was added benzoyl chloride (0.350 g, 2.492 mmol). The reaction mixture was stirred at rt for 30 min., quenched with satd NaHCO₃, and extracted twice with CH₂Cl₂. The combined organic layers were concentrated and the residue was triturated with CH₂Cl₂ to obtain 1.15 g of (R)-benzyl 4-(4-(6-(3-benzamidopiperidin-1-yl)-3-carbamoylpyridin-2-ylamino)phenyl)piperazine-1-carboxylate as an off-white solid. LCMS: (M+H)+=634.40. ¹H NMR (400 MHz, DMSO-d₆) δ ppm 11.08 (1H, s), 8.30 (1H, d, J=8.06 Hz), 7.67-7.96 (3H, m), 7.30-7.37 (3H, m), 7.19-7.30 (7H, m), 6.59 (2H, d, J=9.15 Hz), 6.06 (1H, d, J=9.15 Hz), 4.98 (2H, s), 4.34-4.58 (1H, m), 3.93-4.10 (1H, m), 3.75-3.91 (1H, m), 3.08-3.36 (8H, m), 2.52-2.90 (1H, m), 1.86 (1H, s), 1.59-1.75 (1H, m), 1.47-1.58 (1H, m), 1.40 (1H, d, J=2.93 Hz).

Example 22

(R)-6-(3-Benzamidopiperidin-1-yl)-2-(4-(piperazin-1-yl)phenylamino)nicotinamide

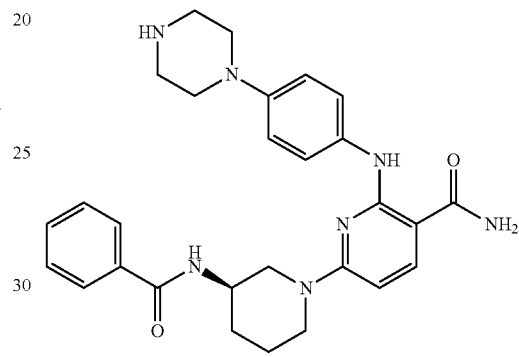

To a suspension of (R)-benzyl 4-(4-(6-(3-benzamidopiperidin-1-yl)-3-carbamoylpyridin-2-ylamino)phenyl)piperazine-1-carboxylate (1.12 g, 1.767 mmol) in EtOAc (10 mL) and EtOH (10.00 mL) was added Pd/C (0.188 g, 0.177 mmol) under nitrogen. The resulting mixture was hydrogenated at 50 psi in a parr shaker overnight. The reaction mixture was filtered and the filtrate was concentrated to give 870 mg of (R)-6-(3-benzamidopiperidin-1-yl)-2-(4-(piperazin-1-yl) phenylamino)nicotinamide. LCMS: (M+H)+=500.14. ¹H NMR (400 MHz, CDCl₃-MIX) δ ppm 10.64 (1H, s), 7.51-7.59 (3H, m), 7.35-7.44 (3H, m), 7.28-7.34 (2H, m), 6.96 (1H, d, J=7.03 Hz), 6.75 (2H, d, J=9.23 Hz), 6.01 (1H, d, J=8.79 Hz), 4.10 (1H, br. s.), 3.75-3.83 (1H, m), 3.66-3.73 (1H, m), 3.58-3.66 (1H, m), 3.47-3.57 (1H, m), 3.15-3.20 (4H, m), 2.88-2.95 (4H, m), 1.82-1.96 (2H, m), 1.65-1.76 (1H, m), 1.54-1.65 (1H, m).

Example 23

(R)-6-(3-Benzamidopiperidin-1-yl)-2-(4-(4-isopropylpiperazin-1-yl)phenylamino)nicotinamide

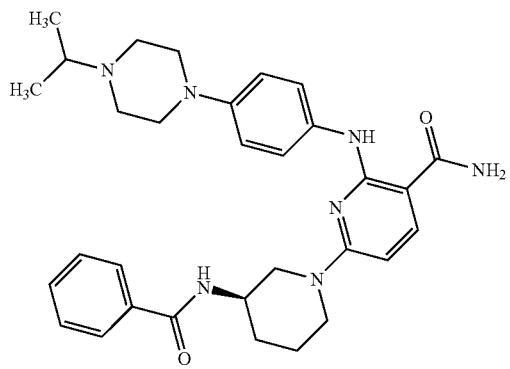 [SMILES: CC(C)N1CCN(c2ccc(Nc3nc(N4CCC[C@@H](NC(=O)c5ccccc5)C4)ccc3C(N)=O)cc2)CC1]

To a mixture of (R)-6-(3-benzamidopiperidin-1-yl)-2-(4-(piperazin-1-yl)phenylamino)nicotinamide (50 mg, 0.100 mmol) and propan-2-one (58.1 mg, 1.001 mmol) in MeOH (1 mL) was added sodium cyanoborohydride (12.58 mg, 0.200 mmol). The reaction mixture was quenched with satd. NaHCO$_3$, extracted twice with CH$_2$Cl$_2$, and concentrated. The residue was purified by prep-HPLC. The product containing fractions were collected, basified with 1N NaOH, extracted with CH$_2$Cl$_2$, and concentrated to give 30 mg of (R)-6-(3-benzamidopiperidin-1-yl)-2-(4-(4-isopropylpiperazin-1-yl)phenylamino)nicotinamide as yellow solid. LCMS: (M+H)+=542.21. $^1$H NMR (500 MHz, CDCl$_{3\text{-}MIX}$) δ ppm 7.57 (2H, d, J=7.15 Hz), 7.53 (1 H, d, J=8.80 Hz), 7.35-7.43 (3H, m), 7.31 (2H, t, J=7.70 Hz), 6.77 (2H, d, J=9.35 Hz), 6.01 (1H, d, J=8.80 Hz), 4.07-4.13 (1H, m), 3.75-3.81 (1H, m), 3.66-3.73 (1H, m), 3.58-3.66 (1H, m), 3.49-3.56 (1H, m), 2.98-3.03 (4H, m), 2.60-2.66 (1H, m), 2.56-2.60 (4H, m), 1.82-1.95 (2H, m), 1.66-1.76 (1H, m), 1.60 (1H, td, J=6.74, 3.57 Hz), 1.03 (6H, d, J=6.05 Hz).

Example 24

(R)-6-(3-Aminopiperidin-1-yl)-4-(4-(morpholine-4-carbonyl)phenylamino)-2-propoxynicotinamide

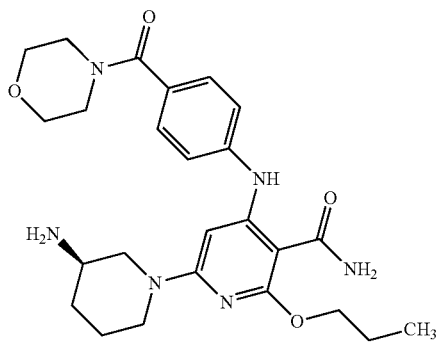 [SMILES: CCCOc1nc(N2CCC[C@@H](N)C2)cc(Nc2ccc(C(=O)N3CCOCC3)cc2)c1C(N)=O]

A. 2,6-Dichloro-4-(4-(morpholine-4-carbonyl)phenylamino)nicotinic acid

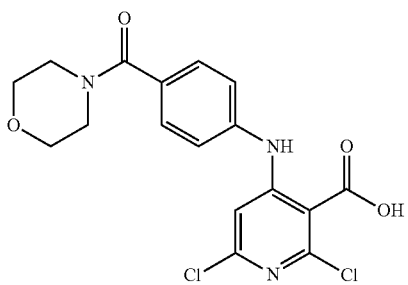 [SMILES: O=C(O)c1c(Nc2ccc(C(=O)N3CCOCC3)cc2)cc(Cl)nc1Cl]

The procedure described in *J. Med. Chem.*, 47:2097-2109 (2004) was employed to prepare 2,4,6-trichloronicotinic acid.

To a suspension of 2,4,6-trichloronicotinic acid (1.0 g, 4.42 mmol) and (4-aminophenyl)(morpholino)methanone (1.91 g, 9.27 mmol) in THF (20 mL) was added sodium bis(trimethylsilyl)amide (14.13 mL, 14.13 mmol) dropwise at −78° C.

The reaction mixture was stirred at −78° C. to rt over 2 h. To the yellow reaction mixture was added 1N HCl (pH=1) and extracted twice with CH$_2$Cl$_2$. The combined organic layers were washed with water and concentrated to give 1.93 g of 2,6-dichloro-4-(4-(morpholine-4-carbonyl)phenylamino) nicotinic acid as a light yellow solid. LCMS: (M+H)+=395.94, 397.88, 399.96 (Cl pattern).

B. 2,6-Dichloro-4-(4-(morpholine-4-carbonyl)phenylamino)nicotinamide

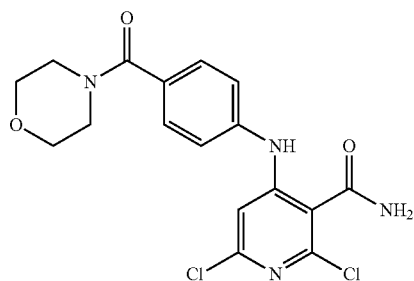 [SMILES: NC(=O)c1c(Nc2ccc(C(=O)N3CCOCC3)cc2)cc(Cl)nc1Cl]

A suspension of 2,6-dichloro-4-(4-(morpholine-4-carbonyl)phenylamino)nicotinic acid (1.926 g, 4.86 mmol), NH$_4$OH (0.94 mL, 24.23 mmol), EDC (1.1 g, 5.8 mmol), and HOBT (0.9 g, 4.9 mmol) in THF (20 mL) was stirred at rt for 2.5 h. The reaction mixture was diluted with CH$_2$Cl$_2$, washed with satd. NaHCO$_3$, water, and concentrated to give 1.6 g of solid. The solids were purified by chromatography (ISCO, 8% NH$_4$OH/MeOH/CH$_2$Cl$_2$, 40 g silica gel column) to give 1.36 g of 2,6-dichloro-4-(4-(morpholine-4-carbonyl)phenylamino)nicotinamide. LCMS: (M+H)+=394.97, 396.91, 398.91 (Cl pattern). $^1$H NMR (400 MHz, CDCl$_3$) δ ppm 9.43 (1H, s), 7.50 (2H, d, J=8.79 Hz), 7.25 (2H, d, J=8.35 Hz), 6.97 (1H, s), 6.72 (1H, br. s.), 6.10 (1H, br. s.), 3.73 (8 H, br. s.).

C. 6-Chloro-4-(4-(morpholine-4-carbonyl)phenylamino)-2-propoxynicotinamide

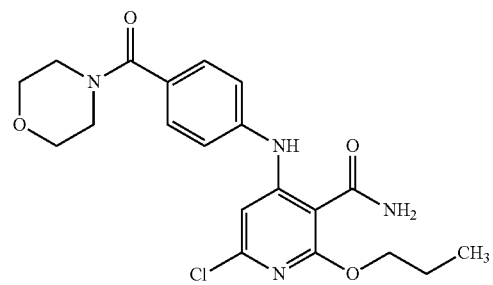 [SMILES: CCCOc1nc(Cl)cc(Nc2ccc(C(=O)N3CCOCC3)cc2)c1C(N)=O]

A mixture of powdered solid sodium hydroxide (121 mg, 3.04 mmol) in 1-propanol (10 mL) was stirred at rt until the solid material dissolved. Then 2,6-dichloro-4-(4-(morpholine-4-carbonyl)phenylamino)nicotinamide (600 mg, 1.518 mmol) was added and the mixture was stirred. The resulting suspension was placed in a heating block at 60° C. for 2 hrs. Next, the reaction mixture was cooled to rt and acidified with HCl (4 ml, 1N) and diluted with water. The cloudy precipitate was extracted into CH$_2$Cl$_2$ and concentrated to give 600 mg of light yellow solid. LCMS: (M+H)$^+$=419.20, 421.19 (Cl pattern).

D. (R)-tert-Butyl 1-(5-carbamoyl-4-(4-(morpholine-4-carbonyl)phenylamino)-6-propoxypyridin-2-yl)piperidin-3-ylcarbamate

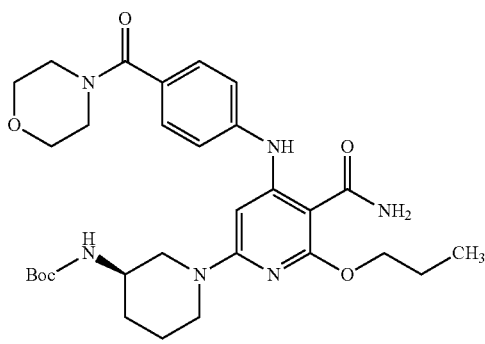 [SMILES: CCCOc1nc(N2CCC[C@@H](NC(=O)OC(C)(C)C)C2)cc(Nc2ccc(C(=O)N3CCOCC3)cc2)c1C(N)=O]

A mixture of 6-chloro-4-(4-(morpholine-4-carbonyl)phenylamino)-2-propoxynicotinamide (500 mg, 1.194 mmol) and (R)-tert-butyl piperidin-3-ylcarbamate (956 mg, 4.77 mmol) in THF (3 mL) was sealed in a vial and heated at 100° C. for 24 hrs. The reaction mixture was dissolved into ethyl acetate, washed with water, and concentrated. The solid material was chromatographed on an ISCO Companion 40 g silica gel column and eluted with (90:9:1 CH$_2$Cl$_2$:MeOH: NH$_4$OH)/CH$_2$Cl$_2$ gradient (10-100%) to give 530 mg of (R)-tert-butyl 1-(5-carbamoyl-4-(4-(morpholine-4-carbonyl)phenylamino)-6-propoxypyridin-2-yl)piperidin-3-ylcarbamate as a white solid. LCMS: (M+H)+=583.46.

E. (R)-6-(3-Aminopiperidin-1-yl)-4-(4-(morpholine-4-carbonyl)phenylamino)-2-propoxynicotinamide A solution of (R)-tert-butyl 1-(5-carbamoyl-4-(4-(morpholine-4-carbonyl)phenylamino)-6-propoxypyridin-2-yl)piperidin-3-ylcarbamate (530 mg, 0.910 mmol) in CH$_2$Cl$_2$ (5 mL) was treated with TFA (5 mL, 64.9 mmol) and stirred at rt for 1 hr. Solvent was removed by evaporation on a rotary evaporator. The residue was dissolved in CH$_2$Cl$_2$ and washed with NaHCO$_3$ and concentrated to give 380 mg of (R)-6-(3-aminopiperidin-1-yl)-4-(4-(morpholine-4-carbonyl)phenylamino)-2-propoxynicotinamide as a white solid. LCMS: (M+H)+=483.36. $^1$H NMR (400 MHz, CDCl$_3$) δ ppm 11.60 (1H, s), 7.94 (1H, br. s.), 7.41 (2H, d, J=8.35 Hz), 7.27 (2H, d, J=8.35 Hz), 6.03 (1H, s), 5.69 (1H, br. s.), 4.36 (2H, t, J=6.48 Hz), 4.06 (1 H, d, J=10.77 Hz), 3.86 (1H, d, J=12.96 Hz), 3.71 (8H, br. s.), 2.81-2.97 (2H, m), 2.75 (1H, dd, J=12.30, 9.23 Hz), 1.89-2.05 (1H, m), 1.80-1.88 (2H, m), 1.70-1.80 (1H, m), 1.53 (1H, ddd, J=10.44, 3.41, 3.30 Hz), 1.25-1.38 (1H, m), 1.05 (3H, t, J=7.36 Hz).

Example 25

(R)-6-(3-(3-(5-Methylthiazol-2-yl)ureido)piperidin-1-yl)-4-(4-(morpholine-4-carbonyl)phenylamino)-2-propoxynicotinamide

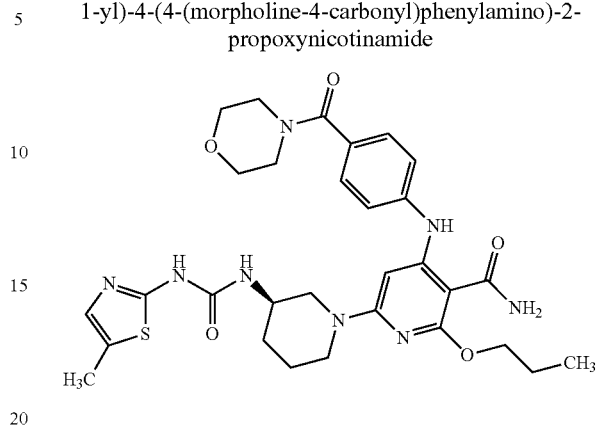

A mixture of (R)-6-(3-aminopiperidin-1-yl)-4-(4-(morpholine-4-carbonyl)phenylamino)-2-propoxynicotinamide (50 mg, 0.104 mmol), phenyl 5-methylthiazol-2-ylcarbamate (29.1 mg, 0.124 mmol), and Et$_3$N (0.014 mL, 0.104 mmol) in THF (3 mL) in a scintillation vial was stirred at 60° C. for 2 hrs, during which time a white precipitate forms. Left standing overnight at rt. The solid were dissolved in a mixture of CH$_2$Cl$_2$ and MeOH and crude mixture was chromatographed (loaded onto an ISCO Companion 40 g silica gel column and eluted with (90:9:1 CH$_2$Cl$_2$:MeOH: NH$_4$OH)/CH$_2$Cl$_2$ gradient (20-100%) to give 40 mg (R)-6-(3-(3-(5-methylthiazol-2-yl)ureido)piperidin-1-yl)-4-(4-(morpholine-4-carbonyl)phenylamino)-2-propoxynicotinamide as a white solid. LCMS: (M+H)$^+$=623.37. $^1$H NMR (400 MHz, CDCl$_3$) δ ppm 11.51 (1H, s), 7.93 (1H, br. s.), 7.38 (2H, d, J=8.57 Hz), 7.24 (2H, d, J=8.57 Hz), 6.80 (1H, s), 6.03 (1H, s), 5.94 (1H, br. s.), 4.23-4.37 (2H, m), 3.85-4.05 (2H, m), 3.55-3.82 (8H, m), 3.25-3.53 (4H, m), 2.32 (3H, s), 1.65-1.90 (5 H, m), 0.97 (3H, t, J=7.47 Hz).

Example 26

(R)-tert-Butyl 1-(5-carbamoyl-4-(4-(morpholine-4-carbonyl)phenylamino)pyridin-2-yl)piperidin-3-ylcarbamate

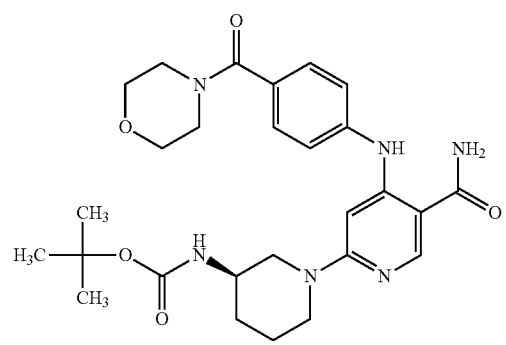 [SMILES: CC(C)(C)OC(=O)N[C@@H]1CCCN(c2cc(Nc3ccc(C(=O)N4CCOCC4)cc3)c(C(N)=O)cn2)C1]

A. Ethyl 6-chloro-4-(4-(morpholine-4-carbonyl)phenylamino)nicotinate

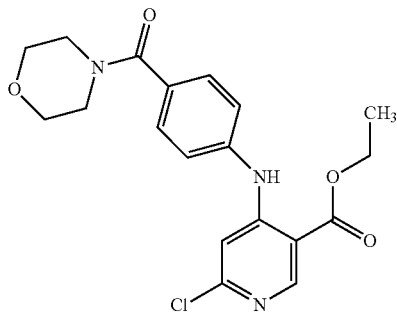 [SMILES: CCOC(=O)c1cnc(Cl)cc1Nc1ccc(C(=O)N2CCOCC2)cc1]

A mixture of ethyl 4,6-dichloronicotinate (500 mg, 2.272 mmol) and (4-aminophenyl)(morpholino)methanone (469 mg, 2.272 mmol) in N,N-Dimethylacetamide (5 mL) was treated with DIEA (0.794 mL, 4.54 mmol) and sealed in a large microwave vial and heated in a heating block at 120° C. overnight. The reaction mixture is removed from heating block, cooled to rt and diluted with water and extracted into CH$_2$Cl$_2$. Washed with water and concentrated to give dark oil which was chromatographed (ISCO Companion 40 g silica gel column and eluted with EtOAc/Hexane gradient (0-100%) to give 300 mg of ethyl 6-chloro-4-(4-(morpholine-4-carbonyl)phenylamino)nicotinate as a light yellow solid. LCMS: (M+H)$^+$=390.02, 392.02 (Cl pattern). $^1$H NMR (400 MHz, CDCl$_3$) δ ppm 1.43 (t, J=7.14 Hz, 3H) 3.74 (br. s, 8H) 4.41 (q, J=7.03 Hz, 2H) 7.00 (s, 1H) 7.30 (d, J=8.35 Hz, 2H) 7.51 (d, J=8.35 Hz, 2H) 8.80 (s, 1H) 9.99 (s, 1H).

B. 6-Chloro-4-(4-(morpholine-4-carbonyl)phenylamino)nicotinic acid

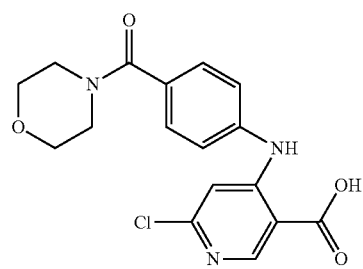 [SMILES: O=C(O)c1cnc(Cl)cc1Nc1ccc(C(=O)N2CCOCC2)cc1]

A solution of ethyl 6-chloro-4-(4-(morpholine-4-carbonyl)phenylamino)nicotinate (300 mg, 0.770 mmol) in EtOH (6 mL) and THF (6.00 mL) was treated with 30% aqueous sodium hydroxide (2 mL, 26.0 mmol) and stirred at rt for 3 hrs. Remove most of the solvent on rotary evaporator and acidified with 1N HCl (no precipitate formed) and extracted into CH$_2$Cl$_2$ several times and the combined extracts were concentrated to give 240 mg of 6-chloro-4-(4-(morpholine-4-carbonyl)phenylamino)nicotinic acid. LCMS: (M+H)$^+$=362.02, 363.93 (Cl pattern).

C. 6-Chloro-4-(4-(morpholine-4-carbonyl)phenylamino)nicotinamide

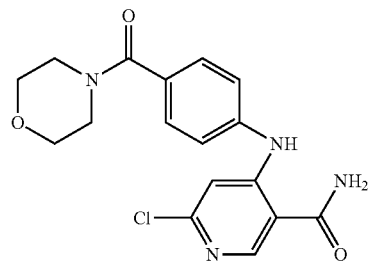 [SMILES: NC(=O)c1cnc(Cl)cc1Nc1ccc(C(=O)N2CCOCC2)cc1]

A mixture of 6-chloro-4-(4-(morpholine-4-carbonyl)phenylamino)nicotinic acid (280 mg, 0.774 mmol) in DMF (10 mL) was treated with NH$_4$OH 0.5 M solution in dioxane (7.74 mL, 3.87 mmol) and DIEA (0.676 mL, 3.87 mmol) to give a cloudy suspension. Then added HATU (589 mg, 1.548 mmol) and stirred at rt for 24 hrs. Diluted with water and extracted into ethyl acetate and washed with 10% LiCl and concentrated to give 230 mg of 6-chloro-4-(4-(morpholine-4-carbonyl)phenylamino)nicotinamide as a white solid. LCMS: (M+H)$^+$=361.03, 363.02 (Cl pattern).

D. (R)-tert-Butyl 1-(5-carbamoyl-4-(4-(morpholine-4-carbonyl)phenylamino) pyridin-2-yl)piperidin-3-ylcarbamate A solution of 6-chloro-4-(4-(morpholine-4-carbonyl)phenylamino)nicotinamide (230 mg, 0.637 mmol) and (R)-tert-butyl piperidin-3-ylcarbamate (166 mg, 0.829 mmol) in N-methyl-2-pyrrolidinone (2 mL) was treated with N-ethyl-N-isopropylpropan-2-amine (107 mg, 0.829 mmol) in a vial, sealed and heated in a heating block at 120° C. for 2 days. The mixture was diluted with ethyl acetate and washed with water. Concentrated and the dark residue was chromatographed (ISCO Companion 12 g silica gel column and eluted with ethyl acetate) to give 140 mg of (R)-tert-butyl 1-(5-carbamoyl-4-(4-(morpholine-4-carbonyl)phenylamino)pyridin-2-yl)piperidin-3-ylcarbamate as a white solid. LCMS: (M+H)+ =525.21. $^1$H NMR (400 MHz, CDCl$_3$) δ ppm 1.43 (s, 9H) 1.50-1.65 (m, 2H) 1.68-1.81 (m, 1H) 1.91 (d, J=10.77 Hz, 1H) 3.16-3.36 (m, 2H) 3.55-3.80 (m, 10H) 3.88 (dd, J=12.85, 3.41 Hz, 1H) 4.68 (d, J=6.81 Hz, 1H) 5.75 (s, 2H) 6.41 (s, 1H) 7.30 (d, J=8.57 Hz, 2H) 7.44 (d, J=8.57 Hz, 2H) 8.32 (s, 1H) 10.33 (s, 1H).

Example 27

(R)-6-(3-(3-(5-Methylthiazol-2-yl)ureido)piperidin-1-yl)-4-(4-(morpholine-4-carbonyl)phenylamino) nicotinamide

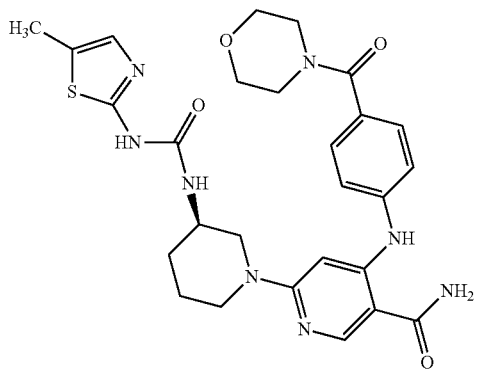 [SMILES: Cc1cnc(NC(=O)N[C@@H]2CCCN(c3cc(Nc4ccc(C(=O)N5CCOCC5)cc4)c(C(N)=O)cn3)C2)s1]

A. (R)-6-(3-Aminopiperidin-1-yl)-4-(4-(morpholine-4-carbonyl)phenylamino)nicotinamide

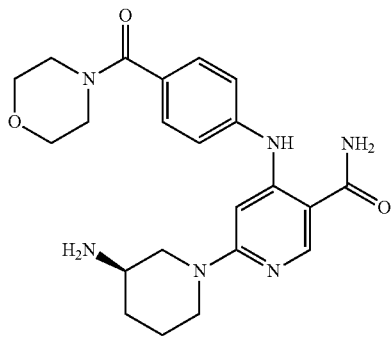 [SMILES: NC(=O)c1cnc(N2CCC[C@@H](N)C2)cc1Nc1ccc(C(=O)N2CCOCC2)cc1]

A solution of (R)-tert-butyl 1-(5-carbamoyl-4-(4-(morpholine-4-carbonyl)phenylamino)pyridin-2-yl)piperidin-3-ylcarbamate (110 mg, 0.210 mmol) in $CH_2Cl_2$ (2 mL) was treated with TFA (4 mL, 51.9 mmol) and stirred at rt for 4 hrs. The mixture is evaporated to dryness and the residue was dissolved in $CH_2Cl_2$ and washed with bicarbonate, water, and brine. Concentrated to give 72 mg of (R)-6-(3-aminopiperidin-1-yl)-4-(4-(morpholine-4-carbonyl)phenylamino)nicotinamide.

LCMS: $(M+H)^+$=425.15.

B. (R)-6-(3-(3-(5-Methylthiazol-2-yl)ureido)piperidin-1-yl)-4-(4-(morpholine-4-carbonyl)phenylamino)nicotinamide A mixture of (R)-6-(3-aminopiperidin-1-yl)-4-(4-(morpholine-4-carbonyl)phenylamino)nicotinamide (34 mg, 0.080 mmol) and phenyl 5-methylthiazol-2-ylcarbamate (24.39 mg, 0.104 mmol) in THF (2 mL) was added $Et_3N$ (0.015 mL, 0.104 mmol) and capped in a vial and stirred at rt overnight. The reaction mixture was chromatographed (ISCO Companion 40 g silica gel column and eluted with $NH_4OH$/MeOH/$CH_2Cl_2$ gradient (4-10%) to give 20 mg of (R)-6-(3-(3-(5-methylthiazol-2-yl)ureido)piperidin-1-yl)-4-(4-(morpholine-4-carbonyl)phenylamino)nicotinamide as a white solid. LCMS: $(M+H)+$=565.19. $^1$H NMR (400 MHz, $CDCl_3$) δ ppm 10.35 (1H, s), 8.36 (1H, br. s.), 7.40 (2H, d, J=8.35 Hz), 7.24 (2H, d, J=8.57 Hz), 6.83 (1H, s), 6.35 (1H, s), 3.31-4.02 (13H, m), 2.30 (3H, s), 1.94 (1H, br. s.), 1.53-1.80 (3H, m).

Example 28

2-((4-(Methylsulfonyl)phenyl)amino)-6-(1-piperidinyl)nicotinamide

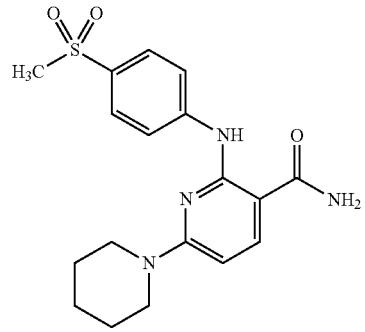 [SMILES: CS(=O)(=O)c1ccc(Nc2nc(N3CCCCC3)ccc2C(N)=O)cc1]

A. 6-Chloro-2-(4-(methylthio)phenylamino)nicotinamide

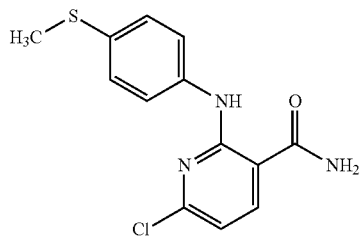 [SMILES: CSc1ccc(Nc2nc(Cl)ccc2C(N)=O)cc1]

A 1 M THF solution of LiHMDS (6.06 mL, 6.06 mmol) was added dropwise to a mixture of 2,6-dichloronicotinamide (331 mg, 1.733 mmol) and 4-(methylthio)aniline (289 mg, 2.079 mmol) in THF (20 mL) at 0° C. The resulting brown solution was stirred at 0° C. for 5 min, at room temperature for 30 min, quenched with saturated $NH_4Cl$ (50 mL) and extracted with EtOAc (3×25 mL). The combined extracts were washed with brine (5 mL), dried ($MgSO_4$), and concentrated. Silica gel chromatography, eluting with 30-70% EtOAc in hexanes, gave the desired product as tan solid (376 mg, 74% yield). LCMS: $(M+H)^+$=293.9. $^1$H NMR (400 MHz, chloroform-d) δ ppm 10.74 (1H, s), 7.54-7.73 (3H, m), 7.20-7.36 (2H, m), 6.68 (1H, d, J=8.03 Hz), 5.84 (2H, br. s.), 2.48 (3H, s).

B. 6-Chloro-2-(4-(methylsulfonyl)phenylamino)nicotinamide

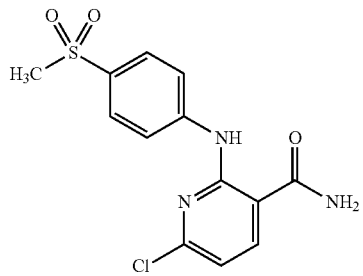 [SMILES: CS(=O)(=O)c1ccc(Nc2nc(Cl)ccc2C(N)=O)cc1]

A mixture of 6-chloro-2-(4-(methylthio)phenylamino)nicotinamide (356 mg, 1.212 mmol), 77% mCPBA (815 mg, 3.64 mmol) and acetic acid (15 mL) was stirred at room temperature for 5 h and concentrated. The residue was diluted with $CH_2Cl_2$ (150 mL), washed with 1 N $Na_2SO_3$ (2×25 mL), 1 N NaOH (2×25 mL), water (25 mL), brine (25 mL), dried ($MgSO_4$) and concentrated to give a white solid (371 mg, 94% yield). LCMS: $(M+H)^+$=325.9. $^1$H NMR (400 MHz, DMSO-$d_6$) δ ppm 11.82 (1H, s), 8.43 (1H, br. s.), 8.25 (1H, d, J=8.28 Hz), 7.76-8.01 (5H, m), 7.08 (1H, d, J=8.03 Hz), 3.17 (3H, s).

C. 2-((4-(Methylsulfonyl)phenyl)amino)-6-(1-piperidinyl)nicotinamide

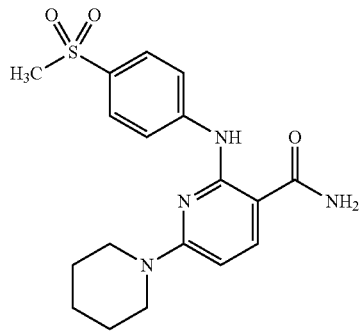 [SMILES: CS(=O)(=O)c1ccc(Nc2nc(N3CCCCC3)ccc2C(N)=O)cc1]

A mixture of 6-chloro-2-(4-(methylsulfonyl)phenylamino)nicotinamide (19.4 mg, 0.060 mmol) and piperidine (2 mL) in a sealed tube was stirred in a 90° C. oil bath for 5 h. The mixture was diluted with EtOAc (25 mL), washed with saturated NH$_4$Cl(2×5 mL), brine (5 mL), dried (MgSO$_4$), and concentrated. After addition of CH$_2$Cl$_2$ (2 mL), white solid precipitated from the solution upon sitting. The solid was collected by filtration (14.1 mg, 60%). LCMS: (M+H)$^+$=375.1. $^1$H NMR (400 MHz, acetone-d$_6$) δ ppm 12.20 (1H, s), 7.90-8.09 (3H, m), 7.78-7.89 (2H, m), 6.33 (1H, d, J=8.78 Hz), 3.58-3.89 (4H, m), 3.07 (3H, s), 1.52-1.85 (6H, m).

Example 29

2-((4-(Methylsulfonyl)phenyl)amino)-6-(3-phenyl-1-oxa-2,7-diazaspiro[4.5]dec-2-en-7-yl)nicotinamide

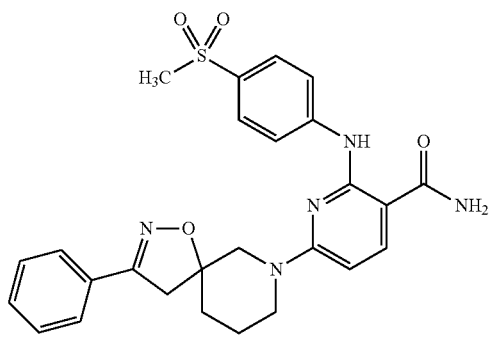 [SMILES: CS(=O)(=O)c1ccc(Nc2nc(N3CCCC4(CC(c5ccccc5)=NO4)C3)ccc2C(N)=O)cc1]

A. tert-Butyl 3-methylenepiperidine-1-carboxylate

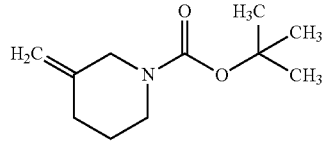

A 2.5 M hexane solution of n-BuLi (4.86 mL, 12.15 mmol) was added to a suspension of methyltriphenylphosphonium bromide (4.34 g, 12.15 mmol) in Et$_2$O (100 mL) at 0° C. The mixture was stirred at room temperature for 10 min. A solution of tert-butyl 3-oxopiperidine-1-carboxylate (2.2 g, 11.04 mmol) in ether (10 mL) was added dropwise. The resultant mixture was stirred at room temperature for 1 h, at reflux for 30 min, and cooled to room temperature. After the addition of water (30 mL), the two phases were separated. The aqueous phase was extracted with ether (3×60 mL). The combined ether extracts were washed with brine (20 mL), dried (MgSO$_4$) and concentrated. Silica gel chromatography, eluting with 0 to 15% ethyl acetate in hexane, gave a colorless liquid (1.0 g, 46%). $^1$H NMR (400 MHz, chloroform-d) δ ppm 4.61-4.96 (2H, m), 3.87 (2H, s), 3.25-3.55 (2H, m), 2.09-2.39 (2H, m), 1.54-1.73 (2H, m), 1.46 (9H, s).

B. tert-Butyl 3-phenyl-1-oxa-2,7-diazaspiro[4.5]dec-2-ene-7-carboxylate

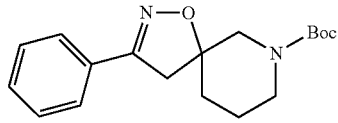 [SMILES: CC(C)(C)OC(=O)N1CCCC2(CC(c3ccccc3)=NO2)C1]

A 10% aqueous sodium hypochlorite solution (2.88 mL, 4.66 mmol) was added dropwise to a solution of tert-butyl 3-methylenepiperidine-1-carboxylate (230 mg, 1.166 mmol) and benzaldehyde oxime (282 mg, 2.332 mmol) in CH$_2$Cl$_2$ (5 mL) at 0° C. After 2 h at 0° C., the mixture was diluted CH$_2$Cl$_2$ (50 mL) and washed with water (10 mL). The aqueous phase was extracted with CH$_2$Cl$_2$ (3×20 mL). The combined organic extracts were washed with brine (10 mL), dried (MgSO$_4$) and concentrated. Silica gel chromatography, eluting with 0 to 15% ethyl acetate in hexanes, gave the expected product as a colorless oil (270 mg, 73% yield). LCMS: (M+Na)$^+$=339.12. $^1$H NMR (400 MHz, chloroform-d) δ ppm 7.55-7.79 (2H, m), 7.31-7.47 (3H, m), 3.57-3.93 (2H, m), 2.90-3.29 (4H, m), 1.78-2.04 (2H, m), 1.51-1.65 (2H, m), 1.46 (9H, s).

C. 3-Phenyl-1-oxa-2,7-diazaspiro[4.5]dec-2-ene

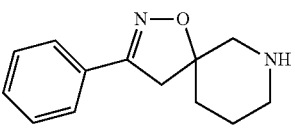 [SMILES: c1ccc(C2=NOC3(CCCNC3)C2)cc1]

Trifluoroacetic acid (2 mL, 26.0 mmol) was added dropwise to a solution of tert-butyl 3-phenyl-1-oxa-2,7-diazaspiro[4.5]dec-2-ene-7-carboxylate (270 mg, 0.853 mmol) in CH$_2$Cl$_2$ (5 mL) at room temperature. After 1 h at room temperature, the mixture was concentrated to give the expected product as TFA salt (280 mg, 99% yield). LCMS: (M+H)$^+$=217.15. $^1$H NMR (400 MHz, methanol-d$_4$) δ ppm 7.62-7.78 (2H, m), 7.36-7.51 (3H, m), 3.35-3.49 (4H, m), 3.00-3.24 (2H, m), 2.04-2.22 (2H, m), 1.85-2.07 (2H, m).

D. 2-((4-(Methylsulfonyl)phenyl)amino)-6-(3-phenyl-1-oxa-2,7-diazaspiro[4.5]dec-2-en-7-yl)nicotinamide

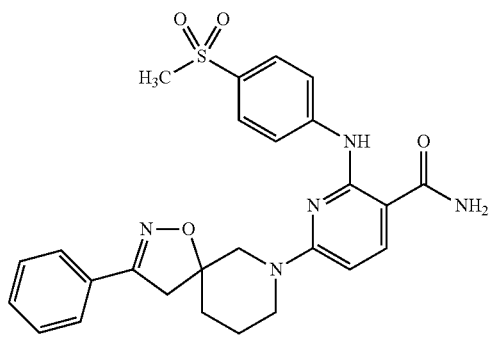 [SMILES: CS(=O)(=O)c1ccc(Nc2nc(N3CCCC4(CC(c5ccccc5)=NO4)C3)ccc2C(N)=O)cc1]

A mixture of 6-chloro-2-(4-(methylsulfonyl)phenylamino)nicotinamide (30 mg, 0.092 mmol), 3-phenyl-1-oxa-2,7-diazaspiro[4.5]dec-2-ene TFA salt (30.4 mg, 0.092 mmol) and N,N-diisopropylethylamine (0.064 mL, 0.368 mmol) in DMF (1 mL) was stirred at 120° C. for 20 h. The mixture was cooled to room temperature and purified by reverse phase HPLC, using Sunfire S10 30×250 mm column and eluting with 40% to 100% solvent B (10% MeOH-90% H$_2$O-0.1% TFA) in solvent A (90% MeOH-10% H$_2$O-0.1% TFA), to give a brown solid (12 mg, 21%). LCMS: (M+H)$^+$=506.10. $^1$H NMR (400 MHz, acetonitrile-d$_3$) δ ppm 7.69-7.80 (3H, m), 7.62-7.69 (2H, m), 7.55 (2H, d, J=9.03 Hz), 7.36-7.44 (3H, m), 6.28 (1H, d, J=9.04 Hz), 3.50-3.95 (4H, m), 3.08-3.38 (2H, m), 2.85 (3H, s), 2.01-2.13 (2H, m), 1.65-1.83 (2H, m).

Example 30

2-((3-(Methyl(phenylsulfonyl)amino)phenyl)amino)-6-(1-pyrrolidinyl)nicotinamide

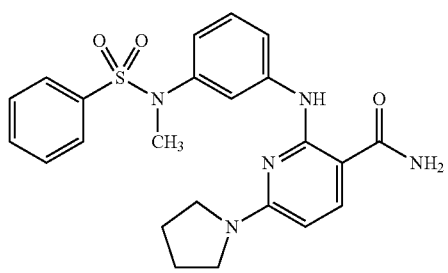 [SMILES: CN(c1cccc(Nc2nc(N3CCCC3)ccc2C(N)=O)c1)S(=O)(=O)c1ccccc1]

A. N-(3-nitrophenyl)benzenesulfonamide

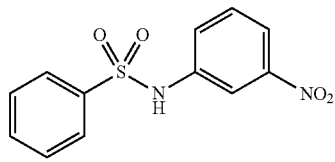 [SMILES: O=[N+]([O-])c1cccc(NS(=O)(=O)c2ccccc2)c1]

Benzenesulfonyl chloride (6.01 mL, 46.8 mmol) was added to a solution of 3-nitroaniline (6.47 g, 46.8 mmol) in pyridine (50 mL) at room temperature. The mixture was heated to 100° C. for 1 h. Most of the pyridine was evaporated under reduced pressure. The resulting brown oil was dissolved in CH$_2$Cl$_2$ (100 mL) and washed with aqueous HCl (150 mL, 50 mmol). A tan solid precipitated out from the acidic aqueous phase. The solid was collected by filtration, washed with CH$_2$Cl$_2$ and dried under vacuum (10.41 g, 80% yield). $^1$H NMR (400 MHz, DMSO-d$_6$) δ ppm 10.95 (1H, s), 7.93 (1H, s), 7.85-7.89 (1H, m), 7.79-7.83 (2H, m), 7.61-7.67 (1H, m), 7.49-7.61 (4H, m).

B. N-Methyl-N-(3-nitrophenyl)benzenesulfonamide

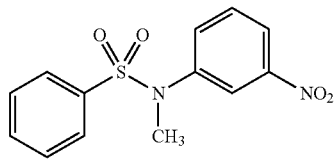 [SMILES: CN(c1cccc([N+](=O)[O-])c1)S(=O)(=O)c1ccccc1]

A 60% suspension of NaH (0.47 g, 11.75 mmol) was added to a solution of N-(3-nitrophenyl)benzenesulfonamide (2.56 g, 9.20 mmol) and iodomethane (2.61 g, 18.4 mmol) in DMF (50 mL) at room temperature. The yellow solution changed to a bright brown color. After 1.5 h at room temperature, the reaction mixture was quenched with careful addition of water (100 mL) and extracted with EtOAc (2×50 mL). The combined extracts were washed with saturated NH$_4$Cl, brine, dried (MgSO$_4$) and concentrated to give N-methyl-N-(3-nitrophenyl)benzenesulfonamide (3.09 g). LCMS: (M+MeCN+Na)$^+$=356.0. $^1$H NMR (400 MHz, DMSO-d$_6$) δ ppm 8.16 (1H, ddd, J=8.03, 2.26, 1.25 Hz), 7.94 (1H, t, J=2.13 Hz), 7.70-7.76 (1H, m), 7.66 (1H, t, J=8.03 Hz), 7.57-7.62 (3H, m), 7.52-7.56 (2H, m), 3.21 (3H, s).

C. N-(3-Aminophenyl)-N-methylbenzenesulfonamide

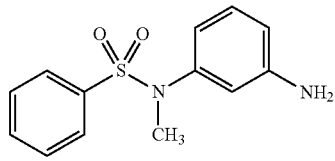

A suspension of N-methyl-N-(3-nitrophenyl)benzenesulfonamide (2.69 g, 9.20 mmol), zinc (6.02 g, 92 mmol) and ammonium chloride (4.92 g, 92 mmol) in MeOH (15 mL) and THF (15.00 mL) was stirred at room temperature for 15 h. The mixture was filtered through a short pad of CELITE® and the pad was washed with MeOH. The combined filtrate was concentrated and purified by silica gel chromatography, eluting with 0-60% EtOAc in hexanes to give a yellow oil (2.37 g, 98% yield). LCMS: (M+MeCN+H)$^+$=304.0. $^1$H NMR (400 MHz, DMSO-d$_6$) δ ppm 7.66-7.72 (1H, m), 7.52-7.61 (4H, m), 6.91 (1H, t, J=7.91 Hz), 6.44 (1H, dd, J=8.03, 1.25 Hz), 6.35 (1H, t, J=2.13 Hz), 6.10 (1H, dd, J=7.78, 1.25 Hz), 5.19 (2H, s), 3.05 (3H, s).

D. 6-Chloro-2-(3-(N-methylphenylsulfonamido) phenylamino)nicotinamide

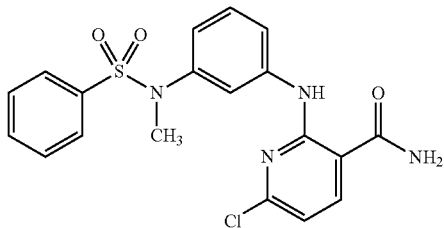 [SMILES: CN(c1cccc(Nc2nc(Cl)ccc2C(N)=O)c1)S(=O)(=O)c1ccccc1]

A 1 M THF solution of LiHMDS (2.302 mL, 2.302 mmol) was added dropwise to a suspension of 2,6-dichloronicotinamide (163 mg, 0.855 mmol) and N-(3-aminophenyl)-N-methylbenzenesulfonamide (172.5 mg, 0.658 mmol) in THF (3 mL) at room temperature. After 18 h at room temperature, the mixture was diluted with EtOAc and washed with saturated NH$_4$Cl (5 mL). The EtOAc phase was concentrated and purified by silica gel chromatography, eluting with 20-100% EtOAc in hexanes, to give a yellow solid (218.8 mg, 51% yield). LCMS: (M+H)$^+$=417.0.

$^1$H NMR (400 MHz, DMSO-d$_6$) δ ppm 11.42 (1H, s), 8.18 (1H, d, J=8.03 Hz), 7.99 (1H, d, J=8.03 Hz), 7.64 (1H, d), 7.55-7.59 (5H, m), 7.48-7.53 (2H, m), 7.28 (1H, t, J=8.03 Hz), 6.94 (1H, d, J=8.03 Hz), 6.75 (1H, d), 3.15 (3H, s).

E. 6-Chloro-2-(3-(N-methylphenylsulfonamido)phenylamino)nicotinamide

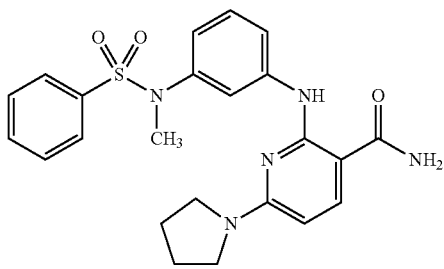 [SMILES: CN(c1cccc(Nc2nc(N3CCCC3)ccc2C(N)=O)c1)S(=O)(=O)c1ccccc1]

A solution of 6-chloro-2-(3-(N-methylphenylsulfonamido)phenylamino)nicotinamide (56.5 mg, 0.086 mmol) in pyrrolidine (0.5 mL) in a sealed tube was stirred at 80° C. for 2 h. The pyrrolidine was evaporated. The crude mixture was dissolved in TFA-MeOH and purified by reverse phase HPLC, using Sunfire S10 30×250 mm column and eluting with 70% to 100% solvent B (10% MeOH-90% H$_2$O-0.1% TFA) in solvent A (90% MeOH-10% H$_2$O-0.1% TFA), to give an off-white solid (27.4 mg, 47% yield), assumed as bis-TFA salt. LCMS: (M+H)$^+$=452.1. $^1$H NMR (400 MHz, chloroform-d) δ ppm 10.86 (1H, br. s.), 7.79 (1H, s), 7.53-7.65 (4H, m), 7.40-7.51 (3H, m), 7.22 (1H, t, J=8.03 Hz), 6.70 (2H, d, J=7.78 Hz), 6.44 (1H, br. s.), 5.87 (1H, d, J=8.78 Hz), 3.49 (4H, t, J=6.27 Hz), 3.18 (3H, s), 2.01 (4H, t, J=6.53 Hz).

Example 31

3-Fluoro-6-(4-(4-methylpiperazin-1-yl)phenylamino)-2,4'-bipyridine-5-carboxamide

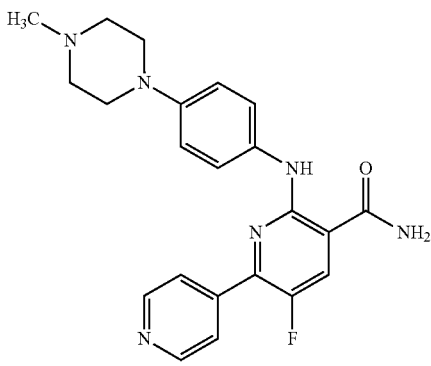 [SMILES: CN1CCN(c2ccc(Nc3nc(-c4ccncc4)c(F)cc3C(N)=O)cc2)CC1]

A. 6-Chloro-5-fluoro-2-(4-(4-methylpiperazin-1-yl) phenylamino)nicotinamide

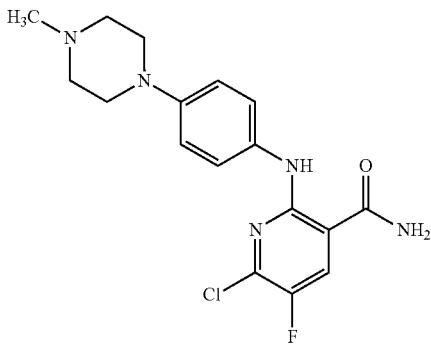 [SMILES: CN1CCN(c2ccc(Nc3nc(Cl)c(F)cc3C(N)=O)cc2)CC1]

To a mixture of 2,6-dichloro-5-fluoronicotinamide (1 g, 4.78 mmol) and 4-(4-methylpiperazin-1-yl)aniline (1.007 g, 5.26 mmol) in THF (30 mL) was added lithium bis(trimethylsilyl)amide (16.75 mL, 16.75 mmol) portionwise at −78° C. The mixture was stirred at −78° C. for 20 min and then removed from the dry ice bath. Next, the mixture was stirred at rt for 30 min. Two isomeric products were formed. The reaction mixture was quenched with water, extracted with ethyl acetate twice, washed the combined organic with water, and concentrated. The dark brown residue was triturated with methylene chloride, to give 570 mg of 2-chloro-5-fluoro-6-(4-(4-methylpiperazin-1-yl)phenylamino)nicotinamide as light brown solid. The mother liquor was concentrated and triturated again with methylene chloride to give 540 mg of 6-chloro-5-fluoro-2-(4-(4-methylpiperazin-1-yl)phenylamino)nicotinamide as brown solid. The mother liquor was purified twice by mPLC (ISCO, 7% ammonia/methanol/methylene chloride, 40 g+12 g stacked columns) to give an additional 490 mg of 6-chloro-5-fluoro-2-(4-(4-methylpiperazin-1-yl)phenylamino)nicotinamide as brown solid.

B. 3-Fluoro-6-(4-(4-methylpiperazin-1-yl)phenylamino)-2,4'-bipyridine-5-carboxamide A mixture of 6-chloro-5-fluoro-2-(4-(4-methylpiperazin-1-yl)phenylamino)nicotinamide (70 mg, 0.192 mmol), pyridin-4-ylboronic acid (23.65 mg, 0.192 mmol), K$_2$CO$_3$ (53.2 mg, 0.385 mmol) and Pd(Ph$_3$P)$_4$ (11.12 mg, 9.62 μmol) in THF (1 mL) was heated at 90° C. overnight in a sealed vial. The reaction mixture was extracted between saturated NaHCO$_3$ and methylene chloride, concentrated and the residue was purified by prep-HPLC. The product containing fractions were collected, basified with 1N NaOH, extracted with methylene chloride, concentrated to give 26 mg of product as orange-red solid. LC-MS: (M+H)$^+$=407.11. $^1$H NMR (400 MHz, chloroform-d$_{MIX}$) δ ppm 8.55-8.60 (2H, m), 7.91 (2H, d, J=5.71 Hz), 7.76 (1H, d, J=11.42 Hz), 7.52 (2H, d, J=9.23 Hz), 6.89 (2H, d, J=8.79 Hz), 3.08-3.16 (4H, m), 2.51-2.60 (4H, m), 2.29 (3H, s).

Example 32

5-Fluoro-2-(4-morpholinophenylamino)-6-(3-oxocyclohex-1-enyl)nicotinamide

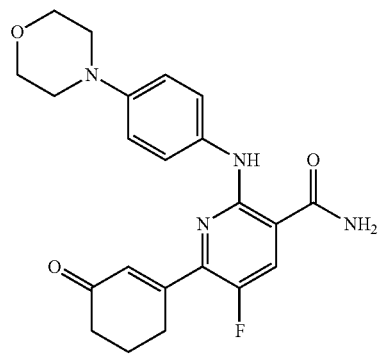 [SMILES: NC(=O)c1cc(F)c(C2=CC(=O)CCC2)nc1Nc1ccc(N2CCOCC2)cc1]

A solution of 6-chloro-5-fluoro-2-(4-morpholinophenylamino)nicotinamide (80 mg, 0.228 mmol), 3-(tributylstannyl)cyclohex-2-enone (105 mg, 0.274 mmol) (synthesized according to literature procedure: *Tet. Lett.*, 31:1837-1840 (1990)), and dichloro bis(triphenylphosphine)palladium (II) (16.05 mg, 0.023 mmol) in DMF (2 mL) was microwaved at 160° C. for 1 h. The reaction mixture was diluted with methylene chloride, washed with satd. NaHCO$_3$, water, and concentrated. The residue was purified prep-HPLC. The product containing fractions were collected, basified with 1N NaOH, and extracted with methylene chloride twice. The combined organic fractions were washed with water, concentrated, and further purified by MPLC (ISCO, 5% ammonia/methanol/methylene chloride, 40 g silica gel column) to give 22 mg brown solid. LC-MS: (M+H)$^+$=411.25. $^1$H NMR (500 MHz, DMSO-d$_6$) δ ppm 10.76-10.84 (1H, m), 8.28-8.39 (1H, m), 8.13-8.21 (1H, m), 7.83-7.91 (1H, m), 7.45-7.53 (2H, m), 6.88-6.96 (2H, m), 6.52-6.57 (1H, m), 3.67-3.77 (4H, m), 3.04 (4H, d, J=4.95 Hz), 2.76-2.85 (2H, m), 2.39-2.46 (2H, m), 2.01-2.09 (2H, m).

Example 33

5-Fluoro-2-(4-morpholinophenylamino)-6-(3-(3-thiazol-2-ylureido)cyclohex-1-enyl)nicotinamide

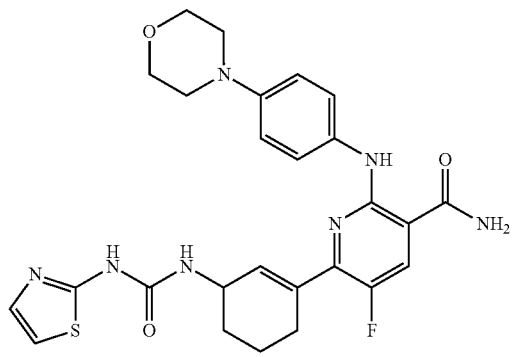 [SMILES: NC(=O)c1cc(F)c(C2=CC(NC(=O)Nc3nccs3)CCC2)nc1Nc1ccc(N2CCOCC2)cc1]

A. 6-(3-Aminocyclohex-1-enyl)-5-fluoro-2-(4-morpholinophenylamino)nicotinamide

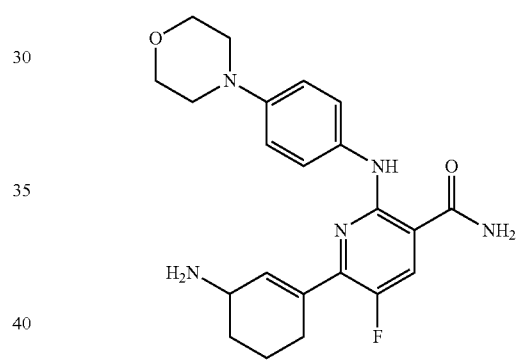

A solution of 5-fluoro-2-(4-morpholinophenylamino)-6-(3-oxocyclohex-1-enyl)nicotinamide (1.2 g, 2.92 mmol), ammonium acetate (2.254 g, 29.2 mmol) and titanium(IV) isopropoxide (2.57 mL, 8.77 mmol) in DMF (0.8 mL) was stirred at rt overnight. To the above solution were added sodium borohydride (0.221 g, 5.85 mmol) and 0.2 mL of MeOH. Violent bubbling occurred and the reaction mixture became warm. The reaction mixture was stirred at rt for 1 h. To the reaction mixture was added 1N NaOH (10 mL). A precipitate formed and was filtered through CELITE®, washed with a mixture of methylene chloride, and MeOH (50% each cosolvent) many times until the filter cake was white. The filtrate was washed with water; the aqueous fraction was back extracted 3 times with methylene chloride. The combined organic fractions were concentrated and the residue was purified by MPLC (ISCO, 5%-20% gradient ammonia/methanol/methylene chloride, 40 g silica gel column) to yield 105 mg of product as a yellow solid.

B. 5-Fluoro-2-(4-morpholinophenylamino)-6-(3-(3-thiazol-2-ylureido)cyclohex-1-enyl)nicotinamide A mixture of 6-(3-aminocyclohex-1-enyl)-5-fluoro-2-(4-morpholinophenylamino)nicotinamide (100 mg, 0.243 mmol), phenyl thiazol-2-ylcarbamate (80 mg, 0.365 mmol), and DIEA (0.085 mL, 0.486 mmol) in THF (2 mL) was stirred at rt overnight. The mixture was heated at 60° C. for 2 h to complete the reaction. The reaction mixture was diluted with methylene chloride, washed with satd. NaHCO$_3$ and water, and then concentrated. The residue was purified with MPLC (ISCO, 6% ammonia/MeOH/CH$_2$Cl$_2$, 40 g silica gel column) to give 65 mg of product as an orange solid. LC-MS: 2.76 min (RT). (M+H)$^+$=538.15. $^1$H NMR (400 MHz, chloroform-d$_{MIX}$) δ ppm 7.77 (1H, d, J=11.86 Hz), 7.60 (2H, d, J=9.23 Hz), 7.29 (1H, d, J=3.52 Hz), 6.94 (2H, d, J=9.23 Hz), 6.87 (1H, d, J=3.52 Hz), 6.57-6.62 (1H, m), 4.58-4.67 (1H, m), 3.84-3.93 (4H, m), 3.09-3.19 (4H, m), 2.54-2.64 (2H, m), 2.01-2.12 (1H, m), 1.79-1.95 (2H, m), 1.60-1.71 (1H, m).

The sample was separated on a chiral column: Chiralpak AS-H 25×3 cm, 5 μm; Column Temp. 40° C.; Flow rate: 150 mL/min; Mobile Phase: CO$_2$/MeOH=65/35; to give the two enantiomers. Example 33: (R)-5-fluoro-2-(4-morpholinophenylamino)-6-(3-(3-thiazol-2-ylureido)cyclohex-1-enyl)nicotinamide and Example 440: (S)-5-fluoro-2-(4-morpholinophenylamino)-6-(3-(3-thiazol-2-ylureido)cyclohex-1-enyl)nicotinamide.

Example 34

2-((3-(Methyl(methylsulfonyl)amino)-4-(4-morpholinylcarbonyl)phenyl)amino)-6-(4-morpholinyl)nicotinamide

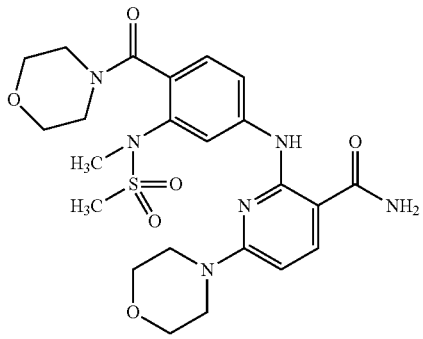 [SMILES: CN(c1cc(Nc2nc(N3CCOCC3)ccc2C(N)=O)ccc1C(=O)N1CCOCC1)S(C)(=O)=O]

A. (2-Amino-4-nitrophenyl)(morpholino)methanone

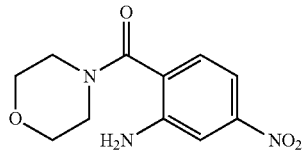 [SMILES: Nc1cc([N+](=O)[O-])ccc1C(=O)N1CCOCC1]

Morpholine (2.152 mL, 24.71 mmol) was added to a stirred suspension of 2-amino-4-nitrobenzoic acid (1.5 g, 8.24 mmol) and HATU (3.44 g, 9.05 mmol) in acetonitrile (15 mL) at room temperature. After 1 h at room temperature, the mixture was quenched with saturated NH$_4$Cl (50 mL) and extracted with EtOAc (100 mL). The EtOAc layer was washed with saturated NH$_4$Cl (10 mL) and brine (10 mL), dried (MgSO$_4$), and concentrated. The resulting syrup was triturated with hot CH$_2$Cl$_2$ and a yellow solid precipitated out. The solid was washed with CH$_2$Cl$_2$ and collected by filtration (1.7195 g, 83% yield). LCMS: (M+H)$^+$=252.0. $^1$H NMR (400 MHz, DMSO-d$_6$) δ ppm 7.54 (1H, d, J=2.26 Hz), 7.35 (1H, dd, J=8.28, 2.26 Hz), 7.24 (1 H, d, J=8.53 Hz), 5.86 (2H, s), 3.60 (8H, br. s.).

B. N-(2-(Morpholine-4-carbonyl)-5-nitrophenyl)methanesulfonamide

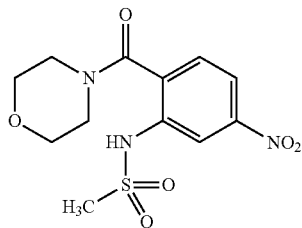 [SMILES: CS(=O)(=O)Nc1cc([N+](=O)[O-])ccc1C(=O)N1CCOCC1]

Methanesulfonyl chloride (0.179 mL, 2.302 mmol) was added to a solution of (2-amino-4-nitrophenyl)(morpholino)methanone (0.5783 g, 2.302 mmol) in pyridine (3 mL) at 0° C. After 30 min at 0° C., the pyridine solvent was evaporated under reduced pressure. The resulting brown oil was triturated with hot CH$_2$Cl$_2$ and filtered. The filtrate was concentrated and purified by silica gel chromatography, eluting with 30-100% EtOAc in hexanes, to give the expected product as yellow solid (108 mg, 14% yield). LCMS: (M+H)$^+$=330.0. $^1$H NMR (400 MHz, DMSO-d$_6$) δ ppm 9.83 (1H, s), 8.24 (1H, d, J=2.26 Hz), 8.07 (1H, dd, J=8.41, 1.88 Hz), 7.61 (1 H, d, J=8.53 Hz), 3.69 (2H, d, J=4.02 Hz), 3.61 (2H, br. s.), 3.57 (2H, d, J=4.27 Hz), 3.16-3.22 (2H, m), 3.10 (3H, s).

C. N-Methyl-N-(2-(morpholine-4-carbonyl)-5-nitrophenyl)methanesulfonamide

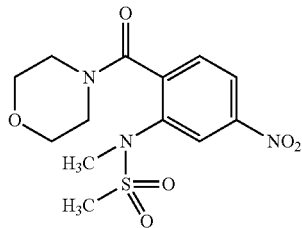 [SMILES: CN(c1cc([N+](=O)[O-])ccc1C(=O)N1CCOCC1)S(C)(=O)=O]

Iodomethane (0.040 mL, 0.643 mmol) was added to a solution of N-(2-(morpholine-4-carbonyl)-5-nitrophenyl)methanesulfonamide (108 mg, 0.321 mmol) and 60% suspension of NaH (16.5 mg, 0.413 mmol) in DMF (0.5 mL) at room temperature. After 1.5 h at room temperature, the mixture was carefully quenched with water (10 mL) and extracted with EtOAc (3×4 mL). The combined EtOAc phase was concentrated, purified by silica gel chromatography, and eluted with 10-100% EtOAc in hexanes to give a yellow oil (101.3 mg, 92% yield). LCMS: (M+H)$^+$=344.0. $^1$H NMR (400 MHz, DMSO-d$_6$) δ ppm 8.39 (1H, d, J=2.26 Hz), 8.27 (1H, dd, J=8.53, 2.26 Hz), 7.71 (1H, d, J=8.53 Hz), 3.69-3.78 (2H, m), 3.47-3.61 (4H, m), 3.10-3.30 (2H, m), 3.21 (3H, s), 3.17 (3H, s).

D. N-(5-Amino-2-(morpholine-4-carbonyl)phenyl)-N-methylmethanesulfonamide

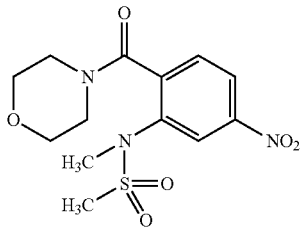 [SMILES: CN(c1cc([N+](=O)[O-])ccc1C(=O)N1CCOCC1)S(C)(=O)=O]

A suspension of N-methyl-N-(2-(morpholine-4-carbonyl)-5-nitrophenyl)methanesulfonamide (101.3 mg, 0.295 mmol), zinc (193 mg, 2.95 mmol), ammonium chloride (158 mg, 2.95 mmol) in MeOH (0.5 mL), and THF (0.5 mL) was stirred at room temperature for 16 h. The crude material was loaded onto a silica gel cartridge and dried in vacuo. The dry cartridge was then connected to an ISCO cartridge, eluting with 2-10% MeOH in $CH_2Cl_2$ to give the desired product as white solid (68.2 mg, 74% yield). LCMS: $(M+H)^+=314.0$. $^1H$ NMR (400 MHz, DMSO-$d_6$) δ ppm 6.94 (1H, d, J=8.28 Hz), 6.61 (1H, br. s.), 6.53 (1H, dd, J=8.28, 2.01 Hz), 5.52 (2H, s), 3.51 (4H, br. s.), 3.19-3.26 (1H, m), 3.15-3.18 (3H, m), 3.08 (3H, br. s.), 3.03 (3H, br. s.).

E. 6-Chloro-2-(3-(N-methylmethylsulfonamido)-4-(morpholine-4-carbonyl)phenylamino)nicotinamide

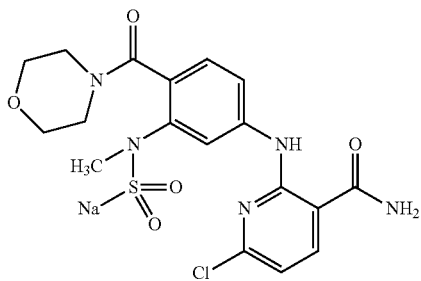

A 1 M THF solution of LiHMDS (0.762 mL, 0.762 mmol) was added dropwise to a suspension of 2,6-dichloronicotinamide (54.0 mg, 0.283 mmol) and N-(5-amino-2-(morpholine-4-carbonyl)phenyl)-N-methylmethanesulfonamide (68.2 mg, 0.218 mmol) in THF (0.5 mL) at 0° C. After 21 h at room temperature, LCMS analysis showed that the reaction was less than 50% complete. Additional portions of LiHMDS (0.054 mL) were added at 22, 23, and 24 h time points. After a total of 28 h, the mixture was quenched by saturated $NH_4Cl$ (2 mL) and extracted with EtOAc (3×2 mL). The combined extracts were loaded onto a silica gel cartridge and dried in vacuo. The dry cartridge was then connected to an ISCO cartridge and eluted with 30-100% EtOAc in hexanes, then 10% MeOH in $CH_2Cl_2$ to give a brown powder (59.3 mg, 58% yield). LCMS: $(M+H)^+=468.0$. $^1H$ NMR (400 MHz, DMSO-$d_6$) δ ppm 11.50 (1H, s), 8.38 (1H, br. s.), 8.21 (1H, d, J=8.28 Hz), 7.95 (1H, d, J=2.26 Hz), 7.85 (1H, br. s.), 7.55 (1H, dd, J=8.41, 2.13 Hz), 7.30 (1H, d, J=8.28 Hz), 7.01 (1H, d, J=8.03 Hz), 3.64-3.78 (2H, m), 3.45-3.59 (4H, m), 3.23 (2H, m), 3.16 (6H, s).

F. 2-((3-(Methyl(methylsulfonyl)amino)-4-(4-morpholinylcarbonyl)phenyl)amino)-6-(4-morpholinyl)nicotinamide

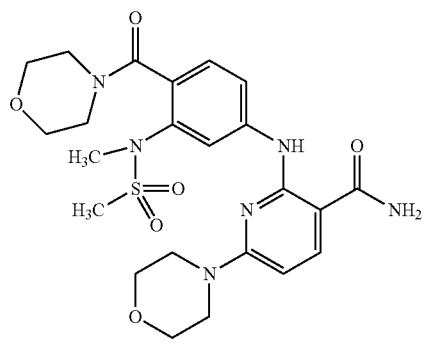 [SMILES: CN(c1cc(Nc2nc(N3CCOCC3)ccc2C(N)=O)ccc1C(=O)N1CCOCC1)S(C)(=O)=O]

A solution of 6-chloro-2-(3-(N-methylmethylsulfonamido)-4-(morpholine-4-carbonyl)phenylamino)nicotinamide (19 mg, 0.041 mmol) in morpholine (0.4 mL) in a sealed tube was stirred at 85° C. for 2 h. The morpholine was evaporated. The crude material was dissolved in 1 N aqueous HCl-MeOH (1:1, total 2 mL) and purified by reverse phase HPLC, using Shimadzu VP-ODS 20×100 mm column and eluting with 20% to 100% solvent B (10% MeOH-90% $H_2O$-0.1% TFA) in solvent A (90% MeOH-10% $H_2O$-0.1% TFA), to give the desired product as brown solid (11.7 mg, 38% yield) as bis-TFA salt. LCMS: $(M+H)^+=519.1$. $^1H$ NMR (400 MHz, methanol-$d_4$) δ ppm 8.06 (1H, d, J=2.26 Hz), 7.90 (1H, d, J=8.78 Hz), 7.48 (1H, dd, J=8.41, 2.13 Hz), 7.26 (1H, d, J=8.53 Hz), 6.25 (1H, d, J=9.03 Hz), 3.70-3.93 (7H, m), 3.56-3.69 (7H, m), 3.41 (2H, t, J=4.64 Hz), 3.26 (3H, s), 3.06 (3H, s).

Example 35

2-(4-(1,4-Dimethylpiperidin-4-yl)phenylamino)-5-fluoro-6-(3-phenyl-1-oxa-2,7-diazaspiro[4.5]dec-2-en-7-yl)nicotinamide

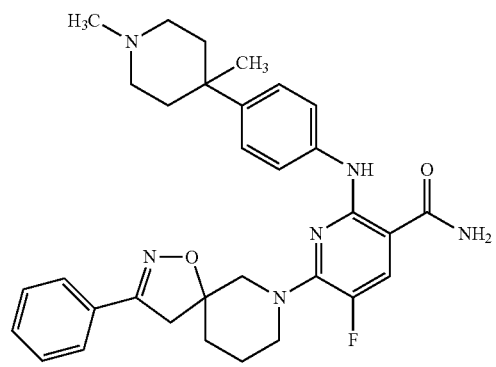 [SMILES: CN1CCC(C)(c2ccc(Nc3nc(N4CCCC5(CC(c6ccccc6)=NO5)C4)c(F)cc3C(N)=O)cc2)CC1]

A. Ethyl 4-(4-bromophenyl)-4-methylpiperidine-1-carboxylate

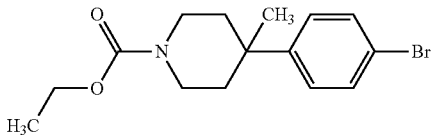

A mixture of ethyl 4-hydroxy-4-methylpiperidine-1-carboxylate (2.81 g, 15.01 mmol), bromobenzene (23.56 g, 150 mmol), and trifluoromethanesulfonic acid (22.52 g, 150 mmol) was stirred at room temperature for 3 h. The reaction mixture was poured into ice, basified with 1N NaOH, extracted with methylene chloride twice. The combined organic phases were washed with water and concentrated. The residue was purified by MPLC (ISCO, hexane/ethyl acetate, 80 g silica gel column) to give 4.28 g of product as a slightly yellow oil. LCMS: $(M+H)^+=326.01, 328.01$.

B. Ethyl 4-(4-aminophenyl)-4-methylpiperidine-1-carboxylate

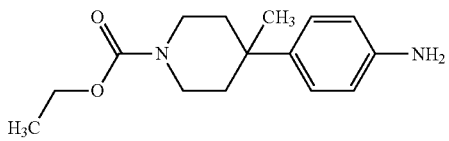

A mixture of ethyl 4-(4-bromophenyl)-4-methylpiperidine-1-carboxylate (2.0 g, 6.13 mmol), biphenyl-2-yldicyclohexylphosphine (0.054 g, 0.153 mmol), 1M LiHMDS in THF (12.26 ml, 12.26 mmol), and $Pd_2(dba)_3$ (0.056 g, 0.061 mmol) was heated in a sealed vial at 65° C. overnight. The mixture was cooled to room temperature and treated with 1N aq. HCl (30.7 mL, 30.7 mmol) and stirred for 5 min. The mixture made basic with 1N NaOH and extracted twice with methylene chloride. The combined organic extracts were concentrated and the residue was purified by MPLC (ISCO, hexane/ethyl acetate, 24+40 g stacked silica gel columns) to give 924 mg (57%) of product as a yellow oil.

C. 4-(1,4-Dimethylpiperidin-4-yl)aniline

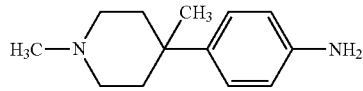

To a solution of ethyl 4-(4-aminophenyl)-4-methylpiperidine-1-carboxylate (444 mg, 1.692 mmol) in THF (10 mL) was added solid LAH (321 mg, 8.46 mmol) portion-wise. The formation of bubbles were observed during addition. The reaction mixture was stirred at room temperature for 20 min. The reaction mixture was diluted with methylene chloride and 15 mL of 1N NaOH was added slowly to destroy excess LAH. The resulting mixture was separated by separatory funnel. The organic layer was washed with water and concentrated. The residue was purified by MPLC (ISCO, 6% ammonia/MeOH/$CH_2Cl_2$, 40 g silica gel column) to give 267 mg colorless oil. $(M+H)^+=205.18$.

D. 6-Chloro-2-(4-(1,4-dimethylpiperidin-4-yl)phenylamino)-5-fluoronicotinamide

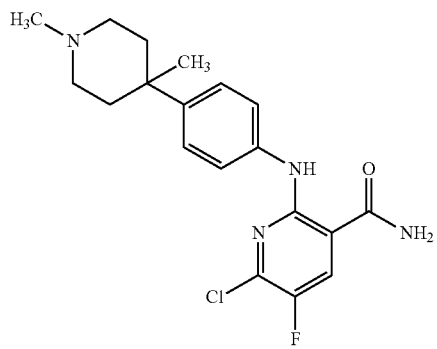 [SMILES: CN1CCC(C)(c2ccc(Nc3nc(Cl)c(F)cc3C(N)=O)cc2)CC1]

To a solution of 2,6-dichloro-5-fluoronicotinamide (287 mg, 1.372 mmol) and 4-(1,4-dimethylpiperidin-4-yl)aniline (267 mg, 1.307 mmol) in THF (10 mL) was added lithium bis(trimethylsilyl)amide (4.57 mL, 4.57 mmol) at room temperature. After 30 min, the reaction was quenched by the addition of satd. $NH_4Cl$. The mixture was extracted with methylene chloride twice, the combined organic layers were washed with water and brine, and then concentrated. The residue was purified by MPLC (ISCO, 6-10% ammonia/methanol/methylene chloride, 40 g silica gel column) to give 229 mg of product as yellow solid.

E. 2-(4-(1,4-Dimethylpiperidin-4-yl)phenylamino)-5-fluoro-6-(3-phenyl-1-oxa-2,7-diazaspiro[4.5]dec-2-en-7-yl)nicotinamide A solution of 6-chloro-2-(4-(1,4-dimethylpiperidin-4-yl)phenylamino)-5-fluoronicotinamide (40 mg, 0.106 mmol), 3-phenyl-1-oxa-2,7-diazaspiro[4.5]dec-2-ene (42.1 mg, 0.127 mmol), and DIEA (0.074 mL, 0.425 mmol) in NMP (1 mL) was heated at 120° C. for 3 h and at 130° C. for 2 h. The reaction mixture was cooled, diluted with water. The resulting brown solid precipitate was filtered and purified by prep-HPLC. The product containing fractions were collected, basified with 1N NaOH, and extracted with methylene chloride twice. The combined organic factions were washed with water and concentrated to give 12 mg yellow solid. LC-MS: 3.04 min (RT). $(M+H)^+=557.28$. $^1H$ NMR (400 MHz, chloroform-d) δ ppm 10.66 (1H, s), 7.67 (2H, dd, J=6.81, 2.86 Hz), 7.50 (2H, d, J=8.79 Hz), 7.36-7.44 (3H, m), 7.22-7.25 (1H, m), 7.13 (2H, d, J=8.79 Hz), 5.43 (2H, br. s.), 3.79-3.90 (2H, m), 3.69-3.75 (1H, m), 3.57-3.67 (1H, m), 3.32 (1H, d, J=16.70 Hz), 3.05 (1H, d, J=16.70 Hz), 2.27-2.45 (4H, m), 2.22 (3H, s), 1.92-2.13 (4H, m), 1.57-1.79 (4H, m), 1.12 (3 H, s).

The compounds in Tables 1 to 43 were prepared by procedures analogous to those described above. The molecular mass of the compounds were determined by MS (ES) by the formula m/z.

TABLE 1
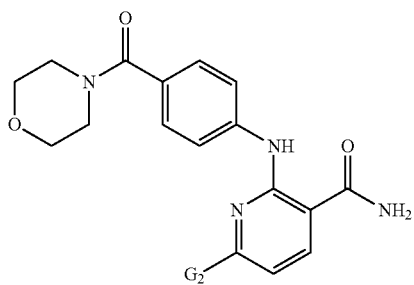
| Ex. | G₂ | FW | (M + H)⁺ Obs. MS |
|---|---|---|---|
| 36 | 4-Cl-phenyl | 436.89 | 437.22 |
| 37 | 3-(4-t-Bu-benzamido)phenyl | 577.67 | 578.43 |
| 38 | 3-aminophenyl | 417.46 | 418.27 |
| 39 | (R)-3-(4-t-Bu-benzamido)piperidin-1-yl | 584.71 | 585.50 |
| 40 | 3-phenylpyrrolidin-1-yl | 471.55 | 472.37 |
| 41 | 2-(N-Boc-N-isopropylamino)thiazol-5-yl | 566.67 | 567.41 |
| 42 | 2-(isopropylamino)thiazol-5-yl | 466.56 | 467.15 |
| 43 | (R)-3-(4-CF₃-benzamido)piperidin-1-yl | 596.60 | 597.42 |

TABLE 1-continued

| Ex. | G₂ | FW | (M + H)⁺ Obs. MS |
|---|---|---|---|
| 44 | t-BuO-C(O)-NH-pyrrolidinyl | 510.59 | 511.38 |
| 45 | H₂N-pyrrolidinyl | 410.47 | 411.30 |
| 46 | 3-CF₃-C₆H₄-C(O)-NH-piperidinyl | 596.60 | 597.39 / 597.08 |
| 47 | H₃C-C(O)-NH-piperidinyl | 466.53 | 467.32 |
| 48 | (H₃C)₂CH-C(O)-NH-piperidinyl | 494.59 | 495.40 |
| 49 | 2-CF₃-C₆H₄-C(O)-NH-piperidinyl | 596.60 | 597.33 |
| 50 | 4-CF₃-C₆H₄-C(O)-NH-pyrrolidinyl | 582.57 | 583.41 |
| 51 | cyclohexyl-C(O)-NH-piperidinyl | 534.65 | 535.41 |

TABLE 1-continued
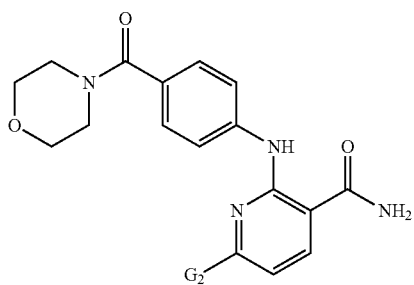
| Ex. | G₂ | FW | (M + H)⁺ Obs. MS |
|---|---|---|---|
| 52 | (benzamido-pyrrolidinyl) | 514.58 | 515.37 |
| 53 | (phenylureido-piperidinyl) | 543.62 | 544.43 |
| 54 | (t-BuO-carbonyl-piperidinyl-carboxamido-piperidinyl) | 635.75 | 636.50 |
| 55 | (piperidinyl-carboxamido-piperidinyl) | 535.64 | 536.44 |
| 56 | (3-methoxyphenyl-ureido-piperidinyl) | 573.64 | 574.41 |
| 57 | (benzamido-phenyl) | 521.57 | 522.28 |
| 58 | (piperidinyl) | 409.48 | 410.34 |
| 59 | (phenyl) | 402.45 | 403.23 |

TABLE 1-continued

| Ex. | G₂ | FW | (M + H)⁺ Obs. MS |
|---|---|---|---|
| 60 | | 564.66 | 565.38 |
| 61 | | 548.59 | 549.39 |
| 62 | | 542.63 | 543.37 |
| 63 | | 473.52 | 474.31 |
| 64 | | 549.28 | 550.29 |
| 65 | | 535.59 | 536.28 |
| 66 | | 611.79 | 612.26 |
| 67 | | 495.55 | 496.20 |

TABLE 1-continued

| Ex. | G₂ | FW | (M + H)⁺ Obs. MS |
|---|---|---|---|
| 68 | | 547.61 | 548.35 |
| 69 | | 578.69 | 579.32 |
| 70 | | 636.72 | 637.32 |
| 71 | | 431.49 | 432.25 |
| 72 | | 565.65 | 566.29 |
| 73 | | 619.62 | 620.21 |
| 74 | | 564.66 | 565.24 |
| 75 | | 535.59 | 536.24 |

TABLE 1-continued

| Ex. | G₂ | FW | (M + H)⁺ Obs. MS |
|---|---|---|---|
| 76 | 5-amino-2-methylphenyl | 431.49 | 432.21 |
| 77 | 3-(phenylsulfonylamino)-4-methylphenyl | 571.65 | 572.12 |
| 78 | 3-(3-phenylureido)-2-methylphenyl | 550.61 | 551.15 |
| 79 | 3-benzamido-4-methylphenyl | 535.59 | 536.15 |
| 80 | 3-(phenylsulfonylamino)-2-methylphenyl | 571.65 | 572.10 |
| 81 | (3R)-3-[3-(3-methylisoxazol-5-yl)ureido]piperidin-1-yl | 548.59 | 549.19 |
| 82 | (3R)-3-[3-(5-bromothiazol-2-yl)ureido]piperidin-1-yl | 629.53 | 630.96 |

TABLE 1-continued
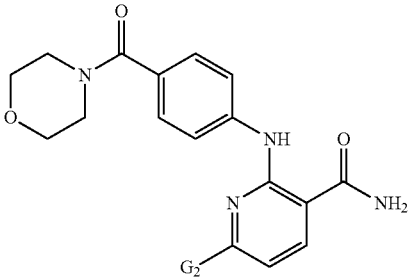
| Ex. | G₂ | FW | (M + H)⁺ Obs. MS |
|---|---|---|---|
| 83 | 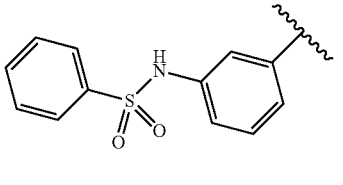 [SMILES: *c1cccc(NS(=O)(=O)c2ccccc2)c1] | 557.62 | 558.08 |
| 84 | 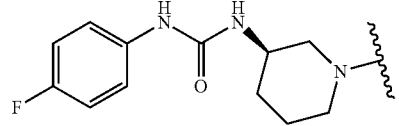 [SMILES: *N1CCC[C@@H](NC(=O)Nc2ccc(F)cc2)C1] | 431.49 | 432.08 |
| 85 | 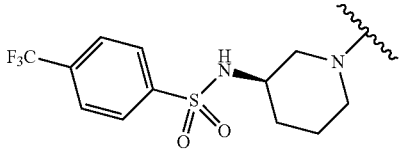 [SMILES: *N1CCC[C@@H](NS(=O)(=O)c2ccc(C(F)(F)F)cc2)C1] | 561.62 | 561.97 |
| 86 | 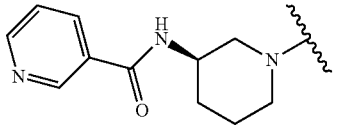 [SMILES: *N1CCC[C@@H](NC(=O)c2cccnc2)C1] | 632.66 | 632.94 |
| 87 | 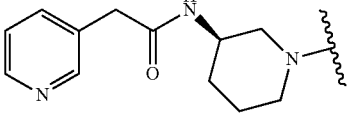 | 529.60 | 529.98 |
| 88 | 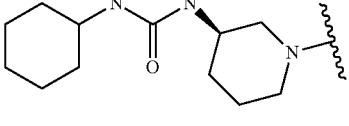 | 543.63 | 544.01 |
| 89 | 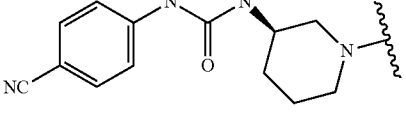 | 549.67 | 549.96 |
| 90 | | 568.64 | 568.91 |

TABLE 1-continued
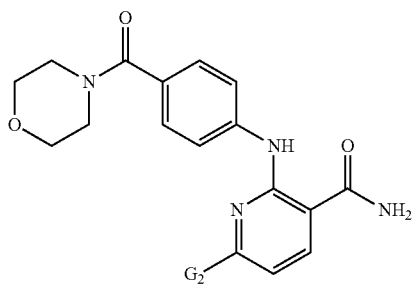
| Ex. | G₂ | FW | (M + H)⁺ Obs. MS |
|---|---|---|---|
| 91 | [2-CF₃-phenyl-NH-C(O)-NH-(3-piperidinyl)] | 611.62 | 611.90 |
| 92 | [3-CF₃-phenyl-NH-C(O)-NH-(3-piperidinyl)] | 611.62 | 611.91 |
| 93 | [4-CF₃-phenyl-NH-C(O)-NH-(3-piperidinyl)] | 611.62 | 611.90 |
| 94 | [phenethyl-NH-C(O)-NH-(3-piperidinyl)] | 571.68 | 571.96 |
| 95 | [4-t-Bu-phenyl-NH-C(O)-NH-(3-piperidinyl)] | 599.73 | 600.00 |
| 96 | [benzyl-NH-C(O)-NH-(3-piperidinyl)] | 557.65 | 557.94 |
| 97 | [2-CF₃-phenyl-SO₂-NH-(3-piperidinyl)] | 632.66 | 632.88 |
| 98 | [3-CF₃-phenyl-SO₂-NH-(3-piperidinyl)] | 632.66 | 632.86 |

TABLE 1-continued

| Ex. | G₂ | FW | (M + H)⁺ Obs. MS |
|---|---|---|---|
| 99 | thiophene-2-sulfonamide-(3-piperidinyl) | 570.69 | 570.79 |
| 100 | 3,5-dimethylisoxazole-4-sulfonamide-(3-piperidinyl) | 583.67 | 583.89 |
| 101 | N-(3,4-dimethylphenyl)-N'-(3-piperidinyl)urea | 571.68 | 571.95 |
| 102 | N-(4-chlorophenyl)-N'-(3-piperidinyl)urea | 578.07 | 577.84 |
| 103 | N-(furan-2-ylmethyl)-N'-(3-piperidinyl)urea | 547.61 | 574.90 |
| 104 | N-cyclopentyl-N'-(3-piperidinyl)urea | 535.65 | 535.95 |
| 105 | N-(pyridin-3-yl)-N'-(3-piperidinyl)urea | 544.61 | 544.91 |
| 106 | N-(3-(methylthio)phenyl)-N'-(3-piperidinyl)urea | 589.72 | 589.91 |

TABLE 1-continued
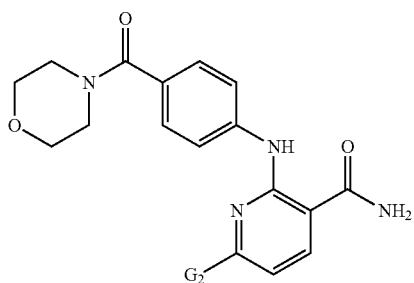
| Ex. | G₂ | FW | (M + H)⁺ Obs. MS |
|---|---|---|---|
| 107 | | 568.66 | 568.88 |
| 108 | | 567.65 | 567.95 |
| 109 | | 563.68 | 563.94 |
| 110 | | 544.61 | 544.96 |
| 111 | | 546.63 | 546.96 |
| 112 | | 519.56 | 519.94 |
| 113 | | 535.63 | 535.89 |

TABLE 1-continued

| Ex. | G₂ | FW | (M + H)⁺ Obs. MS |
|---|---|---|---|
| 114 | 5-methylisoxazole-3-carboxamide-N-(piperidin-3-yl) | 533.59 | 533.90 |
| 115 | 2,5-dimethyloxazole-4-carboxamide-N-(piperidin-3-yl) | 547.61 | 547.96 |
| 116 | isonicotinamide-N-(piperidin-3-yl) | 529.60 | 529.94 |
| 117 | pyridazine-4-carboxamide-N-(piperidin-3-yl) | 530.59 | 530.89 |
| 118 | 1,5-dimethyl-1H-pyrazole-3-carboxamide-N-(piperidin-3-yl) | 546.63 | 546.96 |
| 119 | 2-(1-methyl-1H-indol-3-yl)-N-(piperidin-3-yl)acetamide | 595.70 | 596.00 |
| 120 | pyrimidine-5-carboxamide-N-(piperidin-3-yl) | 530.59 | 530.90 |

TABLE 1-continued

| Ex. | G₂ | FW | (M + H)⁺ Obs. MS |
|---|---|---|---|
| 121 | [1-methylimidazole-2-carboxamide-N-(piperidin-3-yl)] | 532.60 | 532.94 |
| 122 | [oxazole-5-carboxamide-N-(piperidin-3-yl)] | 519.56 | 519.89 |
| 123 | [4-methoxyphenyl] | 432.48 | 432.92 |
| 124 | [4-phenoxyphenyl] | 494.55 | 494.94 |
| 125 | [3-methoxyphenyl] | 432.48 | 432.94 |
| 126 | [2-methoxyphenyl] | 432.48 | 432.94 |
| 127 | [3-ethoxyphenyl] | 446.50 | 446.95 |
| 128 | [3-hydroxyphenyl] | 418.45 | 418.92 |
| 129 | [4-acetylphenyl] | 444.49 | 474.98 |

TABLE 1-continued
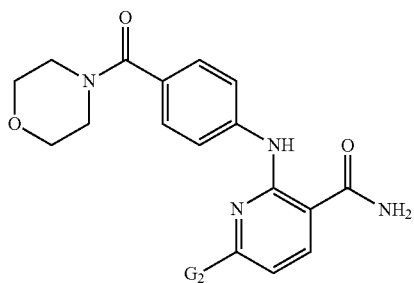
| Ex. | G₂ | FW | (M + H)⁺ Obs. MS |
|---|---|---|---|
| 130 | 3-acetylphenyl | 444.49 | 444.91 |
| 131 | 5-isopropyl-2-methoxyphenyl | 474.56 | 474.98 |
| 132 | 2-acetylphenyl | 444.49 | 444.92 |
| 133 | 4-methoxy-3-methylphenyl | 446.50 | 446.95 |
| 134 | 4-(N,N-dimethylcarbamoyl)phenyl | 473.53 | 473.94 |
| 135 | 4-(tert-butoxycarbonyl)phenyl | 502.57 | 502.95 |
| 136 | 3-(N,N-dimethylcarbamoyl)phenyl | 473.53 | 473.92 |
| 137 | 4-methoxy-2,6-dimethylphenyl | 460.53 | 460.95 |

TABLE 1-continued
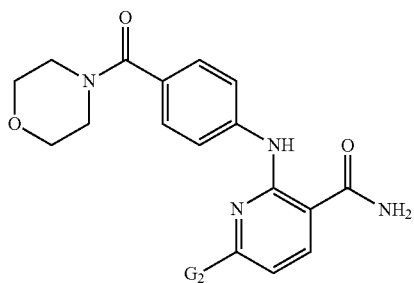
| Ex. | G₂ | FW | (M + H)⁺ Obs. MS |
|---|---|---|---|
| 138 | 3-(N-methylcarbamoyl)phenyl | 459.50 | 459.95 |
| 139 | 4-(N-(furan-2-ylmethyl)carbamoyl)phenyl | 525.56 | 525.90 |
| 140 | 3-(pyrrolidine-1-carbonyl)phenyl | 499.57 | 499.97 |
| 141 | 3-(3-(pyridin-2-yl)ureido)piperidin-1-yl | 544.61 | 545.50 |
| 142 | 3-chloro-4-fluorophenyl | 454.89 | 454.85 |
| 143 | 4-chloro-3-(trifluoromethyl)phenyl | 504.89 | 504.85 |
| 144 | 3-chloro-4-isopropoxyphenyl | 494.98 | 494.88 |
| 145 | 3-chloro-4-methoxyphenyl | 466.92 | 466.85 |

TABLE 1-continued
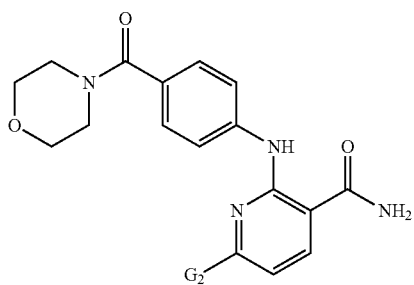
| Ex. | G$_2$ | FW | (M + H)$^+$ Obs. MS |
|---|---|---|---|
| 146 | 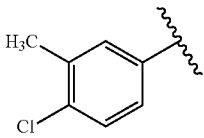 [SMILES: *c1ccc(Cl)c(C)c1] | 450.92 | 450.86 |
| 147 | 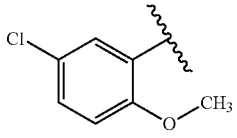 [SMILES: *c1cc(Cl)ccc1OC] | 466.92 | 466.86 |
| 148 | 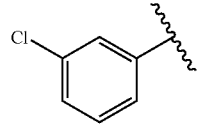 [SMILES: *c1cccc(Cl)c1] | 436.90 | 436.86 |
| 149 | 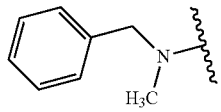 | 445.51 | 446.06 |
| 150 | 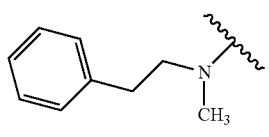 [SMILES: *N(C)CCc1ccccc1] | 459.54 | 460.12 |
| 151 | 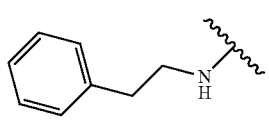 | 445.51 | 446.12 |
| 152 | 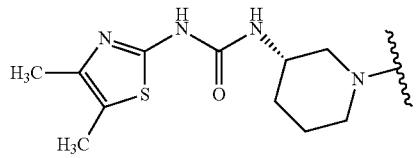 [SMILES: *N1CCC[C@H](NC(=O)Nc2nc(C)c(C)s2)C1] | 578.69 | 579.09 |
| 153 | 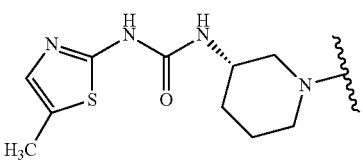 [SMILES: *N1CCC[C@H](NC(=O)Nc2ncc(C)s2)C1] | 564.66 | 565.05 |

TABLE 1-continued
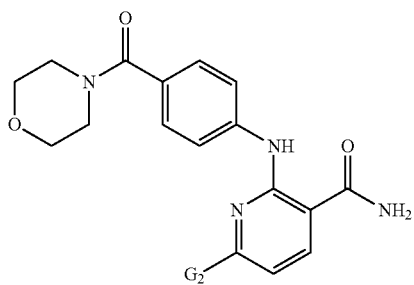
| Ex. | G₂ | FW | (M + H)⁺ Obs. MS |
|---|---|---|---|
| 154 | 3-cyano-4-fluorophenyl | 445.45 | 446.03 |
| 155 | 2,3-dichlorophenyl | 471.34 | 472.45 |
| 156 | 3-cyanophenyl | 427.46 | 427.86 |
| 157 | 4-cyanophenyl | 427.46 | 427.86 |
| 158 | (3-thiazol-2-yl-ureido)piperidinyl | 550.63 | 551.08 |
| 159 | (3-[1,3,4]thiadiazol-2-yl-ureido)piperidinyl | 551.62 | 552.03 |
| 160 | (3-(5-methylthiazol-2-yl)-ureido)pyrrolidinyl | 550.63 | 551.07 |
| 161 | 3-(4-tert-butylbenzoylamino)-2-methylphenyl | 591.70 | 592.23 |

TABLE 1-continued

| Ex. | G₂ | FW | (M + H)⁺ Obs. MS |
|---|---|---|---|
| 162 | t-Bu-C₆H₄-C(O)NH-aryl(CH₃)- | 591.70 | 592.21 |
| 163 | t-Bu-C₆H₄-NHC(O)-pyrrolidinyl- | 570.68 | 571.33 |
| 164 | t-Bu-C₆H₄-NHC(O)-piperidinyl- | 584.71 | 585.32 |
| 165 | HOOC-piperidinyl- | 453.49 | 454.16 |
| 166 | HOOC-pyrrolidinyl- | 439.46 | 440.16 |
| 167 | Ph-NHC(O)-pyrrolidinyl- | 514.02 | 551.24 |
| 168 | biphenyl-C(O)NH-piperidinyl- | 604.70 | 605.43 |
| 169 | (3-pyridyl)phenyl-C(O)NH-piperidinyl- | 605.69 | 606.44 |

TABLE 1-continued

| Ex. | G₂ | FW | (M + H)⁺ Obs. MS |
|---|---|---|---|
| 170 | [3-(1H-pyrazol-1-yl)phenyl]-C(O)NH-piperidinyl | 594.66 | 595.43 |
| 171 | [3-(thiophen-2-yl)phenyl]-C(O)NH-piperidinyl | 610.73 | 611.41 |
| 172 | [3,5-dimethoxyphenyl]-C(O)NH-piperidinyl | 588.66 | 589.14 |
| 173 | [3-hydroxyphenyl]-C(O)NH-piperidinyl | 544.61 | 545.11 |
| 174 | [3,5-dihydroxyphenyl]-C(O)NH-piperidinyl | 560.61 | 561.09 |
| 175 | [3-benzoylphenyl]-C(O)NH-piperidinyl | 632.72 | 633.15 |

TABLE 1-continued

| Ex. | G₂ | FW | (M + H)⁺ Obs. MS |
|---|---|---|---|
| 176 | 3-methylbenzamide-piperidinyl | 542.64 | 543.15 |
| 177 | 3,5-dimethylbenzamide-piperidinyl | 556.66 | 557.16 |
| 178 | naphthalene-2-carboxamide-piperidinyl | 578.67 | 579.11 |
| 179 | 6-methylpyridine-3-carboxamide-piperidinyl | 543.63 | 544.11 |
| 180 | 3,4-difluorobenzamide-piperidinyl | 564.59 | 565.09 |
| 181 | 3-acetamidobenzamide-piperidinyl | 585.66 | 586.13 |
| 182 | 3-(methoxycarbonyl)benzamide-piperidinyl | 586.65 | 587.10 |

TABLE 1-continued
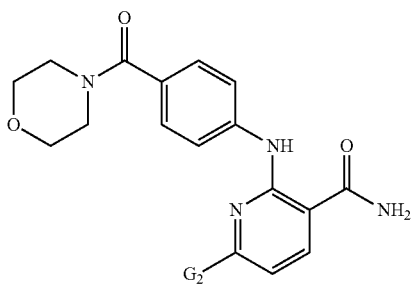
| Ex. | G2 | FW | (M + H)+ Obs. MS |
|---|---|---|---|
| 183 | | 604.71 | 605.10 |
| 184 | | 570.65 | 571.14 |
| 185 | | 579.66 | 580.11 |
| 186 | | 612.71 | 613.10 |
| 187 | | 576.63 | 577.10 |
| 188 | | 614.60 | 615.09 |
| 189 | | 640.82 | 641.21 |

TABLE 1-continued

| Ex. | G₂ | FW | (M + H)⁺ Obs. MS |
|---|---|---|---|
| 190 | 4-methylthiophene-2-carboxamide-(3-piperidinyl) | 548.67 | 549.09 |
| 191 | benzothiazole-6-carboxamide-(3-piperidinyl) | 585.69 | 586.09 |
| 192 | anthracene-2-carboxamide-(3-piperidinyl) | 628.73 | 629.15 |
| 193 | 3-(1,1,2,2-tetrafluoroethoxy)benzamide-(3-piperidinyl) | 644.62 | 645.08 |
| 194 | 2-chloropyridine-4-carboxamide-(3-piperidinyl) | 564.04 | 564.08 |
| 195 | 3-bromo-5-iodobenzamide-(3-piperidinyl) | 733.40 | 732.90 |
| 196 | 1H-indole-6-carboxamide-(3-piperidinyl) | 567.65 | 586.11 |

TABLE 1-continued

| Ex. | G₂ | FW | (M + H)⁺ Obs. MS |
|---|---|---|---|
| 197 | | 606.70 | 607.05 |
| 198 | | 643.74 | 644.17 |
| 199 | | 672.74 | 673.17 |
| 200 | | 586.65 | 587.09 |
| 201 | | 597.60 | 598.08 |
| 202 | | 582.66 | 583.13 |

TABLE 1-continued

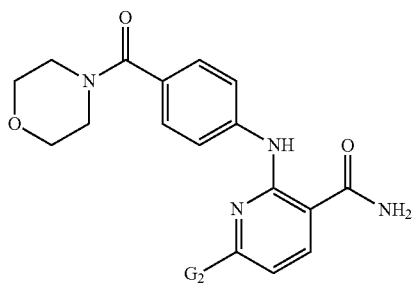

| Ex. | G₂ | FW | (M + H)⁺ Obs. MS |
|---|---|---|---|
| 203 | 1,2-dimethyl-benzimidazole-5-carboxamide-piperidine | 596.69 | 597.15 |
| 204 | quinoxaline-6-carboxamide-piperidine | 580.65 | 581.10 |
| 205 | 3-bromo-5-fluorobenzamide-piperidine | 625.50 | 625.00 |
| 206 | 1-isopropyl-benzotriazole-5-carboxamide-piperidine | 611.70 | 612.13 |
| 207 | 1-isopropyl-2-trifluoromethyl-benzimidazole-5-carboxamide-piperidine | 678.71 | 679.13 |
| 208 | 4-fluoro-3-methyl-benzamide-piperidine | 560.63 | 561.09 |
| 209 | 4-chloro-3-trifluoromethyl-benzamide-piperidine | 631.05 | 631.04 |

TABLE 1-continued

| Ex. | G₂ | FW | (M + H)⁺ Obs. MS |
|---|---|---|---|
| 210 | 4-hydroxyphenyl-phenyl-C(O)NH-piperidinyl | 620.71 | 621.11 |
| 211 | 3-isopropoxyphenyl-C(O)NH-piperidinyl | 586.69 | 587.11 |
| 212 | 2-oxo-2H-chromen-3-yl-phenyl-C(O)NH-piperidinyl | 672.74 | 673.11 |
| 213 | 1-methyl-1H-benzotriazol-5-yl-C(O)NH-piperidinyl | 583.65 | 584.10 |
| 214 | 4-chlorophenyl-phenyl-C(O)NH-piperidinyl | 639.15 | 639.08 |
| 215 | 3-(1H-imidazol-1-yl)phenyl-C(O)NH-piperidinyl | 594.67 | 595.10 |

TABLE 1-continued
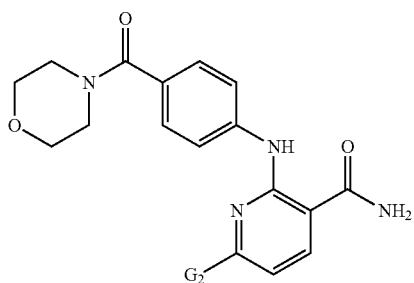
| Ex. | G₂ | FW | (M + H)⁺ Obs. MS |
|---|---|---|---|
| 216 | 3-fluorophenyl urea piperidine | 561.62 | 562.08 |
| 217 | 3,4-dichlorophenyl urea piperidine | 612.52 | 612.03 |
| 218 | 3-methylphenyl urea piperidine | 557.65 | 558.08 |
| 219 | 3,5-bis(trifluoromethyl)phenyl urea piperidine | 679.62 | 680.17 |
| 220 | 3-cyanophenyl urea piperidine | 568.64 | 569.04 |
| 221 | 3-chloro-4-methylphenyl urea piperidine | 592.10 | 592.08 |
| 222 | ethyl 3-(ureido)benzoate piperidine | 615.69 | 616.15 |

TABLE 1-continued
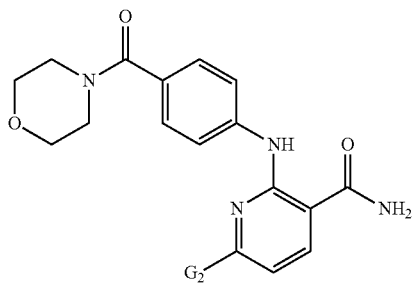
| Ex. | G$_2$ | FW | (M + H)$^+$ Obs. MS |
|---|---|---|---|
| 223 | | 585.66 | 586.10 |
| 224 | | 571.68 | 572.11 |
| 225 | | 476.31 | 572.10 |
| 226 | | 646.07 | 646.10 |
| 227 | | 596.65 | 597.10 |
| 228 | | 596.06 | 596.04 |
| 229 | | 684.79 | 685.03 |

TABLE 1-continued
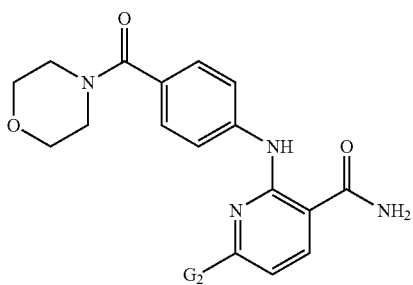
| Ex. | G₂ | FW | (M + H)⁺ Obs. MS |
|---|---|---|---|
| 230 | (3-fluoro-4-methylphenyl urea piperidine) | 575.64 | 576.09 |
| 231 | (3,4-difluorophenyl urea piperidine) | 579.61 | 580.07 |
| 232 | (3-cyclopentyloxy-4-methoxyphenyl urea piperidine) | 657.77 | 658.23 |
| 233 | (3-trifluoromethyl-5-fluorophenyl urea piperidine) | 629.61 | 630.09 |
| 234 | (3-chloro-4-methoxyphenyl urea piperidine) | 608.10 | 608.09 |
| 235 | (3,4-dimethoxyphenyl urea piperidine) | 603.68 | 604.14 |
| 236 | (3-t-butoxycarbonylphenyl urea piperidine) | 643.74 | 644.15 |

TABLE 1-continued
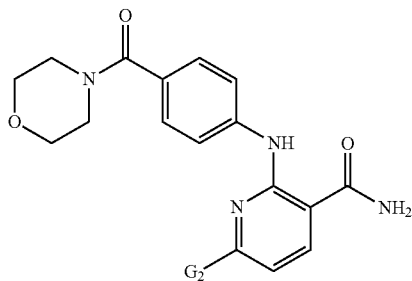
| Ex. | G₂ | FW | (M + H)⁺ Obs. MS |
|---|---|---|---|
| 237 | 3,5-dibromobenzamide-piperidinyl | 686.40 | 686.97 |
| 238 | 3',4'-dichlorobiphenyl-4-carboxamide-piperidinyl | 673.60 | 673.09 |
| 239 | 3',5'-dichlorobiphenyl-3-carboxamide-piperidinyl | 673.60 | 673.09 |
| 240 | 3-(4-methylpiperazin-1-yl)benzamide-piperidinyl | 626.76 | 627.17 |
| 241 | 3-(trifluoromethyl)quinoxaline-6-carboxamide-piperidinyl | 648.64 | 649.14 |
| 242 | 3,5-bis(trifluoromethyl)benzamide-piperidinyl | 664.60 | 665.10 |

TABLE 1-continued
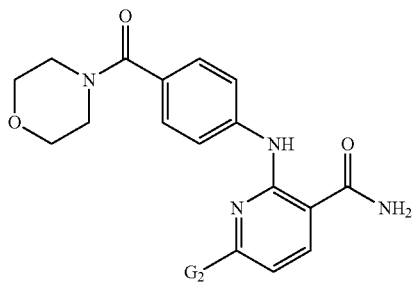
| Ex. | G$_2$ | FW | (M + H)$^+$ Obs. MS |
|---|---|---|---|
| 243 | | 630.70 | 631.09 |
| 244 | | 563.06 | 563.00 |
| 245 | | 597.50 | 596.97 |
| 246 | | 620.71 | 621.16 |
| 247 | | 632.72 | 633.13 |
| 248 | | 608.70 | 609.09 |

TABLE 1-continued
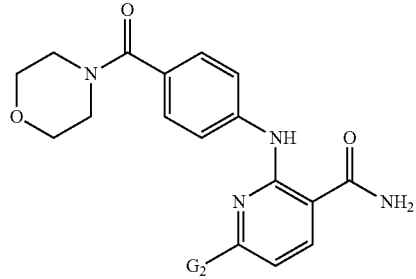
| Ex. | G₂ | FW | (M + H)⁺ Obs. MS |
|---|---|---|---|
| 249 | 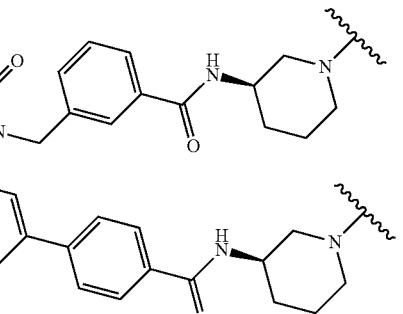 | 657.77 | 658.21 |
| 250 | 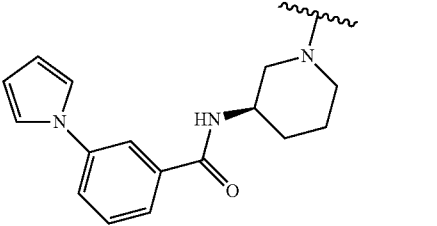 [SMILES: *N1CCC[C@@H](NC(=O)c2cccc(-n3cccc3)c2)C1] | 622.70 | 623.11 |
| 251 | 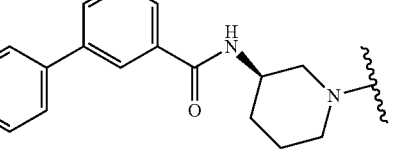 | 593.69 | 594.07 |
| 252 | 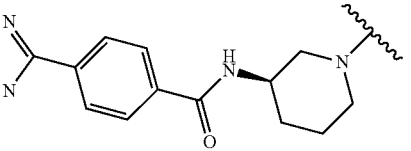 | 643.74 | 644.15 |
| 253 | 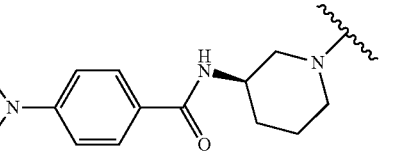 | 610.67 | 611.07 |
| 254 | 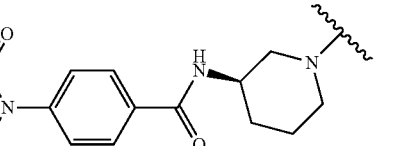 | 644.73 | 645.15 |
| 255 | | 621.70 | 622.10 |

TABLE 1-continued

| Ex. | G₂ | FW | (M + H)⁺ Obs. MS |
|---|---|---|---|
| 256 | 4-fluorobenzamide piperidine | 546.60 | 547.02 |
| 257 | 3-dimethylaminobenzamide piperidine | 571.68 | 572.05 |
| 258 | 3-methoxybenzamide piperidine | 558.64 | 559.05 |
| 259 | 3,4-dimethoxybenzamide piperidine | 588.66 | 589.07 |
| 260 | 3,5-difluorobenzamide piperidine | 564.59 | 565.02 |
| 261 | benzimidazole-5-carboxamide piperidine | 568.64 | 596.03 |
| 262 | benzotriazole-5-carboxamide piperidine | 569.62 | 570.03 |

TABLE 1-continued
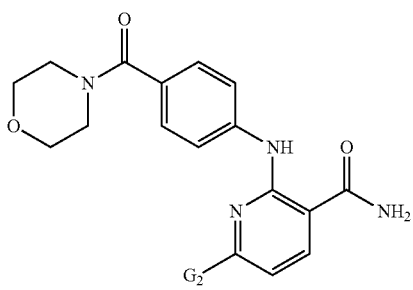
| Ex. | G₂ | FW | (M + H)⁺ Obs. MS |
|---|---|---|---|
| 263 | | 644.73 | 645.15 |
| 264 | | 610.68 | 611.13 |
| 265 | | 606.68 | 607.09 |
| 266 | | 599.71 | 600.05 |
| 267 | | 595.66 | 596.07 |
| 268 | | 597.50 | 597.03 |

TABLE 1-continued

| Ex. | G₂ | FW | (M + H)⁺ Obs. MS |
|---|---|---|---|
| 269 | 3,5-diiodo-benzamide-piperidinyl | 780.39 | 780.91 |
| 270 | 2'-methyl-biphenyl-3-carboxamide-piperidinyl | 618.73 | 619.15 |
| 271 | 2-oxo-1,2-dihydroquinoline-6-carboxamide-piperidinyl | 595.66 | 596.15 |
| 272 | 3-(1H-tetrazol-5-yl)benzamide-piperidinyl | 596.65 | 597.05 |
| 273 | 2-amino-1H-benzimidazole-5-carboxamide-piperidinyl | 583.65 | 584.09 |
| 274 | 3-(hydroxymethyl)piperidinyl | 439.51 | 440.16 |
| 275 | 3-(aminomethyl)piperidinyl | 438.53 | 439.20 |
| 276 | 3-((Boc-amino)methyl)piperidinyl | 538.65 | 539.20 |

TABLE 1-continued

| Ex. | G₂ | FW | (M + H)⁺ Obs. MS |
|---|---|---|---|
| 277 | (3-methylenepiperidin-1-yl) | 421.50 | 422.13 |
| 278 | (1-phenyl-2-oxo-1,7-diazaspiro[4.5]decan-7-yl) | 554.65 | 555.20 |
| 279 | (3-phenyl-1-oxa-2,8-diazaspiro[4.5]dec-2-en-8-yl) | 540.62 | 541.40 |

TABLE 2

| Ex. | G₂ | FW | M + H |
|---|---|---|---|
| 280 | N-(4,5-dimethylthiazol-2-yl)urea-piperidinyl | 591.73 | 592.15 |
| 281 | 2-fluorobenzyl | 433.48 | 434.09 |

TABLE 3

| Ex. | G₂ | FW | M + H |
|---|---|---|---|
| 282 | 4-(trifluoromethyl)benzamido-piperidinyl | 581.63 | 582.23 |
| 283 | N-(3,4-dimethylphenyl)urea-piperidinyl | 556.70 | 557.27 |

TABLE 3-continued
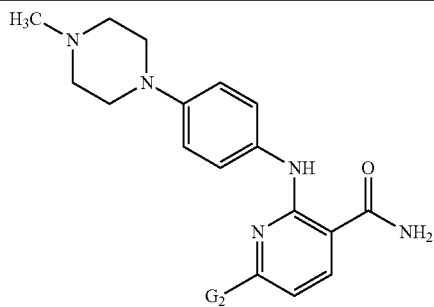
| Ex. | G2 | FW | M + H |
|---|---|---|---|
| 284 | | 535.66 | 536.20 |
| 285 | | 563.72 | 564.23 |
| 286 | | 614.56 | 613.2 / 615.2 |
| 287 | | 575.79 | 576.37 |
| 288 | | 536.65 | 537.20 |
| 289 | | 451.56 | 452.17 |
| 290 | | 513.63 | 514.21 |
| 291 | | 477.60 | 478.25 |
TABLE 3-continued
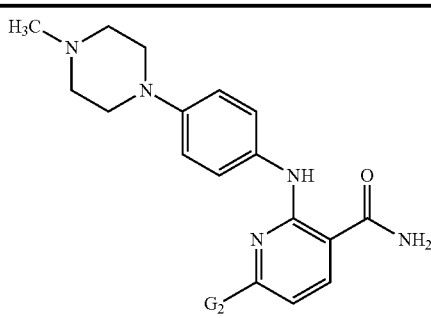
| Ex. | G2 | FW | M + H |
|---|---|---|---|
| 292 | | 394.51 | 395.14 |
| 293 | | 387.48 | 388.15 |
| 294 | | 421.92 | 422.08 |
TABLE 4
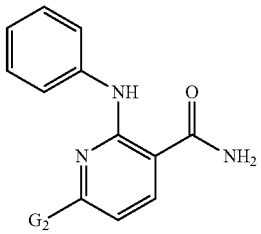
| Ex. | G2 | FW | M + H |
|---|---|---|---|
| 295 | | 411.50 | 412.22 |
| 296 | | 451.54 | 452.12 |
| 297 | | 465.57 | 466.13 |
| 298 | | 318.37 | 319.14 |

TABLE 4-continued

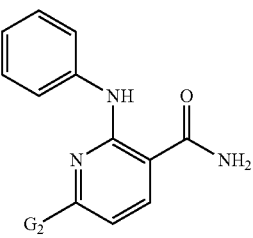

| Ex. | G2 | FW | M + H |
|---|---|---|---|
| 299 | (3-aminopiperidin-1-yl) | 311.38 | 312.25 |
| 300 | (3-(3-(3,4-dimethylphenyl)ureido)piperidin-1-yl) | 458.56 | 459.31 |

TABLE 5

| Ex. | G2 | FW | M + H |
|---|---|---|---|
| 301 | (3-(3-(4,5-dimethylthiazol-2-yl)ureido)piperidin-1-yl) | 490.58 | 491.05 |
| 302 | (3-aminopiperidin-1-yl) | 336.39 | 337.24 |
| 303 | (3-(3-(3,4-dimethylphenyl)ureido)piperidin-1-yl) | 483.56 | 484.37 |

TABLE 6

| Ex. | G2 | FW | M + H |
|---|---|---|---|
| 304 | (3-(3-(4-methylthiazol-2-yl)ureido)piperidin-1-yl) | 522.67 | 523.23 |
| 305 | (3-(3-(thiazol-2-yl)ureido)piperidin-1-yl) | 508.64 | 509.15 |
| 306 | (3-(3-(1,3,4-thiadiazol-2-yl)ureido)piperidin-1-yl) | 509.63 | 510.19 |
| 307 | (3-(3-(3,4-dimethylphenyl)ureido)piperidin-1-yl) | 529.68 | 530.29 |
| 308 | (3-(5-t-Bu-1-methyl-1H-pyrazole-3-carboxamido)piperidin-1-yl) | 546.71 | 547.30 |
| 309 | (3-(5-t-Bu-1-methyl-1H-pyrazole-3-carboxamido)piperidin-1-yl) | 546.71 | 547.27 |
| 310 | (3-(4-(trifluoromethyl)benzamido)piperidin-1-yl) | 554.61 | 555.23 |

TABLE 7

Core structure: 2-(G₁-NH)-6-(pyrrolidin-1-yl)pyridine-3-carboxamide

| Ex. | G₁ | FW | M + H |
|---|---|---|---|
| 311 | 3-[N-methyl-N-(methylsulfonyl)amino]phenyl | 389.48 | 390.10 |
| 312 | 3-(methylsulfonylamino)phenyl | 375.45 | 376.00 |
| 313 | 4-(morpholine-4-carbonyl)-3-(methylsulfonylamino)phenyl | 488.57 | 489.10 |

TABLE 8

Core structure: 2-(G₁-NH)-6-(piperidin-1-yl)pyridine-3-carboxamide

| Ex. | G₁ | FW | M + H |
|---|---|---|---|
| 314 | 4-(t-BuO-C(O))phenyl | 396.48 | 397.20 |
| 315 | 4-(HOOC)phenyl | 340.38 | 341.08 |
| 316 | 4-(pyrrolidine-1-carbonyl)phenyl | 393.48 | 394.22 |

TABLE 8-continued

| Ex. | G₁ | FW | M + H |
|---|---|---|---|
| 317 | 4-(piperidine-1-carbonyl)phenyl | 407.51 | 408.21 |
| 318 | 4-(t-Bu-NH-C(O))phenyl | 395.50 | 396.17 |
| 319 | 4-(4-methylpiperazine-1-carbonyl)phenyl | 422.52 | 423.14 |
| 320 | 4-[(2-dimethylaminoethyl)aminocarbonyl]phenyl | 410.51 | 411.16 |
| 321 | 4-[4-(2-hydroxyethyl)piperazine-1-carbonyl]phenyl | 452.55 | 453.14 |
| 322 | 4-(cyclopropylaminocarbonyl)phenyl | 379.46 | 380.13 |
| 323 | 4-(phenylaminocarbonyl)phenyl | 415.49 | 416.10 |
| 324 | 4-(N,N-dimethylaminocarbonyl)phenyl | 367.44 | 368.17 |

TABLE 8-continued

[Core structure: G₁-NH-pyridine-carboxamide with piperidinyl group]

| Ex. | G₁ | FW | M + H |
|-----|-----|------|--------|
| 325 | [4-(2-hydroxyethylcarbamoyl)phenyl] | 387.44 | 384.19 |
| 326 | [4-(azetidin-1-ylcarbonyl)phenyl] | 379.46 | 380.11 |
| 327 | [4-(piperidin-4-yl)phenyl] | 379.50 | 380.17 |
| 328 | [4-(1-methylpiperidin-4-yl)phenyl] | 393.53 | 394.17 |
| 329 | [4-(4-hydroxy-1,3,3-trimethylpiperidin-4-yl)phenyl] | 437.58 | 438.24 |

TABLE 9

[Core structure: 4-methylthiazol-2-yl-NH-C(O)-NH-(3-piperidinyl)-pyridine-carboxamide with G₁-NH]

| Ex. | G₁ | FW | M + H |
|-----|-----|------|--------|
| 330 | [4-methoxyphenyl] | 481.57 | 482.06 |
| 331 | [3-methoxyphenyl] | 481.57 | 482.04 |
| 332 | [2-methoxyphenyl] | 481.57 | 482.05 |
| 333 | [4-acetamidophenyl] | 508.60 | 509.08 |
| 334 | [4-acetylphenyl] | 493.58 | 494.08 |
| 335 | [3-(N-methylcarbamoyl)phenyl] | 508.60 | 509.11 |
| 336 | [4-(morpholinomethyl)phenyl] | 550.68 | 551.23 |
| 337 | [4-morpholinophenyl] | 536.65 | 537.06 |
| 338 | [4-aminophenyl] | 466.56 | 467.08 |
| 339 | [4-(pyrrolidin-1-yl)phenyl] | 520.65 | 521.11 |
| 340 | [4-ethylphenyl] | 479.60 | 480.30 |

TABLE 10
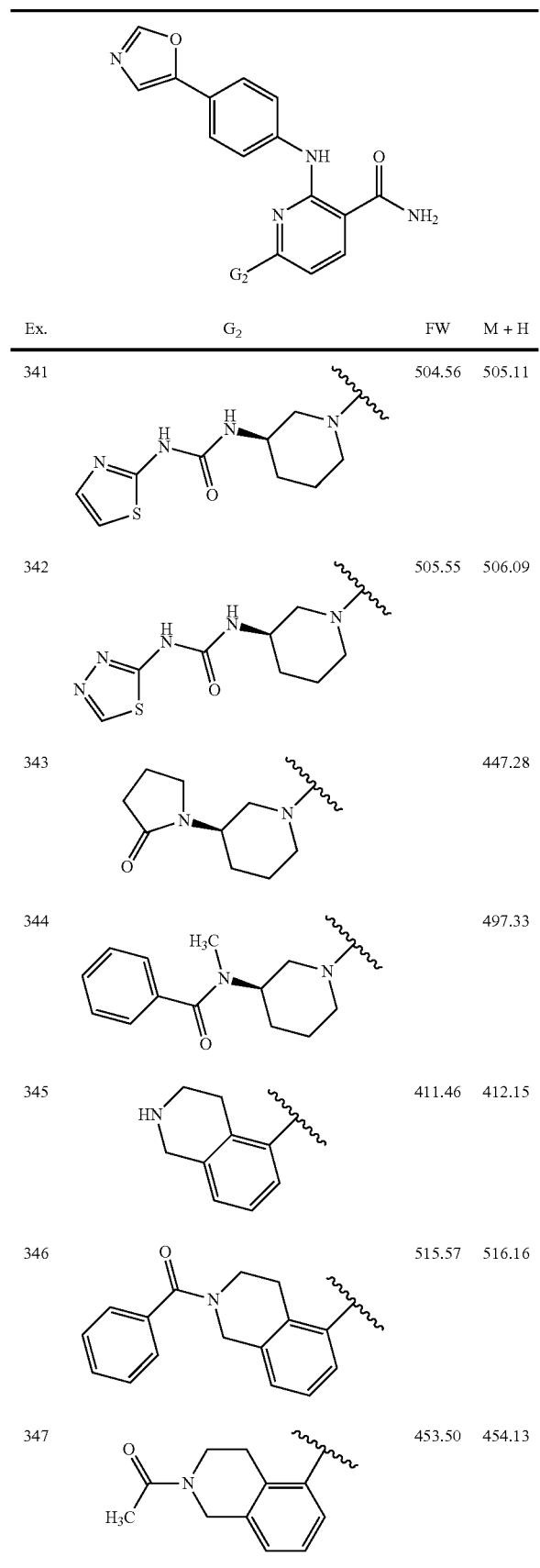
| Ex. | G₂ | FW | M + H |
|---|---|---|---|
| 341 | | 504.56 | 505.11 |
| 342 | | 505.55 | 506.09 |
| 343 | | | 447.28 |
| 344 | | | 497.33 |
| 345 | | 411.46 | 412.15 |
| 346 | | 515.57 | 516.16 |
| 347 | | 453.50 | 454.13 |
TABLE 10-continued
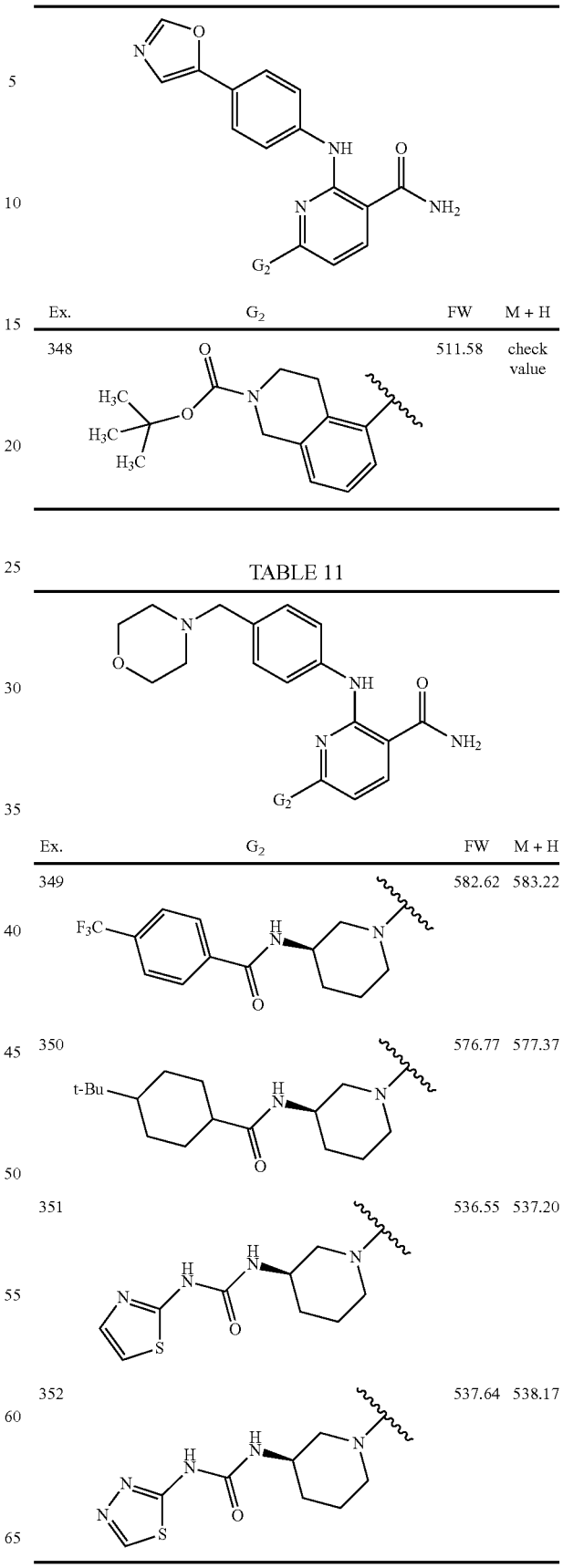
| Ex. | G₂ | FW | M + H |
|---|---|---|---|
| 348 | | 511.58 | check value |
TABLE 11
| Ex. | G₂ | FW | M + H |
|---|---|---|---|
| 349 | | 582.62 | 583.22 |
| 350 | | 576.77 | 577.37 |
| 351 | | 536.55 | 537.20 |
| 352 | | 537.64 | 538.17 |

TABLE 12
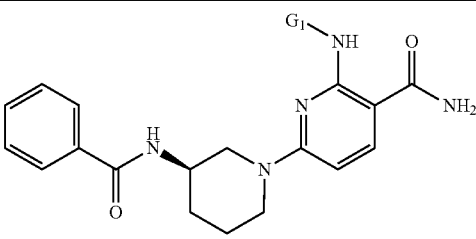
| Ex. | G₁ | FW | M + H |
|---|---|---|---|
| 353 | 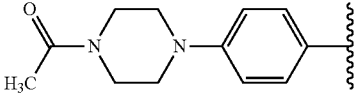 | 541.64 | 542.12 |
| 354 | 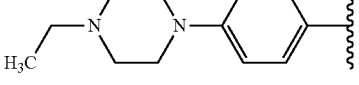 | 527.66 | 528.20 |
| 355 | 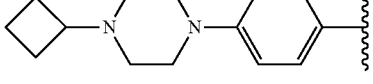 | 553.70 | 554.21 |
| 356 | 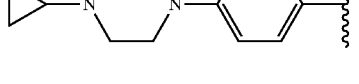 | 539.67 | 540.32 |
| 357 | 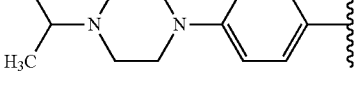 | 541.7 | 542.21 |
TABLE 13
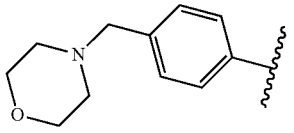 [SMILES: *c1ccc(CN2CCOCC2)cc1]
| Ex. | G₁ | FW | M + H |
|---|---|---|---|
| 358 | 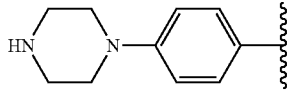 | 557.69 | 558.26 |
| 359 | 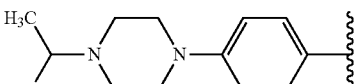 | 542.68 | 543.18 |
| 360 | 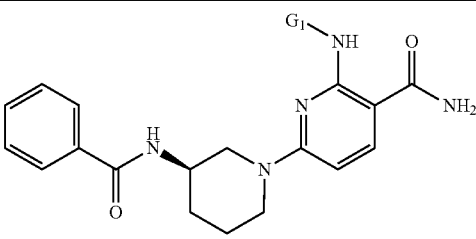 | 584.75 | 585.25 |
TABLE 13-continued
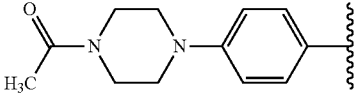
| Ex. | G₁ | FW | M + H |
|---|---|---|---|
| 361 | 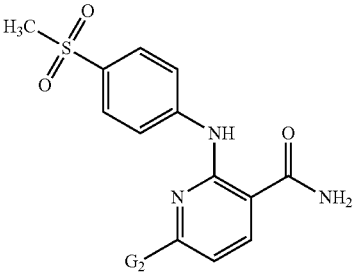 | 584.71 | 585.20 |
TABLE 14
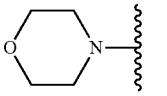
| Ex. | G₂ | FW | M + H |
|---|---|---|---|
| 362 | 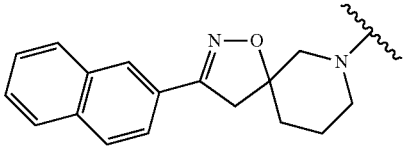 [SMILES: *N1CCCC2(CC(c3ccc4ccccc4c3)=NO2)C1] | 376.44 | 377.00 |
| 363 | 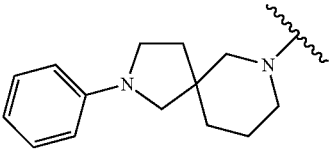 [SMILES: *N1CCCC2(CCN(c3ccccc3)C2)C1] | 555.66 | 556.18 |
| 364 | 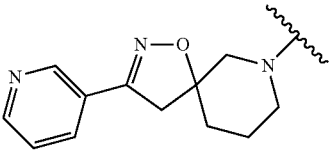 [SMILES: *N1CCCC2(CC(c3cccnc3)=NO2)C1] | 505.64 | 506.10 |
| 365 | 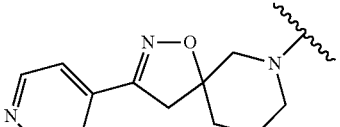 | 506.58 | 507.11 |
| 366 | | 506.58 | 507.11 |

TABLE 14-continued
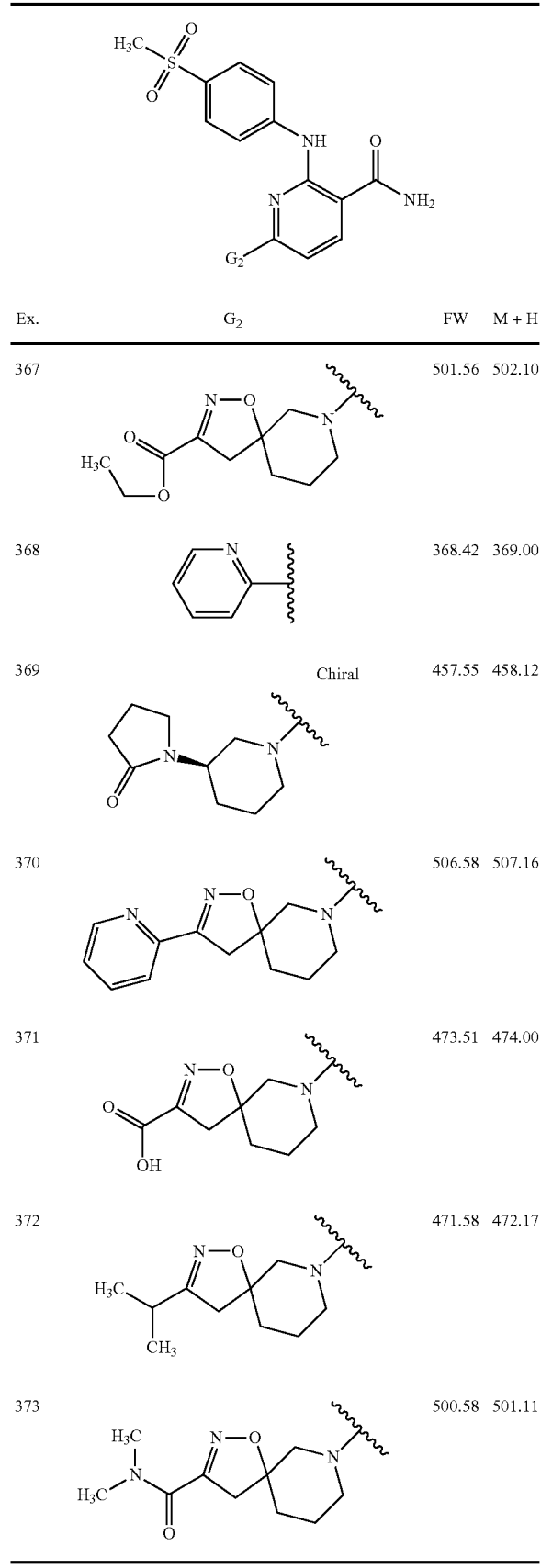
| Ex. | G2 | FW | M + H |
|---|---|---|---|
| 367 | | 501.56 | 502.10 |
| 368 | | 368.42 | 369.00 |
| 369 | Chiral | 457.55 | 458.12 |
| 370 | | 506.58 | 507.16 |
| 371 | | 473.51 | 474.00 |
| 372 | | 471.58 | 472.17 |
| 373 | | 500.58 | 501.11 |
TABLE 15
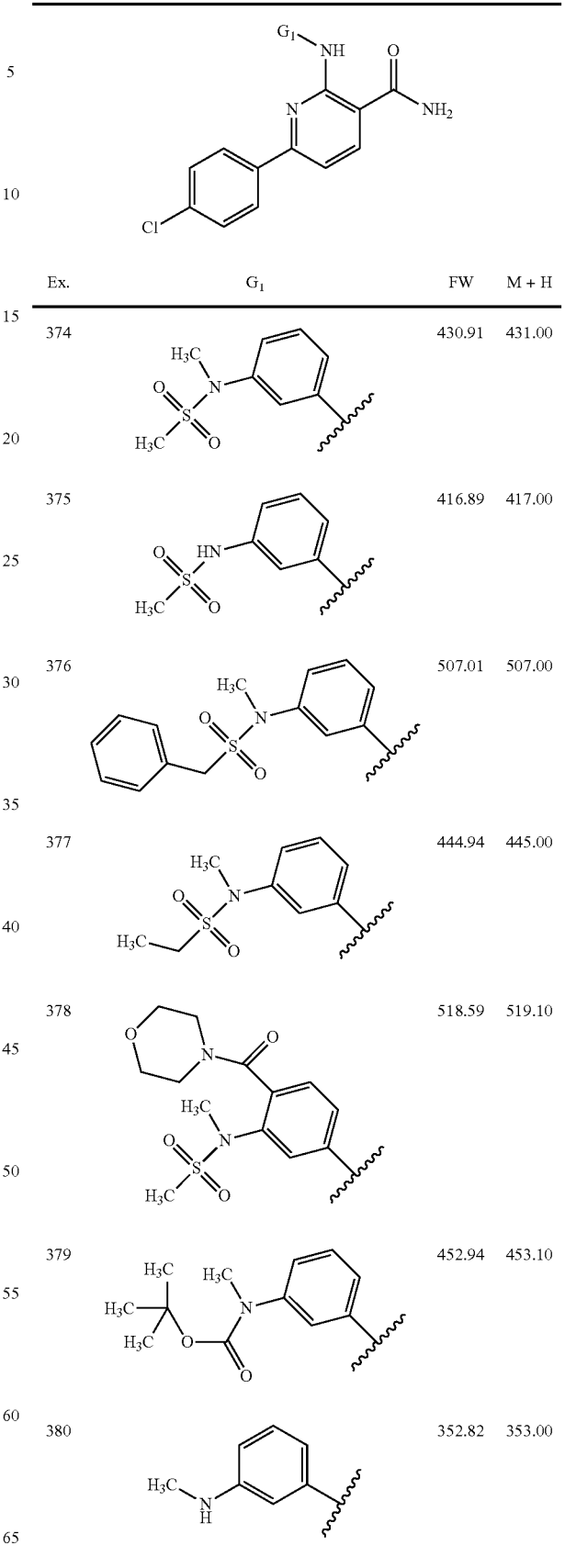
| Ex. | G1 | FW | M + H |
|---|---|---|---|
| 374 | | 430.91 | 431.00 |
| 375 | | 416.89 | 417.00 |
| 376 | | 507.01 | 507.00 |
| 377 | | 444.94 | 445.00 |
| 378 | | 518.59 | 519.10 |
| 379 | | 452.94 | 453.10 |
| 380 | | 352.82 | 353.00 |

TABLE 15-continued
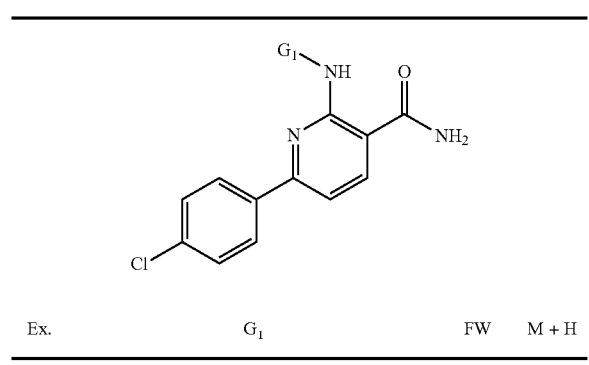
| Ex. | G₁ | FW | M + H |
|---|---|---|---|
| 381 | 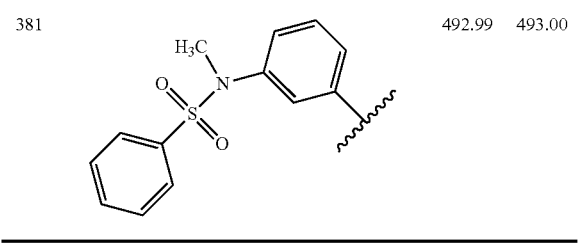 | 492.99 | 493.00 |
TABLE 16
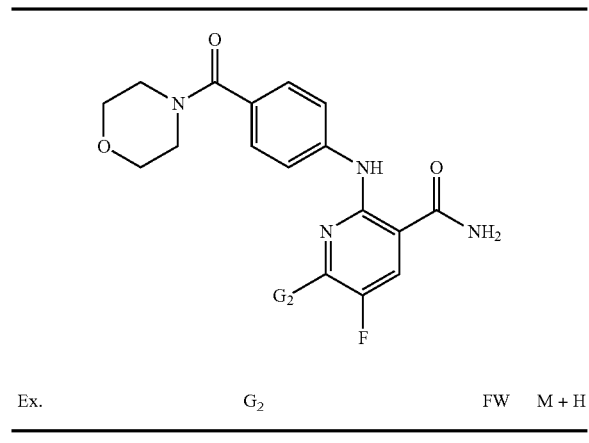
| Ex. | G₂ | FW | M + H |
|---|---|---|---|
| 382 | 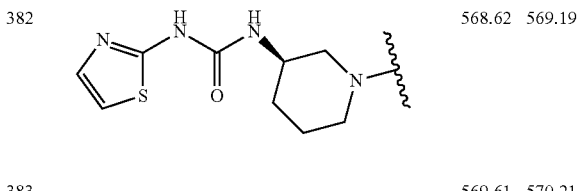 | 568.62 | 569.19 |
| 383 | 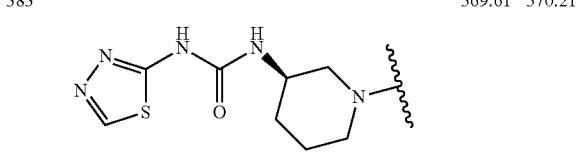 | 569.61 | 570.21 |
| 384 | 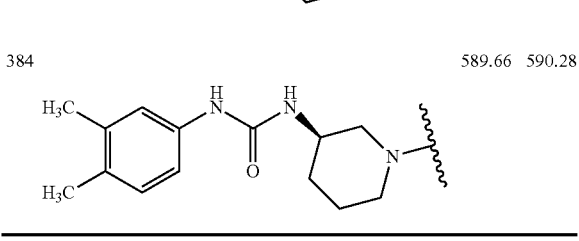 | 589.66 | 590.28 |
TABLE 17
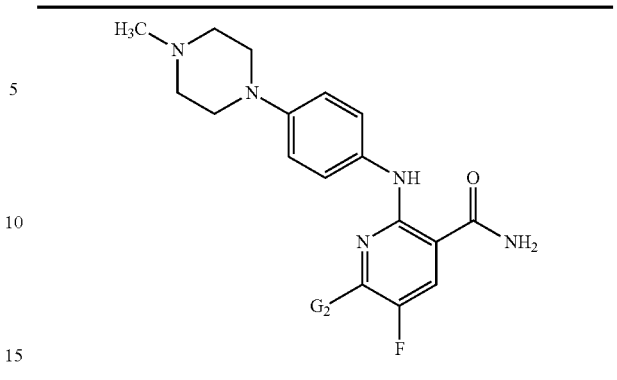
| Ex. | G₂ | FW | M + H |
|---|---|---|---|
| 385 | 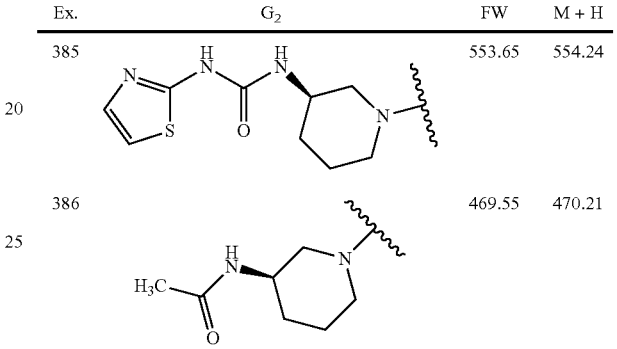 | 553.65 | 554.24 |
| 386 | 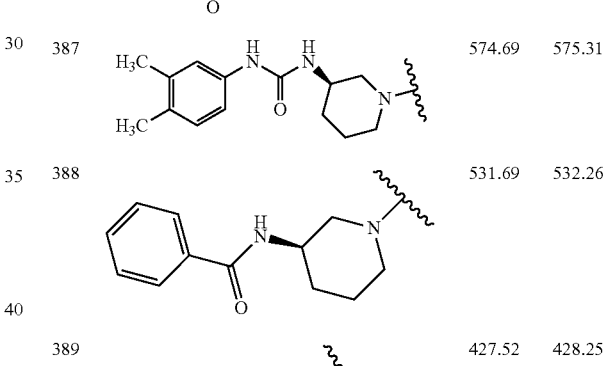 | 469.55 | 470.21 |
| 387 | | 574.69 | 575.31 |
| 388 | 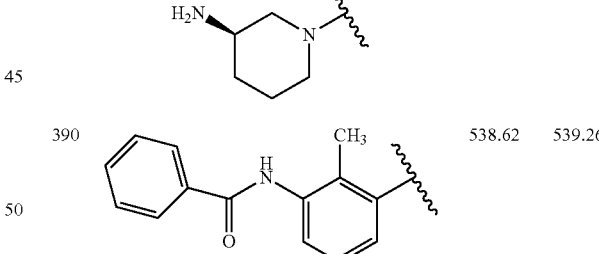 | 531.69 | 532.26 |
| 389 | 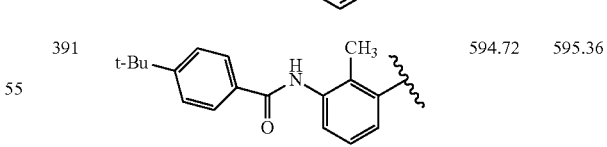 | 427.52 | 428.25 |
| 390 | | 538.62 | 539.26 |
| 391 | 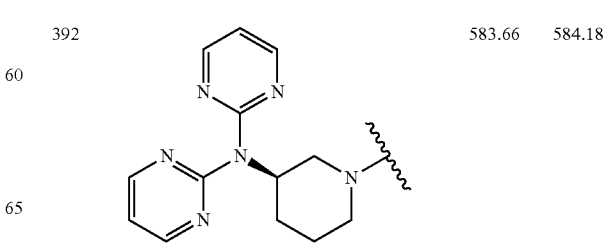 | 594.72 | 595.36 |
| 392 | | 583.66 | 584.18 |

TABLE 17-continued
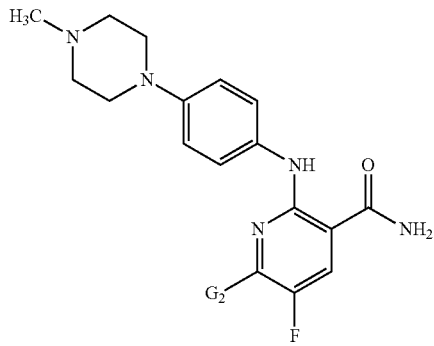
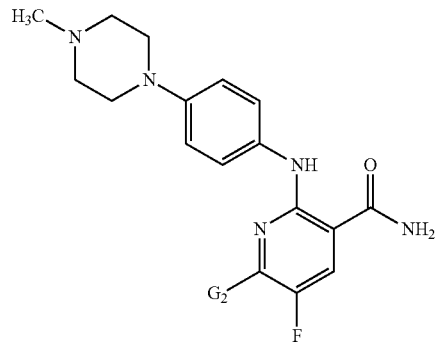
| Ex. | G₂ | FW | M + H | Ex. | G₂ | FW | M + H |
|---|---|---|---|---|---|---|---|
| 393 | piperidin-1-yl | 412.50 | 413.10 | 403 | thiophen-3-yl | 411.50 | 412.08 |
| 394 | phenyl | 405.47 | 406.10 | 404 | 1-methyl-1H-pyrazol-5-yl | 409.46 | 410.12 |
| 395 | pyrrolidin-1-yl | 398.48 | 399.12 | 405 | 4,4-difluoropiperidin-1-yl | 448.48 | 449.08 |
| 396 | 2,3-dichlorophenyl | 474.36 | 474.02 | 406 | 3,3-difluoropyrrolidin-1-yl | 434.46 | 435.09 |
| 397 | isoindolin-2-yl | 446.52 | 447.14 | 407 | 4-hydroxypiperidin-1-yl | 428.50 | 429.14 |
| 398 | benzofuran-2-yl | 445.49 | 446.04 | 408 | 5-amino-2-methylphenyl | 434.51 | 435.13 |
| 399 | 4-chlorophenyl | 439.91 | 440.04 | | | | |
| 400 | 3-amino-2-methylphenyl | 434.51 | 435.13 | 409 | 2-(methoxymethyl)phenyl | 449.52 | 450.11 |
| 401 | naphthalen-2-yl | 455.53 | 456.12 | 410 | 2-azaspiro[5.5]undecan-2-yl | 480.62 | 481.19 |
| 402 | 1H-indol-5-yl | 444.50 | 445.13 | 411 | cyclohex-1-en-1-yl | 409.51 | 410.16 |

TABLE 17-continued

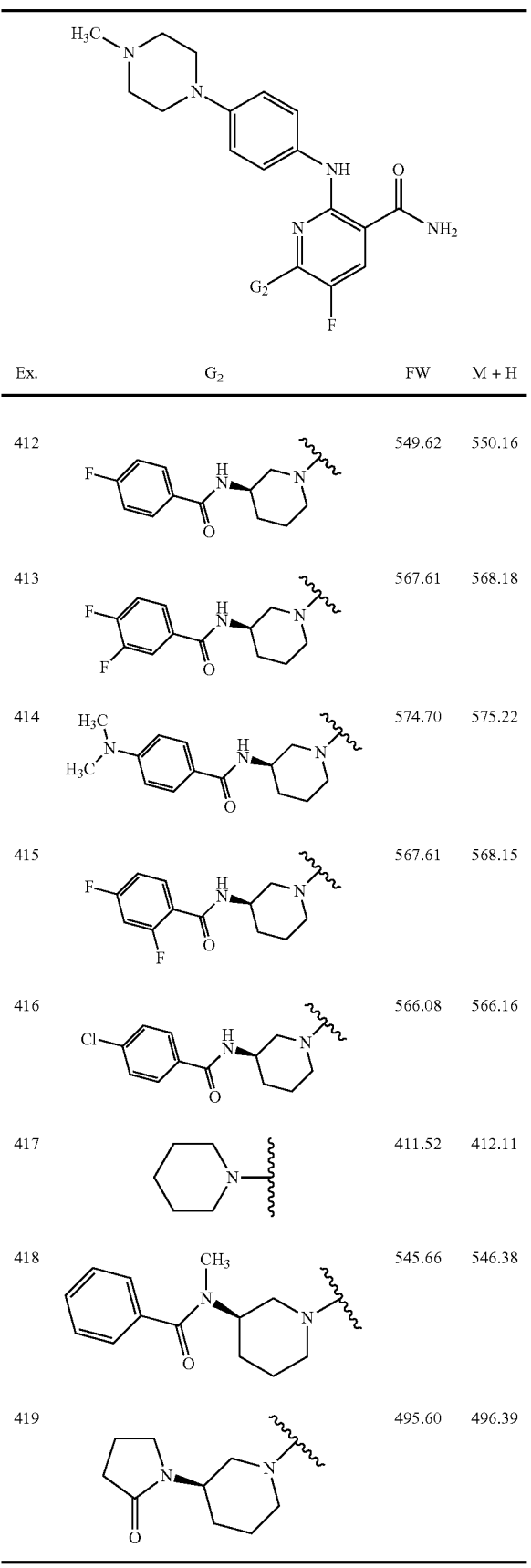

| Ex. | G₂ | FW | M + H |
|---|---|---|---|
| 412 | 4-fluorobenzamido-piperidinyl | 549.62 | 550.16 |
| 413 | 3,4-difluorobenzamido-piperidinyl | 567.61 | 568.18 |
| 414 | 4-(dimethylamino)benzamido-piperidinyl | 574.70 | 575.22 |
| 415 | 2,4-difluorobenzamido-piperidinyl | 567.61 | 568.15 |
| 416 | 4-chlorobenzamido-piperidinyl | 566.08 | 566.16 |
| 417 | piperidinyl | 411.52 | 412.11 |
| 418 | N-methylbenzamido-piperidinyl | 545.66 | 546.38 |
| 419 | 2-oxopyrrolidinyl-piperidinyl | 495.60 | 496.39 |

TABLE 18

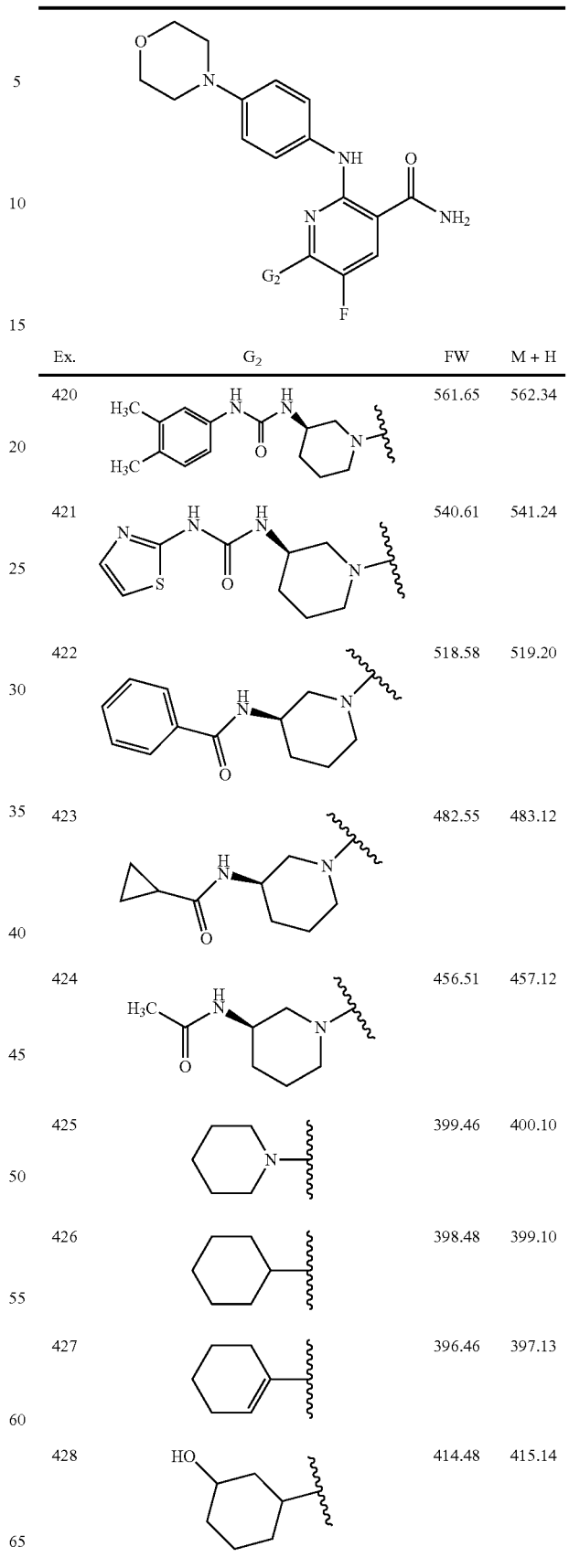

| Ex. | G₂ | FW | M + H |
|---|---|---|---|
| 420 | 3,4-dimethylphenyl-urea-piperidinyl | 561.65 | 562.34 |
| 421 | thiazol-2-yl-urea-piperidinyl | 540.61 | 541.24 |
| 422 | benzamido-piperidinyl | 518.58 | 519.20 |
| 423 | cyclopropanecarboxamido-piperidinyl | 482.55 | 483.12 |
| 424 | acetamido-piperidinyl | 456.51 | 457.12 |
| 425 | piperidinyl | 399.46 | 400.10 |
| 426 | cyclohexyl | 398.48 | 399.10 |
| 427 | cyclohexenyl | 396.46 | 397.13 |
| 428 | 3-hydroxycyclohexyl | 414.48 | 415.14 |

TABLE 18-continued

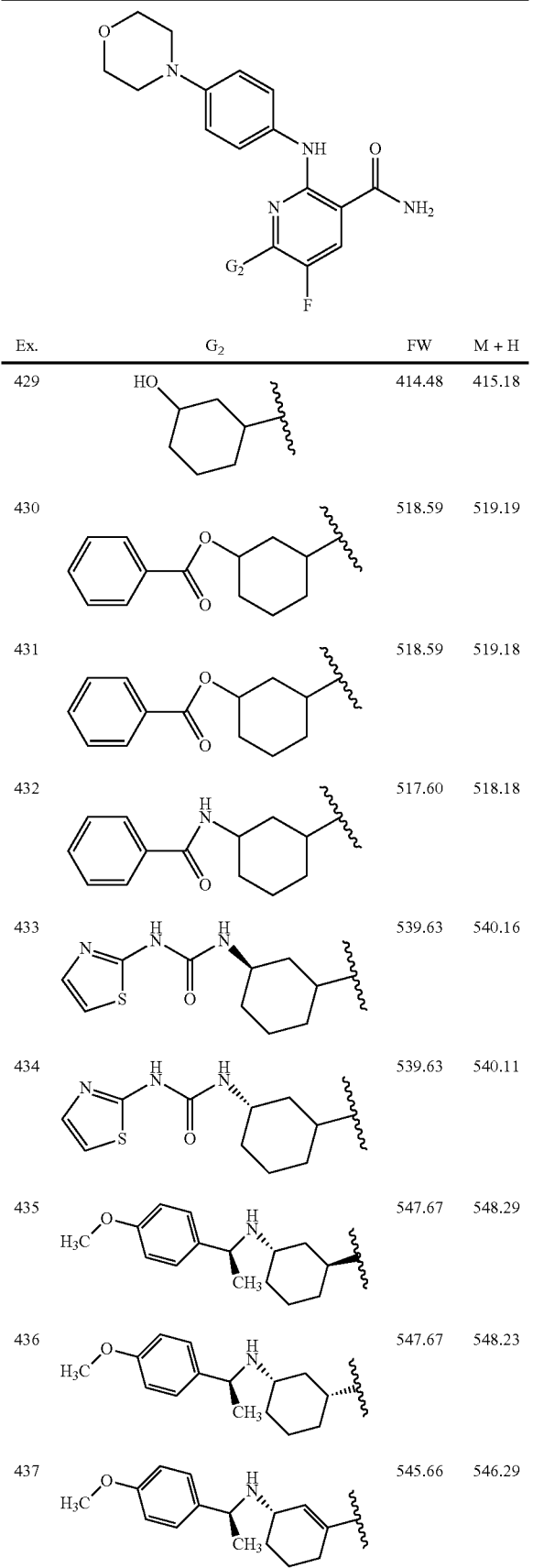

| Ex. | G2 | FW | M + H |
|---|---|---|---|
| 429 | (HO-cyclohexyl) | 414.48 | 415.18 |
| 430 | (benzoate-cyclohexyl) | 518.59 | 519.19 |
| 431 | (benzoate-cyclohexyl) | 518.59 | 519.18 |
| 432 | (benzamide-cyclohexyl) | 517.60 | 518.18 |
| 433 | (thiazolyl urea cyclohexyl) | 539.63 | 540.16 |
| 434 | (thiazolyl urea cyclohexyl) | 539.63 | 540.11 |
| 435 | (methoxyphenethylamino cyclohexyl) | 547.67 | 548.29 |
| 436 | (methoxyphenethylamino cyclohexyl) | 547.67 | 548.23 |
| 437 | (methoxyphenethylamino cyclohexenyl) | 545.66 | 546.29 |
| 438 | (methoxyphenethylamino cyclohexenyl) | 545.66 | 546.27 |
| 439 | (thiazolyl urea cyclohexenyl) | 537.62 | 538.25 |
| 440 | (thiazolyl urea cyclohexenyl) | 537.62 | 538.27 |

TABLE 19

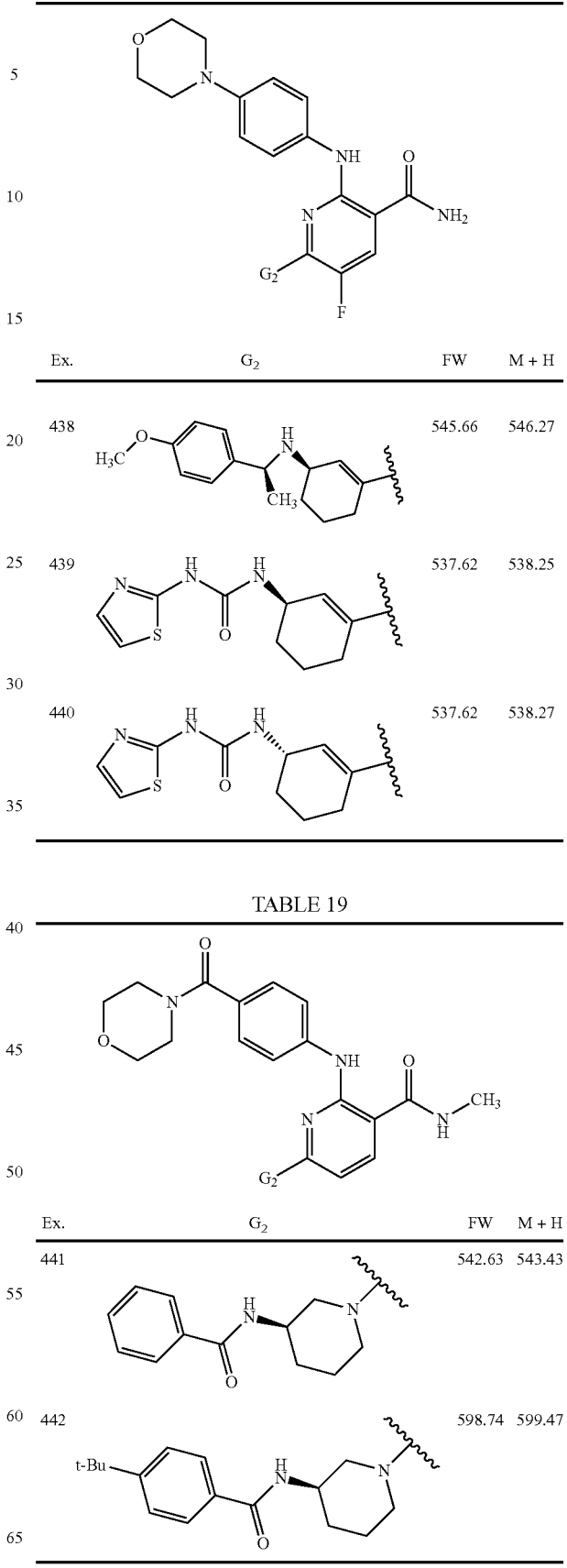

| Ex. | G2 | FW | M + H |
|---|---|---|---|
| 441 | (benzamide piperidinyl) | 542.63 | 543.43 |
| 442 | (t-Bu-benzamide piperidinyl) | 598.74 | 599.47 |

TABLE 20
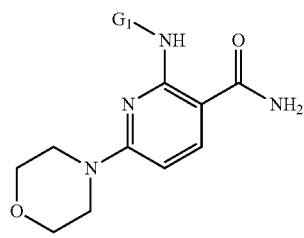
| Ex. | G₁ | FW | M + H |
|---|---|---|---|
| 443 | 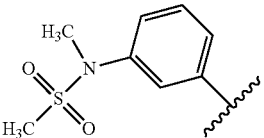 | 405.48 | 406.10 |
| 444 | 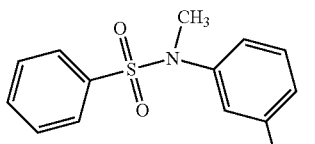 | 467.55 | 468.10 |
| 445 | 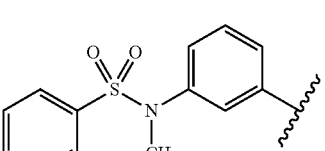 | 468.54 | 469.10 |
TABLE 21
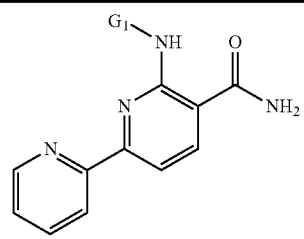
| Ex. | G₁ | FW | M + H |
|---|---|---|---|
| 446 | 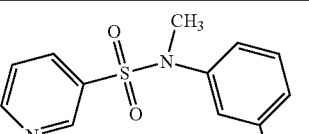 | 460.52 | 461.00 |
| 447 | 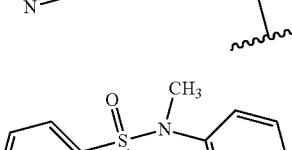 | 459.53 | 460.00 |
TABLE 22
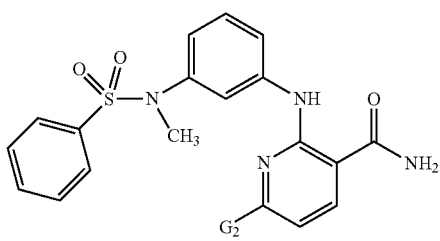
| Ex. | G₂ | FW | M + H |
|---|---|---|---|
| 448 | 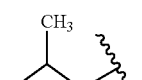 | 465.58 | 466.10 |
| 449 |  | 467.55 | 468.10 |
TABLE 23
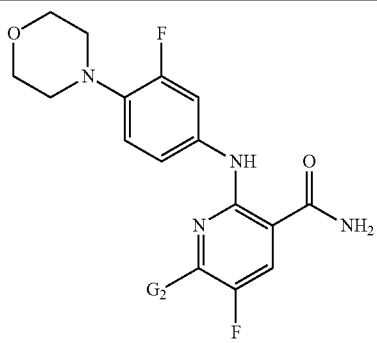
| Ex. | G₂ | FW | M + H |
|---|---|---|---|
| 450 | 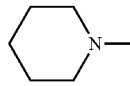 | 417.46 | 418.15 |
| 451 | 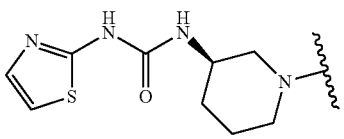 [SMILES: *N1CCC[C@@H](NC(=O)Nc2nccs2)C1] | 558.61 | 559.13 |
| 452 | 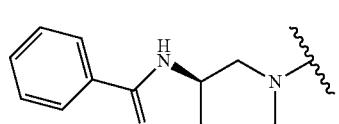 | 536.58 | 537.00 |
| 453 | 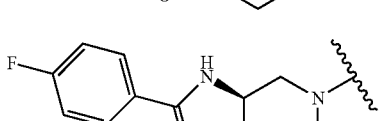 | 554.57 | 554.00 |

TABLE 24

| Ex. | G₂ | FW | M + H |
|---|---|---|---|
| 454 | 4-F-C₆H₄-C(O)NH-(3-piperidinyl)- | 469.47 | 470.26 |
| 455 | 2,4-diF-C₆H₃-C(O)NH-(3-piperidinyl)- | 487.46 | 488.26 |
| 456 | 3-Cl-4-F-C₆H₃-C(O)NH-(3-piperidinyl)- | 503.91 | 504.25 |

TABLE 25

| Ex. | G₂ | FW | M + H |
|---|---|---|---|
| 457 | C₆H₅-C(O)NH-(3-piperidinyl)- | 504.61 | 527.09 |
| 458 | thiazol-2-yl-NHC(O)NH-(3-piperidinyl)- | 526.64 | 527.09 |

TABLE 25-continued

| Ex. | G₂ | FW | M + H |
|---|---|---|---|
| 459 | 4-F-C₆H₄-C(O)NH-(3-piperidinyl)- | 522.60 | 522.00 |
| 460 | piperidinyl | 385.48 | 386.28 |
| 461 | pyrrolidinyl | 371.46 | 372.21 |
| 462 | 1,3,4-thiadiazol-2-yl-NHC(O)NH-(3-piperidinyl)- | 527.63 | 528.26 |
| 463 | 4-(Me₂N)-C₆H₄-C(O)NH-(3-piperidinyl)- | 547.68 | 548.35 |
| 464 | CH₃C(O)NH-(3-piperidinyl)- | 442.54 | 443.23 |
| 465 | 2-oxopyrrolidin-1-yl-(3-piperidinyl)- | 468.57 | 469.22 |
| 466 | 3-amino-piperidinyl | 400.50 | 401.19 |
| 467 | ethyl 2-(piperidin-3-yl)acetate | 471.57 | 472.03 |

TABLE 25-continued

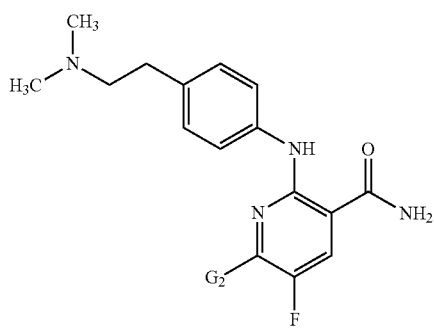

| Ex. | G₂ | FW | M + H |
|---|---|---|---|
| 468 | (1S,4S)-tert-butyl 2,5-diazabicyclo[2.2.1]heptane-2-carboxylate | 498.60 | 499.18 |
| 469 | 3-phenoxypiperidine | 477.58 | 478.00 |
| 470 | (R)-tert-butyl pyrrolidin-3-ylcarbamate | 486.59 | 487.22 |
| 471 | (S)-tert-butyl pyrrolidin-3-ylcarbamate | 486.59 | 487.40 |
| 472 | (R)-1-(pyrrolidin-3-yl)-3-(thiazol-2-yl)urea | 512.61 | 513.15 |
| 473 | (S)-1-(pyrrolidin-3-yl)-3-(thiazol-2-yl)urea | 512.61 | 513.15 |
| 474 | 2,5-diazabicyclo[2.2.1]heptane-thiazol-2-yl urea | 524.62 | 525.16 |
| 475 | 3,3-difluoropiperidine | 421.46 | 422.03 |

TABLE 25-continued

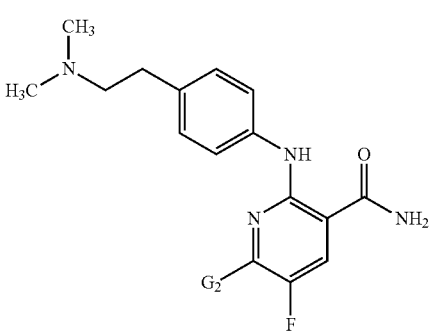

| Ex. | G₂ | FW | M + H |
|---|---|---|---|
| 476 | tert-butyl 2-(piperidin-3-yl)ethylcarbamate | 528.67 | 529.01 |
| 477 | 3-(1H-indol-1-yl)piperidine | 500.62 | 501.01 |
| 478 | 3-(1H-indol-3-yl)piperidine | 500.62 | 500.96 |

TABLE 26

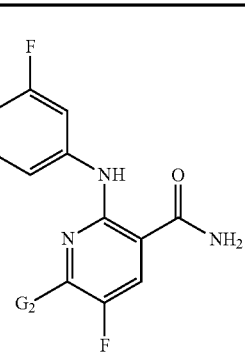

| Ex. | G₂ | FW | M + H |
|---|---|---|---|
| 479 | (R)-N-(piperidin-3-yl)benzamide | 549.62 | 550.00 |

TABLE 26-continued
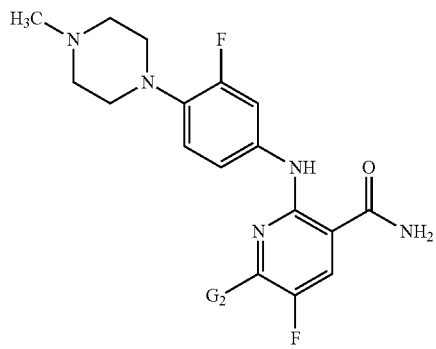
| Ex. | G₂ | FW | M + H |
|---|---|---|---|
| 480 | 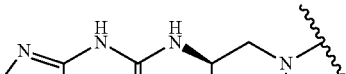 | 571.65 | 572.00 |
| 481 | 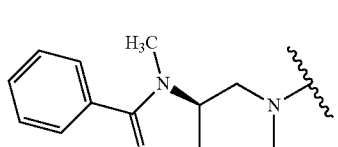 | 563.65 | 564.15 |
| 482 | 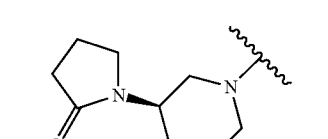 | 513.59 | 514.13 |
TABLE 27
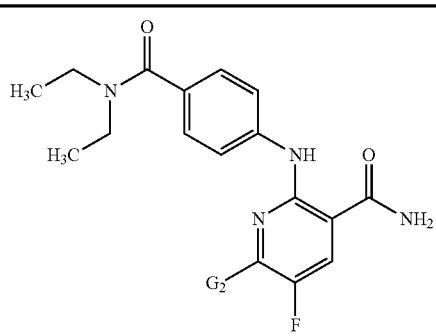
| Ex. | G₂ | FW | M + H |
|---|---|---|---|
| 483 | 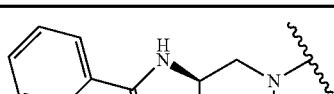 | 532.62 | 533.41 |
| 484 | 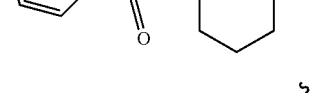 | 554.65 | 555.38 |
TABLE 27-continued
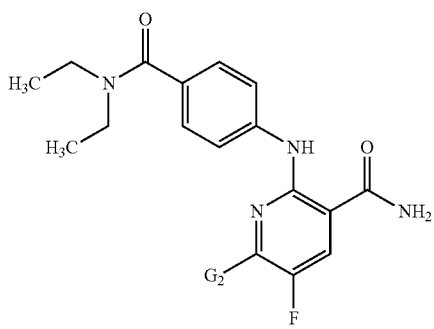
| Ex. | G₂ | FW | M + H |
|---|---|---|---|
| 485 | 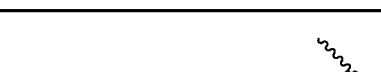 | 550.61 | 551.37 |
TABLE 28
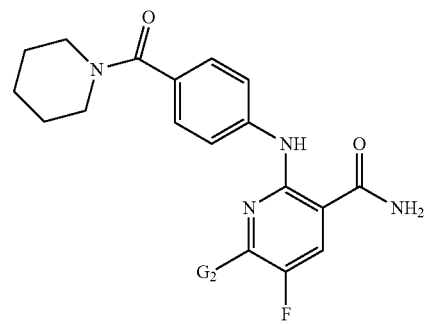
| Ex. | G₂ | FW | M + H |
|---|---|---|---|
| 486 | 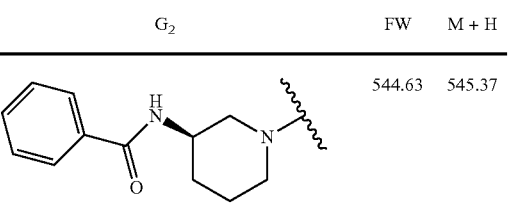 | 544.63 | 545.37 |
| 487 | 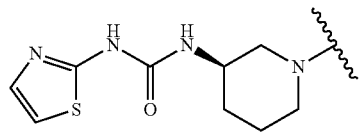 [SMILES: *N1CCC[C@@H](NC(=O)Nc2nccs2)C1] | 566.66 | 567.34 |
| 488 | 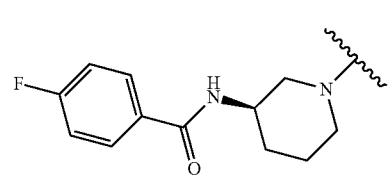 [SMILES: *N1CCC[C@@H](NC(=O)c2ccc(F)cc2)C1] | 562.62 | 563.37 |

TABLE 29
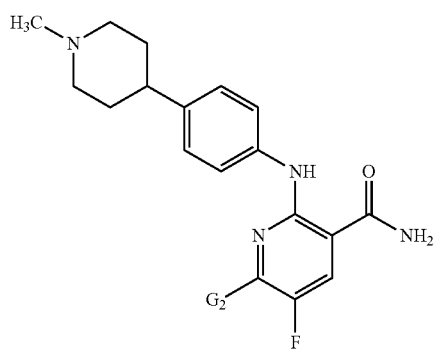
| Ex. | G₂ | FW | M + H |
|---|---|---|---|
| 489 | 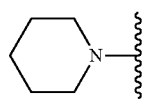 [SMILES: *N1CCCCC1] | 411.52 | 412.25 |
| 490 | 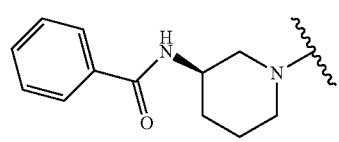 [SMILES: *N1CCC[C@@H](NC(=O)c2ccccc2)C1] | 530.64 | 531.31 |
| 491 | 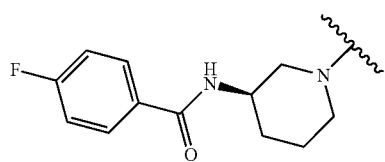 [SMILES: *N1CCC[C@@H](NC(=O)c2ccc(F)cc2)C1] | 548.64 | 549.29 |
| 492 | 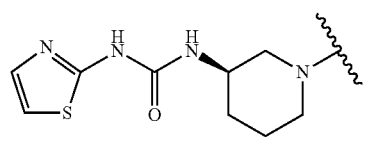 [SMILES: *N1CCC[C@@H](NC(=O)Nc2nccs2)C1] | 552.68 | 553.27 |
| 493 | 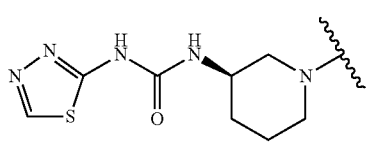 [SMILES: *N1CCC[C@@H](NC(=O)Nc2nncs2)C1] | 553.66 | 554.26 |
TABLE 30
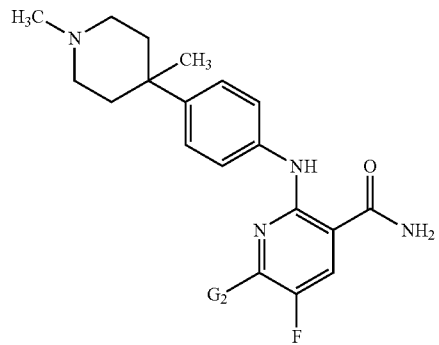
| Ex. | G₂ | FW | M + H |
|---|---|---|---|
| 494 | 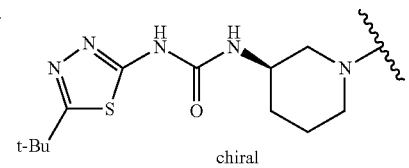 chiral | 623.80 | 624.29 |
| 495 | 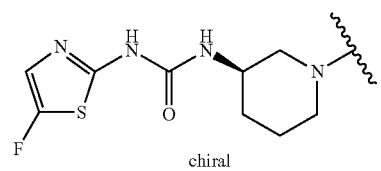 [SMILES: *N1CCC[C@@H](NC(=O)Nc2ncc(F)s2)C1] chiral | 584.69 | 585.18 |
TABLE 31
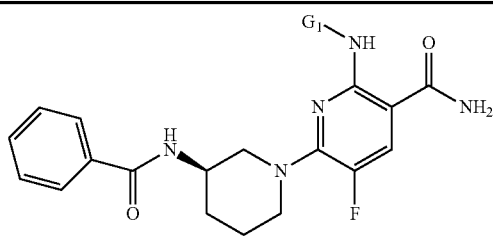
| Ex. | G₁ | FW | M + H |
|---|---|---|---|
| 496 | 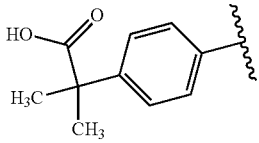 [SMILES: *c1ccc(C(C)(C)C(=O)O)cc1] | 519.57 | 520.06 |
| 497 | 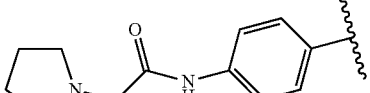 | 559.64 | 560.11 |
| 498 | 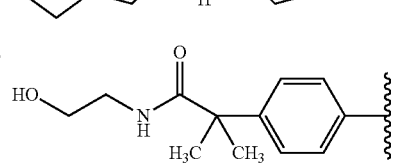 | 562.64 | 563.09 |

TABLE 31-continued
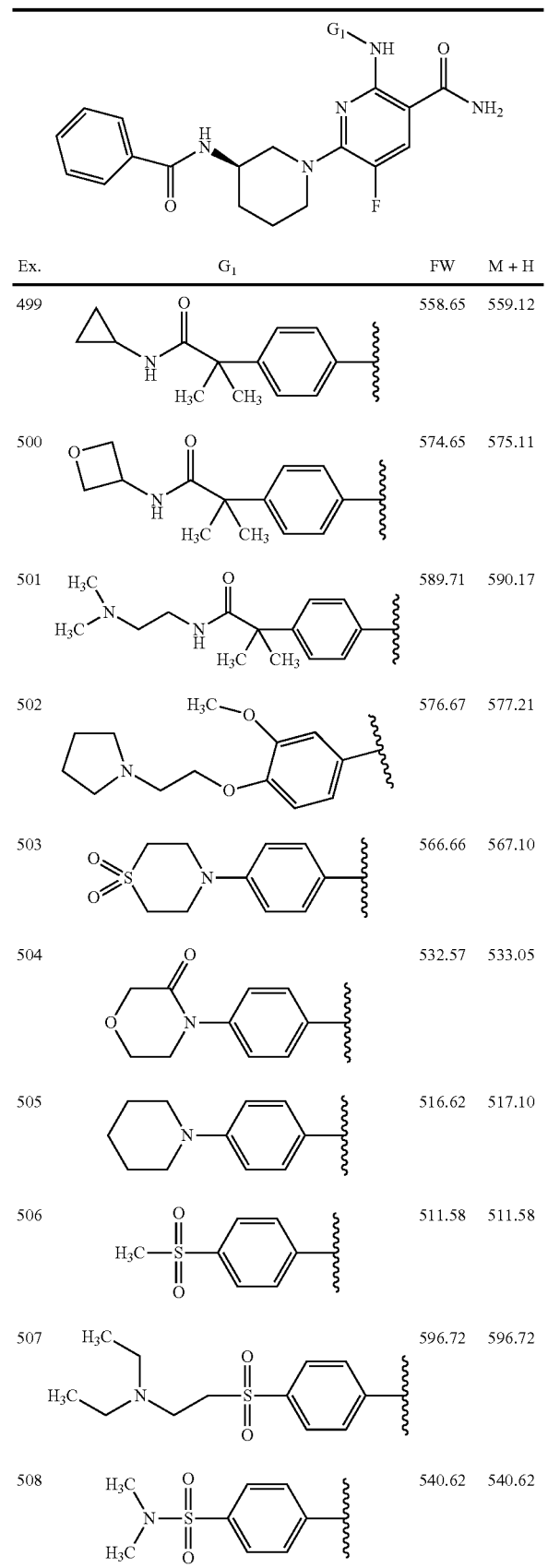
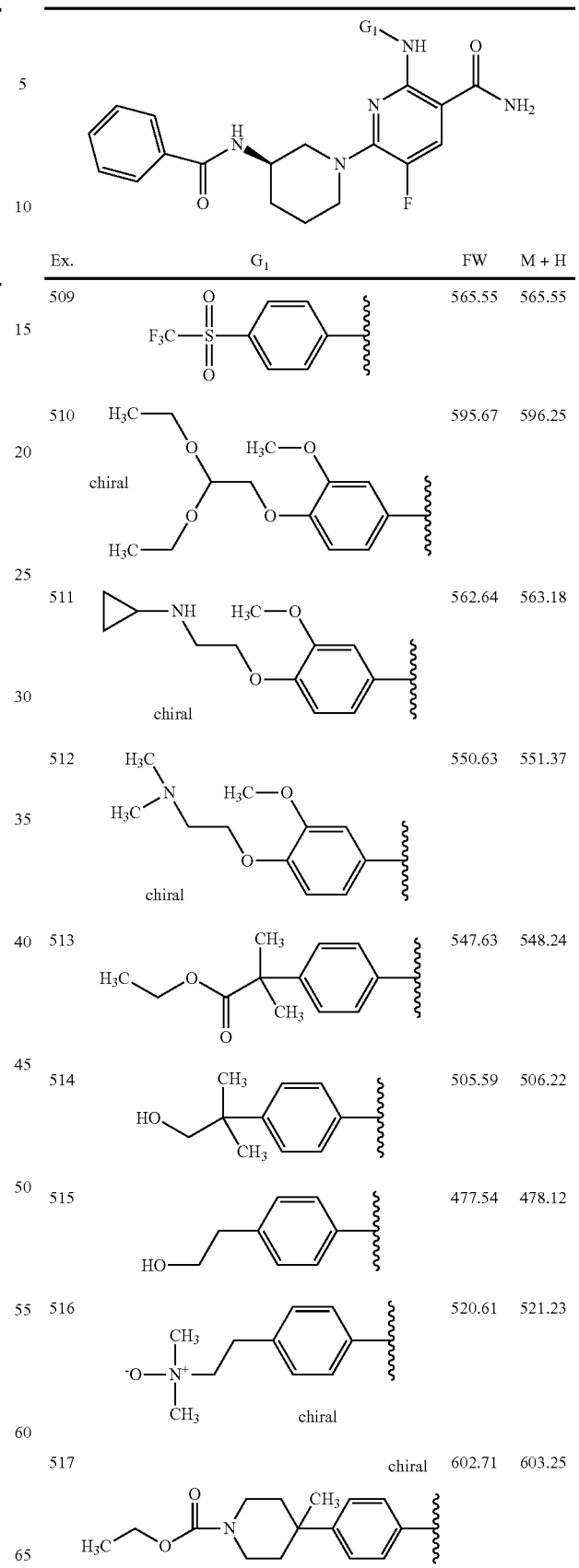
| Ex. | G₁ | FW | M + H |
|---|---|---|---|
| 499 | | 558.65 | 559.12 |
| 500 | | 574.65 | 575.11 |
| 501 | | 589.71 | 590.17 |
| 502 | | 576.67 | 577.21 |
| 503 | | 566.66 | 567.10 |
| 504 | | 532.57 | 533.05 |
| 505 | | 516.62 | 517.10 |
| 506 | | 511.58 | 511.58 |
| 507 | | 596.72 | 596.72 |
| 508 | | 540.62 | 540.62 |
| 509 | | 565.55 | 565.55 |
| 510 | | 595.67 | 596.25 |
| 511 | | 562.64 | 563.18 |
| 512 | | 550.63 | 551.37 |
| 513 | | 547.63 | 548.24 |
| 514 | | 505.59 | 506.22 |
| 515 | | 477.54 | 478.12 |
| 516 | | 520.61 | 521.23 |
| 517 | | 602.71 | 603.25 |

TABLE 31-continued

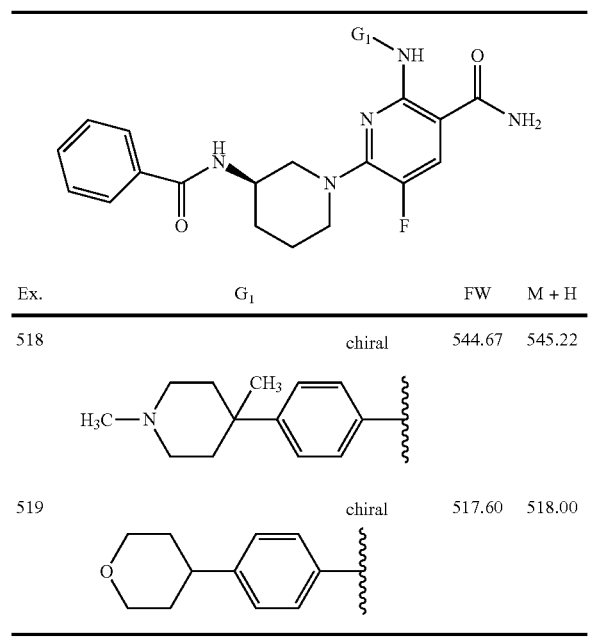

| Ex. | G₁ | FW | M + H |
|---|---|---|---|
| 518 | chiral (N-methyl-4-methylpiperidinyl-phenyl) | 544.67 | 545.22 |
| 519 | chiral (tetrahydropyranyl-phenyl) | 517.60 | 518.00 |

TABLE 32

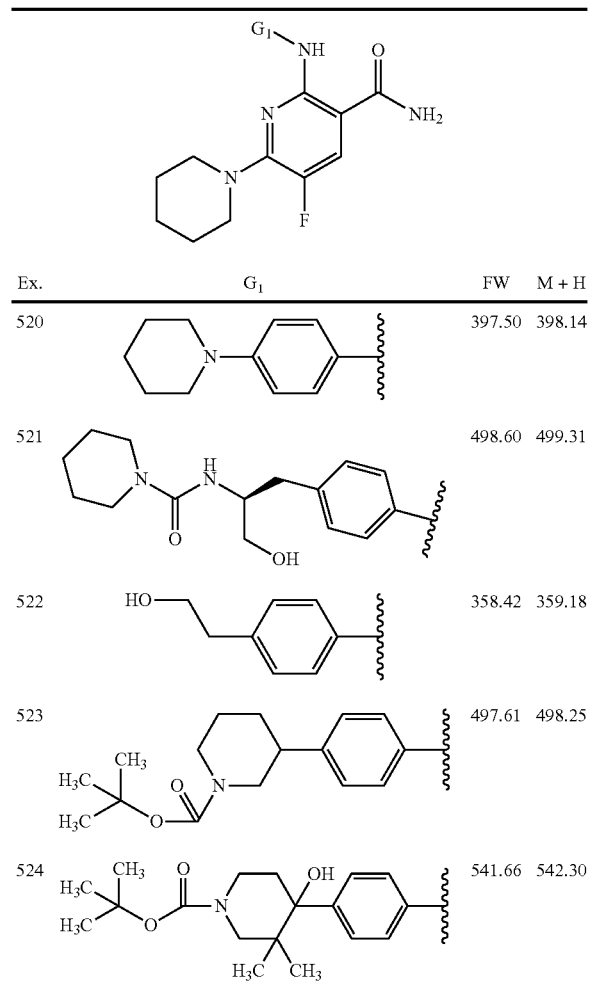

| Ex. | G₁ | FW | M + H |
|---|---|---|---|
| 520 | piperidinyl-phenyl | 397.50 | 398.14 |
| 521 | piperidine-carboxamide-CH₂CH(CH₂OH)-phenyl | 498.60 | 499.31 |
| 522 | HO-CH₂CH₂-phenyl | 358.42 | 359.18 |
| 523 | Boc-piperidinyl-phenyl | 497.61 | 498.25 |
| 524 | Boc-(4-OH, 3,3-dimethyl)piperidinyl-phenyl | 541.66 | 542.30 |

TABLE 32-continued

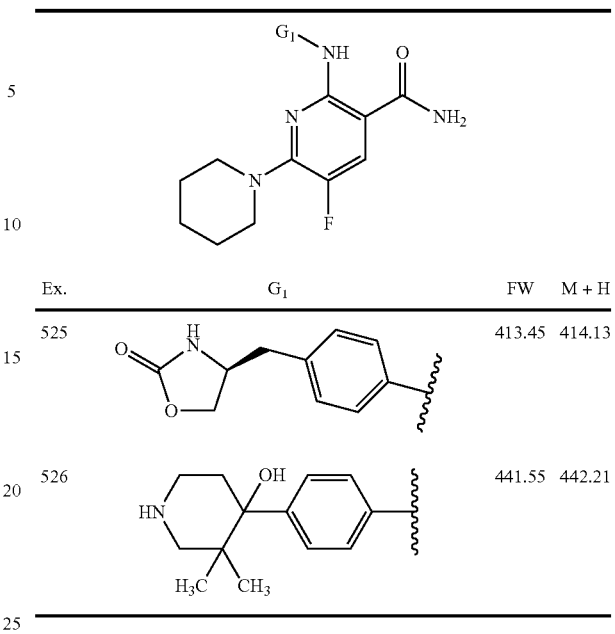

| Ex. | G₁ | FW | M + H |
|---|---|---|---|
| 525 | oxazolidinone-CH₂-phenyl | 413.45 | 414.13 |
| 526 | (4-OH, 3,3-dimethyl)piperidinyl-phenyl | 441.55 | 442.21 |

TABLE 33

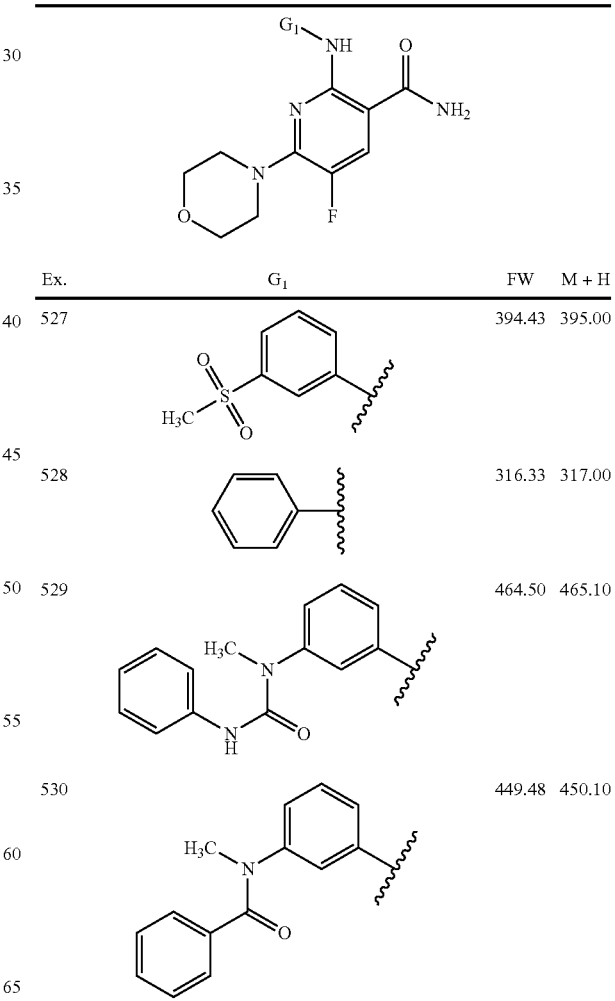

| Ex. | G₁ | FW | M + H |
|---|---|---|---|
| 527 | methylsulfonyl-phenyl | 394.43 | 395.00 |
| 528 | phenyl | 316.33 | 317.00 |
| 529 | N-methyl-N-phenyl-urea-phenyl | 464.50 | 465.10 |
| 530 | N-methyl-N-benzoyl-phenyl | 449.48 | 450.10 |

TABLE 33-continued
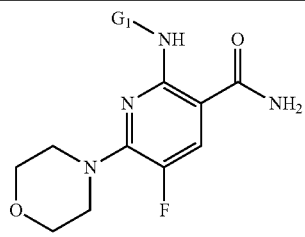
| Ex. | G₁ | FW | M + H |
|---|---|---|---|
| 531 | | 485.54 | 486.00 |
| 532 | | 471.51 | 472.00 |
| 533 | | 463.53 | 464.10 |
| 534 | | 413.41 | 414.00 |
| 535 | | 612.53 | 613.90 |
| 536 | | 471.94 | 472.00 |
| 537 | | 561.64 | 562.00 |
TABLE 33-continued
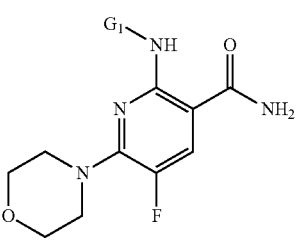
| Ex. | G₁ | FW | M + H |
|---|---|---|---|
| 538 | | 535.60 | 536.10 |
| 539 | | 535.60 | 536.10 |
| 540 | | 503.53 | 504.00 |
| 541 | | 503.53 | 504.10 |
| 542 | | 526.01 | 525.90 |
| 543 | | 489.53 | 490.10 |

TABLE 34
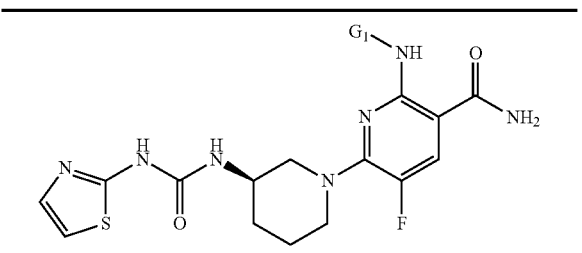
| Ex. | G₁ | FW | M + H |
|---|---|---|---|
| 544 | | 581.67 | 582.22 |
| 545 | | 499.57 | 500.10 |
| 546 | | 533.61 | 533.98 |
| 547 | | 538.65 | 539.13 |
| 548 | | 549.63 | 550.18 |
| 549 | | 552.68 | 553.15 |
| 550 | chiral | 554.69 | 555.23 |
| 551 | chiral | 624.74 | 625.23 |
| 552 | chiral | 542.64 | 543.12 |
TABLE 34-continued
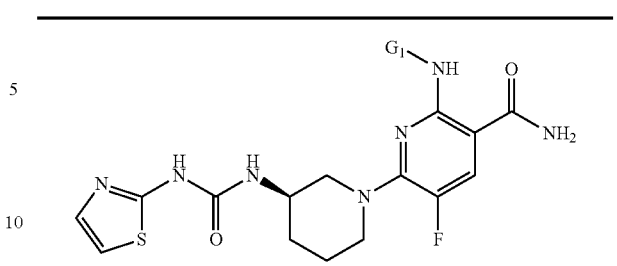
| Ex. | G₁ | FW | M + H |
|---|---|---|---|
| 553 | chiral | 556.62 | 557.08 |
| 554 | chiral | 566.70 | 567.21 |
| 555 | chiral | 539.63 | 540.16 |
TABLE 35
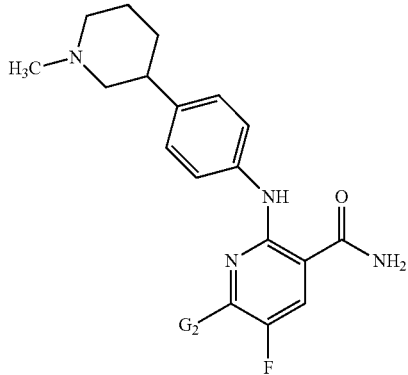
| Ex. | G₂ | FW | M + H |
|---|---|---|---|
| 556 | | 411.52 | 412.18 |
| 557 | | 552.68 | 553.16 |

TABLE 35-continued
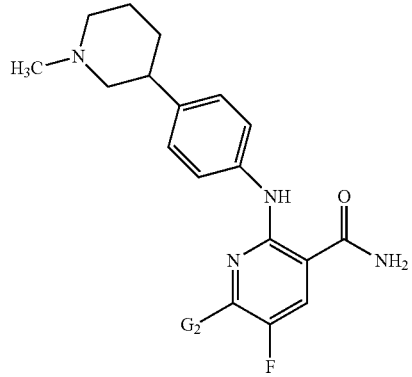
| Ex. | G₂ | FW | M + H |
|---|---|---|---|
| 558 | 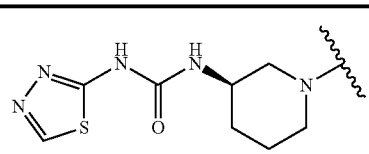 | 553.66 | 554.16 |
| 559 | 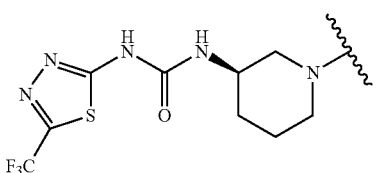 | 621.66 | 622.18 |
| 560 | 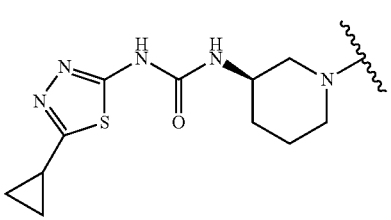 [SMILES: *N1CCC[C@@H](NC(=O)Nc2nnc(C3CC3)s2)C1] | 593.73 | 594.21 |
| 561 | 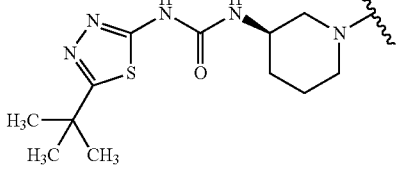 | 609.77 | 610.24 |
| 562 | 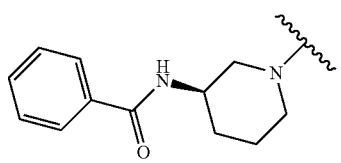 [SMILES: *N1CCC[C@@H](NC(=O)c2ccccc2)C1] | 530.64 | 531.21 |
| 563 | 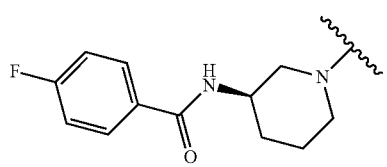 [SMILES: *N1CCC[C@@H](NC(=O)c2ccc(F)cc2)C1] | 548.64 | 549.18 |
TABLE 35-continued
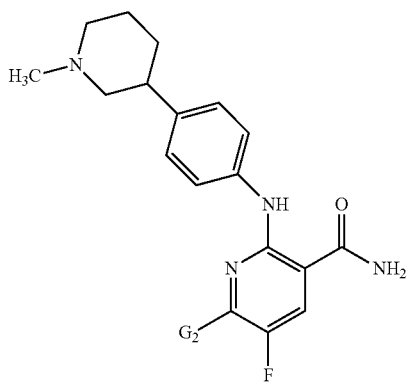
| Ex. | G₂ | FW | M + H |
|---|---|---|---|
| 564 | 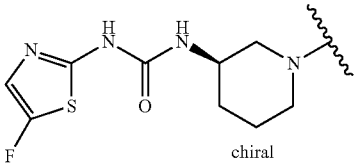 [SMILES: *N1CCC[C@@H](NC(=O)Nc2ncc(F)s2)C1] chiral | 570.67 | 571.17 |
TABLE 36
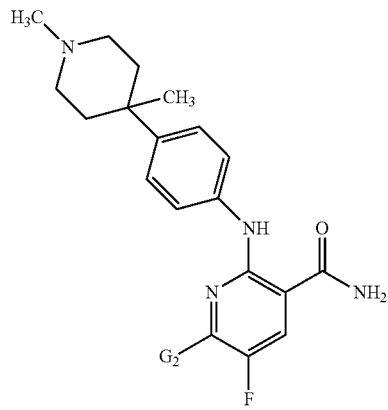
| Ex. | G₂ | FW | M + H |
|---|---|---|---|
| 565 | 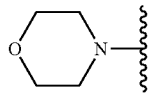 [SMILES: *N1CCOCC1] | 427.52 | 428.15 |
| 566 | 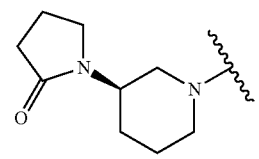 chiral | 508.64 | 509.25 |

TABLE 37

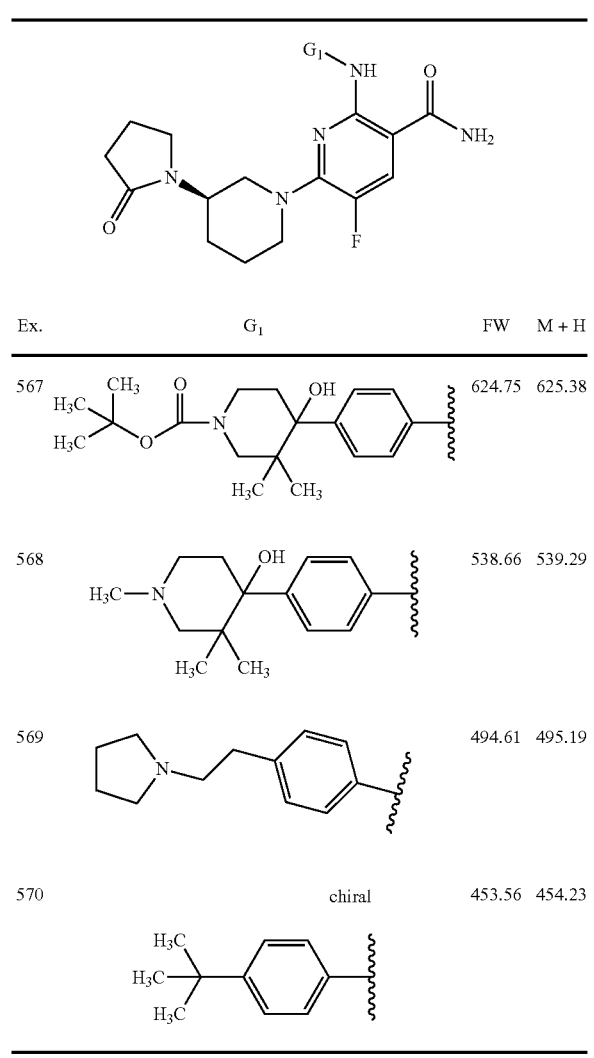

| Ex. | G₁ | FW | M + H |
|---|---|---|---|
| 567 | (tert-butyl carbamate piperidinol dimethyl phenyl) | 624.75 | 625.38 |
| 568 | (N-methyl piperidinol dimethyl phenyl) | 538.66 | 539.29 |
| 569 | (pyrrolidinyl ethyl phenyl) | 494.61 | 495.19 |
| 570 | chiral (tert-butyl phenyl) | 453.56 | 454.23 |

TABLE 38

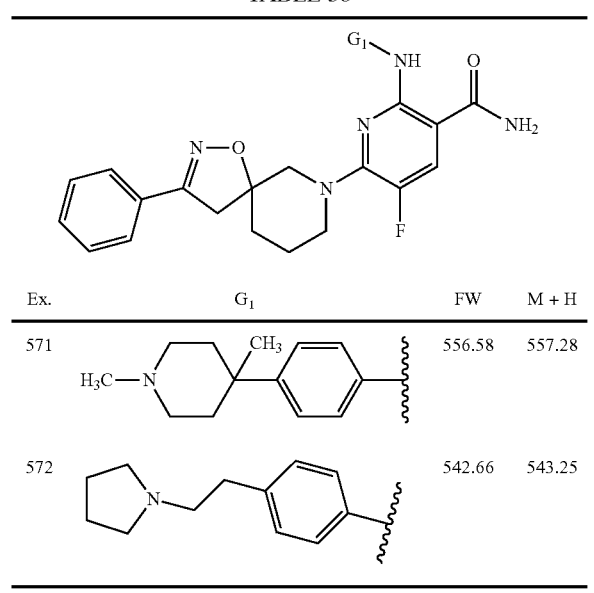

| Ex. | G₁ | FW | M + H |
|---|---|---|---|
| 571 | (N-methyl-4-methylpiperidinyl phenyl) | 556.58 | 557.28 |
| 572 | (pyrrolidinyl ethyl phenyl) | 542.66 | 543.25 |

TABLE 39

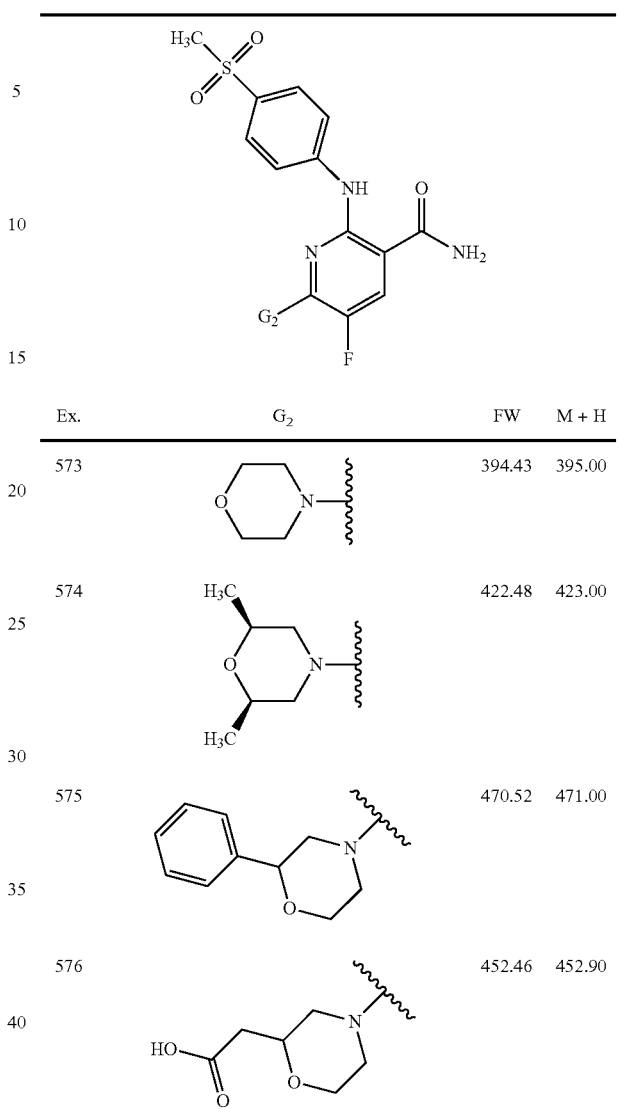

| Ex. | G₂ | FW | M + H |
|---|---|---|---|
| 573 | morpholinyl | 394.43 | 395.00 |
| 574 | (2,6-dimethyl morpholinyl) | 422.48 | 423.00 |
| 575 | (2-phenyl morpholinyl) | 470.52 | 471.00 |
| 576 | (morpholinyl acetic acid) | 452.46 | 452.90 |
| 577 | (phenyl carbamoylmethyl morpholinyl) | 527.57 | 528.08 |
| 578 | (oxopiperazinyl) | 526.01 | 525.90 |
| 579 | (phenylsulfonylmethyl morpholinyl) | 548.61 | 549.06 |

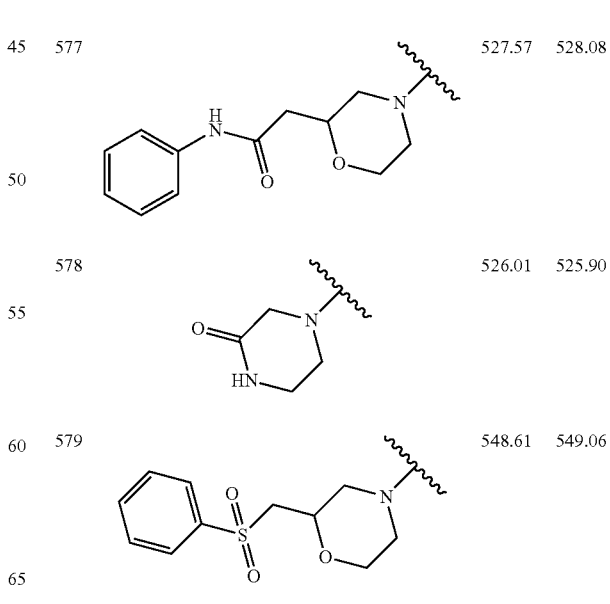

TABLE 39-continued
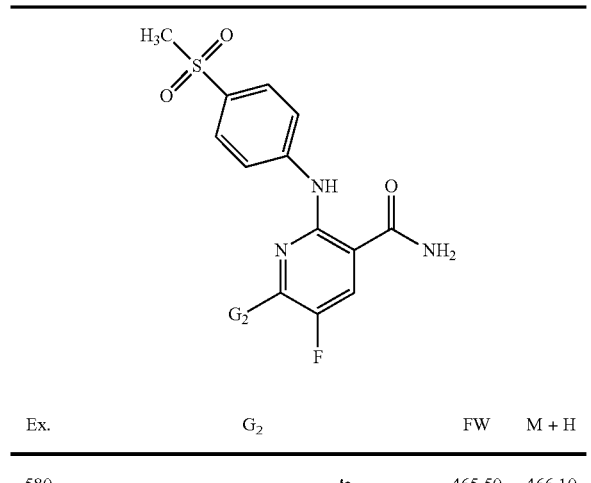
| Ex. | G$_2$ | FW | M + H |
|---|---|---|---|
| 580 | | 465.50 | 466.10 |
| 581 | | 479.53 | 480.07 |
| 582 | | 429.43 | 430.02 |
TABLE 40
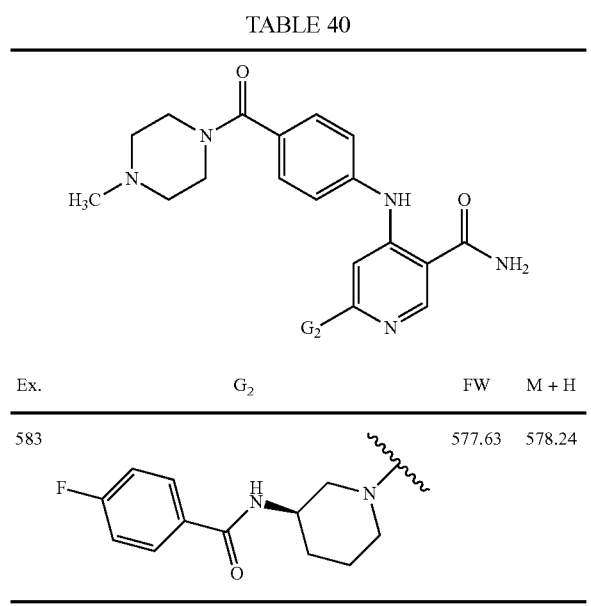
| Ex. | G$_2$ | FW | M + H |
|---|---|---|---|
| 583 | | 577.63 | 578.24 |
TABLE 41
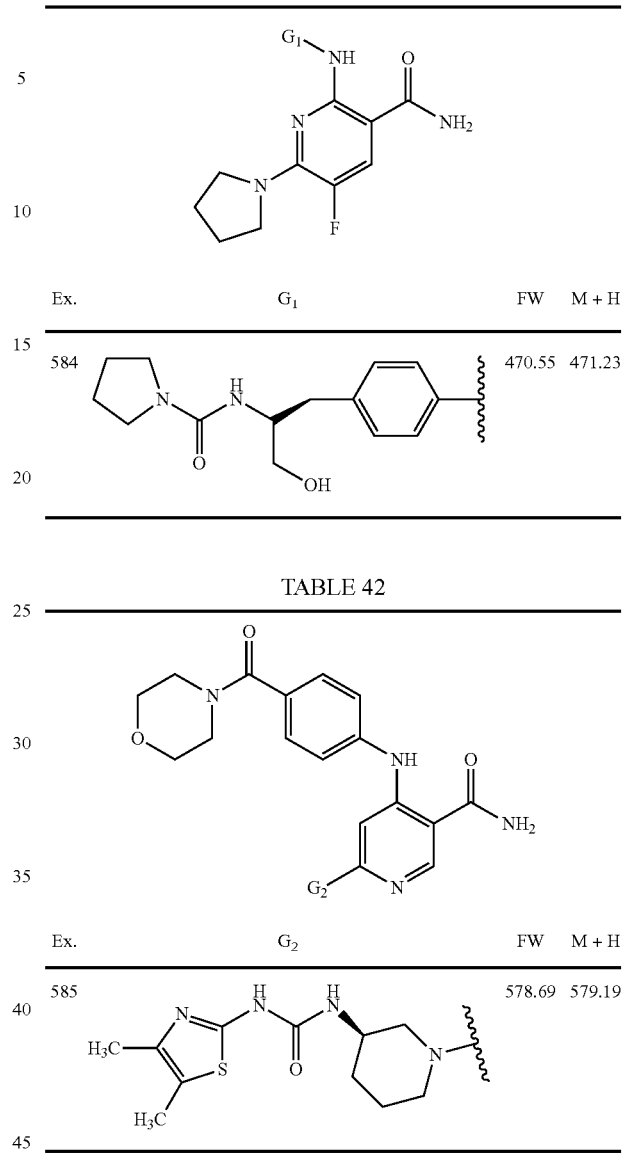
| Ex. | G$_1$ | FW | M + H |
|---|---|---|---|
| 584 | | 470.55 | 471.23 |
TABLE 42
| Ex. | G$_2$ | FW | M + H |
|---|---|---|---|
| 585 | | 578.69 | 579.19 |
TABLE 43
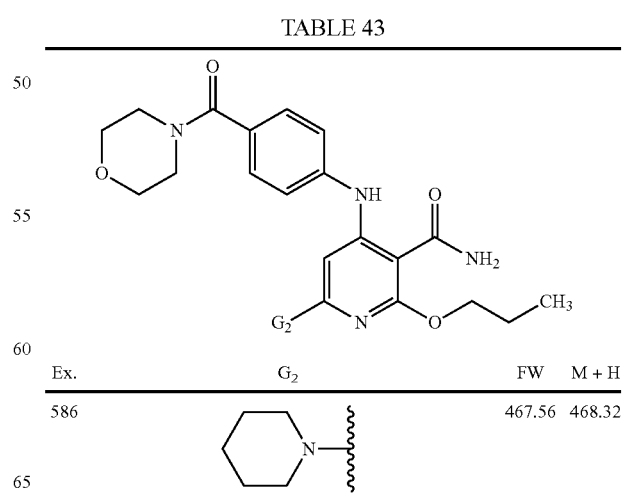
| Ex. | G$_2$ | FW | M + H |
|---|---|---|---|
| 586 | | 467.56 | 468.32 |

TABLE 43-continued

| Ex. | G₂ | FW | M+H |
|---|---|---|---|
| 587 | 4,5-dimethylthiazol-2-yl urea (H₃C, H₃C on thiazole) | 636.76 | 637.41 |
| 588 | 3,4-dimethylphenyl urea (H₃C, H₃C on phenyl) | 629.75 | 630.42 |

Table 44 below lists $IC_{50}$ values for the following examples of the invention measured in the Human Recombinant BTK enzyme assay (LLE_BTK) and/or the NFAT-bla RA1 Reporter assay (Ramos-NFAT), each of which is described herein above.

TABLE 44

| Ex. | LLE_BTK (IC50, uM) | IMM Ramos-NFAT (IC50, uM) |
|---|---|---|
| 10 | 1.8 | — |
| 12 | 0.007 | 0.04 |
| 15 | 0.87 | — |
| 29 | 0.001 | 0.16 |
| 37 | 1.4 | — |
| 44 | 0.75 | — |
| 45 | 2.1 | — |
| 50 | 0.74 | — |
| 132 | 1.0 | — |
| 143 | 1.2 | — |
| 162 | 1.4 | — |
| 163 | 1.5 | — |
| 164 | 2.7 | — |
| 165 | 2.9 | — |
| 167 | 1.8 | — |
| 263 | 0.0009 | 5.7 |
| 283 | 0.01 | 0.12 |
| 284 | 0.007 | 0.06 |
| 295 | 1.7 | — |
| 298 | 12 | — |
| 299 | 1.5 | — |
| 300 | 1.3 | — |
| 302 | 0.88 | — |
| 314 | 1.8 | — |
| 323 | 0.78 | — |
| 331 | 0.78 | — |
| 337 | 0.76 | — |
| 345 | 0.9 | 0.92 |
| 346 | 2.9 | 10 |
| 347 | 2.0 | 10 |
| 354 | 0.004 | 0.1 |
| 357 | 0.004 | 0.1 |
| 361 | 0.009 | 0.1 |
| 375 | 1.2 | — |
| 376 | 6.9 | — |
| 380 | 3.2 | — |
| 381 | 1.0 | — |
| 382 | 0.002 | 0.8 |
| 385 | 0.003 | 0.02 |
| 386 | 0.01 | 0.11 |
| 388 | 0.004 | 0.07 |
| 393 | 0.02 | 0.12 |
| 407 | 0.03 | 0.12 |
| 412 | 0.001 | 0.18 |
| 413 | 0.001 | 0.24 |
| 414 | 0.002 | 0.23 |
| 418 | 0.002 | 0.38 |
| 419 | 0.001 | 0.18 |
| 421 | 0.002 | 0.04 |
| 422 | 0.02 | 0.12 |
| 430 | 0.74 | 10 |
| 435 | 1.3 | 4.5 |
| 436 | 2.2 | 7.9 |
| 437 | 0.74 | 2.9 |
| 442 | 2.6 | — |
| 442 | 2.6 | — |
| 451 | 0.0008 | 0.08 |
| 456 | 4.3 | 10 |
| 458 | 0.0006 | 0.03 |
|  | 0.0006 | 0.05 |
| 462 | 0.002 | 0.25 |
| 475 | 0.02 | 0.1 |
| 479 | 0.001 | 0.07 |
| 480 | 0.0002 | 0.04 |
| 482 | 0.002 | 0.17 |
| 489 | 0.01 | 0.1 |
| 490 | 0.003 | 0.27 |
| 491 | 0.002 | 0.2 |
| 492 | 0.001 | 0.02 |
| 493 | 0.0007 | 0.13 |
| 494 | 0.0006 | — |
| 495 | 0.001 | 0.08 |
| 503 | 0.007 | 0.08 |
| 506 | 0.002 | 0.15 |
| 508 | 0.0008 | 0.14 |
| 511 | 0.73 | — |
| 518 | 0.002 | 0.03 |
| 523 | 3.7 | 10 |
| 524 | 1.6 | 5.7 |
| 529 | 1.0 | — |
| 533 | 22 | — |
| 535 | 0.98 | — |
| 537 | 1.1 | — |
| 538 | 1.2 | — |
| 544 | 0.0009 | 0.56 |
| 545 | 0.002 | 0.16 |
| 546 | 0.003 | 0.23 |
| 547 | 0.001 | 0.05 |
| 548 | 0.002 | 0.27 |
| 549 | 0.0007 | 0.03 |
| 550 | 0.002 | 0.12 |
| 552 | 0.001 | 5.4 |
| 554 | 0.0007 | 0.04 |
| 555 | 0.003 | 0.19 |
| 557 | 0.002 | 0.06 |
| 558 | 0.002 | 0.38 |
| 559 | 0.002 | 0.07 |
| 560 | 0.0008 | 0.18 |
| 561 | 0.0009 | 0.14 |
| 564 | 0.001 | 0.10 |
| 566 | 0.003 | 0.09 |
| 568 | 0.001 | 0.12 |
| 571 | 0.002 | 0.15 |

What is claimed is:

1. A compound having Formula (I):

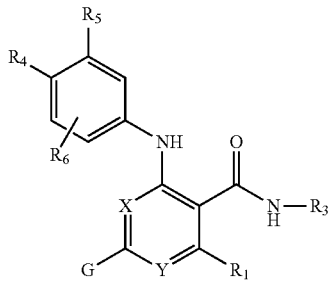

or stereoisomers or pharmaceutically acceptable salts thereof, wherein:

X is N; and Y is $CR_2$;

G is
  a cyclic group selected from 1- to 2-ring carbocyclyl, 1- to 2-ring aryl, 1- to 2-ring heterocyclyl, and 1- to 2-ring heteroaryl, each substituted with zero to 3 $R_f$;

$R_1$ is H or $-OR_a$;

$R_2$ is H, $-OCH_3$, halo, $-CH_3$, $-CF_3$, $-OCF_3$, or $-CN$;

$R_3$ is H or $-CH_3$;

$R_6$ is H, alkoxy, halo, $-CH_3$, $-CF_3$, $-OCF_3$, or $-CN$;

one of $R_4$ and $R_5$ is H, halo, $-CH_3$, $-CF_3$, $-CN$, $-NH_2$, $-OH$, alkoxy, $-OCF_3$, $-NR_dR_d$, $-NR_bS(O)_2$(alkyl), $-NR_bS(O)_2$(aryl), $-NR_bC(O)$(phenyl), $-NR_bC(O)NR_b$(phenyl), $-S(O)_2(C_{1-4}$alkyl), $-NR_bS(O)_2$(heterocyclyl), $-NR_bS(O)_2(C_{1-4}$ haloalkyl), $-NR_bS(O)_2$(fluorophenyl), $-NR_bS(O)_2$(biphenyl), $-NR_bS(O)_2$(heteroaryl), $-NR_bS(O)_2$(benzyl), $-N(S(O)_2(C_{1-4}$haloalkyl))$_2$, pyrrolidine-2,5-dione, $-NR_bC(O)O$(alkyl) or -L-C(O)-A;

and the other of $R_4$ and $R_5$ is:
  a) H, halo, $-CN$, or alkoxy;
  b) -L-A; or
  c) -L-C(O)-A;

wherein L is a bond or $-(CR_cR_c)_t-$; and A is selected from $A_1$, $A_2$, and $A_3$, wherein:

$A_1$ is alkyl or cycloalkyl, each independently substituted with 0 to 5 substituents independently selected from $-OH$, $=O$, alkyl, $-OH$, alkoxy, $-C(O)$(alkyl), $-C(O)OR_d$, $-NR_dR_d$, $-C(O)NR_dR_d$, $-C(O)NR_b$(hydroxyalkyl), $-C(O)NR_b$(heterocyclyl), $-C(O)NR_b(CR_bR_b)_qNR_dR_d$, and/or $-NR_bC(O)$(alkyl);

$A_2$ is heterocyclyl or heteroaryl having 1- to 3-heteroatoms independently selected from N, O, and/or S, and substituted with zero to 5 substituents independently selected from $-OH$, $=O$, alkyl, hydroxyalkyl, cycloalkyl, $-C(O)$(alkyl), $-NR_dR_d$, $-C(O)NR_dR_d$, $-C(O)NR_b$(hydroxyalkyl), $-C(O)NR_b$(cycloalkyl), $-C(O)NR_b(CR_bR_b)_qNR_dR_d$, $-C(O)NR_b$(phenyl), $-NR_bC(O)$(alkyl), $-C(O)O$(alkyl), and/or $-C(O)O$(benzyl);

$A_3$ is $-OH$, alkoxy, $-NR_dR_d$, di-$(C_{1-2}$alkyl) N-oxide, $-NR_b$(hydroxyalkyl), $-NR_b$(cycloalkyl), $-NR_b(CR_bR_b)_qNR_dR_d$, $-NR_b$(phenyl), $-NR_bC(O)$(alkyl), $-S$(alkyl), $-S(O)_2$(alkyl), $-S(O)_2$(fluoroalkyl), $-S(O)_2NR_dR_d$, $-S(O)_2(CR_bR_b)_qNR_dR_d$, $-O(CR_bR_b)_qCR_b$(alkoxy)$_2$, $-O(CR_bR_b)_qNR_b$(cycloalkyl), $-O(CR_bR_b)_qNR_dR_d$, $-NR_bS(O)_2$(alkyl), $-NR_bS(O)_2$(aryl), $-NR_bS(O)_2$(heteroaryl), $-NR_bC(O)NR_bA_2$, $-NR_bC(O)A_2$, $-NR_bA_2$, $-NR_bC(O)(CR_bR_b)_qA_2$, or $-O(CR_cR_c)_qA_2$;

$R_a$ is H, alkyl, hydroxyalkyl, or $-(CH_2)_n$phenyl, wherein said phenyl in turn is substituted with zero to 4 $R_h$;

each $R_b$ is independently H and/or $-CH_3$;

each $R_c$ is independently H, $-OH$, $-CH_3$, F, and/or $-CH_2OH$;

each $R_d$ is independently H and/or alkyl;

each $R_f$ is independently H, $Q_1$, $R_g$, $-C(O)Q_2$, $-C(O)(CR_bR_b)_qQ_2$, $-C(O)NR_bQ_2$, $-C(O)N(Q_2)_2$, $-NR_bQ_2$, $-NR_bCR_bR_bQ_2$, $-N(Q_2)_2$, $-(CR_bR_b)_qQ_2$, $-(CR_bR_b)_tNR_bC(O)Q_2$, $-C(O)NR_b(CR_bR_b)_tQ_2$, $-NR_bS(O)_2Q_2$, $-NR_bS(O)_2Q_2$, $-(CR_bR_b)_tNR_bQ_2$, and/or 5- to 6-membered heterocyclyl substituted with 0-3 $R_g$;

each $R_g$ is independently $Q_2$, $=O$, $=CR_bR_b$, $-OH$, halo, $-CN$, alkyl, hydroxyalkyl, haloalkyl, aminoalkyl, phenyl, phenoxy, alkoxy, aryl, heteroaryl, heterocyclyl, $-NR_dR_d$, $-C(O)$(alkyl), $-C(O)CR_bR_b$(phenyl), $-CR_bR_bC(O)$(phenyl), and/or $-C(O)NR_dR_d$; and/or two $R_g$ together with the carbon atom to which they are attached form a 5- to 7-membered cycloalkyl or heterocyclyl ring substituted with zero to 2 substituents independently selected from $-OH$, alkyl, cycloalkyl, halo, fluoroalkyl, $=O$, 1- to 2-ring aryl, and/or 1- to 2-ring heteroaryl each $Q_1$ is independently:

a) H, $-OH$, $-C(O)OR_d$, $-C(O)NR_b$(phenyl), $-C(O)NR_b$(alkyl phenyl), $-OC(O)$(phenyl), $-O$(phenyl), phenyl, $-NR_dR_d$, $-NR_b$(pyrimidinyl), $-N$(pyrimidinyl)$_2$, hydroxyalkyl, aminoalkyl, $-(CR_bR_b)_qC(O)O$(alkyl), $-(CR_bR_b)_qNR_bC(O)O$(alkyl), indolyl, imidazolidinonyl, and/or pyrrolidinonyl;
  b) $-NR_dC(O)-Q_2$;
  c) $-NR_bC(O)(CR_bR_b)_t-Q_2$;
  d)

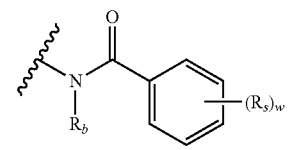

wherein each $R_s$ is independently selected from alkyl, fluoroalkyl, halo, $-OH$, $-C(O)$(alkyl), $-NR_bC(O)$(alkyl), $-C(O)OR_d$, alkoxy, fluoroalkoxy, $-NR_dR_d$, $-S(O)_2$(alkyl), $-NR_bC(O)O$(alkyl), phenoxy, $-CR_bR_bNR_bC(O)$(alkyl), and/or a cyclic group independently selected from aryl, heteroaryl, and/or heterocyclyl, wherein said cyclic group is substituted with zero or more substituents independently selected from alkyl, $-OH$, halo, haloalkyl, $-NR_dR_d$, alkoxy, $=O$, and/or $-CN$;

e) $-NR_bS(O)_2-Q_2$;
  f) $-(CR_bR_b)_tC(O)-Q_2$;
  g) $-NR_bC(O)NR_b-Q_2$; and/or
  h) $-(CR_bR_b)_tC(O)NR_b-Q_2$;

each $Q_2$ is independently:

a) H, $-OH$, alkyl, haloalkyl, $-NR_dR_d$, alkoxy, phenoxy, and/or benzophenonyl;
  b) cycloalkyl, aryl, heterocyclyl, and/or heteroaryl, each of which is substituted with zero or more substituents independently selected from alkyl, fluoroalkyl, cycloalkyl, halo, $-CN$, $-OH$, $=O$, $-NR_dR_d$, alkoxy, fluoroalkoxy, $-C(O)$(alkyl), $-C(O)O$(alkyl), phenoxy, $-O$(cycloalkyl), $-NR_bC(O)$ (alkyl), —S(alkyl), —S(O)₂(alkyl), —NR_bC(O)O (alkyl), —CR_bR_bNR_bC(O)(alkyl), and/or a cyclic group independently selected from aryl, heteroaryl, and/or heterocyclyl, wherein said cyclic group is substituted with zero or more substituents independently selected from alkyl, —OH, halo, —NR_dR_d, alkoxy, =O, —CN, and/or haloalkyl; and/or c) —(CR_bR_b)_qN(alkyl)₂, —(CR_bR_b)_q(aryl), and/or —(CR_bR_b)_q(heteroaryl);

each $R_h$ is independently —OH, —NH₂, alkyl, halo, haloalkyl, alkoxy, and/or haloalkoxy;

n is zero, 1, 2, 3, 4, 5, or 6;

each q is independently 1, 2, and/or 3;

each t is independently 1, 2, 3, and/or 4; and w is zero, 1, 2, or 3.

2. The compound according to claim 1 or stereoisomers or pharmaceutically acceptable salts thereof, wherein:

G is:

i) 1- to 2-ring heteroaryl or 1- to 2-ring heterocyclyl substituted with zero to 3 substituents independently selected from alkyl, phenyl, —NR_dR_d, —NR_dC(O)O(alkyl), —C(O)(alkyl), —C(O)(phenyl), and/or —C(O)(benzyl);

ii)

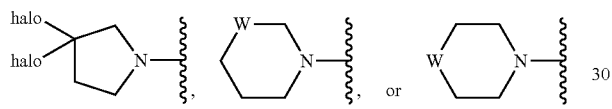

wherein W is CR_b(OR_b), C=CR_bR_b, NR_d, or NC(O)CR_bR_b(phenyl); or W is CR_gR_g and a) each $R_g$ is halo; or b) $R_g$ and $R_g$ together with the carbon atom to which they are attached, form a 5- to 7-membered cycloalkyl or heterocyclyl ring substituted with zero to 2 substituents independently selected from —OH, alkyl, cycloalkyl, halo, —CF₃, =O, —C(O)OH, —C(O)(C_{1-6}alkyl), 1- to 2-ring aryl, and/or 1- to 2-ring heteroaryl;

iii) naphthalenyl; or phenyl substituted with zero to 3 substituents independently selected from —OH, alkyl, fluoroalkyl, halo, —CN, —NR_bR_b, —C(O)OH, alkoxy, —CR_bR_bO(alkyl), —CH₂NR_bC(O)(alkyl), —CH₂NR_bC(O)(phenyl), —C(O)(alkyl), —C(O)(heterocyclyl), phenoxy, —C(O)O(alkyl), —C(O)NR_b(alkyl), —C(O)N(alkyl)₂, —C(O)NR_bCR_bR_b(heteroaryl), —NR_bS(O)₂(alkyl), —NR_bS(O)₂(phenyl), —NR_bC(O)(phenyl), —NR_bC(O)(alkyl phenyl), and/or —NR_bC(O)NR_b(phenyl); or iv)

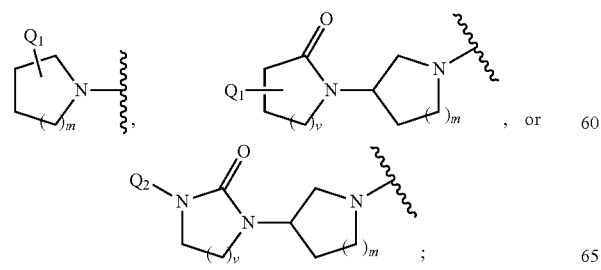

v) cycloalkyl or cycloalkenyl substituted with zero to 2 substituents independently selected from —OH, halo, —CF₃, =O, —OC(O)(phenyl), —NR_bC(O)(phenyl), —NR_bCR_bR_b(methoxyphenyl), —NR_bC(O)NR_b(thiazolyl),

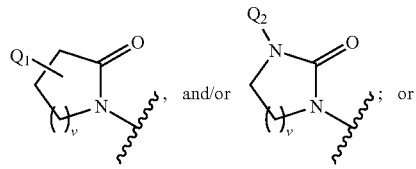

vi)

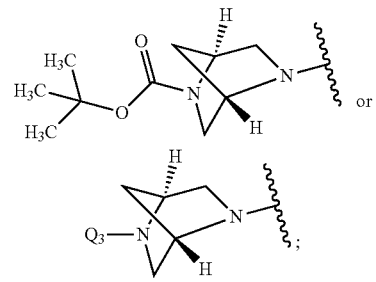

$Q_3$ is H, —C(O)O(C_{1-4}alkyl), —C(O)NR_b(C_{1-4}alkyl), or —C(O)NR_b(1-ring heteroaryl);

each $R_d$ is independently H and/or C_{1-6}alkyl;

m is 1 or 2; and v is 1 or 2.

3. The compound according to claim 2 or stereoisomers or pharmaceutically acceptable salts thereof, wherein:

$R_a$ is H, C_{1-6}alkyl, C_{1-6}hydroxyalkyl, or —(CH₂)_nphenyl, wherein said phenyl in turn is substituted with zero to 4 $R_h$;

one of $R_4$ and $R_5$ is H, halo, —CH₃, —CF₃, —CN, —NH₂, —OH, C_{1-3}alkoxy, —OCF₃, —C(O)NR_b(C_{1-2}alkyl), —NR_b(C_{1-2}alkyl), —NR_bS(O)₂(C_{1-2}alkyl), —NR_bS(O)₂(phenyl), —NR_bC(O)(phenyl), pyrrolidine-2,5-dione, —NR_bC(O)NR_b(phenyl), —NR_bS(O)₂(pyrrolidinyl), —S(O)₂(C_{1-4}alkyl), —NR_bS(O)₂(C_{1-4}alkyl), —NR_bS(O)₂(fluorophenyl), —NR_bS(O)₂(biphenyl), —NR_bS(O)₂(naphthalenyl), —NR_bS(O)₂(imidazolyl), —NR_bS(O)₂(chlorothiophenyl), —NR_bS(O)₂(benzyl), —NR_bS(O)₂(pyridinyl), —NR_b(S(O)₂(C_{1-4}haloalkyl), —N(S(O)₂(C_{1-4}haloalkyl))₂, or —NR_bC(O)O(C_{1-4}alkyl);

and the other of $R_4$ and $R_5$ is:

a) H, halo, —CN, or C_{1-6}alkoxy;

b) -L-A; or c) -L-C(O)-A;

wherein L is a bond or —(CR_cR_c)_t—; and A is selected from A₁, A₂, and A₃, wherein:

A₁ is C_{1-6}alkyl or C_{5-7}cycloalkyl, each independently substituted with 0 to 3 substituents independently selected from —OH, —NH₂, C_{1-3}alkoxy, —C(O)NH₂, —C(O)(C_{1-6}alkyl), —C(O)OR_b, —NH(C_{1-6}alkyl), —N(C_{1-6}alkyl)₂, —C(O)NR_b(C_{1-6}alkyl), —C(O)NR_b(C_{1-6}hydroxyalkyl), —C(O)NR_b(heterocyclyl), —NR_bC(O)(C_{1-6}alkyl), —C(O)NR_b(CR_bR_b)_qNH(C_{1-6}alkyl), and/or —C(O)NR_b(CR_bR_b)_qN(C_{1-6}alkyl)₂;

A₂ is 4- to 6-membered heterocyclyl or 5- to 6-membered heteroaryl having 1- to 3-heteroatoms independently selected from N, O, and/or S, and substituted with zero to 4 substituents independently selected from —OH, =O, C₁₋₆alkyl, C₁₋₄-hydroxyalkyl, C₃₋₆cycloalkyl, —C(O)(C₁₋₆alkyl), —NH(C₁₋₆alkyl), —N(C₁₋₆alkyl)₂, —C(O)NR$_b$(C₁₋₆alkyl), —C(O)NR$_b$(C₁₋₆hydroxyalkyl), —C(O)NR$_b$(C₃₋₆cycloalkyl), —C(O)NR$_b$(CR$_b$R$_b$)$_q$NH(C₁₋₆alkyl), —C(O)NR$_b$(phenyl), —C(O)NR$_b$(CR$_b$R$_b$)$_q$N(C₁₋₆alkyl)₂, —C(O)NR$_b$R$_b$, —NR$_b$C(O)(C₁₋₆alkyl), —C(O)O(C₁₋₄alkyl), and/or —C(O)O(benzyl);

A₃ is —OH, —NH₂, C₁₋₆alkoxy, —NH(C₁₋₆alkyl), —N(C₁₋₆alkyl)₂, di-(C₁₋₂alkyl) N-oxide, —NR$_b$(C₁₋₆hydroxyalkyl), —NR$_b$(C₃₋₇cycloalkyl), —NR$_b$(CR$_b$R$_b$)$_q$NH(C₁₋₆alkyl), —NR$_b$(CR$_b$R$_b$)$_q$N(C₁₋₆alkyl)₂, —NR$_b$(phenyl), —NR$_b$C(O)(C₁₋₆alkyl), —S(C₁₋₆alkyl), —S(O)₂(C₁₋₆alkyl), —S(O)₂(C₁₋₄fluoroalkyl), —S(O)₂NR$_d$R$_d$, —S(O)₂(CR$_b$R$_b$)$_q$N(C₁₋₂alkyl)₂, —O(CR$_b$R$_b$)$_q$CR$_b$(C₁₋₂alkoxy)₂, —O(CR$_b$R$_b$)$_q$NR$_b$(C₃₋₆cycloalkyl), —O(CR$_b$R$_b$)$_q$N(C₁₋₂alkyl)₂, —NR$_b$C(O)NR$_b$A₂, —NR$_b$C(O)A₂, —NR$_b$A₂, —NR$_b$C(O)(CR$_b$R$_d$)$_q$A₂, or —O(CR$_c$R$_c$)$_q$A₂;

G is:

i) 1- to 2-ring heteroaryl or 1- to 2-ring heterocyclyl substituted with zero to 3 substituents independently selected from —OH, =O, C₁₋₆alkyl, —CR$_b$R$_b$C(O)OH, —CR$_b$R$_b$C(O)O(C₁₋₄alkyl), —CR$_b$R$_b$C(O)NH(phenyl), —CR$_b$R$_b$S(O)₂(phenyl), phenyl, —NR$_b$(C₁₋₆alkyl), —N(C₁₋₆alkyl)C(O)O(C₁₋₆alkyl), —C(O)(C₁₋₄alkyl), —C(O)(phenyl), and/or —C(O)(benzyl);

ii)

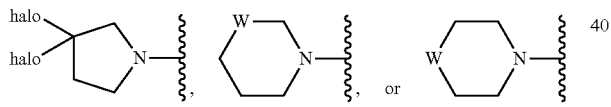

wherein W is CR$_b$(OR$_b$), C=CR$_b$R$_b$, NH, N(C₁₋₆alkyl), or NC(O)CR$_b$R$_b$(phenyl); or W is CR$_g$R$_g$ and a) each R$_g$ is halo; or b) R$_g$ and R$_g$ together with the carbon atom to which they are attached, form a 5- to 7-membered cycloalkyl or heterocyclyl ring substituted with zero to 2 substituents independently selected from —OH, —C(O)OH, —C(O)(C₁₋₄alkyl), C₁₋₆alkyl, C₃₋₆cycloalkyl, halo, —CF₃, =O, 1- to 2-ring aryl, and/or 1- to 2-ring heteroaryl;

iii) naphthalenyl; or phenyl substituted with zero to 3 substituents independently selected from —OH, C₁₋₆alkyl, C₁₋₄fluoroalkyl, halo, —CN, —NR$_b$R$_b$, C₁₋₄alkoxy, —C(O)OH, —CR$_b$R$_b$O(C₁₋₆alkyl), —CH₂NR$_b$C(O)(C₁₋₆alkyl), —CH₂NR$_b$C(O)(phenyl), —C(O)(C₁₋₆alkyl), —C(O)(heterocyclyl), phenoxy, —C(O)O(C₁₋₆alkyl), —C(O)NR$_b$(C₁₋₆alkyl), —C(O)N(C₁₋₆alkyl)₂, —C(O)NR$_b$CR$_b$R$_b$(heteroaryl), —NR$_b$S(O)₂(C₁₋₆alkyl), —NR$_b$S(O)₂(phenyl), —NR$_b$C(O)(phenyl), —NR$_b$C(O)(C₁₋₆alkyl phenyl), and/or —NR$_b$C(O)NR$_b$(phenyl); or iv)

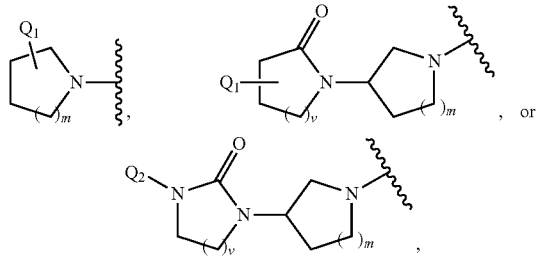

v) C₃₋₆cycloalkyl or C₄₋₆cycloalkenyl substituted with zero to 2 substituents independently selected from —OH, halo, —CF₃, =O, —OC(O)(phenyl), —NR$_b$C(O)(phenyl), —NR$_b$CR$_b$R$_b$(methoxyphenyl), —NR$_b$C(O)NR$_b$(thiazolyl),

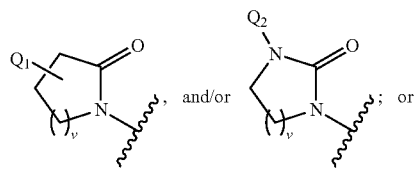

vi)

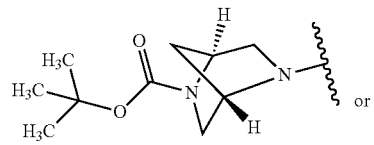

Q₁ is:

a) H, —OH, —C(O)OR$_b$, —C(O)NR$_b$(phenyl), —C(O)NR$_b$(C₁₋₆alkyl phenyl), —OC(O)(phenyl), —O(phenyl), phenyl, —NR$_b$R$_b$, —NR$_b$(pyrimidinyl), —N(pyrimidinyl)₂, C₁₋₄hydroalkyl, C₁₋₄aminoalkyl, —(CR$_b$R$_b$)$_q$C(O)O(C₁₋₄alkyl), —(CR$_b$R$_b$)$_q$NR$_b$C(O)O(C₁₋₄alkyl), indolyl, imidazolidinonyl, or pyrrolidinonyl;

b) —NR$_b$C(O)-Q₂;

c) —NR$_b$C(O)CR$_b$R$_b$-Q₂;

d)

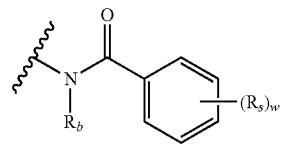

wherein each R$_s$ is independently selected from C₁₋₆alkyl, C₁₋₆fluoroalkyl, halo, —OH, —C(O)

($C_{1-6}$alkyl), —$NR_bC(O)(C_{1-6}$alkyl), —C(O)O($C_{1-6}$alkyl), $C_{1-6}$alkoxy, $C_{1-6}$fluoroalkoxy, —$NR_bR_b$, —N($C_{1-6}$alkyl)$_2$, —S(O)$_2$($C_{1-6}$alkyl), —$NR_bC(O)O(C_{1-6}$alkyl), phenoxy, —$CR_bR_bNR_bC(O)(C_{1-6}$alkyl), and/or a cyclic group independently selected from aryl, heteroaryl, and/or heterocyclyl, wherein said cyclic group is substituted with zero or more substituents independently selected from $C_{1-6}$alkyl, —OH, halo, $C_{1-2}$haloalkyl, —$NR_bR_b$, $C_{1-4}$alkoxy, =O, and/or —CN;

e) —$NR_bS(O)_2$-$Q_2$; or f) —$NR_bC(O)NR_b$-$Q_2$;

$Q_2$ is:
  a) H, $C_{1-6}$alkyl, $C_{1-6}$haloalkyl, —N($C_{1-6}$alkyl)$_2$, $C_{1-6}$alkoxy, phenoxy, or benzophenonyl;
  b) $C_{3-7}$cycloalkyl, aryl, heterocyclyl, or heteroaryl, each of which is substituted with zero or more substituents independently selected from $C_{1-6}$alkyl, $C_{3-7}$cycloalkyl, halo, —CN, —OH, =O, —$NR_bR_b$, $C_{1-6}$fluoroalkyl, $C_{1-6}$alkoxy, —S($C_{1-6}$alkyl), —C(O)($C_{1-6}$alkyl), —C(O)O($C_{1-6}$alkyl), —O($C_{3-7}$cycloalkyl), $C_{1-6}$alkylphenyl, hydroxyphenyl, halophenyl, ($C_{1-6}$fluoroalkyl)phenyl, and/or pyridinyl; or
  c) —$(CR_bR_b)_q$N($C_{1-6}$alkyl)$_2$, —$(CR_bR_b)_q$(phenyl), or —$(CR_bR_b)_q$(furanyl); and each $R_h$ is independently —OH, —$NH_2$, $C_{1-6}$alkyl, halo, $C_{1-6}$haloalkyl, $C_{1-6}$alkoxy, and/or $C_{1-6}$haloalkoxy.

4. The compound according to claim 3, or stereoisomers or pharmaceutically acceptable salts thereof, $R_6$ is H or $C_{1-2}$alkoxy;

one of $R_4$ and $R_5$ is H, halo, $C_{1-2}$alkoxy, —C(O)$NR_b$($C_{1-2}$alkyl), —$NR_b$($C_{1-2}$alkyl), —$NR_bS(O)_2$($C_{1-2}$alkyl), —$NR_bS(O)_2$(phenyl), —C(O)NH($C_{1-2}$alkyl), —N(CH$_3$)C(O)(phenyl), pyrrolidine-2,5-dione, —$NR_bC(O)NR_b$(phenyl), —$CH_2S(O)_2$(pyrrolidinyl), —S(O)$_2$($C_{1-2}$alkyl), —$NR_bS(O)_2$($C_{1-2}$alkyl), —$NR_bS(O)_2$(fluorophenyl), —$NR_bS(O)_2$(biphenyl), —$NR_bS(O)_2$(naphthalenyl), —$NR_bS(O)_2$(imidazolyl), —$NR_bS(O)_2$(chlorothiophenyl), —$NR_bS(O)_2$(benzyl), —$NR_bS(O)_2$(pyridinyl), —$NR_b(S(O)_2(C_{1-4}$chloroalkyl), —N(S(O)$_2$($C_{1-4}$chloroalkyl))$_2$, or —$NR_bC(O)O(C_{1-4}$alkyl);

and the other of $R_4$ and $R_5$ is:
  a) H, halo, —CN, or $C_{1-2}$alkoxy;
  b) -L-A; or
  c) -L-C(O)-A;

wherein L is a bond or —$(CR_cR_c)_t$—; and A is selected from $A_1$, $A_2$, and $A_3$, wherein:

$A_1$ is $C_{1-4}$alkyl or $C_{5-7}$cycloalkyl, each independently substituted with 0 to 2 substituents independently selected from —OH, —$NH_2$, $C_{1-2}$alkoxy, —C(O)($C_{1-6}$alkyl), —C(O)$OR_b$, —NH($C_{1-4}$alkyl), —N($C_{1-6}$alkyl)$_2$, —C(O)$NR_b$($C_{1-6}$alkyl), —C(O)$NR_b$($C_{1-6}$hydroxyalkyl), —C(O)$NR_b$(heterocyclyl), —C(O)$NR_b(CR_bR_b)_q$NH($C_{1-6}$alkyl), —C(O)$NR_b(CR_bR_b)_q$N($C_{1-6}$alkyl)$_2$, and/or —$NR_bC(O)(C_{1-6}$alkyl);

$A_2$ is 4- to 6-membered heterocyclyl or 5- to 6-membered heteroaryl having 1- to 3-heteroatoms independently selected from N, O, and/or S, and substituted with zero to 4 substituents independently selected from —OH, =O, $C_{1-4}$alkyl, $C_{1-4}$hydroxyalkyl, $C_{3-5}$cycloalkyl, —C(O)($C_{1-4}$alkyl), —NH($C_{1-4}$alkyl), —N($C_{1-4}$alkyl)$_2$, —C(O)$NR_b$($C_{1-4}$alkyl), —C(O)$NR_b$($C_{1-4}$-hydroxyalkyl), —C(O)$NR_b$($C_{3-4}$cycloalkyl), —C(O)$NR_b(CR_bR_b)_q$NH($C_{1-4}$alkyl), —C(O)$NR_b$(phenyl), —C(O)$NR_b(CR_bR_b)_q$N($C_{1-4}$alkyl)$_2$, —C(O)$NR_bR_b$, —$NR_bC(O)(C_{1-4}$alkyl), —C(O)O($C_{1-4}$alkyl), and/or —C(O)O(benzyl);

$A_3$ is —OH, —$NH_2$, $C_{1-4}$alkoxy, —NH($C_{1-6}$alkyl), —N($C_{1-6}$alkyl)$_2$, di-($C_{1-2}$alkyl) N-oxide, —$NR_b$($C_{1-4}$-hydroxyalkyl), —$NR_b$($C_{3-6}$cycloalkyl), —$NR_b(CR_bR_b)_q$NH($C_{1-4}$alkyl), —$NR_b(CR_bR_b)_q$N($C_{1-4}$alkyl)$_2$, —$NR_b$(phenyl), —$NR_bC(O)(C_{1-4}$alkyl), —$NR_bC(O)(C_{1-4}$alkyl), —S($C_{1-4}$alkyl), —S(O)$_2$($C_{1-4}$alkyl), —S(O)$_2$($C_{1-3}$fluoroalkyl), —S(O)$_2NR_dR_d$, —S(O)$_2(CR_bR_b)_qN(C_{1-2}$alkyl)$_2$, —O($CR_bR_b)_qCR_b(C_{1-2}$alkoxy)$_2$, —O($CR_bR_b)_qNR_b$($C_{3-6}$cycloalkyl), —O($CR_bR_b)_qN(C_{1-2}$alkyl)$_2$, —$NR_bC(O)NR_bA_2$, —$NR_bC(O)A_2$, —$NR_bA_2$, —$NR_bC(O)(CR_bR_d)_qA_2$, or —O($CR_cR_c)_qA_2$;

G is:

i) 1- to 2-ring heteroaryl or heterocyclyl substituted with zero to 3 substituents independently selected from —OH, =O, $C_{1-6}$alkyl, —$CR_bR_bC(O)OH$, —$CR_bR_bC(O)O(C_{1-4}$alkyl), —$CR_bR_bC(O)NH$(phenyl), —$CR_bR_bS(O)_2$(phenyl), phenyl, —$NR_b(C_{1-6}$alkyl), —N($C_{1-6}$alkyl)C(O)O($C_{1-6}$alkyl), —C(O)($C_{1-4}$alkyl), —C(O)(phenyl), and/or —C(O)(benzyl);

ii)

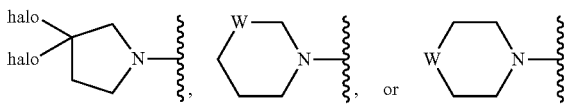

wherein W is $CR_b(OR_b)$, C=$CR_bR_b$, NH, N($C_{1-6}$alkyl), or NC(O)$CR_bR_b$(phenyl); or W is $CR_gR_g$ and
  a) each $R_g$ is halo; or
  b) $R_g$ and $R_g$ together with the carbon atom to which they are attached, form a 5- to 7-membered cycloalkyl or heterocyclyl ring substituted with zero to two substituents independently selected from $C_{1-4}$alkyl, —C(O)OH, —C(O)O($C_{1-4}$alkyl), =O, 1- to 2-ring aryl, and/or 1- to 2-ring heteroaryl;

iii) naphthalenyl; or phenyl substituted with zero to 3 substituents independently selected from —OH, $C_{1-6}$alkyl, $C_{1-2}$fluoroalkyl, halo, —CN, —$NR_bR_b$, $C_{1-4}$alkoxy, —C(O)OH, —$CR_bR_bO(C_{1-4}$alkyl), —$CH_2NR_bC(O)(C_{1-4}$alkyl), —$CH_2NR_bC(O)$(phenyl), —C(O)($C_{1-4}$alkyl), —C(O)-(heterocyclyl), phenoxy, —C(O)O($C_{1-6}$alkyl), —C(O)$NR_b$($C_{1-4}$alkyl), —C(O)N($C_{1-4}$alkyl)$_2$, —C(O)$NR_bCR_bR_b$(heteroaryl), —$NR_bS(O)_2(C_{1-4}$alkyl), —$NR_bS(O)_2$(phenyl), —$NR_bC(O)$(phenyl), —$NR_bC(O)(C_{1-6}$alkyl phenyl), and/or —$NR_bC(O)NR_b$(phenyl); or iv)

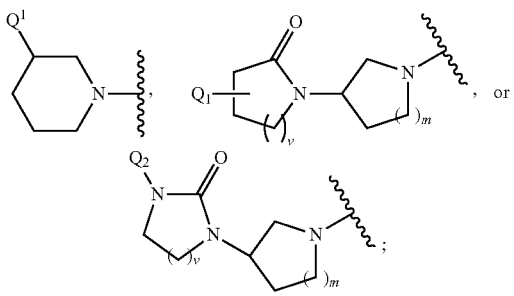

v)

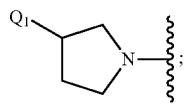

vi) cyclohexyl or cyclohexenyl substituted with zero to 2 substituents independently selected from —OH, =O, —OC(O)(phenyl), —NR$_b$C(O)(phenyl), —NR$_b$CR$_b$R$_b$(methoxyphenyl), —NR$_b$C(O)NR$_b$(thiazolyl),

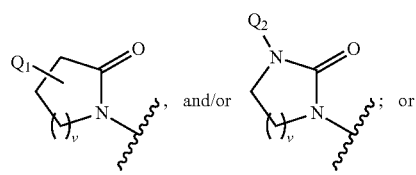

vii)

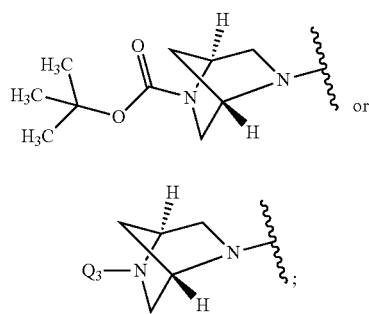

wherein Q$_1$ is:

a) H, —OH, —C(O)OR$_b$, —C(O)NR$_b$(phenyl), —C(O)NR$_b$(C$_{1-6}$alkyl phenyl), —OC(O)(phenyl), —O(phenyl), phenyl, —NR$_b$R$_b$, —NR$_b$(pyrimidinyl), —N(pyrimidinyl)$_2$, C$_{1-4}$hydroalkyl, C$_{1-4}$-aminoalkyl, —(CR$_b$R$_b$)$_q$C(O)O(C$_{1-4}$alkyl), —(CR$_b$R$_b$)$_q$NR$_b$C(O)O(C$_{1-4}$alkyl), indolyl, imidazolidinonyl, or pyrrolidinonyl;

b) —NR$_b$C(O)—B$_1$, wherein B$_1$ is C$_{1-4}$alkyl; C$_{1-4}$alkoxy; C$_{3-6}$cycloalkyl optionally substituted with C$_{1-4}$alkyl or C$_{1-4}$alkoxy; phenoxy; benzophenonyl; or 1- to 3-ring aryl optionally substituted with C$_{1-4}$alkyl, C$_{1-2}$fluoroalkyl, or C$_{1-4}$alkoxy;

c) —NR$_b$C(O)—B$_2$, wherein B$_2$ is 1- to 2-ring heterocyclyl or heteroaryl substituted with zero or more substituents independently selected from C$_{1-4}$alkyl, —NR$_b$R$_b$, halo, C$_{1-2}$fluoroalkyl, —CN, =O, C$_{1-4}$alkoxy, —C(O)(C$_{1-4}$alkyl), and/or pyridinyl;

d) —NR$_b$C(O)CR$_b$R$_b$—B$_3$, wherein B$_3$ is —N(C$_{1-6}$alkyl)$_2$, phenyl, or 1- to 2-ring heteroaryl substituted with zero or more substituents independently selected from C$_{1-4}$alkyl, —OH, —CN, halo, and/or C$_{1-4}$alkoxy;

e)

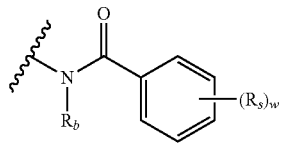

wherein each R$_s$ is independently selected from C$_{1-6}$alkyl, C$_{1-2}$fluoroalkyl, halo, —OH, —C(O)(C$_{1-4}$alkyl), —NR$_b$C(O)(C$_{1-4}$alkyl), —C(O)O(C$_{1-4}$alkyl), C$_{1-4}$alkoxy, C$_{1-4}$fluoroalkoxy, —NR$_b$R$_b$, —N(C$_{1-4}$alkyl)$_2$, —S(O)$_2$(C$_{1-4}$alkyl), —NR$_b$C(O)O(C$_{1-6}$alkyl), —CR$_b$R$_b$NR$_b$C(O)(C$_{1-6}$alkyl), phenoxy, and/or a cyclic group independently selected from aryl, heteroaryl, and/or heterocyclyl, wherein said cyclic group is substituted with zero or more substituents independently selected from C$_{1-6}$alkyl, —OH, halo, C$_{1-2}$haloalkyl, —NR$_b$R$_b$, C$_{1-4}$alkoxy, =O, and/or —CN;

f) —NHS(O)$_2$—B$_4$ wherein B$_4$ is phenyl or 1-ring heteroaryl substituted with zero to 3 substituents independently selected from C$_{1-4}$alkyl, halo, —NR$_b$R$_b$, C$_{1-4}$alkoxy, and/or C$_{1-2}$fluoroalkyl;

g) —NR$_b$C(O)NR$_b$—B$_5$ wherein B$_5$ is phenyl substituted with zero to 2 substituents independently selected from halo, C$_{1-6}$alkyl, —CN, —NR$_b$R$_b$, C$_{1-2}$fluoroalkyl, C$_{1-4}$alkoxy, —C(O)O(C$_{1-6}$alkyl), —S(C$_{1-2}$alkyl), —C(O)(C$_{1-4}$alkyl), and/or —O(C$_{3-6}$cycloalkyl);

h) —NR$_b$C(O)NR$_b$—B$_6$ wherein B$_6$ is a 1-ring heteroaryl substituted with zero to 2 substituents independently selected from C$_{1-4}$alkyl, halo, C$_{1-4}$fluoroalkyl, C$_{3-6}$cycloalkyl, —S(C$_{1-3}$alkyl), and/or —C(O)O(C$_{1-4}$alkyl); or i) —NR$_b$C(O)NR$_b$—B$_7$ wherein B$_7$ is C$_{1-6}$alkyl, C$_{1-4}$haloalkyl, C$_{3-6}$cycloalkyl, —(CR$_b$R$_b$)$_q$(phenyl), or —(CR$_b$R$_b$)$_q$(furanyl); and each R$_h$ is independently —OH, —NH$_2$, C$_{1-6}$alkyl, halo, C$_{1-4}$haloalkyl, C$_{1-4}$alkoxy, and/or C$_{1-4}$haloalkoxy.

5. The compound according to claim 4, or stereoisomers or pharmaceutically acceptable salts thereof, wherein:

R$_1$ is H;

R$_2$ is H, F, or Br;

R$_6$ is C$_{1-2}$alkoxy, R$_5$ is H, and R$_4$ is H; or

R$_6$ is H, R$_5$ is halo, and R$_4$ is 5- to 6-membered heterocyclyl having 1- to 3-heteratoms independently selected from N, O, and/or S, and substituted with zero to 2 substituents independently selected from C$_{1-4}$alkyl, C$_{1-4}$-hydroxyalkyl, and/or —C(O)(C$_{1-4}$alkyl); or R$_6$ is H, R$_5$ is H, —OCH$_3$, —NH(CH$_3$), —C(O)NHCH$_3$, —N(CH$_3$)C(O)(phenyl), pyrrolidine-2,5-dione, —N(CH$_3$)C(O)NH(phenyl), —CH$_2$S(O)$_2$(pyrrolidinyl), —S(O)$_2$CH$_3$, —NR$_b$S(O)$_2$CH$_3$, —NR$_b$S(O)$_2$CH$_2$CH$_3$, —NR$_b$S(O)$_2$(phenyl), —NR$_b$S(O)$_2$(fluorophenyl), —NR$_b$S(O)$_2$(biphenyl), —NR$_b$S(O)$_2$(naphthalenyl), —NR$_b$S(O)$_2$(chlorothiophenyl), —NR$_b$S(O)$_2$(imidazolyl), —NR$_b$S(O)$_2$(benzyl), —NR$_b$S(O)$_2$(pyridinyl), —NR$_b$(S(O)$_2$CH$_2$CH$_2$CH$_2$Cl), —N(S(O)$_2$CH$_2$CH$_2$CH$_2$Cl)$_2$, or —NR$_b$C(O)O(butyl), and R$_4$ is:

a) H, halo, or —CN;

b) -L-A; or c) -L-C(O)-A;

wherein L is a bond or —(CR$_c$R$_c$)$_t$—; and A is selected from A$_1$, A$_2$, and A$_3$; wherein:

A$_1$ is C$_{1-4}$alkyl substituted with 0 to 2 substituents independently selected from —OH, —NH$_2$, —OCH$_3$, —C(O)OH, —NH(C$_{1-2}$alkyl), and/or —N(C$_{1-2}$alkyl)$_2$;

A$_2$ is 4- to 6-membered heterocyclyl or 5- to 6-membered heteroaryl having 1- to 3-heteroatoms independently selected from N, O, and/or S, and substituted with zero to 4 substituents independently selected from —OH, =O, C$_{1-3}$alkyl, C$_{1-2}$hydroxyalkyl, C$_{3-4}$cycloalkyl, —C(O)(C$_{1-2}$alkyl), —C(O)O(C$_{1-4}$alkyl), and/or —C(O)O(benzyl);

A$_3$ is —OH, —NH$_2$, C$_{1-4}$alkoxy, —OCH$_2$CH(OCH$_2$CH$_3$)$_2$, —OCH$_2$CH$_2$NH(cyclopropyl), —OCH$_2$CH$_2$(pyrrolidinyl)), —OCH$_2$CH$_2$N(CH$_3$)$_2$, N,N-dimethylethamine oxide, —NH(C$_{1-4}$alkyl), —N(C$_{1-2}$alkyl)$_2$, —NH(C$_{1-2}$hydroxyalkyl), —NH(C$_{3-6}$cycloalkyl), —NH(CH$_2$)$_q$NH(C$_{1-4}$alkyl), —NH(CH$_2$)$_q$N(C$_{1-2}$alkyl)$_2$, —NH(phenyl), —NHC(O)(C$_{1-2}$alkyl), —S(C$_{1-4}$alkyl), —S(O)$_2$(C$_{1-4}$alkyl), —S(O)$_2$(C$_{1-2}$fluoroalkyl), —S(O)$_2$NR$_d$R$_d$, —S(O)$_2$(CH$_2$)$_q$N(C$_{1-2}$alkyl)$_2$, —NHC(O)A$_2$, —NHA$_2$, —NHC(O)(CH$_2$)$_q$A$_2$, or —O(CH$_2$)$_q$A$_2$;

G is:
i) 1- to 2-ring heteroaryl or heterocyclyl substituted with zero to 3 substituents independently selected from —OH, =O, C$_{1-4}$alkyl, —CH$_2$C(O)OH, —CH$_2$C(O)NH(phenyl), —CH$_2$C(O)O(C$_{1-2}$alkyl), —CH$_2$S(O)$_2$(phenyl), phenyl, —NR$_b$(C$_{1-4}$alkyl), —N(C$_{1-4}$alkyl)C(O)O(C$_{1-4}$alkyl), —C(O)(C$_{1-4}$alkyl), —C(O)(phenyl), and/or —C(O)(benzyl);

ii)

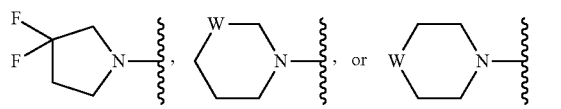

wherein W is CH(OH), C=CH$_2$, NH, N(C$_{1-4}$alkyl), or NC(O)CR$_b$R$_b$(phenyl); or W is CR$_g$R$_g$ and
a) each R$_g$ is halo; or
b) R$_g$ and R$_g$ together with the carbon atom to which they are attached, form a 5- to 6-membered cycloalkyl or heterocyclyl ring substituted with zero to two substituents independently selected from —C(O)OH, —CH(CH$_3$)$_2$, —C(O)OCH$_2$CH$_3$, =O, phenyl, pyridinyl, and/or naphthalenyl;

iii) naphthalenyl; or phenyl substituted with zero to 3 substituents independently selected from —OH, C$_{1-4}$alkyl, C$_{1-2}$fluoroalkyl, halo, —CN, —NR$_b$R$_b$, C$_{1-4}$alkoxy, —CH$_2$O(C$_{1-4}$alkyl), —CH$_2$NHC(O)(C$_{1-4}$alkyl), —CH$_2$NR$_b$C(O)(phenyl), —C(O)(C$_{1-4}$alkyl), —C(O)(heterocyclyl), phenoxy, —C(O)OH, —C(O)O(C$_{1-4}$alkyl), —C(O)NR$_b$(C$_{1-2}$alkyl), —C(O)N(C$_{1-4}$alkyl)$_2$, —C(O)NR$_b$CR$_b$R$_b$(furanyl), —NR$_b$S(O)$_2$(C$_{1-4}$alkyl), —NR$_b$S(O)$_2$(phenyl), —NR$_b$C(O)(phenyl), —NR$_b$C(O)(C$_{1-4}$alkyl phenyl), and/or —NR$_b$C(O)NR$_b$(phenyl);

iv)

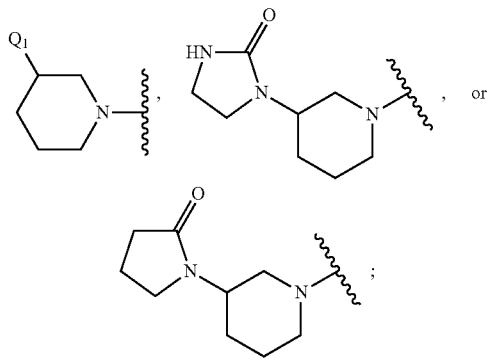

v)

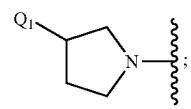

vi) cyclohexyl or cyclohexenyl substituted with zero to 1 substituent selected from —OH, =O, —OC(O)(phenyl), —NHC(O)(phenyl), —NHCH(CH$_3$)(methoxyphenyl), or —NHC(O)NH(thiazolyl); or vii)

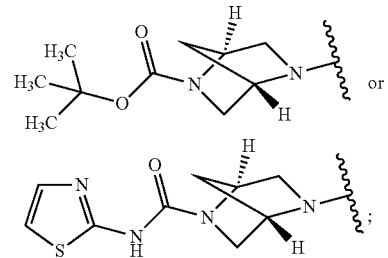

wherein Q$_1$ is:
a) H, —OH, —C(O)OH, —C(O)NR$_b$(phenyl), —C(O)NR$_b$(C$_{1-4}$alkyl phenyl), —OC(O)(phenyl), —O(phenyl), —NR$_b$R$_b$, —NR$_b$(pyrimidinyl), —N(pyrimidinyl)$_2$, —CH$_2$OH, —CH$_2$NH$_2$, —CH$_2$C(O)OCH$_2$CH$_3$, —CH$_2$NHC(O)O(butyl), —CH$_2$CH$_2$NHC(O)O(butyl), phenyl, indolyl, imidazolidinonyl, or pyrrolidinonyl;
b) —NHC(O)—B$_1$, wherein B$_1$ is C$_{1-4}$alkyl; C$_{1-4}$alkoxy; C$_{3-6}$cycloalkyl optionally substituted with C$_{1-4}$alkyl or C$_{1-4}$alkoxy; phenoxy; benzophenonyl; or 2- or 3-ring aryl optionally substituted with C$_{1-4}$alkyl or C$_{1-4}$alkoxy;
c) —NHC(O)—B$_2$, wherein B$_2$ is 1- to 2-ring heterocyclyl or heteroaryl substituted with zero or more substituents independently selected from C$_{1-4}$alkyl, —NR$_b$R$_b$, halo, C$_{1-2}$fluoroalkyl, —CN, =O, C$_{1-4}$alkoxy, —C(O)O(C$_{1-4}$alkyl), and/or pyridinyl;
d) —NHC(O)CH$_2$—B$_3$, wherein B$_3$ is a —N(C$_{1-4}$alkyl)$_2$, phenyl, 1- to 2-ring heteroaryl substituted with zero or more substituents independently selected from C$_{1-4}$alkyl, —OH, —CN, halo, and/or C$_{1-3}$alkoxy;

e)

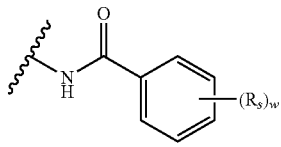

wherein each $R_s$ is independently $C_{1-4}$alkyl, $C_{1-2}$fluoroalkyl, halo, —OH, —C(O)($C_{1-4}$alkyl), —$NR_bC(O)$($C_{1-4}$alkyl), —C(O)O($C_{1-4}$alkyl), $C_{1-4}$alkoxy, —O($C_{1-4}$fluoroalkyl), —$NH_2$, —N($C_{1-4}$alkyl)$_2$, —S(O)$_2$($C_{1-2}$alkyl), —$NR_bC(O)O(C_{1-4}$alkyl), —$CR_bR_bNR_bC(O)(C_{1-4}$alkyl), phenoxy, phenyl, 1- to 3-ring heterocyclyl, or 1- to 3-ring heteroaryl, wherein said phenyl, said heterocyclyl, and said heteroaryl are substituted with zero or more substituents independently selected from $C_{1-4}$alkyl, —OH, halo, $C_{1-2}$haloalkyl, —$NR_bR_b$, $C_{1-4}$alkoxy, =O, and/or —CN;

f) —NHS(O)$_2$—$B_4$ wherein $B_4$ is phenyl or 1-ring heteroaryl substituted with zero to 3 substituents independently selected from $C_{1-4}$alkyl, halo, —$NR_bR_b$, $C_{1-4}$alkoxy, and/or $C_{1-2}$fluoroalkyl;

g) —NHC(O)NH—$B_5$ wherein $B_5$ is phenyl substituted with zero to two substituents independently selected from halo, $C_{1-4}$alkyl, —CN, —$NR_bR_b$, $C_{1-2}$fluoroalkyl, $C_{1-4}$alkoxy, —C(O)O($C_{1-4}$alkyl), —S($C_{1-2}$alkyl), —C(O)($C_{1-4}$alkyl), and/or —O($C_{3-6}$cycloalkyl);

h) —NHC(O)NH—$B_6$ wherein $B_6$ is 1-ring heteroaryl substituted with zero to two substituents independently selected from $C_{1-4}$alkyl, halo, $C_{1-4}$fluoroalkyl, $C_{3-6}$cycloalkyl, —S($C_{1-2}$alkyl), and/or —C(O)O($C_{1-4}$alkyl);

i) —NHC(O)NH—$B_7$ wherein $B_7$ is $C_{1-4}$alkyl, $C_{1-4}$haloalkyl, $C_{3-6}$cycloalkyl, benzyl, —$CR_bR_bCR_bR_b$-(phenyl), or —$CR_bR_b$-(furanyl);

each $R_c$ is independently H, —$CH_3$, and/or —$CH_2OH$;
each q is independently 1 or 2; and
t is 1 or 2.

6. The compound according to claim 1, or stereoisomers or pharmaceutically acceptable salts thereof, wherein: $R_3$ is H.

7. The compound according to claim 1, or stereoisomers or pharmaceutically acceptable salts thereof, wherein:
$R_6$ is —$OCH_3$, $R_5$ is H, and $R_4$ is H; or
$R_6$ is H, $R_5$ is F, and $R_4$ is morpholinyl or N-methyl piperazinyl; or
$R_6$ is H, $R_5$ is —$OCH_3$, and $R_4$ is H, —$OCH_2CH(OCH_2CH_3)_2$, —$OCH_2CH_2N(CH_3)_2$, —$OCH_2CH_2NH$(cyclopropyl), or —$OCH_2CH_2$(pyrrolidinyl); or
$R_6$ is H, $R_5$ is —$NH(CH_3)$, —C(O)$NHCH_3$, —N($CH_3$)C(O)(phenyl), pyrrolidine-2,5-dione, —N($CH_3$)C(O)NH(phenyl), —$CH_2S(O)_2$(pyrrolidinyl), —S(O)$_2CH_3$, —$NR_bS(O)_2CH_3$, —$NR_bS(O)_2CH_2CH_3$, —$NR_bS(O)_2$(phenyl), —N($CH_3$)S(O)$_2$(fluorophenyl), —N($CH_3$)S(O)$_2$(biphenyl), —N($CH_3$)S(O)$_2$(naphthalenyl), —N($CH_3$)S(O)$_2$(imidazolyl), —N($CH_3$)S(O)$_2$(chlorothiophenyl), —N($CH_3$)S(O)$_2$(benzyl), —N($CH_3$)S(O)$_2$(pyridinyl), —NH(S(O)$_2CH_2CH_2CH_2Cl$), —N(S(O)$_2CH_2CH_2CH_2Cl)_2$, or —N($CH_3$)C(O)O(butyl), and $R_4$ is H or —C(O)(morpholinyl); or
$R_6$ is H, $R_5$ is H, and $R_4$ is H, F, —CN, ethyl, butyl, hydroxyethyl, dimethylaminoethyl, N,N-dimethylethamine oxide, —$OCH_3$, —$NHC(O)CH_3$, —$NH_2$, —N(ethyl)$_2$, —C(O)$CH_3$, —C(O)OH, —C(O)O(butyl), —C(O)NH(cyclopropyl), —C(O)NH(butyl), —C(O)NH(phenyl), —C(O)N($CH_3$)$_2$, —C(O)N(ethyl)$_2$, —C(O)$NHCH_2CH_2N(CH_3)_2$, —C(O)NH(hydroxyethyl), —C($CH_3$)$_2CH_2OH$, —C($CH_3$)$_2$C(O)$OCH_2CH_3$, —$CH_2CH_2NH$(butyl), —$CH_2CH_2$(azetidinyl), —$CH_2CH_2$(imidazolyl), —$CH_2CH_2$(pyrrolidinyl), —C($CH_3$)$_2$C(O)NH(oxetanyl), —$CH_2CH(CH_2OH)NHC(O)$(pyrrolidinyl), —$CH_2CH(CH_2OH)NHC(O)$(piperidinyl), —C($CH_3$)$_2$C(O)$NHCH_2CH_2N(CH_3)_2$, —NHC(O)$CH_2$(pyrrolidinyl), —C($CH_3$)$_2$C(O)NH(cyclopropyl), —C($CH_3$)$_2$C(O)$NHCH_2CH_2OH$, —S(O)$_2N(CH_3)_2$, —C($CH_3$)$_2$C(O)OH, —S(O)$_2CH_3$, —S(O)$_2CF_3$, —S(O)$_2CH_2CH_2N(CH_2CH_3)_2$, pyrrolidinyl, oxazolyl, tetrahydropyranyl, morpholinyl, 4-hydroxymorpholinyl, morpholinonyl, piperidinyl, N-methyl piperidinyl, N-(butyl-OC(O))piperidinyl, 1-(ethyl-OC(O))-4-methylpiperidinyl, 1,4-dimethyl piperidinyl, N-acetyl piperazinyl, piperazinyl, N-methyl piperazinyl, N-ethyl piperazinyl, N-propyl piperazinyl, N-cyclopropyl-piperazinyl, N-cyclobutyl piperazinyl, N-(benzyl-OC(O))piperazinyl, —C(O)(azetidinyl), —C(O)(pyrrolidinyl), —C(O)(morpholinyl), —C(O)(piperidinyl), —C(O)(N-methyl piperazinyl), —C(O)(N-hydroxyethyl piperazinyl), —$CH_2$(morpholinyl), —$CH_2$(oxazolidinonyl),

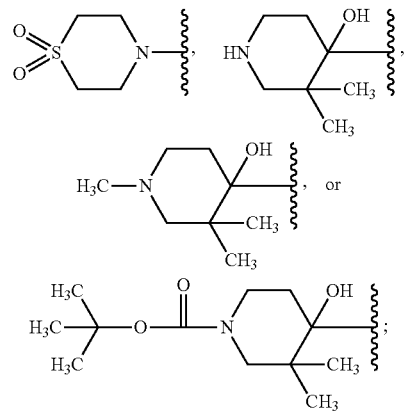

G is:

i) thiophenyl; methylpyrrolidinyl, hydroxypyrrolidinyl, pyridinyl; indolyl; isoindolinyl; benzofuranyl; N-methylpyrazolyl; dimethyl morpholinyl; morpholinyl optionally substituted with phenyl, —$CH_2C(O)OH$, —$CH_2C(O)NH$(phenyl), or —$CH_2S(O)_2$(phenyl); piperazinyl optionally substituted with =O, —$CH_2C(O)OCH_3$, or —C(O)(benzyl); N-methyl piperazinyl substituted with —$CH_2C(O)OCH_3$; thiazolyl substituted with —NH(propyl) or —N(propyl)(C(O)(O-butyl)); or 1,2,3,4-tetrahydroisoquinolinyl substituted with zero or one substituents selected from —C(O)(phenyl), —C(O)$CH_3$, or —C(O)butyl;

ii)

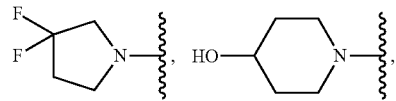

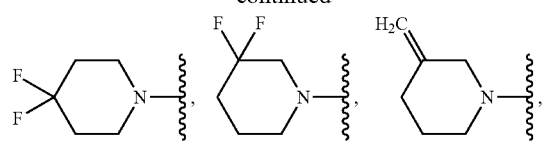
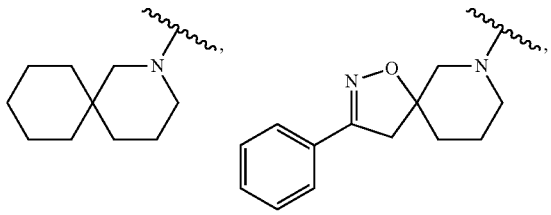
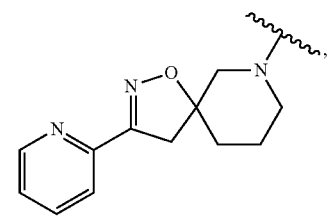
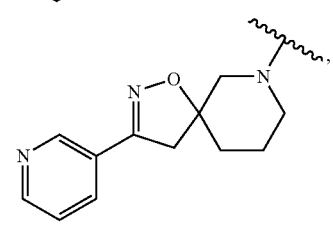
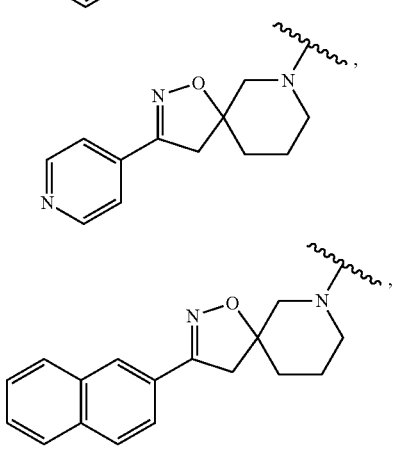
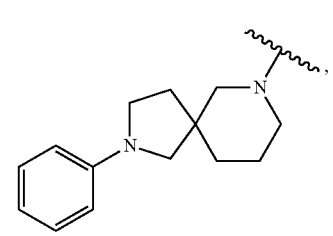

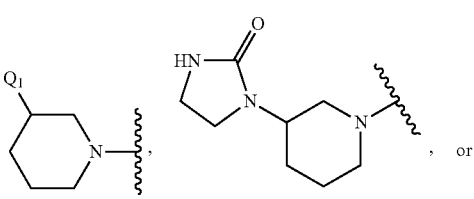

iii) naphthalenyl; or phenyl substituted with zero to 3 substituents independently selected from —OH, —CH₃, propyl, F, Cl, —CF₃, —CN, —NH₂, C₁₋₃alkoxy, —CH₂OCH₃, —CH₂NHC(O)CH₃, —CH₂NHC(O)(phenyl), —C(O)CH₃, —C(O)-(pyrrolidinyl), phenoxy, —C(O)OH, —C(O)O-(t-butyl), —C(O)NHCH₃, —C(O)N(CH₃)₂, —C(O)NHCH₂(furanyl), —NHS(O)₂(CH₃), —NHS(O)₂(phenyl), —NHC(O)(phenyl), —NHC(O)(t-butyl phenyl), and/or —NHC(O)NH(phenyl);

iv)

wherein Q₁ is:

a) H, —C(O)OH, —C(O)NH(t-butyl phenyl), —O(phenyl), —NH₂, —NH(pyrimidinyl), —N(pyrimidinyl)₂, —N(CH₃)C(O)(phenyl), —CH₂OH, —CH₂NH₂, —CH₂C(O)OCH₂CH₃, —CH₂NHC(O)O(butyl), —CH₂CH₂NHC(O)O(butyl), or indolyl;

b) —NHC(O)—B₁, wherein B₁ is —CH₃, propyl, cyclopropyl, cyclohexyl, butyl cyclohexyl, t-butoxy, phenoxy, benzophenonyl, naphthalenyl, methoxynaphthalenyl, or anthracenyl;

c) —NHC(O)—B₂, wherein B₂ is piperidinyl, furanyl, morpholinyl, pyrazinyl, indolyl, benzothiazolyl, benzotriazolyl, benzimidazolyl, quinolinyl, quinolinonyl, quinoxalinyl, 2,3-dihydrobenzodioxinyl, fluorenonyl, thiophenyl, pyrazolyl, imidazolyl, isoxazolyl, oxazolyl, thiazolyl, pyridinyl, pyridazinyl, or pyrimidinyl, each of which is substituted with zero or more substituents independently selected from —CH₃, propyl, butyl, —NH₂, Cl, —CF₃, —C(O)O(butyl), and/or pyridinyl;

d) —NHC(O)CH₂—B₃, wherein B₃ is a —N(CH₃)₂, phenyl, pyridinyl, or methyl indolyl;

e)

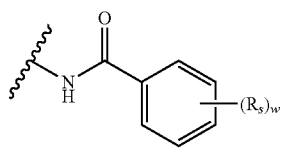

wherein each $R_s$ is independently —CH₃; butyl; —CF₃; halo; —OH; —C(O)CH₃; —NHC(O)CH₃; —C(O)OCH₃; —C(O)OCH₂CH₃; —OCH₃; propoxy; —OCF₂CHF₂; —N(CH₃)₂; —S(O)₂CH₃; —NHC(O)O(butyl); —CH₂NHC(O)(t-butyl); phenoxy; pyrrolyl; thiophenyl; pyrazolyl; imidazolyl; methyl oxadiazolyl; triazolyl; tetrazolyl; methyl tetrazolyl; pyridinyl; pyrimidinyl; pyridinonyl; N-methyl piperazinyl, indolyl, benzimidazolyl, chromenonyl, or phenyl substituted with zero or more substituents independently selected from —CH₃, —OH, F, and/or Cl;

f) —NHS(O)₂—B₄ wherein B₄ is phenyl, trifluoromethyl phenyl, thiophenyl, dimethyl isoxazolyl, or methyl imidazolyl;

g) —NHC(O)NH—B₅ wherein B₅ is phenyl substituted with zero to two substituents independently selected from halo, —CH₃, ethyl, butyl, —CN, —CF₃, —OCH₃, —C(O)O(ethyl), —C(O)O(t-butyl), —SCH₃, —C(O)CH₃, and/or —O(cyclopentyl);

h) —NHC(O)NH—B₆ wherein B₆ is pyrazolyl, isoxazolyl, thiazolyl, thiadiazolyl, tetrazolyl, or pyridinyl, each of which is substituted with zero to two substituents independently selected from —CH₃, butyl, Br, —CF₃, cyclopropyl, —S(ethyl), and/or —C(O)O(ethyl); or i) -NHC(O)NH—B₇ wherein B₇ is propyl, chloroethyl, C₅₋₆cycloalkyl, benzyl, —CH₂CH₂— (phenyl), or —CH₂— (furanyl);

v)

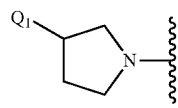

wherein Q₁ is H, —NH₂, phenyl, —C(O)OH, —NHC(O)(t-butyl), —NHC(O)(phenyl), —NHC(O)(trifluoromethyl phenyl), —NHC(O)O(t-butyl), —C(O)NH(phenyl), —C(O)NH(t-butyl phenyl), or —NHC(O)NH(methyl thiazolyl);

vi)

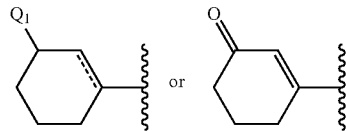

wherein Q₁ is H, —OH, —OC(O)(phenyl), —NHC(O)(phenyl), —NHCH(CH₃)(methoxyphenyl), or —NHC(O)NH(thiazolyl); or vii)

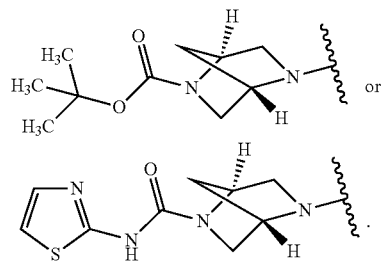

8. A compound having Formula (II):

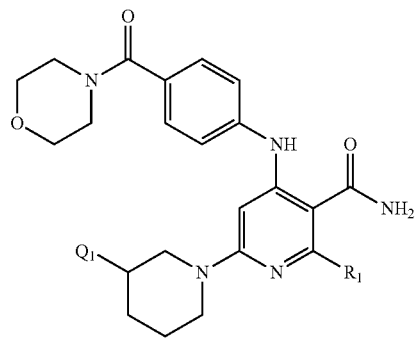

or stereoisomers or pharmaceutically acceptable salts thereof, wherein:

R₁ is H or C₃alkoxy;

Q₁ is: H, —NH₂, —NHC(O)O-(t-butyl), —NHC(O)NH—B₈; and

B₈ is phenyl or thiazolyl, each of which is optionally substituted with one or two methyl groups.

9. A pharmaceutical composition, comprising; a pharmaceutically acceptable carrier and a compound of claim 1, or stereoisomers or pharmaceutically acceptable salts thereof.

10. A method of using a compound of claim 1, or stereoisomers or pharmaceutically acceptable salts thereof, for treatment of an allergic disorder, and/or inflammatory disease.

* * * * *

UNITED STATES PATENT AND TRADEMARK OFFICE
CERTIFICATE OF CORRECTION

PATENT NO. : 8,586,751 B2
APPLICATION NO. : 13/377157
DATED : November 19, 2013
INVENTOR(S) : George DeLucca et al.

Page 1 of 1

It is certified that error appears in the above-identified patent and that said Letters Patent is hereby corrected as shown below:

Title page, "Other Publications":

Col. 2, line 7, delete "nicotinamid" and insert -- nicotinamide --, therefor.

In the Claims:

Claim 3, col. 226, line 50, delete "—$NR_b(S(O)_2(C_{1-4}haloalkyl)$," and insert -- —$NR_bS(O)_2(C_{1-4}haloalkyl)$," --;

Claim 4, col. 229, line 41, delete "—$NR_b(S(O)_2(C_{1-4}chloroalkyl)$," and insert -- —$NR_bS(O)_2(C_{1-4}chloroalkyl)$," --; and Claim 5, col. 232, line 48, delete "3-heratoms" and insert -- 3-heteroatoms --, therefor.

Signed and Sealed this
Twenty-first Day of October, 2014

Michelle K. Lee
*Deputy Director of the United States Patent and Trademark Office*